United States Patent
Ahn et al.

(10) Patent No.: US 11,930,704 B2
(45) Date of Patent: Mar. 12, 2024

(54) ORGANIC ELECTROLUMINESCENT DEVICE COMPRISING AN ELECTRON BUFFER LAYER AND AN ELECTRON TRANSPORT LAYER

(71) Applicant: ROHM AND HAAS ELECTRONIC MATERIALS KOREA LTD., Chungcheongnam-do (KR)

(72) Inventors: Hee-Choon Ahn, Gyeonggi-do (KR); Doo-Hyeon Moon, Gyeonggi-do (KR); Sang-Hee Cho, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 0 days.

(21) Appl. No.: 18/062,715

(22) Filed: Dec. 7, 2022

(65) Prior Publication Data
US 2023/0180604 A1    Jun. 8, 2023

Related U.S. Application Data

(63) Continuation of application No. 16/325,248, filed as application No. PCT/KR2017/010047 on Sep. 13, 2017, now abandoned.

(30) Foreign Application Priority Data

Sep. 13, 2016 (KR) .................. 10-2016-0118007
Sep. 4, 2017 (KR) .................. 10-2017-0112487

(51) Int. Cl.
*H10K 85/60* (2023.01)
*H10K 50/11* (2023.01)
(Continued)

(52) U.S. Cl.
CPC ........ *H10K 85/6572* (2023.02); *H10K 50/11* (2023.02); *H10K 50/171* (2023.02); *H10K 85/626* (2023.02); *H10K 85/633* (2023.02); *H10K 85/636* (2023.02); *H10K 85/654* (2023.02); *H10K 85/657* (2023.02); *H10K 85/6574* (2023.02); *H10K 85/6576* (2023.02); *H10K 50/15* (2023.02); *H10K 50/165* (2023.02); *H10K 50/166* (2023.02);
(Continued)

(58) Field of Classification Search
CPC ............. H01L 51/0072; H01L 51/0071; H01L 51/5004; H01L 51/0067; H01L 51/0058; H01L 51/006; H01L 51/0061; H01L 51/0074; H01L 51/5012; H01L 51/5092; H01L 51/0073; H01L 51/508; H01L 51/5056; H01L 2251/552; H01L 2251/558; H01L 51/5076
See application file for complete search history.

(56) References Cited

U.S. PATENT DOCUMENTS

| 2015/0144897 A1* | 5/2015 | Kang ............... H10K 50/166 257/40 |
| 2017/0250348 A1* | 8/2017 | Jin ............... H10K 85/6572 |

FOREIGN PATENT DOCUMENTS

KR     2014094408 A  *  7/2014  ........... C07D 401/14

* cited by examiner

*Primary Examiner* — Michael Y Sun
(74) *Attorney, Agent, or Firm* — G. Creston Campbell

(57) ABSTRACT

The present disclosure relates to an organic electroluminescent device. The organic electroluminescent device of the present disclosure comprises a specific combination of an electron buffer material and an electron transport material which can provide high efficiency and/or long lifespan.

7 Claims, 2 Drawing Sheets

(51) Int. Cl.
*H10K 50/17* (2023.01)
*H10K 50/15* (2023.01)
*H10K 50/16* (2023.01)
*H10K 50/165* (2023.01)
*H10K 101/30* (2023.01)
*H10K 101/40* (2023.01)
*H10K 102/00* (2023.01)

(52) U.S. Cl.
CPC ..... *H10K 2101/30* (2023.02); *H10K 2101/40* (2023.02); *H10K 2102/351* (2023.02)

ORGANIC ELECTROLUMINESCENT DEVICE COMPRISING AN ELECTRON BUFFER LAYER AND AN ELECTRON TRANSPORT LAYER

CLAIM OF BENEFIT OF PRIOR APPLICATION

This application claims priority under 35 U.S.C. § 120 from U.S. patent application Ser. No. 16/325,248 filed Feb. 13, 2019, which is the Convention Filing of KR10-2017-0112487, filed Sep. 4, 2017 and KR10-2016-0118007, filed Sep. 13, 2016, all of which are incorporated by reference herein in their entirety.

TECHNICAL FIELD

The present disclosure relates to an organic electroluminescent device comprising an electron buffer layer and an electron transport layer.

BACKGROUND ART

An electroluminescent (EL) device is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic EL device changes electric energy into light by the injection of a charge into an organic light-emitting material, and commonly comprises an anode, a cathode, and an organic layer formed between the two electrodes. The organic layer of the organic EL device may be composed of a hole injection layer, a hole transport layer, an electron blocking layer, a light-emitting layer (containing host and dopant materials), an electron buffer layer, a hole blocking layer, an electron transport layer, an electron injection layer, etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by electric voltage, and an exciton having high energy is produced by the recombination of the holes and electrons. The organic light-emitting compound moves into an excited state by the energy and emits light from energy when the organic light-emitting compound returns to the ground state from the excited state.

In an organic EL device, an electron transport material actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. Organic metal complexes having light-emitting function such as $Alq_3$ are excellent in transporting electrons, and thus have been conventionally used as an electron transport material. However, $Alq_3$ has problems in that it moves to other layers and shows reduction of color purity when used in blue light-emitting devices. Therefore, new electron transport materials have been required, which do not have the above problems, are highly electron-affinitive, and quickly transport electrons in organic EL devices to provide organic EL devices having high luminous efficiency.

Further, the electron buffer layer is a layer for solving the problem of a change in luminance caused by the change of a current characteristic of the device when exposed to a high temperature during a process of producing a panel. In order to obtain a similar current characteristic and a stability to high temperature compared to a device without an electron buffer layer, the characteristic of the compound comprised in the electron buffer layer is important.

In addition, a fluorescent material provides lower efficiencies than a phosphorescent material. Accordingly, there have been attempts to improve efficiencies by developing a specific fluorescent material such as a combination of an anthracene-based host and a pyrene-based dopant. However, the proposed combination makes holes become greatly trapped, which can cause light-emitting sites in a light-emitting layer to shift to the side close to a hole transport layer, thereby light being emitted at an interface. The light-emission at the interface decreases lifespan of a device, and efficiencies are not satisfactory. Accordingly, there have been attempts of solving both efficiency and lifespan problems by inserting an electron buffer layer between the light-emitting layer and the electron transport layer as a method to solve the problems of fluorescent materials.

Korean Patent Appln. Laying-Open No. 2015-0080213 A discloses an organic electroluminescent device comprising a bilayer-structured electron transport layer comprising an anthracene-based compound and a heteroaryl-based compound.

Korean Patent Appln. Laying-Open No. 2015-0108330 A discloses an organic electroluminescent device comprising a compound in which a nitrogen-containing heteroaryl is bonded to a carbazole, etc., as an electron buffer material.

Korean Patent Appln. Laying-Open No. 2015-0024491 A and Korean Patent Appln. Laying-Open No. 2015-0099750 A disclose an electron buffer layer or an electron transport layer comprising a compound comprising an azine ring.

However, the above references fail to specifically disclose an organic electroluminescent device comprising a compound comprising a nitrogen-containing heteroaryl as an electron buffer material and a compound in which a 5-membered heteroaryl is fused to a phenanthrene as an electron transport material.

DISCLOSURE OF THE INVENTION

Problems to be Solved

The objective of the present disclosure is to provide an organic electroluminescent device having high efficiency and/or long lifespan by comprising a specific combination of an electron buffer material and an electron transport material.

Solution to Problems

The present inventors found that the above objective can be achieved by an organic electroluminescent device comprising a first electrode, a second electrode facing the first electrode, a light-emitting layer between the first electrode and the second electrode, and an electron transport layer and an electron buffer layer between the light-emitting layer and the second electrode, wherein the electron buffer layer comprises a compound represented by the following formula 1, and the electron transport layer comprises a compound represented by the following formula 2:

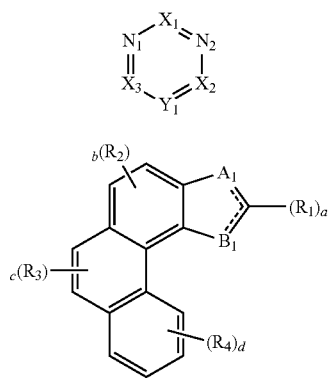

wherein $N_1$ and $N_2$ each independently represent N or $CR_{11}$, with a proviso that at least one of $N_1$ and $N_2$ represent N;

$X_1$ and $X_3$ each independently represent N or $CR_{12}$;

$Y_1$ represents N or $CR_{13}$;

$R_{11}$ to $R_{13}$ each independently represent hydrogen, deuterium, a halogen, a cyano, a substituted or unsubstituted (C1-C30)alkyl, a substituted or unsubstituted (C6-C50)aryl, a substituted or unsubstituted (3- to 50-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur;

$A_1$ represents —N═, —$NR_7$—, —O—, or —S—;

$B_1$ represents —N═, —$NR_8$—, —O—, or —S—, with a proviso that $B_1$ is —$NR_8$—, —O—, or —S— when $A_1$ is —N═, and $B_1$ is —N═, —O—, or —S— when $A_1$ is —$NR_7$—;

$R_1$ represents a substituted or unsubstituted (C6-C30)aryl, or a substituted or unsubstituted (3- to 30-membered)heteroaryl;

$R_2$ to $R_4$, $R_7$, and $R_8$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30) arylamino, or a substituted or unsubstituted (C1-C30)alkyl (C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur;

a represents 1, b and c each independently represent 1 or 2, and d represents an integer of 1 to 4; and the heteroaryl(ene) contains at least one heteroatom selected from B, N, O, S, Si, and P.

Effects of the Invention

The present disclosure provides an organic electroluminescent device having high efficiency and/or long lifespan, and a display system or a lighting system can be produced by using the device.

EMBODIMENTS OF THE INVENTION

Figure 1:
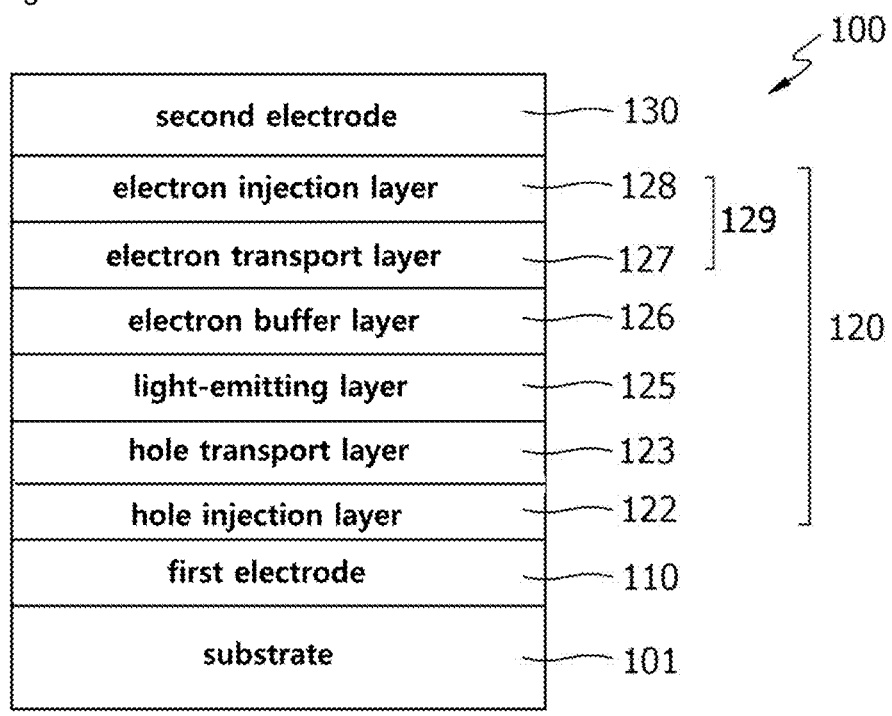
FIG. 1 illustrates a schematic sectional view of an organic electroluminescent device according to one embodiment of the present disclosure.

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

In an organic electroluminescent device comprising first and second electrodes, and a light-emitting layer, an electron buffer layer can be inserted between the light-emitting layer and the second electrode to focus on obtaining high efficiency and/or long lifespan due to electron injection controlled by the LUMO energy level of the electron buffer layer.

Originally, LUMO (lowest unoccupied molecular orbital) energy and HOMO (highest occupied molecular orbital) energy levels have negative values. However, for convenience, LUMO energy level (A) and HOMO energy level are expressed in absolute values in the present disclosure. In addition, the values of the LUMO energy level are compared based on absolute values. Values measured by density functional theory (DFT) are used for LUMO energy levels and HOMO energy levels in the present disclosure.

The LUMO energy levels can be easily measured by known various methods. Generally, LUMO energy levels are measured by cyclic voltammetry or ultraviolet photoelectron spectroscopy (UPS). Therefore, a person skilled in the art can easily comprehend the electron buffer layer, light-emitting layer, and electron transport layer that satisfy the equational relationship of the LUMO energy levels of the present disclosure, and practice the present disclosure. HOMO energy levels can be easily measured by the same method of measuring LUMO energy levels.

The present disclosure is directed to an organic electroluminescent device comprising a first electrode, a second electrode facing the first electrode, a light-emitting layer between the first electrode and the second electrode, and an electron transport layer and an electron buffer layer between the light-emitting layer and the second electrode, wherein the electron buffer layer comprises a compound represented by formula 1, and the electron transport layer comprises a compound represented by formula 2.

The electron buffer layer and the electron transport layer are inserted between the light-emitting layer and the second electrode. The electron buffer layer may be located between the light-emitting layer and the electron transport layer, or between the electron transport layer and the second electrode.

The electron buffer material comprised in the electron buffer layer indicates a material controlling an electron flow. Therefore, the electron buffer material may be, for example, a material which traps electrons, blocks electrons, or lowers an energy barrier between an electron transport zone and a light-emitting layer. In the organic electroluminescent device, the electron buffer material may be used for preparing an electron buffer layer, or may be incorporated to another area such as an electron transport zone or a light-emitting layer. The electron buffer layer may be formed between a light-emitting layer and an electron transport zone, or between an electron transport zone and a second electrode of an organic electroluminescent device. The electron buffer material may further comprise materials which are conventionally used for preparing an organic electroluminescent device besides the compound of formula 1.

The electron transport material comprised in the electron transport layer actively transports electrons from a cathode to a light-emitting layer and inhibits transport of holes which are not recombined in the light-emitting layer to increase recombination opportunity of holes and electrons in the light-emitting layer. Thus, electron-affinitive materials are used as an electron transport material. The electron transport layer may be formed in an electron transport zone between a second electrode and a light-emitting layer of an organic electroluminescent device. The electron transport material may further comprise materials which are conventionally used for preparing an organic electroluminescent device besides the compound of formula 2.

Herein, "(C1-C30)alkyl" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is a monocyclic or fused ring derived from an aromatic hydrocarbon having 6 to 30 ring backbone carbon atoms and may be partially saturated, in which the number of ring backbone carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "(3- to 30-membered)heteroaryl(ene)" is an aryl group having at least one, preferably 1 to 4 heteroatoms selected from the group consisting of B, N, O, S, Si, and P, and 3 to 30 ring backbone atoms, in which the number of ring backbone atoms is preferably 3 to 20, more preferably 5 to 15; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted aryl, the substituted heteroaryl, the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic, aromatic, or a combination of alicyclic and aromatic ring in $R_1$ to $R_4$, $R_7$, $R_8$, and $R_{11}$ to $R_{13}$ in formulae 1 and 2 each independently are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl.

According to one embodiment of the present disclosure, the compound of formula 1 comprised in the electron buffer layer may be represented by the following formula 3:

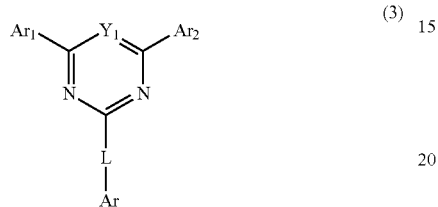

(3)

wherein $Ar_1$ and $Ar_2$ are identical to the definition of $R_{12}$ of formula 1;

$Y_1$ is as defined in formula 1;

L represents a single bond, a substituted or unsubstituted (C6-C50)arylene, or a substituted or unsubstituted (5- to 50-membered)heteroarylene; and Ar represents a substituted or unsubstituted (C6-C50)aryl, or a substituted or unsubstituted (5- to 50-membered)heteroaryl.

According to one embodiment of the present disclosure, the compound of formula 3 comprised in the electron buffer layer may be represented by any one of the following formulae 4 to 8:

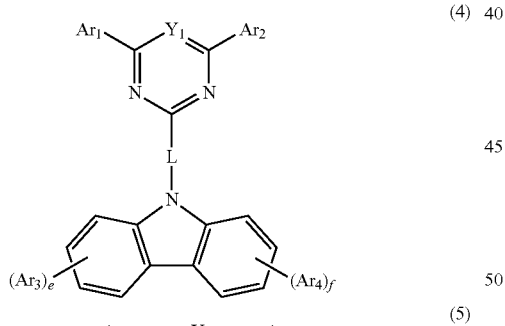

(4)

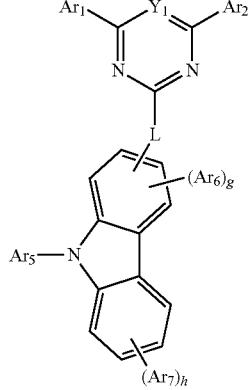

(5)

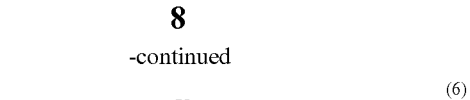

(6)

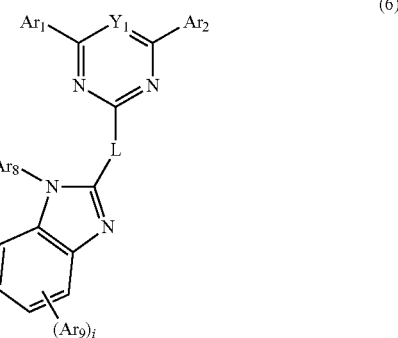

(7)

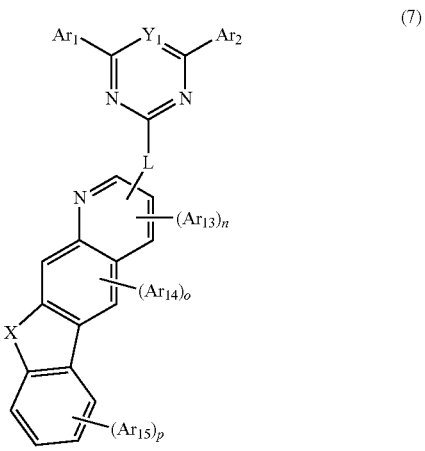

(8)

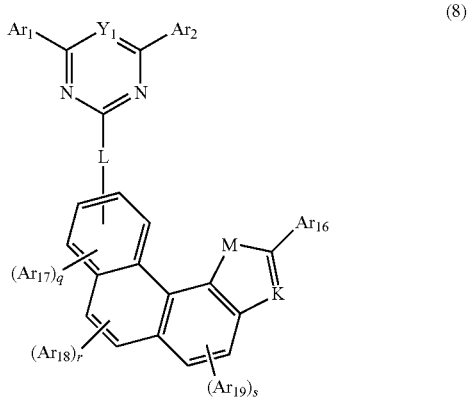

wherein $Ar_1$, $Ar_2$, $Y_1$, and L are as defined in formula 3;

$Ar_3$ to $Ar_9$, and $Ar_{13}$ to $Ar_{19}$ are each independently identical to the definition of $Ar_1$ of formula 3;

X represents CRaRb, NRc, O, or S, wherein Ra, Rb, and Rc are each independently identical to the definition of $Ar_1$ of formula 3;

K represents CRd or N, wherein Rd is identical to the definition of $Ar_1$ of formula 3;

M represents O or S; and e, f, h, i, and p each independently represent an integer of 1 to 4, g and q each independently represent an integer of 1 to 3, and n, o, r, and s each independently represent 1 or 2.

According to one embodiment of the present disclosure, the compound of formula 4 comprised in the electron buffer layer may be represented by any one of the following formulae 10 to 14:

(10)

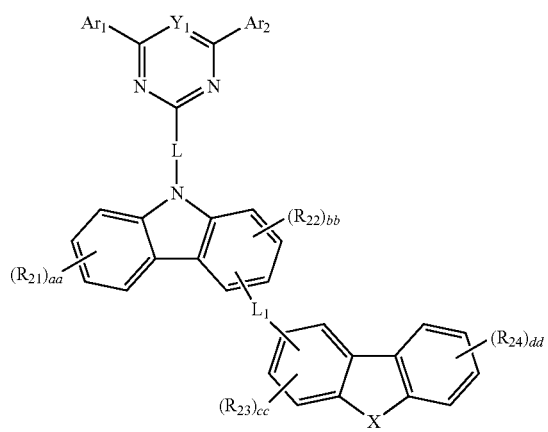

(11)

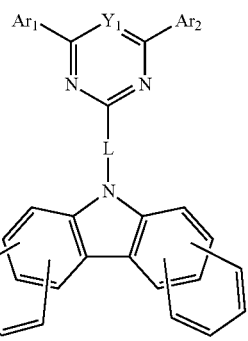

(12)

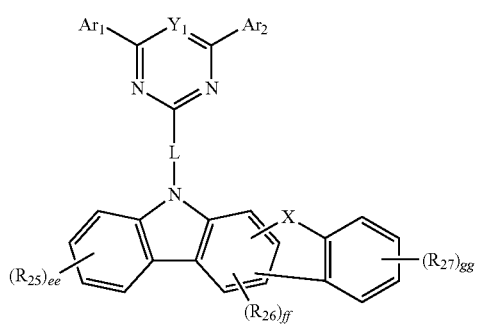

(13)

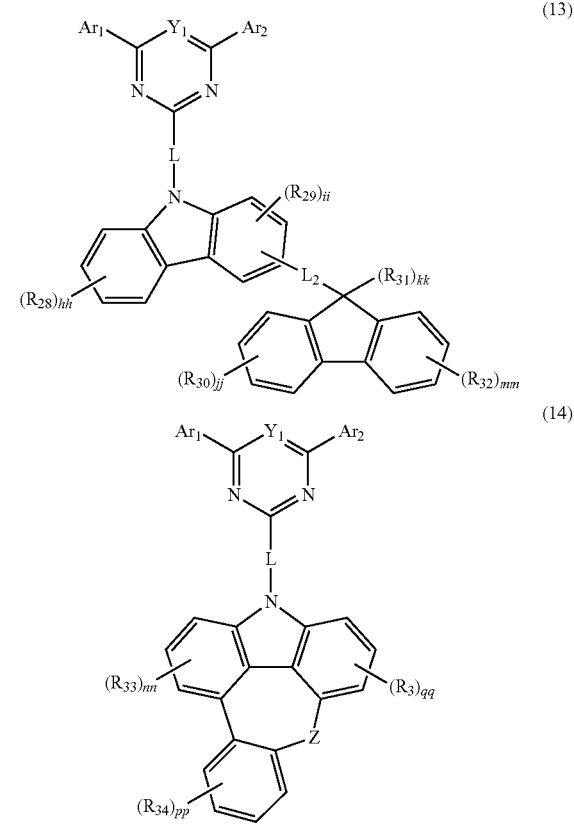

(14)

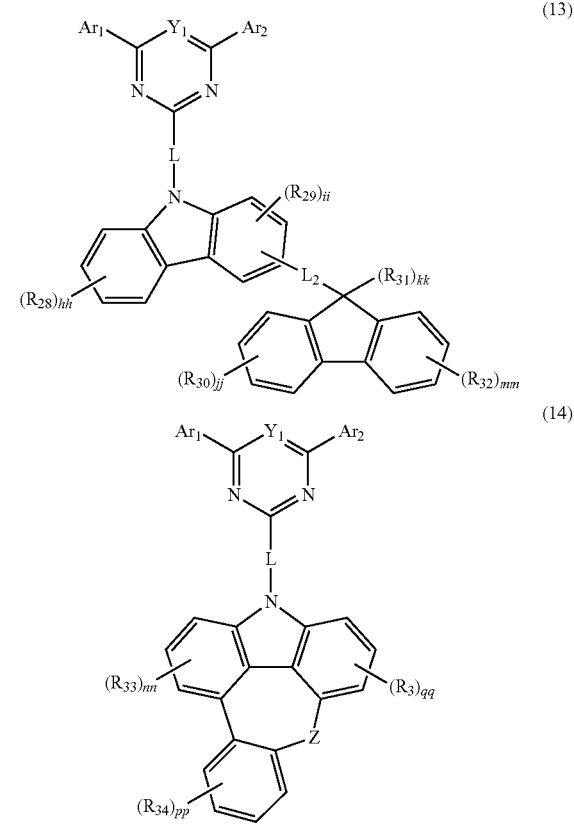

wherein

Ar$_1$, Ar$_2$, Y$_1$, L, and X are as defined in formula 4;

R$_{21}$ to R$_{35}$ are each independently identical to the definition of Ar$_1$ of formula 4;

Z is identical to the definition of X of formula 4;

L$_1$ and L$_2$ are each independently identical to the definition of L of formula 4;

aa, dd, ee, gg, hh, jj, kk, and pp each independently represent an integer of 1 to 4, bb, cc, ii, nn, and qq each independently represent an integer of 1 to 3, and ff represents 1 or 2.

According to one embodiment of the present disclosure, the compound of formula 2 comprised in the electron transport layer may be represented by any one of the following formulae 15 to 17:

(15)

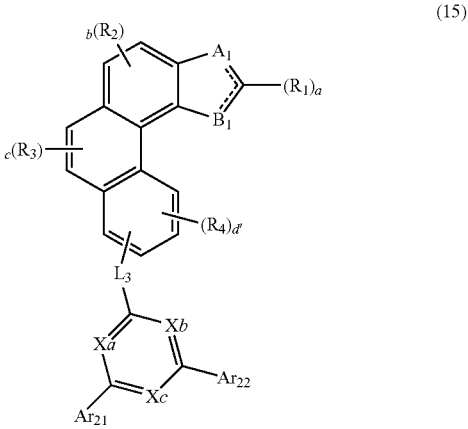

-continued

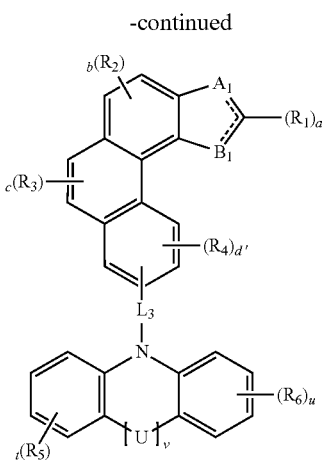

(16)

(17)

wherein $A_1, B_1, R_1$ to $R_4$, and a to o are as defined in formula 2;

$L_3$ represents a single bond, a substituted or unsubstituted (O6-O30)arylene, or a substituted or unsubstituted (3- to 30-membered)heteroarylene;

$X_a$ to $X_c$ each independently represent —N— or —$CR_9$—;

$Ar_{21}$ and $Ar_{22}$ each independently represent a substituted or unsubstituted (C6-C30)aryl, or a substituted or unsubstituted (3- to 30-membered)heteroaryl;

$R_5$, $R_6$, and $R_9$ are identical to the definition of $R_2$ of formula 2;

U represents a single bond, or a substituted or unsubstituted (C1-C6)alkylene;

W represents —NR—, —O—, —S—, or —CR'R"—;

R represents a substituted or unsubstituted (C6-C30)aryl, or a substituted or unsubstituted (3- to 30-membered)heteroaryl;

R' and R" each independently represent a substituted or unsubstituted (C1-C30)alkyl, a substituted or unsubstituted (C6-C30)aryl, or a substituted or unsubstituted (3- to 30-membered)heteroaryl; and d', and w each independently represent an integer of 1 to 3, t and u each independently represent an integer of 1 to 4, and v represents 0 or 1.

In formulae 1, 3 to 8, and 10 to 14, $R_{11}$ to $R_{13}$, $Ar_1$ to $Ar_9$, $Ar_{13}$ to $Ar_{19}$, Ra to Rd, and $R_{21}$ to $R_{35}$ each independently represent hydrogen, deuterium, a halogen, a cyano, a substituted or unsubstituted (C1-C30)alkyl, a substituted or unsubstituted (C6-C50)aryl, a substituted or unsubstituted (3- to 50-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur. $R_{11}$ to $R_{13}$, $Ar_1$ to $Ar_9$, $Ar_{13}$ to $Ar_{19}$, Ra to Rd, and $R_{21}$ to $R_{35}$, preferably, each independently represent hydrogen, a substituted or unsubstituted (C6-C20)aryl, or a substituted or unsubstituted (5- to 40-membered)heteroaryl; or may be linked to an adjacent substituent to form a substituted or unsubstituted, mono- or polycyclic, (C3-C15) alicyclic or aromatic ring; and more preferably, each independently represent hydrogen; a (C6-C20)aryl unsubstituted or substituted with a (C1-C6)alkyl, a (C6-C12)aryl, or a (5- to 15-membered) heteroaryl; or a (5- to 40-membered)heteroaryl unsubstituted or substituted with a (C1-C6)alkyl or a (C6-C12)aryl; or may be linked to an adjacent substituent to form a substituted or unsubstituted, mono- or polycyclic, (C3-C15) aromatic ring. Specifically, $R_{11}$ to $R_{13}$, $Ar_1$ to $Ar_9$, $Ar_{13}$ to $Ar_{19}$, Ra to Rd, and $R_{21}$ to $R_{35}$ each independently may represent hydrogen, phenyl, biphenyl, naphthyl, terphenyl, phenylnaphthyl, naphthylphenyl, anthracenyl, phenanthrenyl, dibenzofuranyl, dibenzothiophenyl, or fluorenyl.

In formulae 3 to 8, and 10 to 14, L represents a single bond, a substituted or unsubstituted (C6-C50)arylene, or a substituted or unsubstituted (5- to 50-membered)heteroarylene. L preferably represents a single bond, a substituted or unsubstituted (C6-C20)arylene, or a substituted or unsubstituted (5- to 40-membered)heteroarylene, and more preferably represents a single bond, a (C6-C20)arylene unsubstituted or substituted with a (C1-C6)alkyl or a (C6-C12)aryl, or a (5- to 40-membered)heteroarylene unsubstituted or substituted with a (C1-C6)alkyl or a (C6-C12)aryl. Specifically, L may represent a single bond, phenylene, biphenylene, naphthylene, phenyl-naphthylene, naphthylphenylene, biphenyl-naphthylene, or naphthyl-biphenylene.

In formulae 2 and 15 to 17, $R_1$ represents a substituted or unsubstituted (C6-C30)aryl, or a substituted or unsubstituted (3- to 30-membered)heteroaryl, preferably represents a substituted or unsubstituted (C6-C30)aryl, or a substituted (5- to 25-membered)heteroaryl, and more preferably represents a substituted or unsubstituted (C6-C30)aryl, or a substituted (5- to 20-membered)heteroaryl. For example, R, may represent an unsubstituted phenyl, an unsubstituted biphenyl, an unsubstituted naphthyl, a fluorenyl substituted with methyl, a benzofluorenyl substituted with methyl, a carbazolyl substituted with phenyl, a benzocarbazolyl substituted with phenyl, an indolocarbazolyl substituted with phenyl, an unsubstituted dibenzofuranyl, an unsubstituted dibenzothiophenyl, a spiro[fluorene-fluorene], or a spiro[fluorene-benzofluorene].

In formulae 2 and 15 to 17, $R_2$ to $R_9$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur. $R_2$ to $R_9$ preferably, each independently represent hydrogen, a substituted or unsubstituted (C6-C25)aryl, a substituted or unsubstituted (5- to 25-membered)heteroaryl, or a substituted or unsubstituted mono- or di-(C6-C25)arylamino, or may be linked to an adjacent substituent to form a substituted or unsubstituted, mono- or polycyclic, (C5-C25) alicyclic or aromatic ring, whose carbon atom(s) may be replaced with at least one heteroatom selected from nitrogen, oxygen, and sulfur, and more preferably, each independently represent hydrogen, a substituted or unsubstituted (C6-C20)aryl, a substituted or unsubstituted (5- to 25-membered)heteroaryl, or a substituted or unsubstituted di(C6-C18)arylamino, or may be linked to an adjacent substituent to form a substituted or unsubstituted, mono- or polycyclic, (C5-C25) alicyclic or aromatic ring, whose carbon atom(s) may be replaced with at least one heteroatom selected from nitrogen and sulfur. For example, $R_2$ to $R_4$ each independently may be selected from the group consisting of hydrogen, a substituted phenyl, a substituted triazinyl, a substituted pyrimidinyl, a substituted or unsubstituted carbazolyl, a substituted benzocarbazolyl, an unsubstituted dibenzocarbazolyl, and a substituted or unsubstituted diphenylamino, or may be linked to an adjacent substituent to form a substituted indene ring or a substituted benzothiophene ring. $R_5$ and $R_6$ each independently may be selected from the group consisting of hydrogen, a substituted or unsubstituted phenyl, a substituted or unsubstituted carbazolyl, an unsubstituted benzocarbazolyl, and an unsubstituted dibenzocarbazolyl, or may be linked to an adjacent substituent to form an unsubstituted benzene ring, an indole ring substituted with phenyl, a benzoindole ring substituted with phenyl, an indene ring substituted with methyl, or a benzoindene ring substituted with methyl.

In formulae 2 and 15 to 17, $A_1$ represents —N═, —NR$_7$—, —O—, or —S—; $B_1$ represents —N═, —NR$_8$—, —O—, or —S—, with a proviso that $B_1$ is —NR$_8$—, —O—, or —S— when $A_1$ is —N═, and $B_1$ is —N═, —O—, or —S— when $A_1$ is —NR$_7$—. $R_7$ and $R_8$ may represent an unsubstituted phenyl.

In formulae 15 to 17, $L_3$ represents a single bond, a substituted or unsubstituted (C6-C30)arylene, or a substituted or unsubstituted (3- to 30-membered)heteroarylene, preferably represents a single bond, or a substituted or unsubstituted (C6-C18)arylene, and more preferably represents a single bond, or an unsubstituted (C6-C12)arylene. For example, $L_3$ may represent a single bond or an unsubstituted phenylene.

In formula 15, $X_a$ to $X_c$ each independently represent —N— or —CR$_9$—, preferably one or more of $X_a$ to $X_c$ represent —N—, and more preferably two or more of $X_a$ to $X_c$ represent —N—. $R_9$ may represent hydrogen.

In formula 15, $Ar_{21}$ and $Ar_{22}$ each independently represent a substituted or unsubstituted (C6-C30)aryl, or a substituted or unsubstituted (3- to 30-membered)heteroaryl, preferably each independently represent a substituted or unsubstituted (C6-C25)aryl, or a substituted or unsubstituted (3- to 25-membered)heteroaryl, and more preferably each independently represent an unsubstituted (C6-C20)aryl, or a substituted or unsubstituted (5- to 20-membered)heteroaryl. For example, $Ar_{21}$ and $Ar_{22}$ may each independently represent an unsubstituted phenyl, an unsubstituted biphenyl, an unsubstituted naphthyl, an unsubstituted dibenzothiophenyl, a fluorenyl substituted with methyl, a benzofluorenyl substituted with methyl, a carbazolyl substituted with phenyl, a benzocarbazolyl substituted with phenyl, or an unsubstituted benzonaphthothiophenyl.

In formulae 16 and 17, U represents a single bond, or a substituted or unsubstituted (C1-C6)alkylene, and preferably represents a single bond.

In formula 18, W represents —NR—, —O—, —S—, or —CR'R"—, and preferably represents —NR—.

In formula 18, R represents a substituted or unsubstituted (C6-C30)aryl, or a substituted or unsubstituted (3- to 30-membered)heteroaryl, preferably represents a substituted or unsubstituted (C6-C20)aryl, and more preferably represents an unsubstituted (C6-C18)aryl. For example, R may represent an unsubstituted phenyl.

In formula 18, R' and R" each independently represent a substituted or unsubstituted (C1-C30)alkyl, a substituted or unsubstituted (C6-C30)aryl, or a substituted or unsubstituted (3- to 30-membered)heteroaryl, preferably each independently represent a substituted or unsubstituted (C1-C20)alkyl, and more preferably each independently represent an unsubstituted (C1-C15)alkyl. For example, R' and R" may each independently represent an unsubstituted methyl.

The compound of formula 2 of the present disclosure may be comprised not only in an electron transport material, but also in an electron buffer material of an electron buffer layer.

The compound represented by formula 1 may be selected from the group consisting of the following compounds, but is not limited thereto:

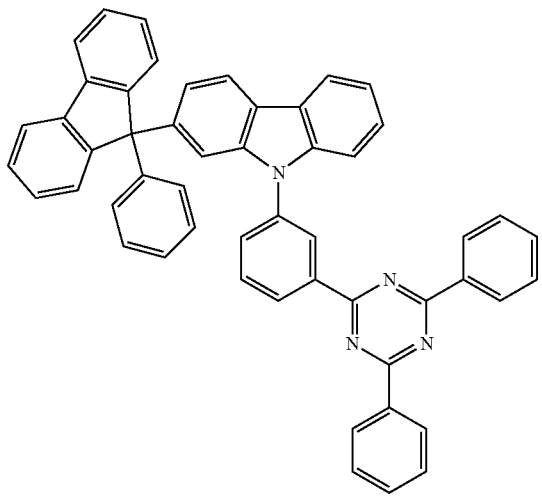

B-1

B-2
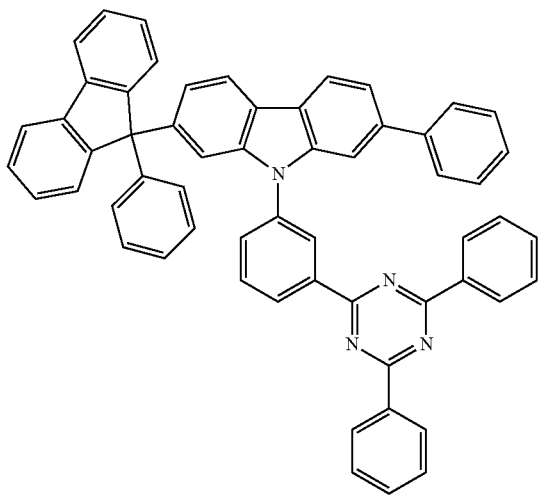
B-3
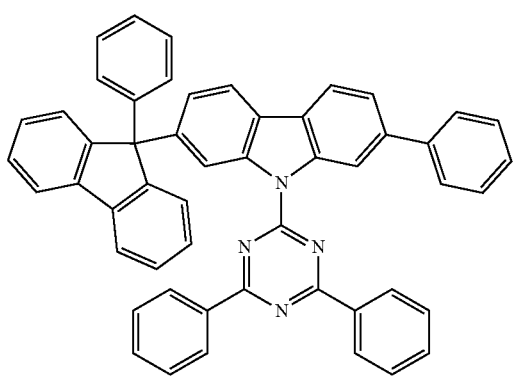
B-4
B-5
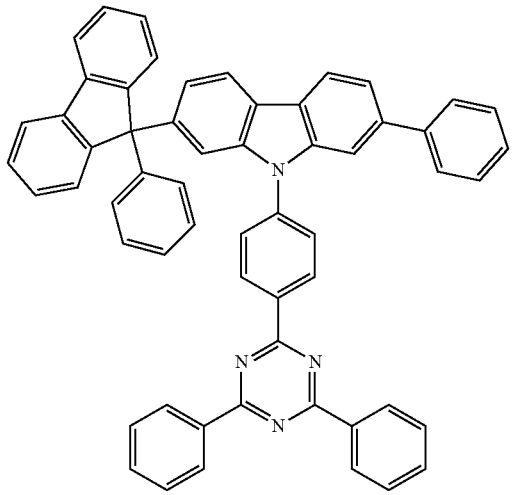
B-6
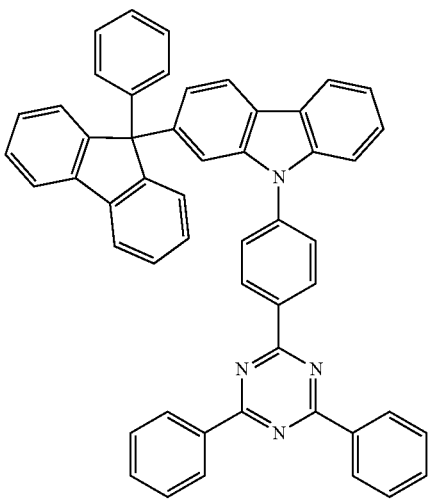
B-7
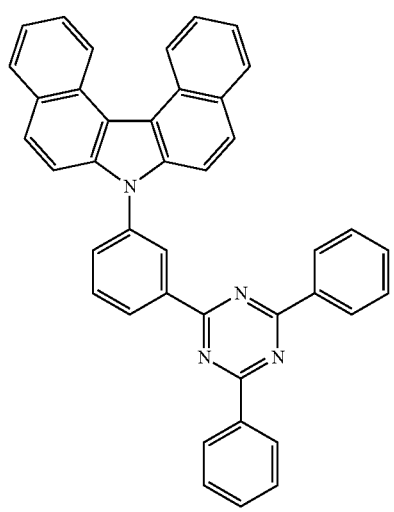

B-8
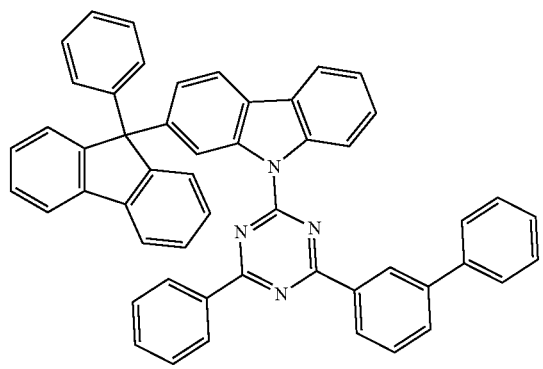
B-9
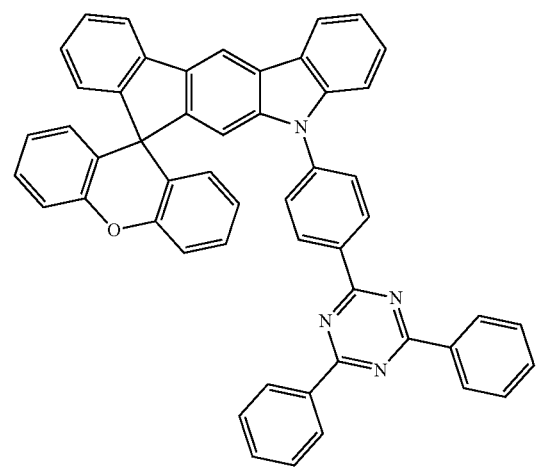
B-10
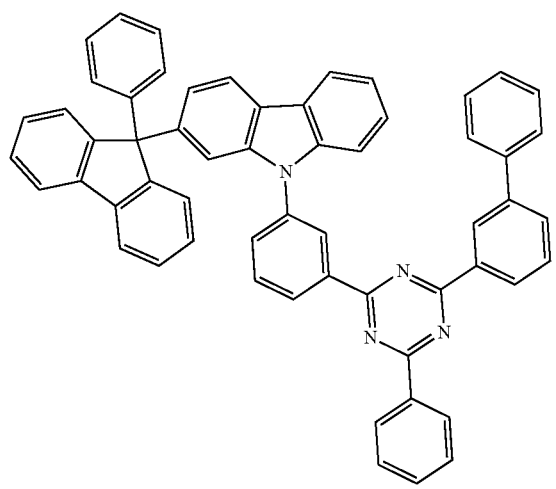
B-11
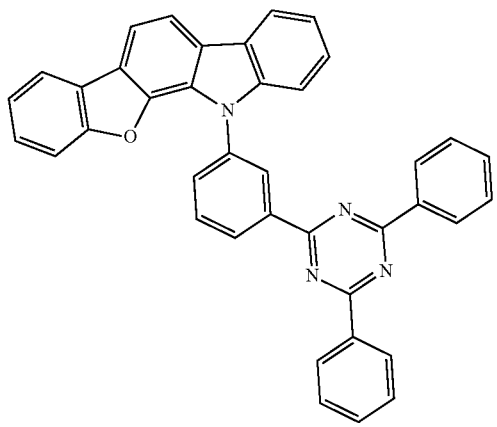
B-12
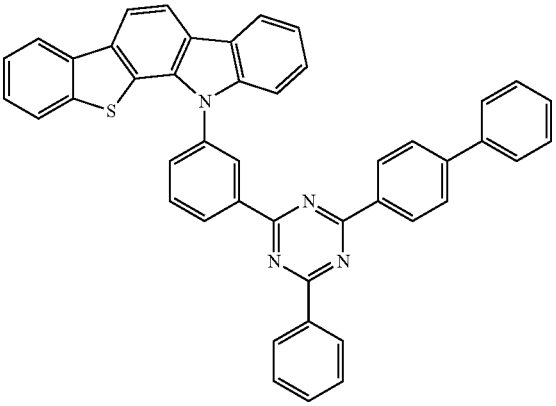
B-13
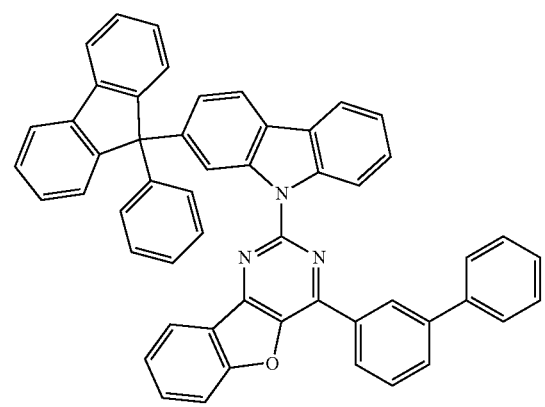

B-14
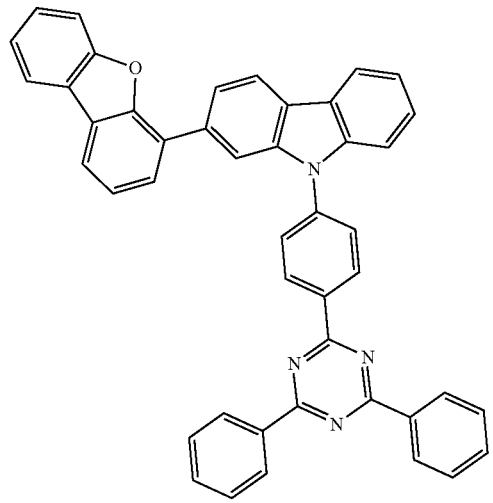
B-18
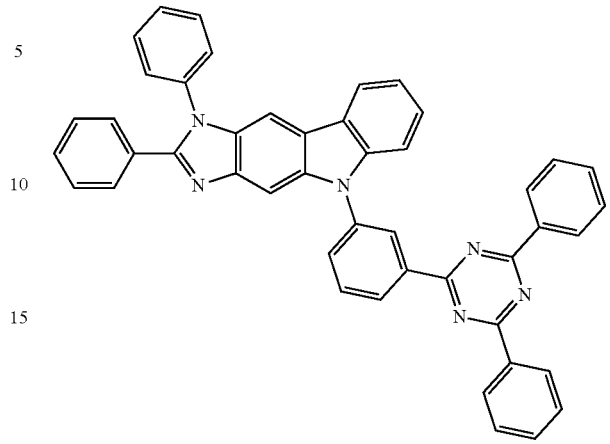
B-15
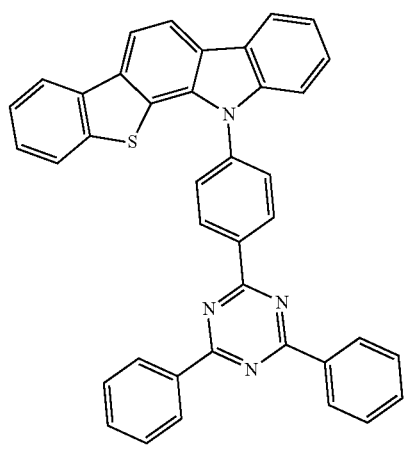
B-19
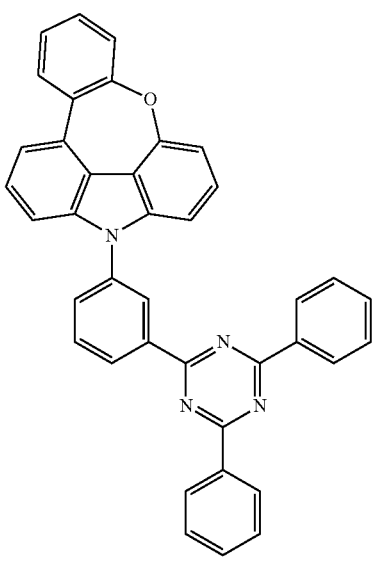
B-16
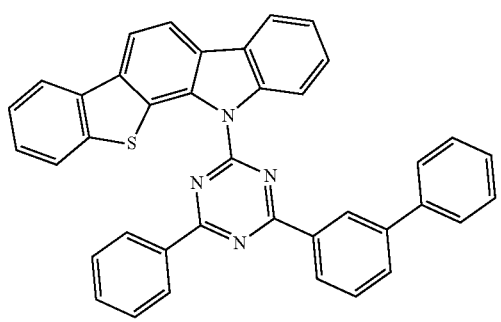
B-20
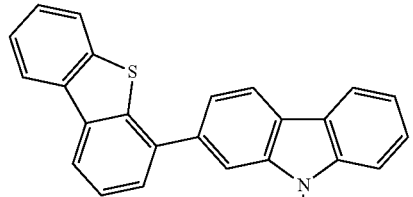
B-17
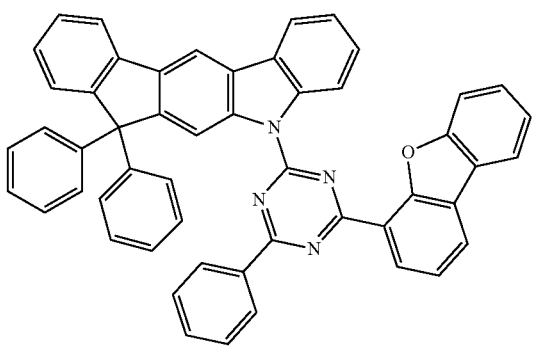

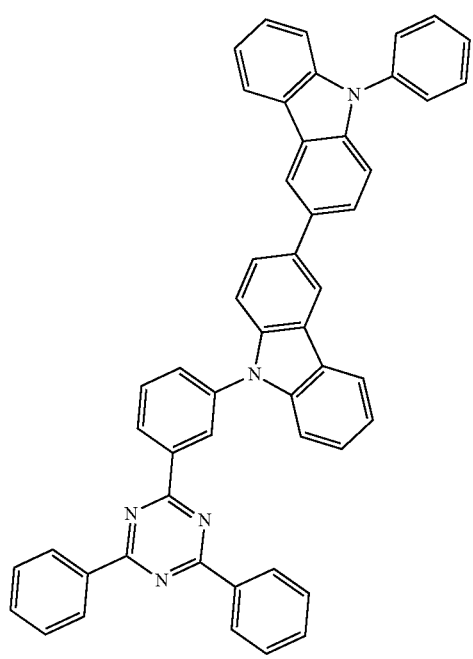
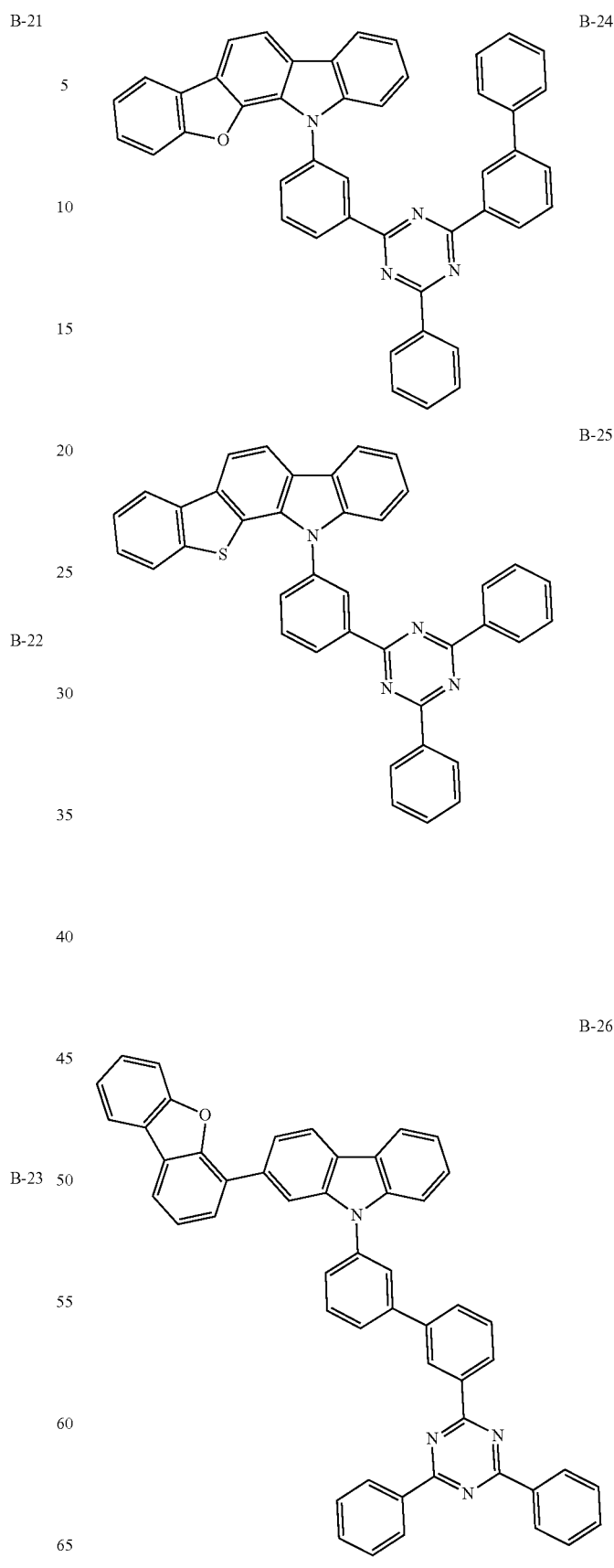

B-27
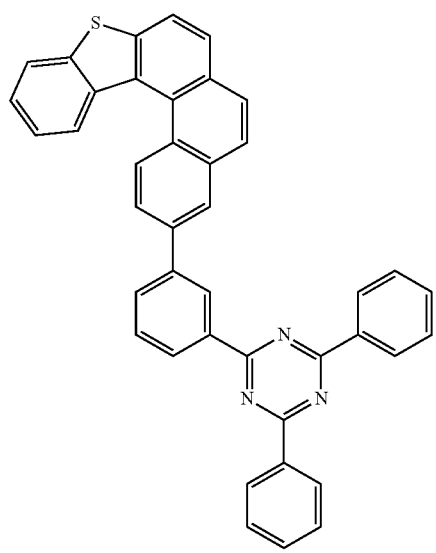
B-28
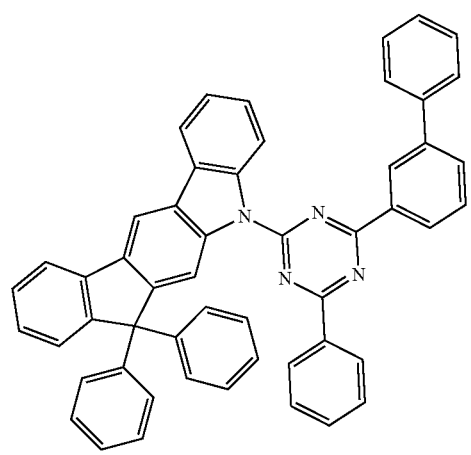
B-29
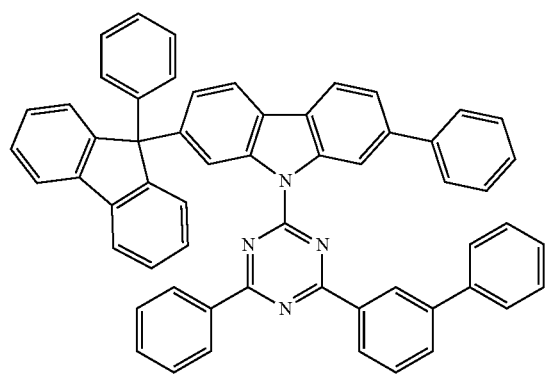
B-30
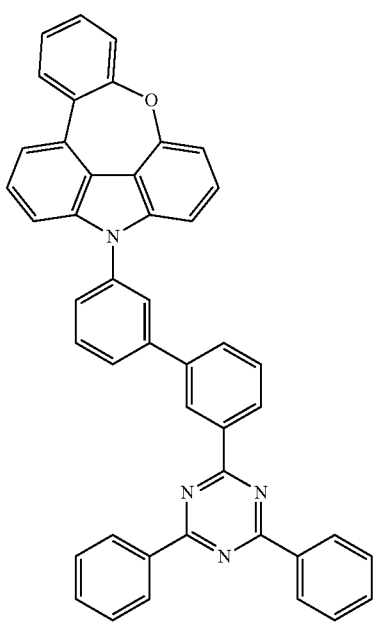
B-31
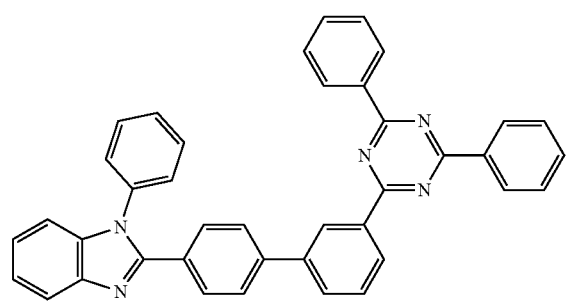
B-32
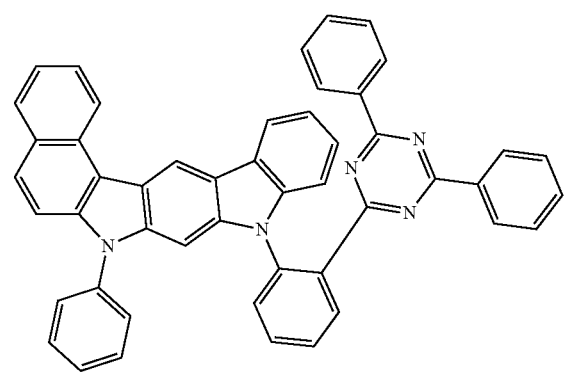

-continued
B-33
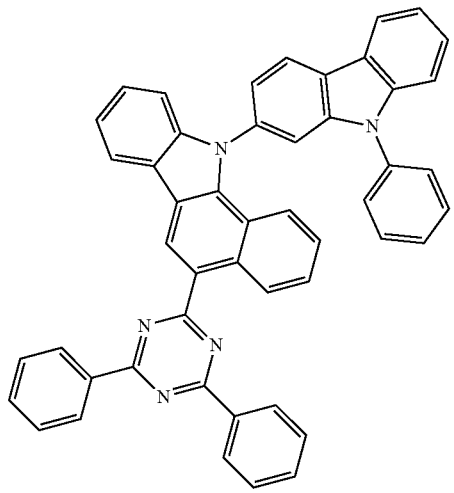
B-34
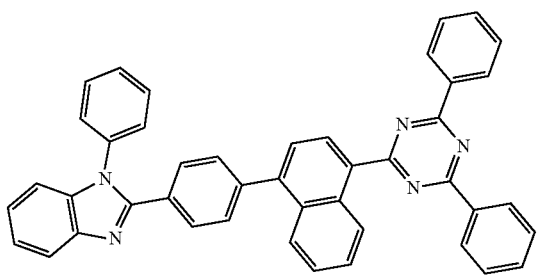
B-35
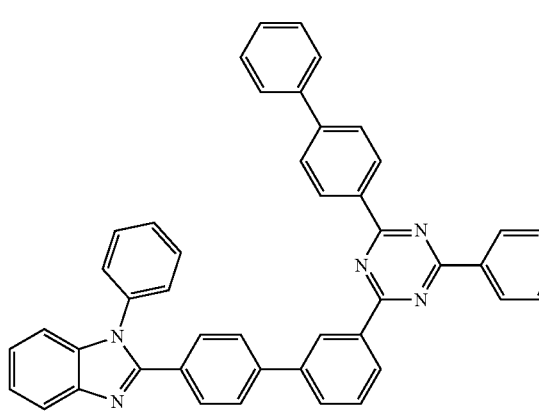
B-36
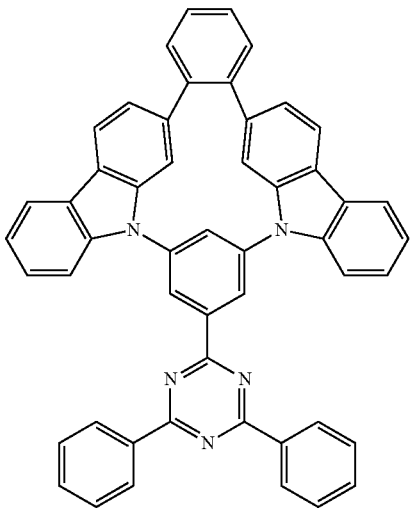
B-37
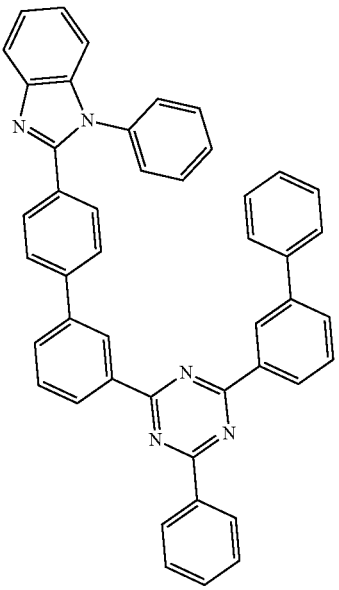
B-38
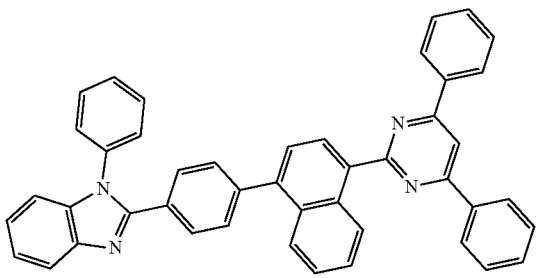

B-39
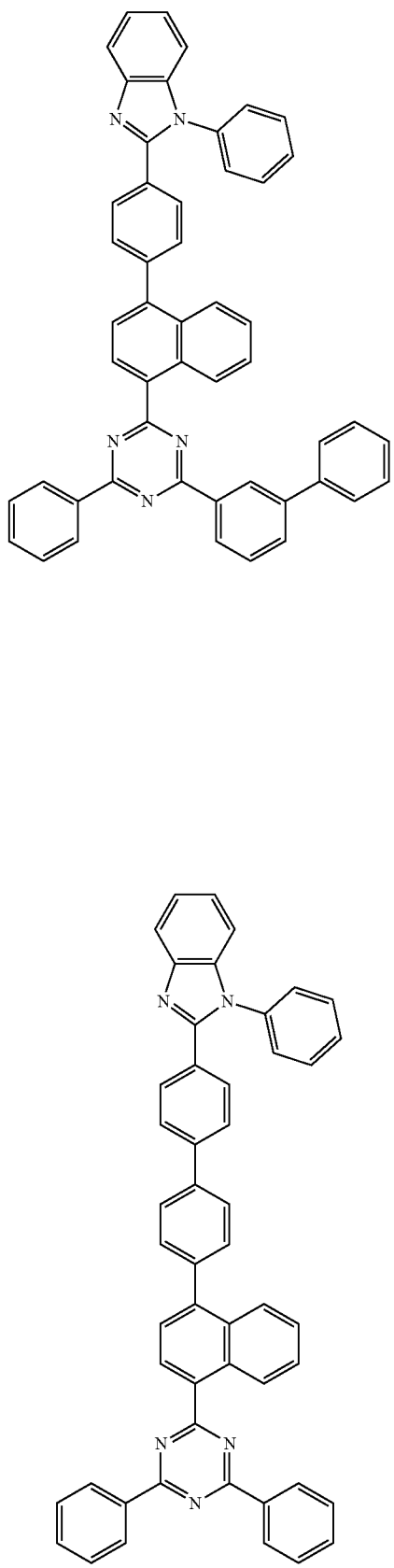
B-40
B-41
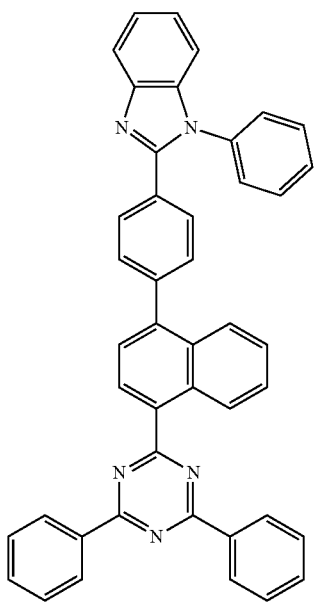
B-42
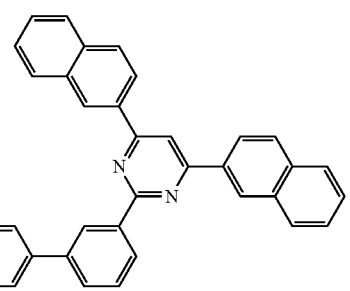
B-43
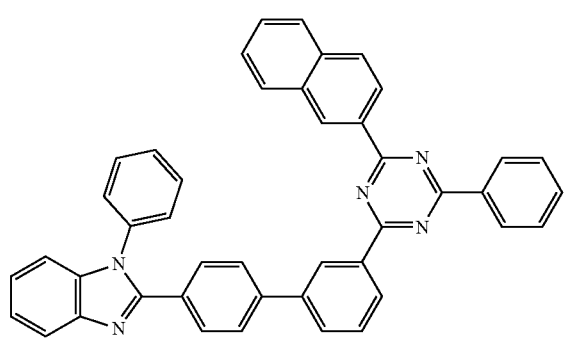

B-44
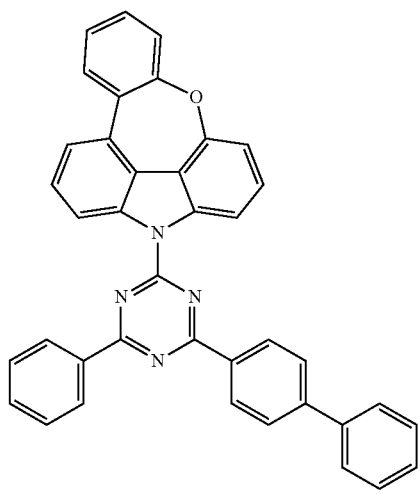
B-45
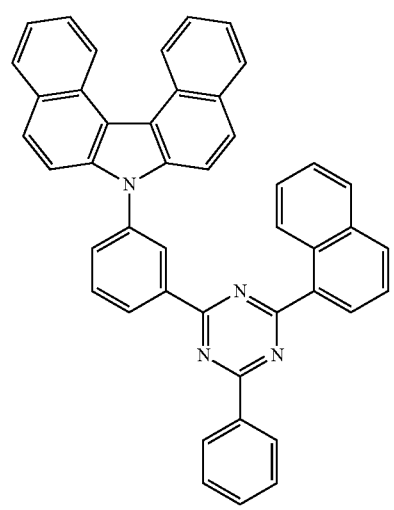
B-46
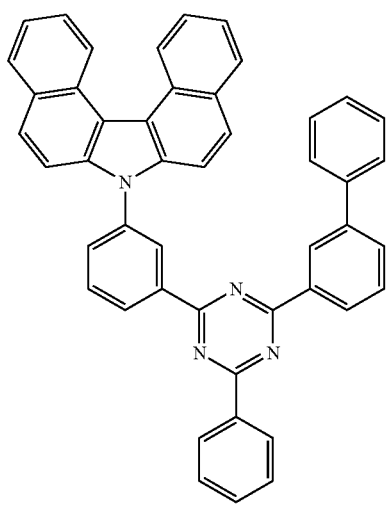
B-47
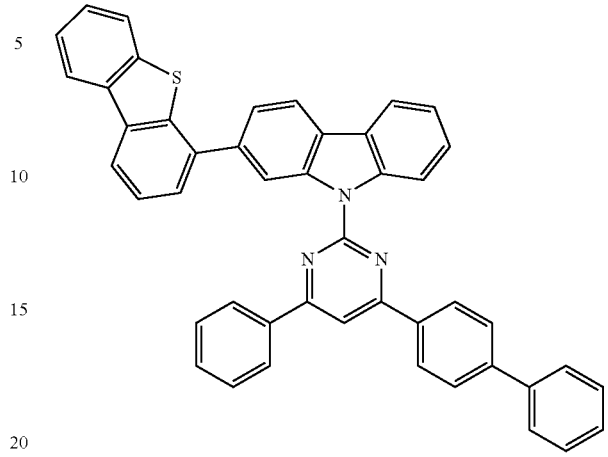
B-48
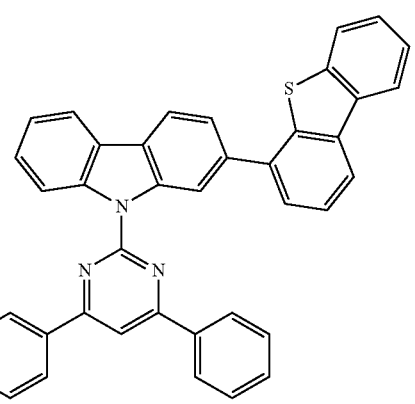
B-49
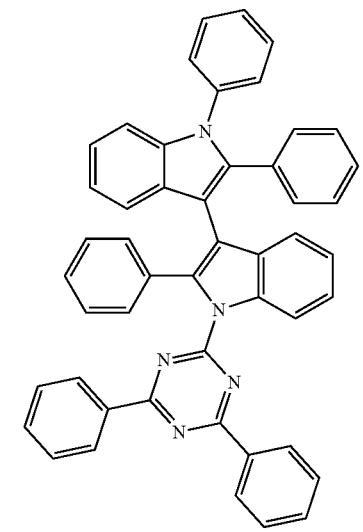

-continued
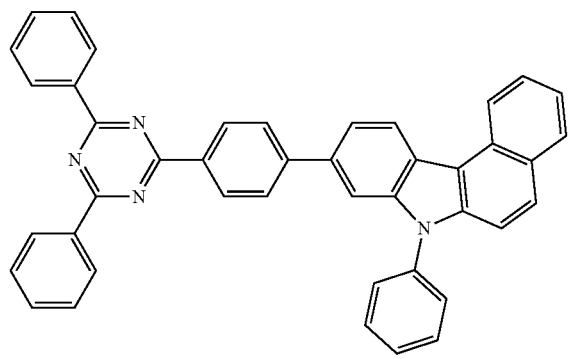
B-50
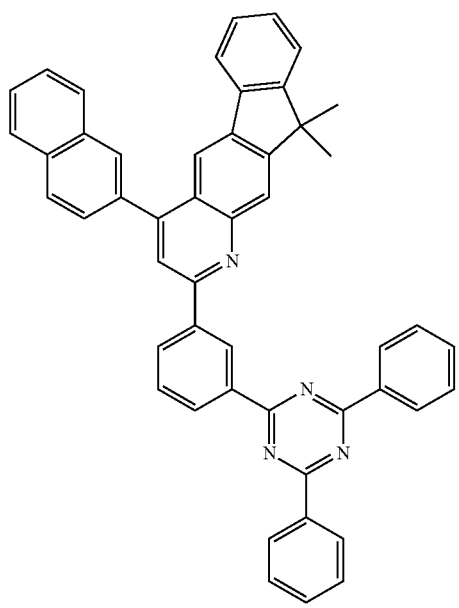
B-51
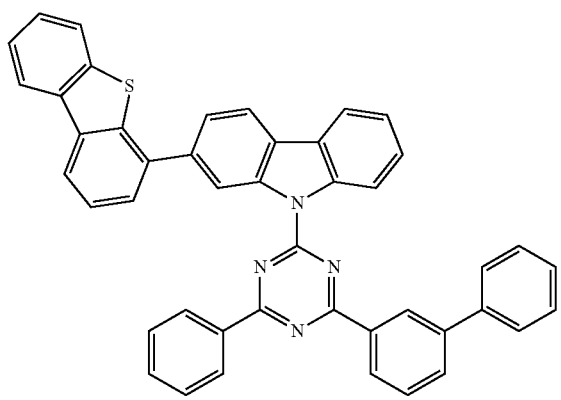
B-52
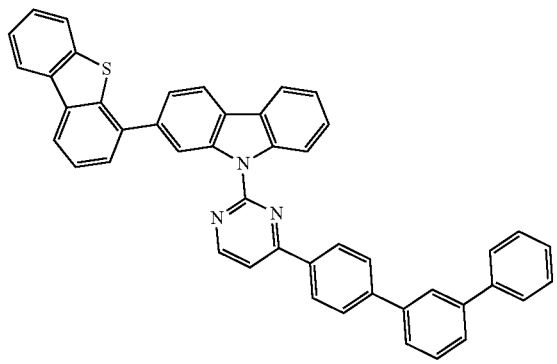
B-53
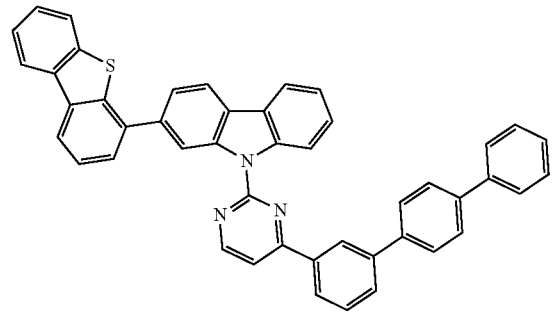
B-54
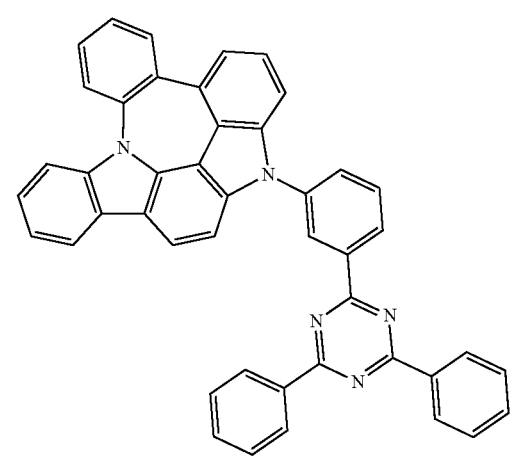
B-55

B-56 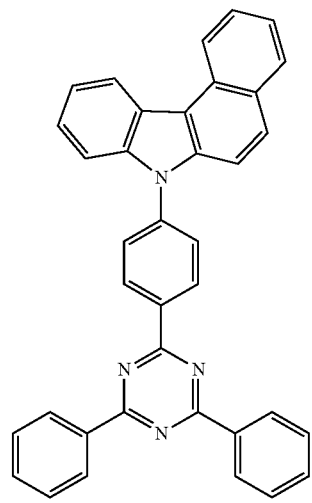
B-59 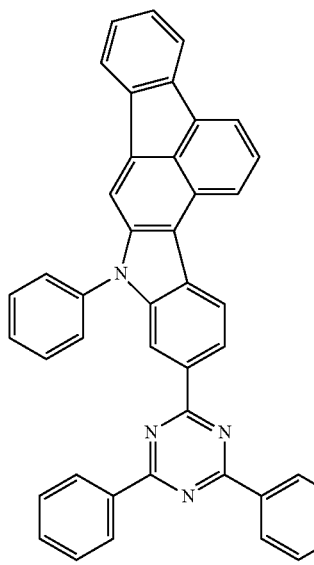
B-57 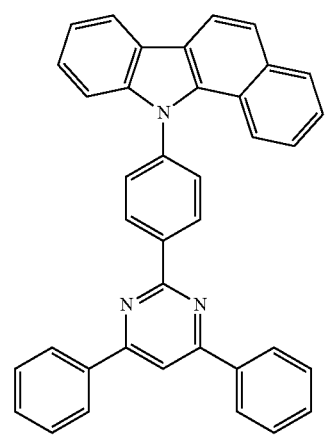
B-60 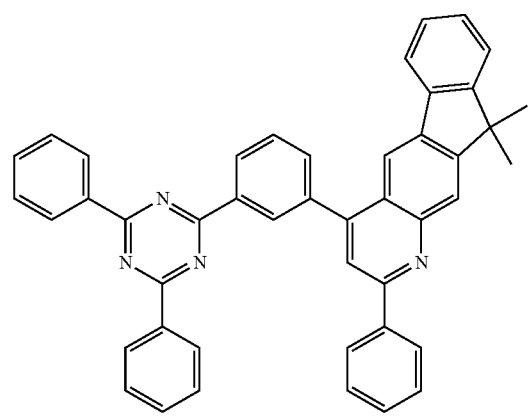
B-58 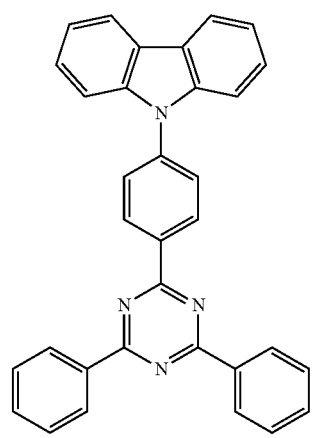
B-61 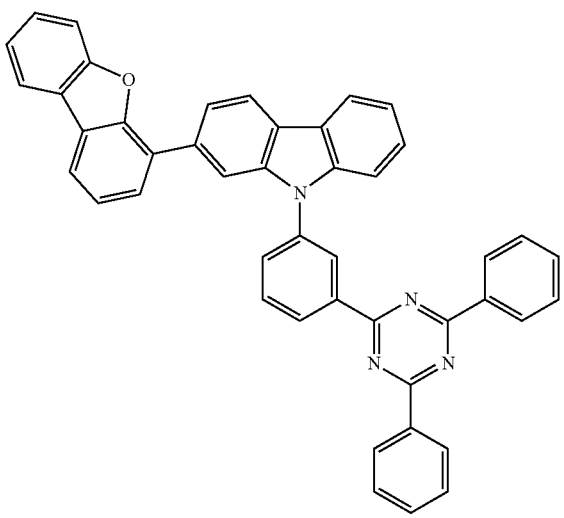

B-62
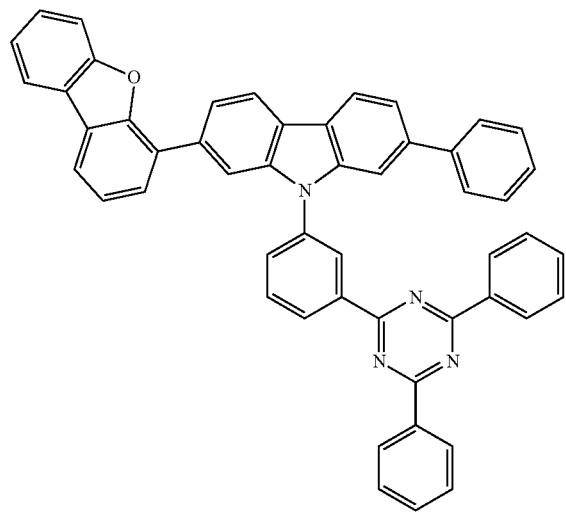
B-63
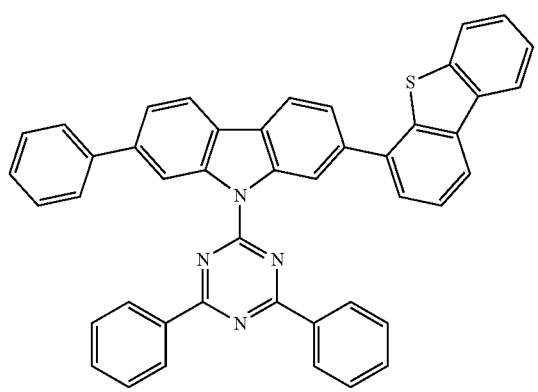
B-64
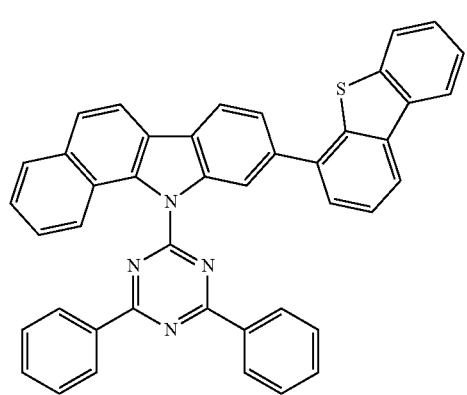
B-65
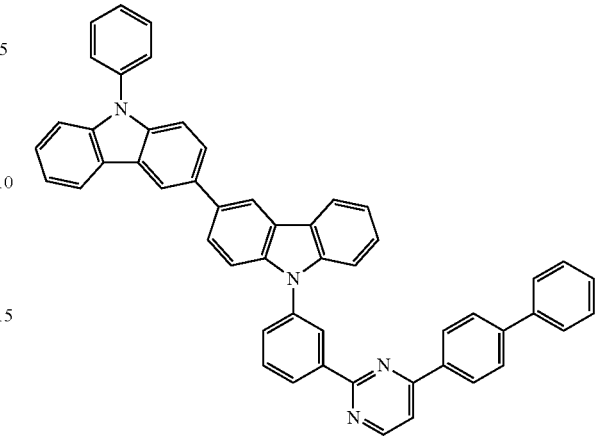
B-66
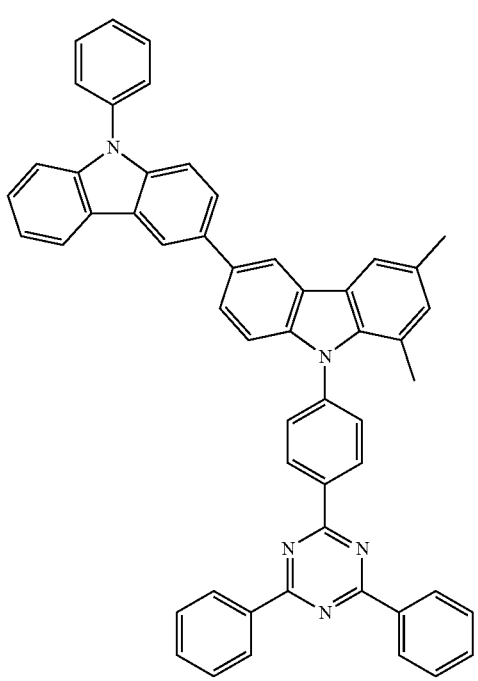
B-67
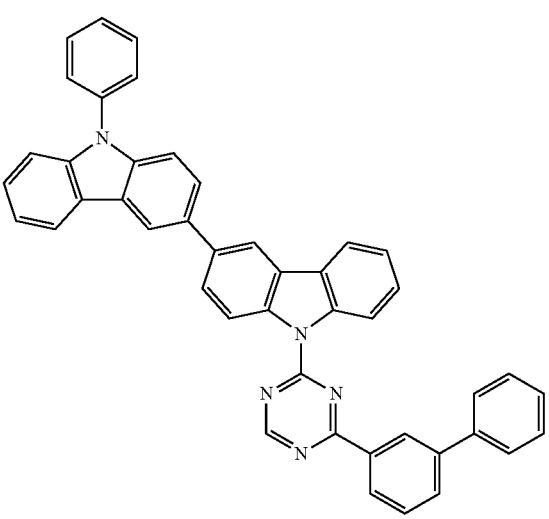

B-68
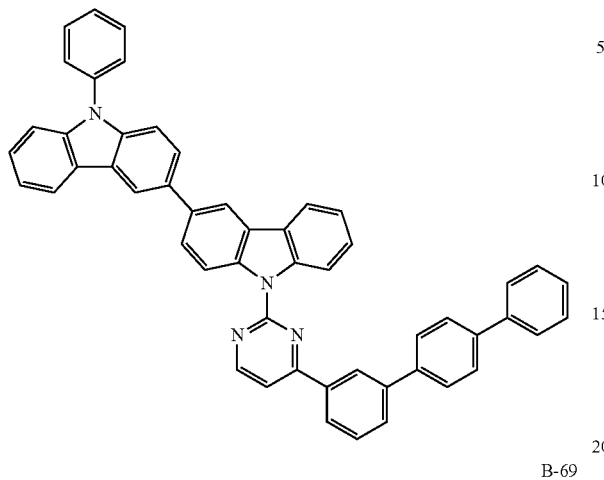
B-69
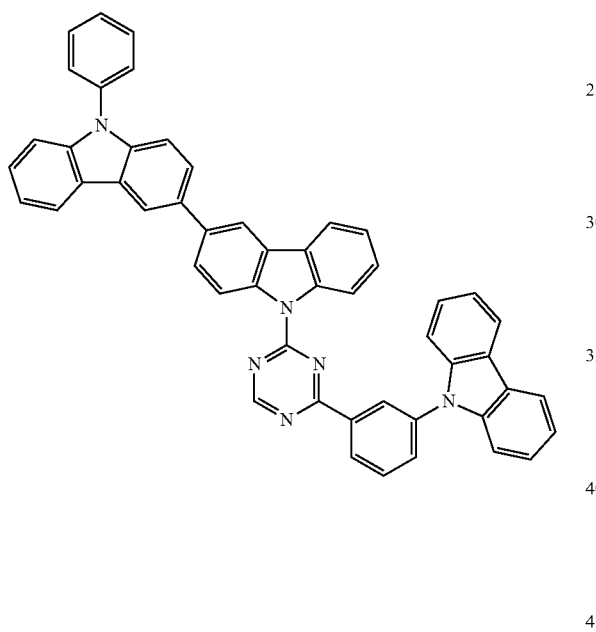
B-70
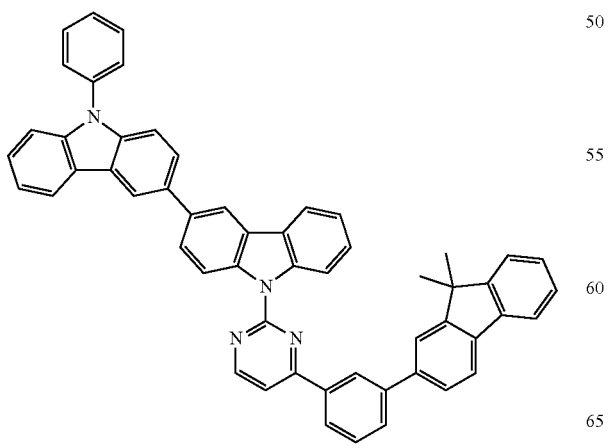
B-71
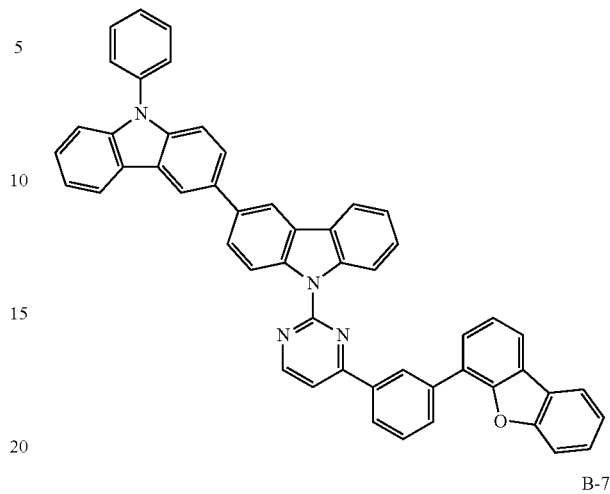
B-72
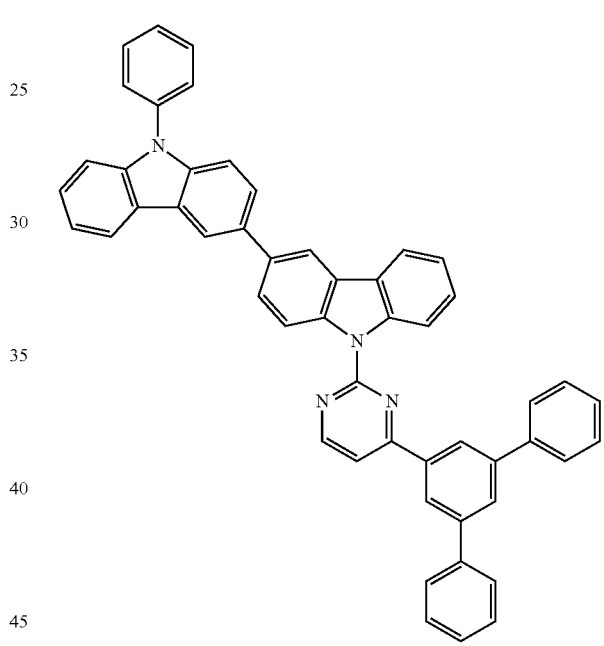
B-73
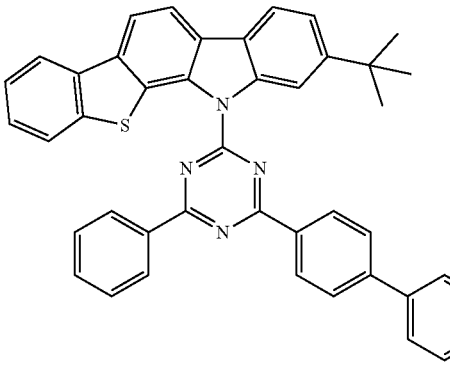

-continued
B-74
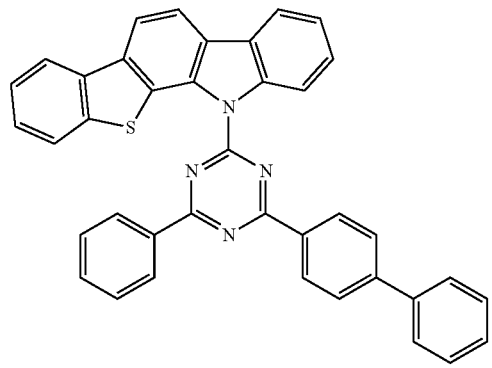
B-75
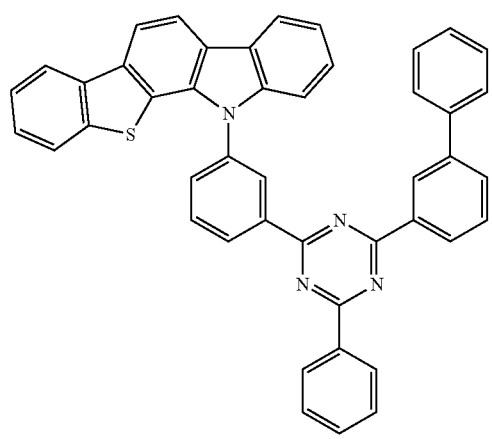
B-76
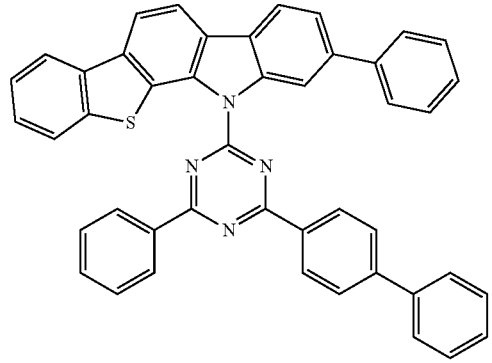
B-77
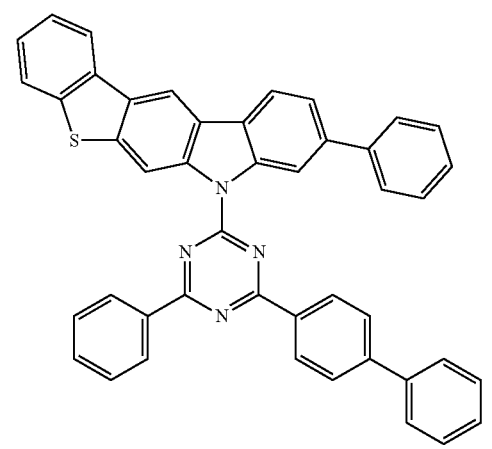
-continued
B-78
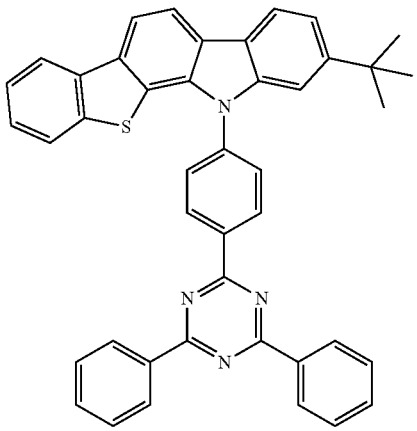
B-79
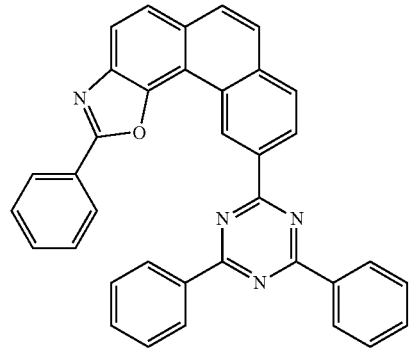
B-80
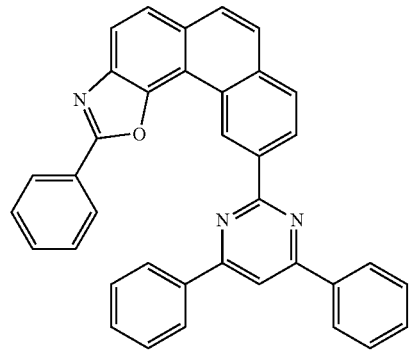
B-81
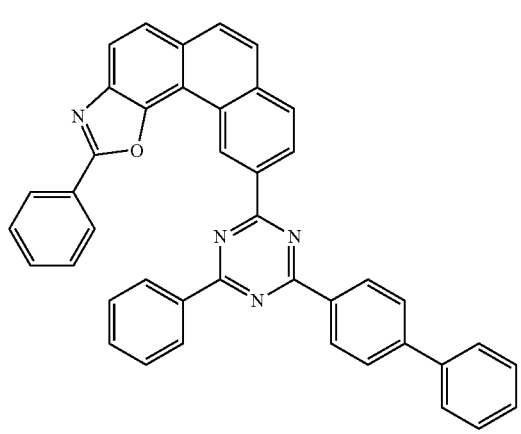

B-82
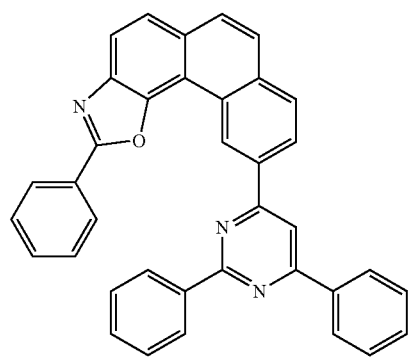
B-83
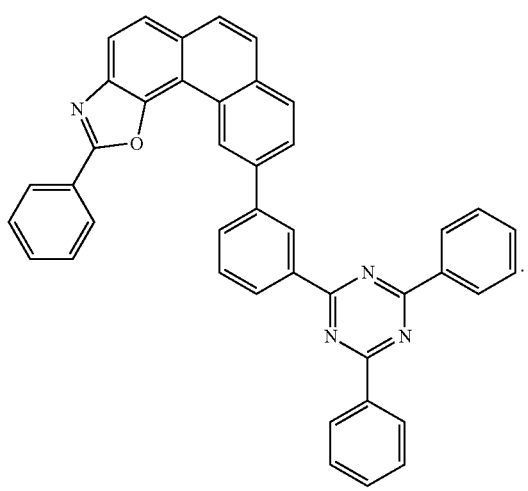
The compound represented by formula 2 may be selected from the group consisting of the following compounds, but is not limited thereto:
C-1
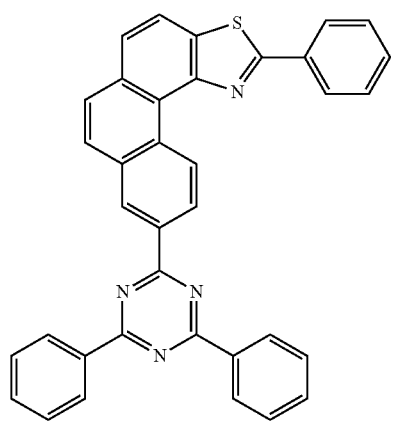
C-2
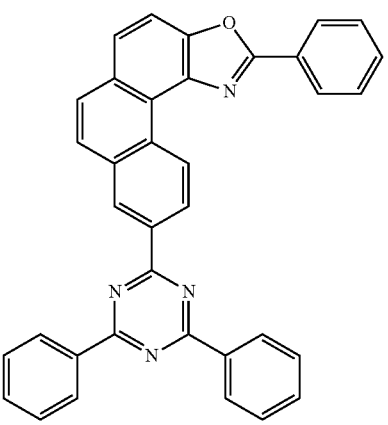
C-3
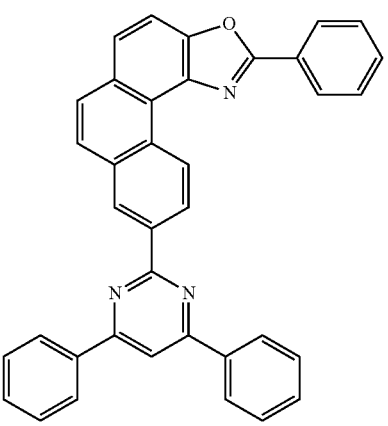
C-4
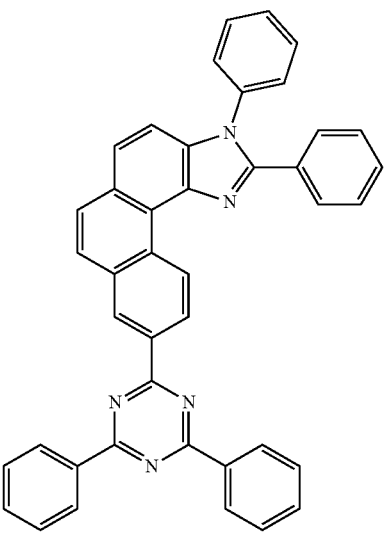

C-5
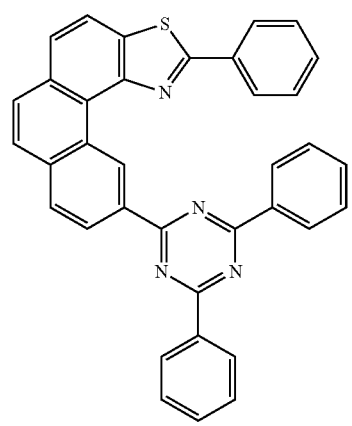
C-6
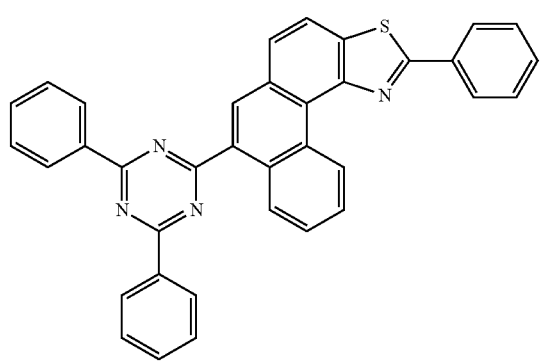
C-7
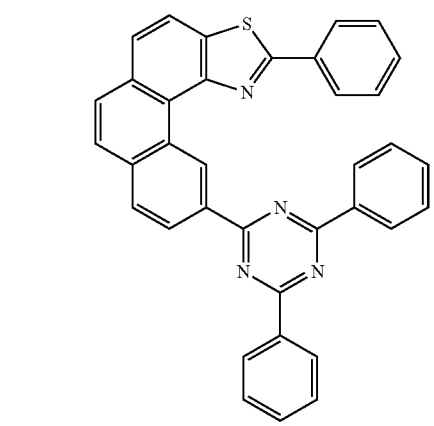
C-8
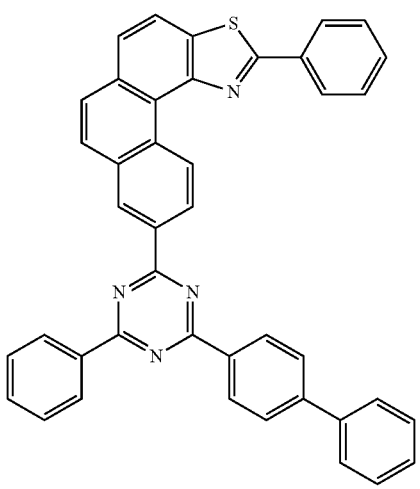
C-9
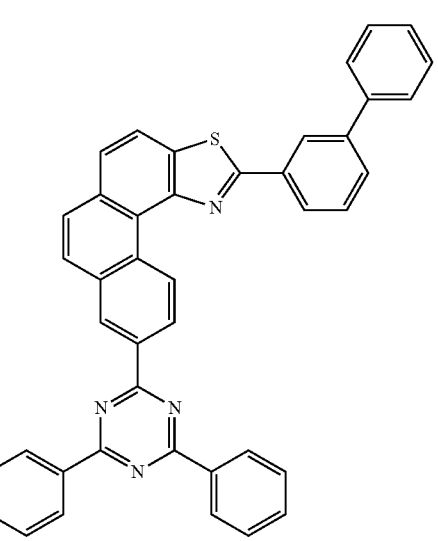
C-10
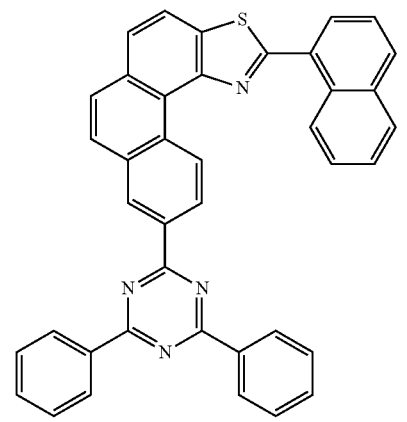

-continued
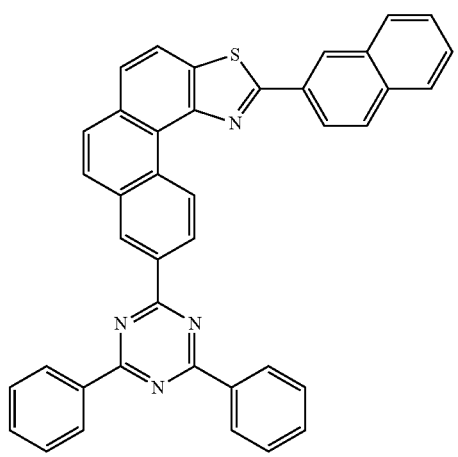
C-11
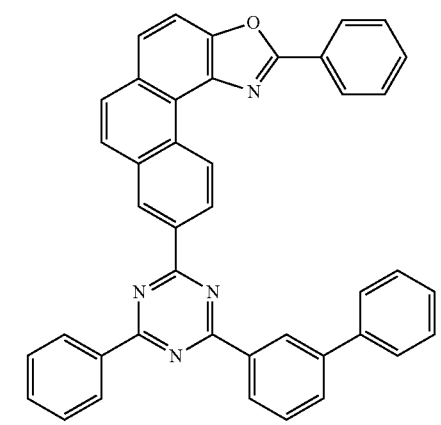
C-12
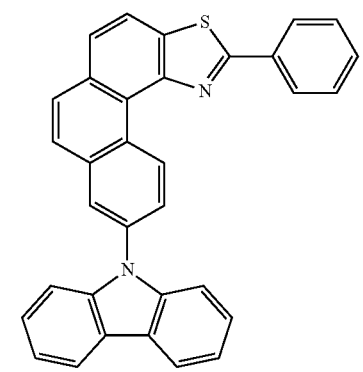
C-13
-continued
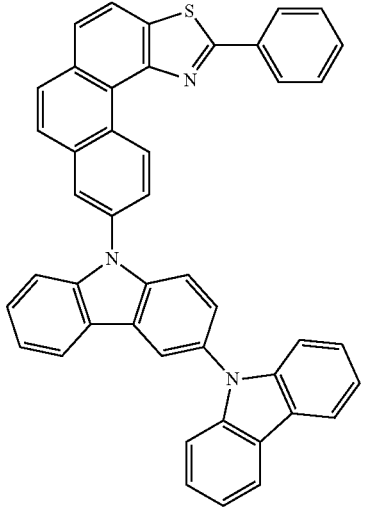
C-14
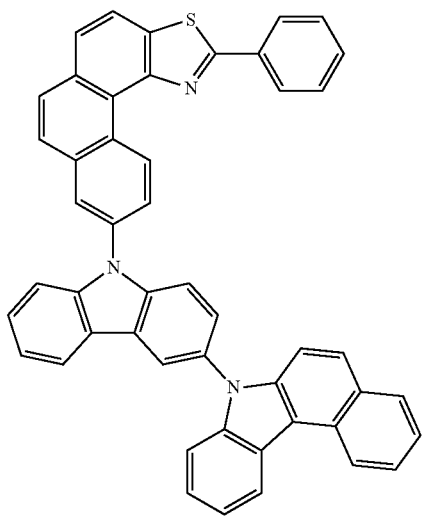
C-15
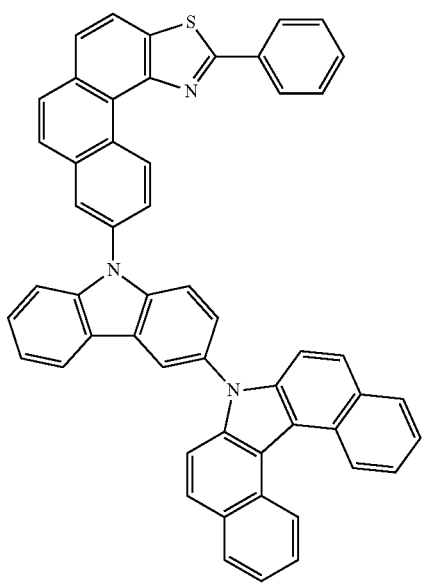
C-16

C-17
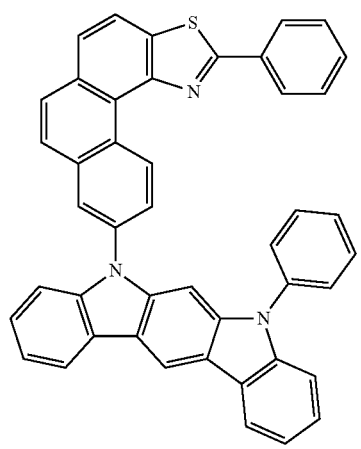
C-18
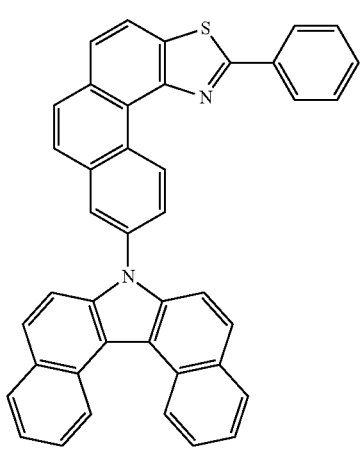
C-19
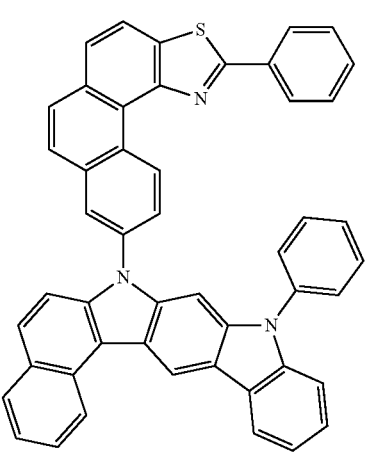
C-20
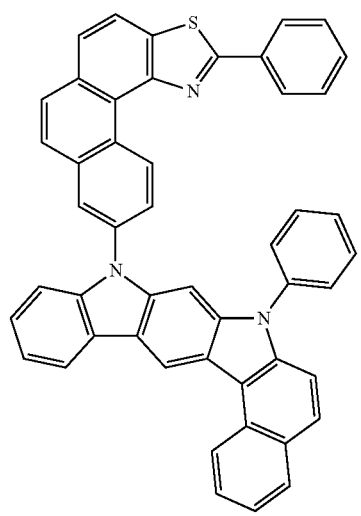
C-21
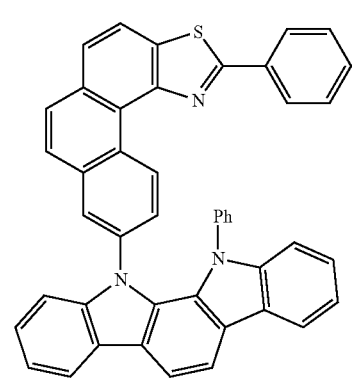
C-22
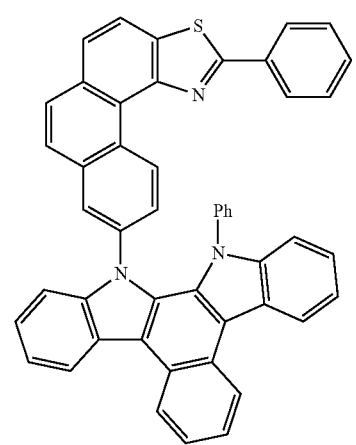

C-23
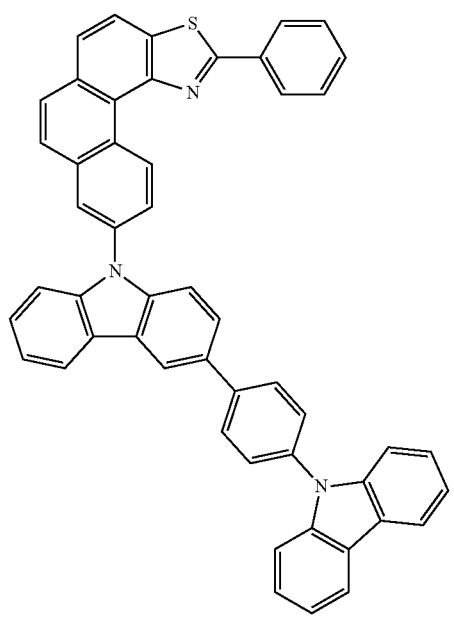
C-25
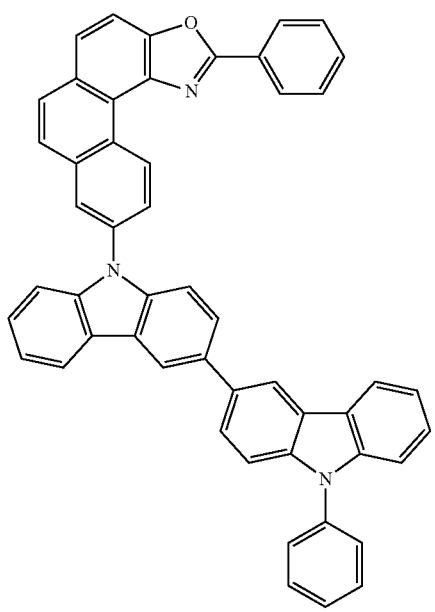
C-24
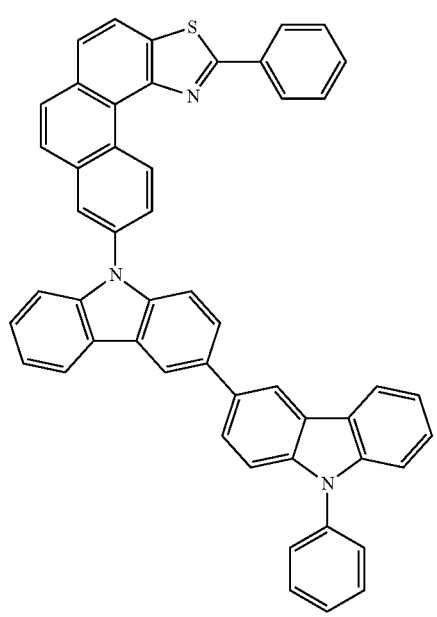
C-26
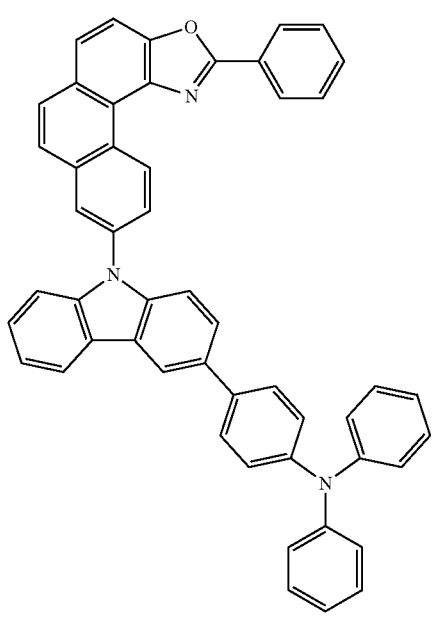

C-27
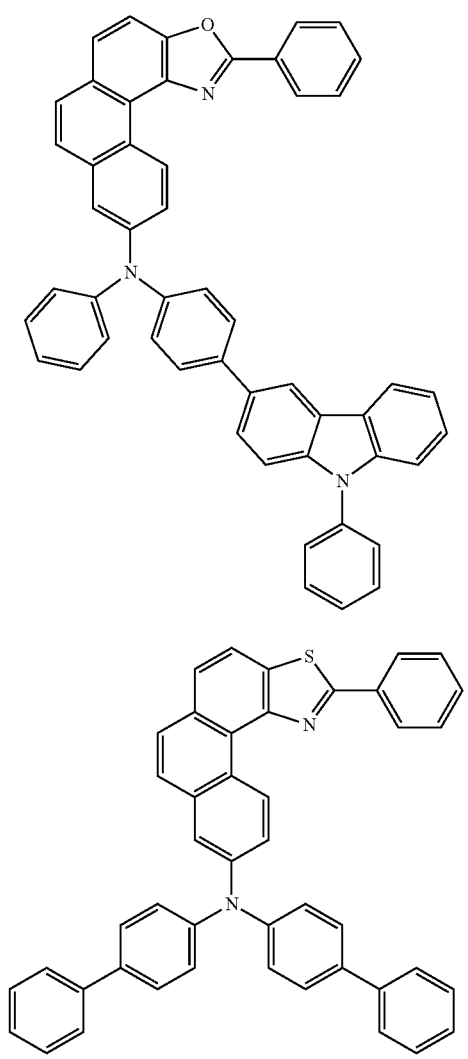
C-28
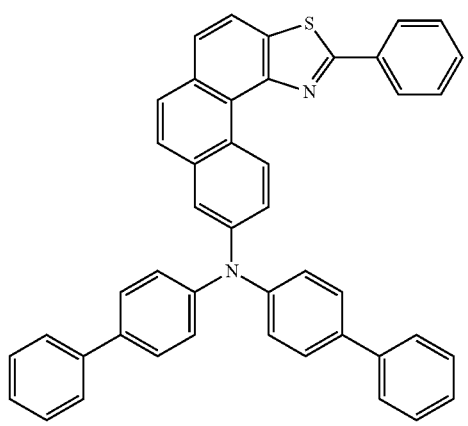
C-29
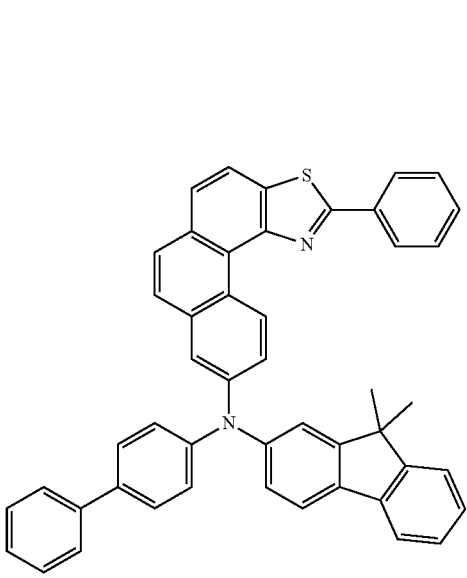
C-30
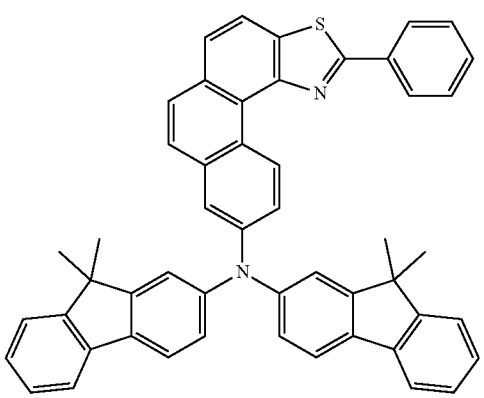
C-31
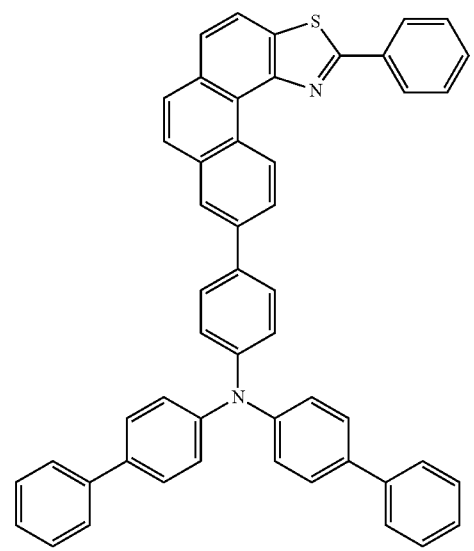
C-32
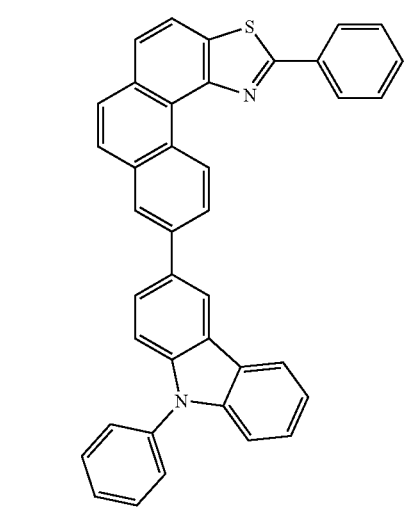

C-33
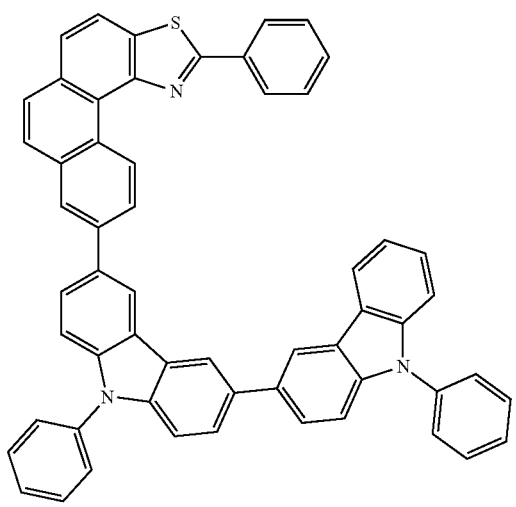
C-34
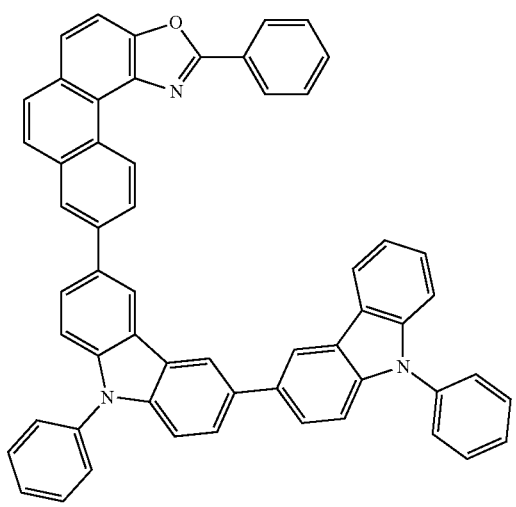
C-35
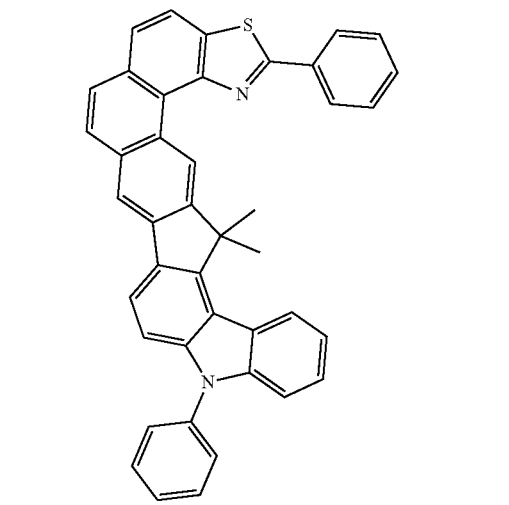
C-36
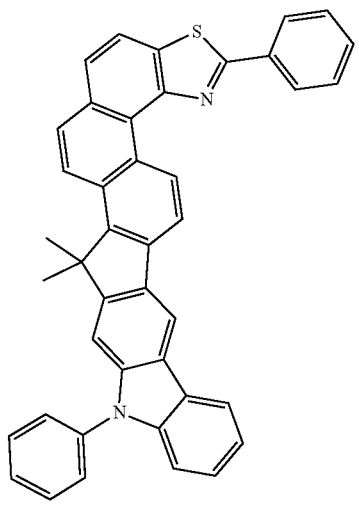
C-37
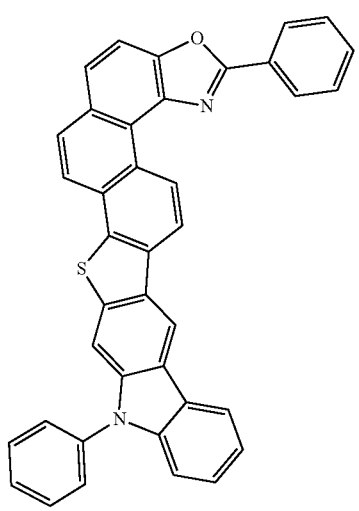
C-38
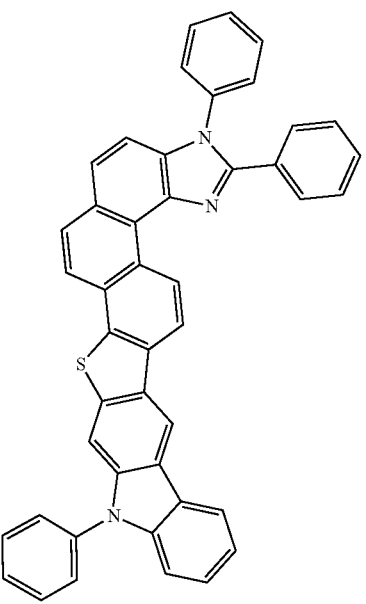

-continued
C-39
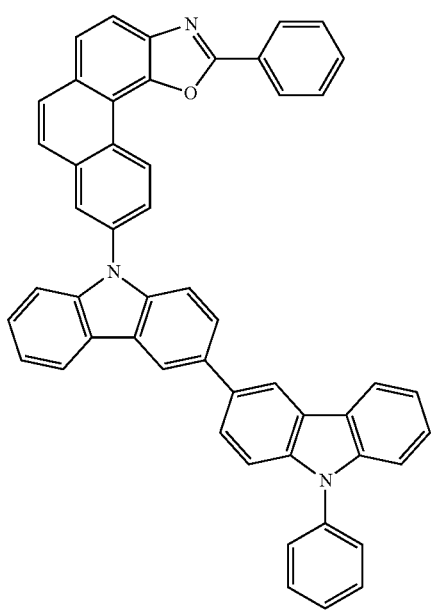
C-40
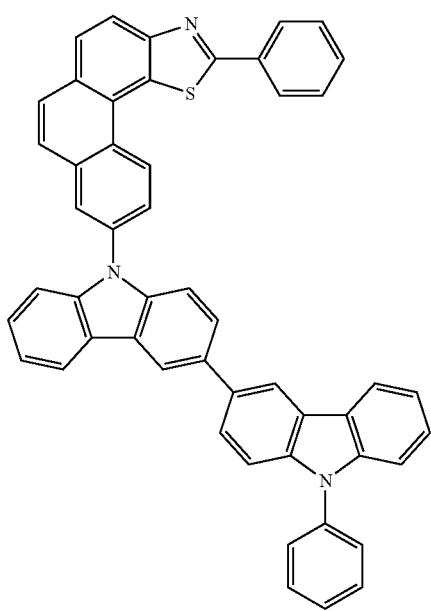
C-41
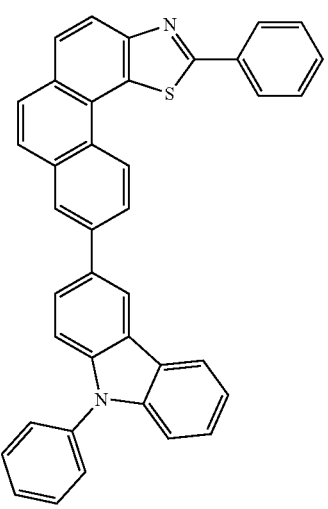
C-42
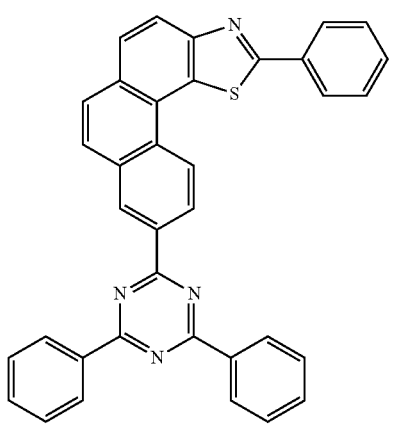
C-43
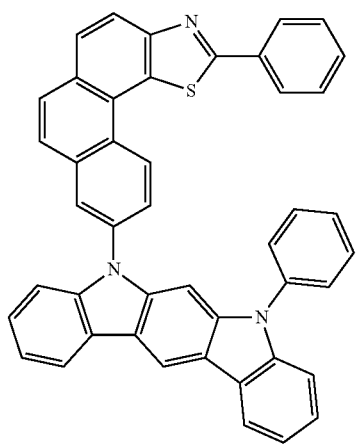

C-44
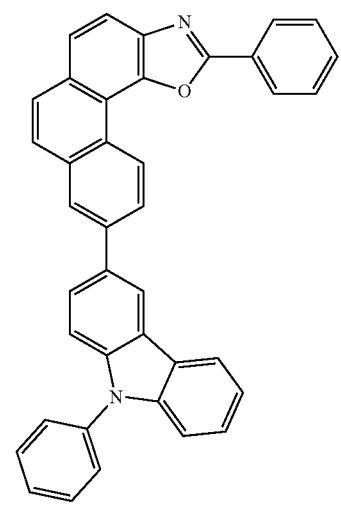
C-45
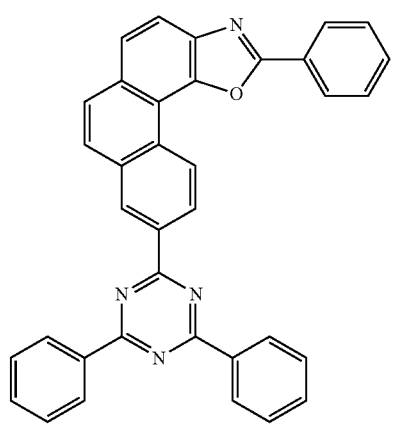
C-46
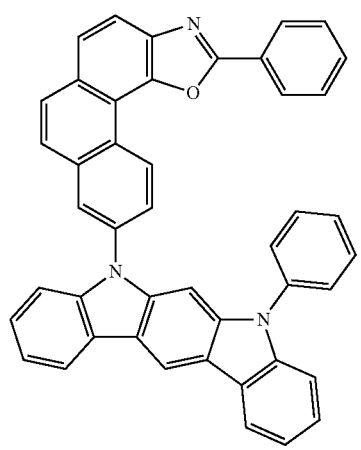
C-47
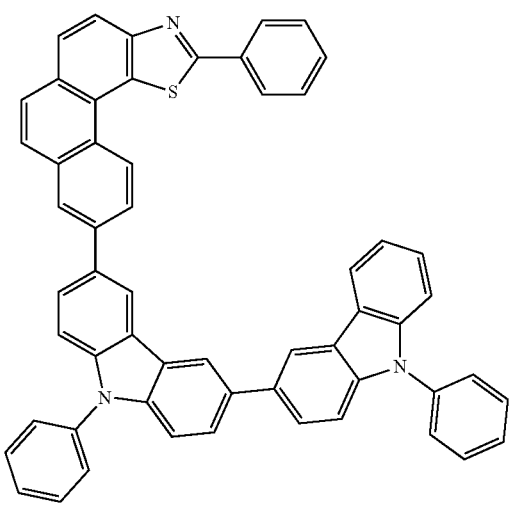
C-48
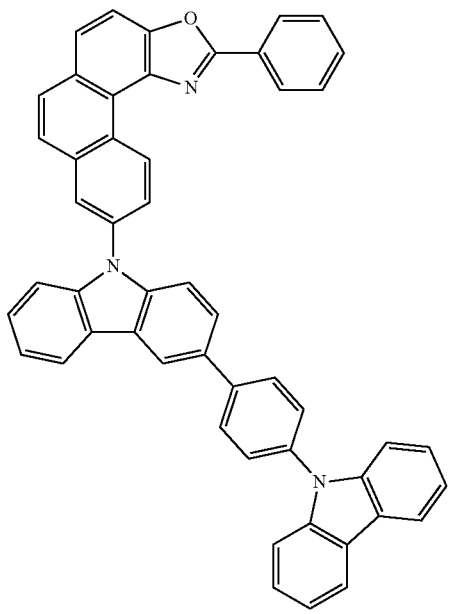
C-49
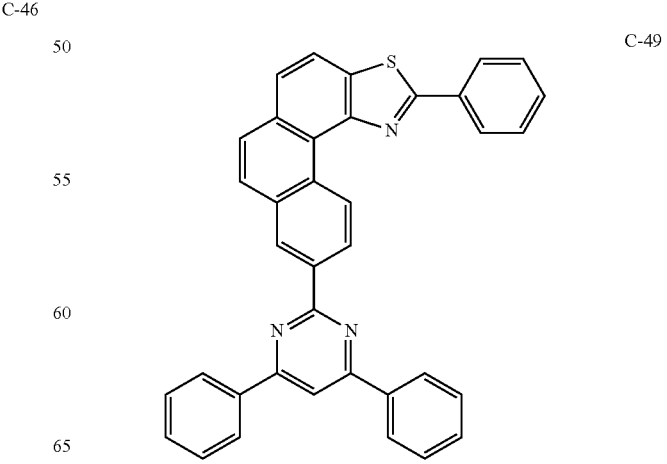

C-50
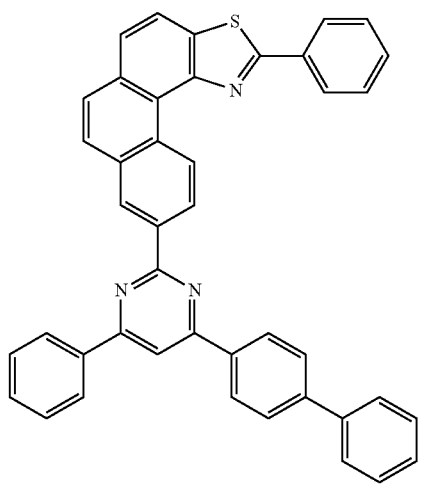
C-51
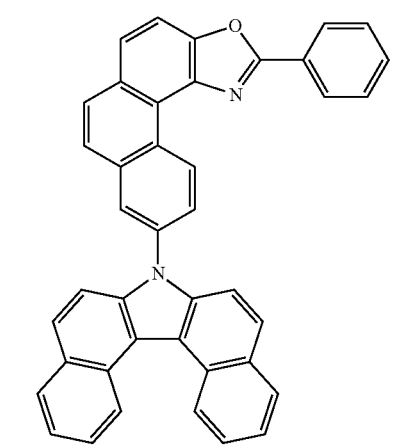
C-52
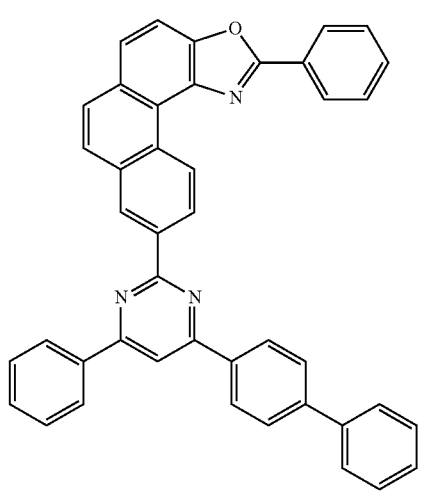
C-53
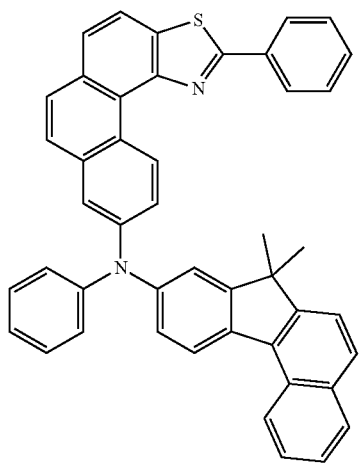
C-54
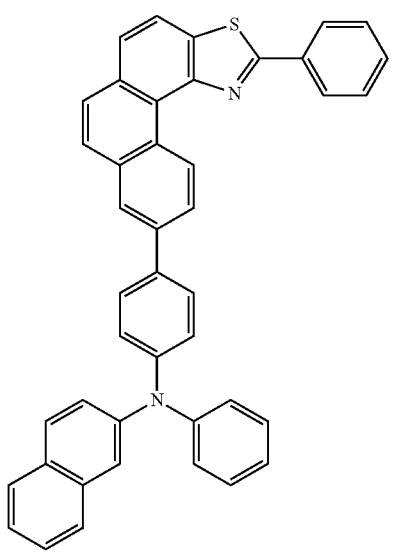
C-55
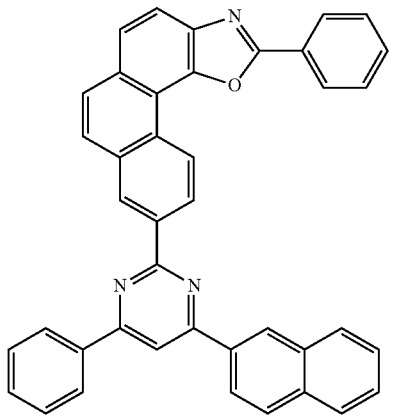

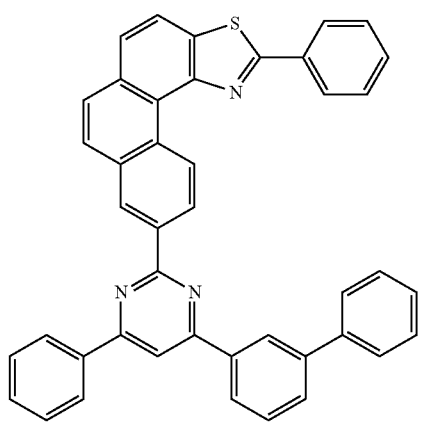
C-56
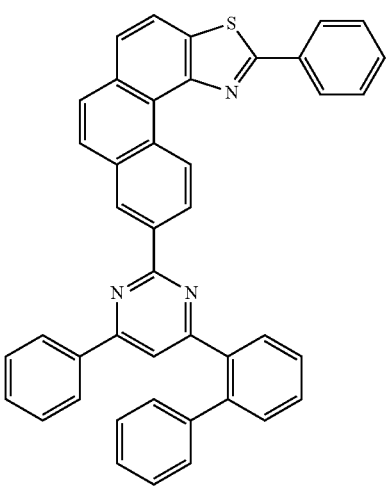
C-59
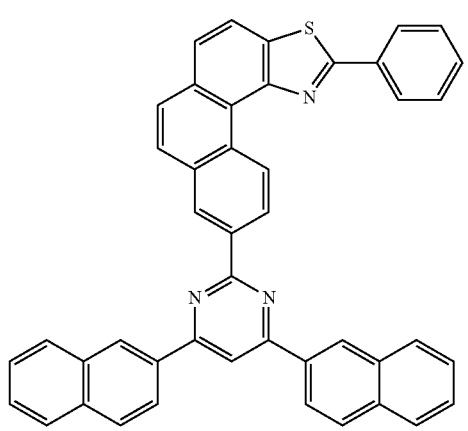
C-57
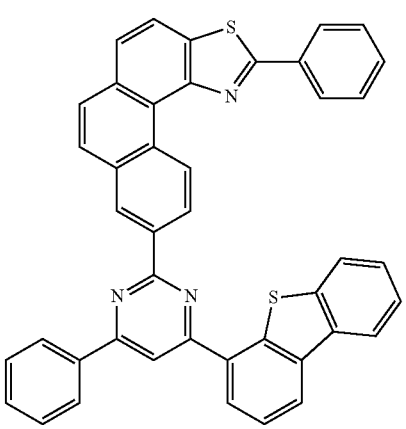
C-60
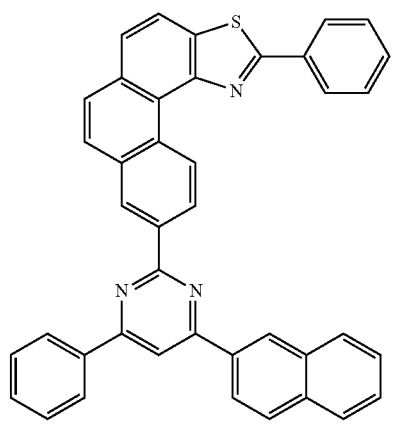
C-58
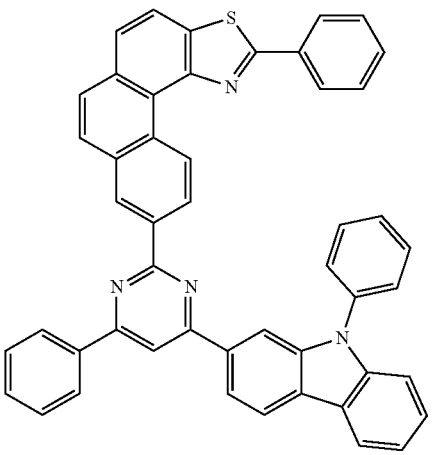
C-61

-continued
C-62
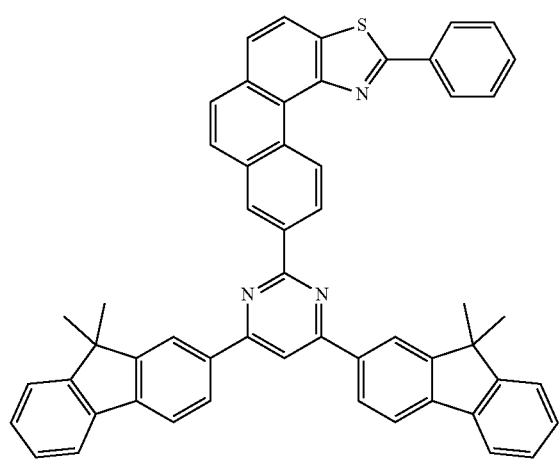
C-63
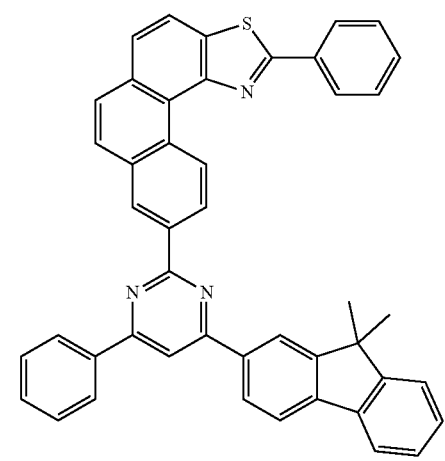
C-64
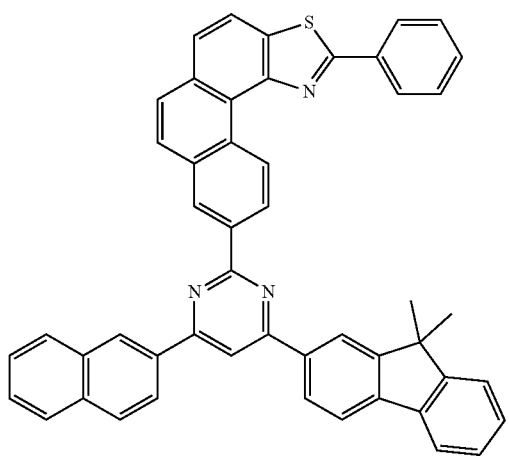
C-65
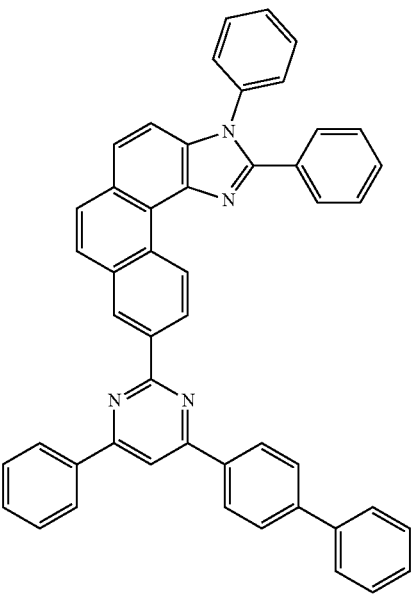
C-66
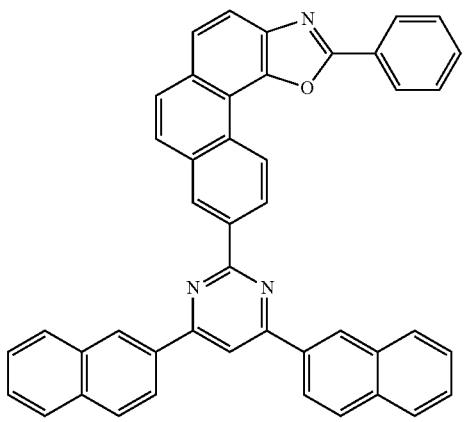
C-67
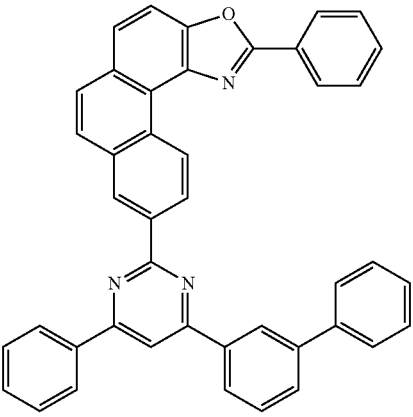

-continued
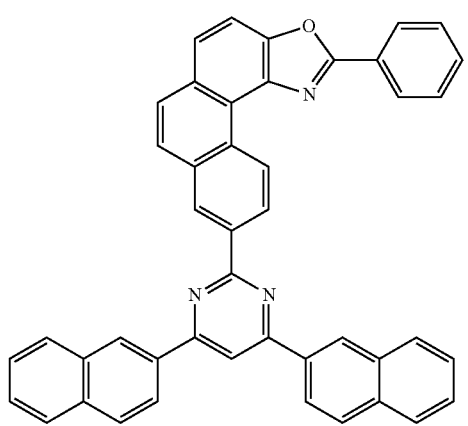
C-68
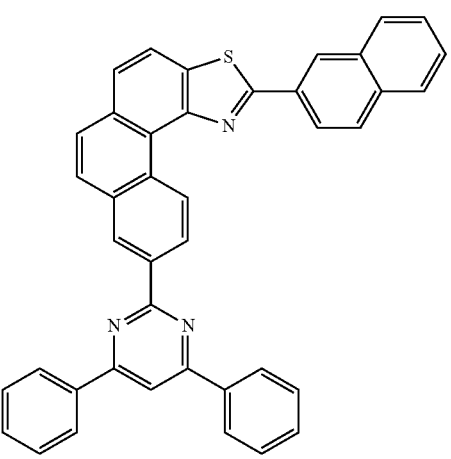
C-71
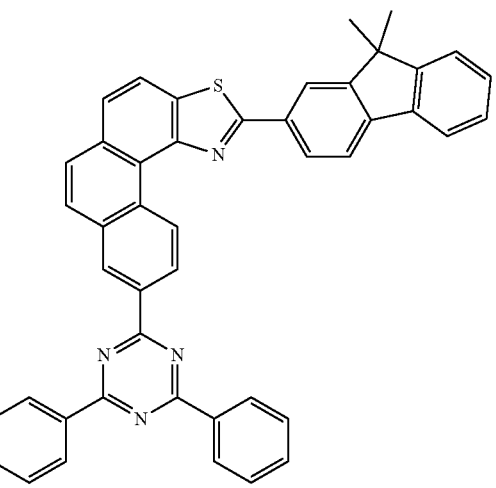
C-72
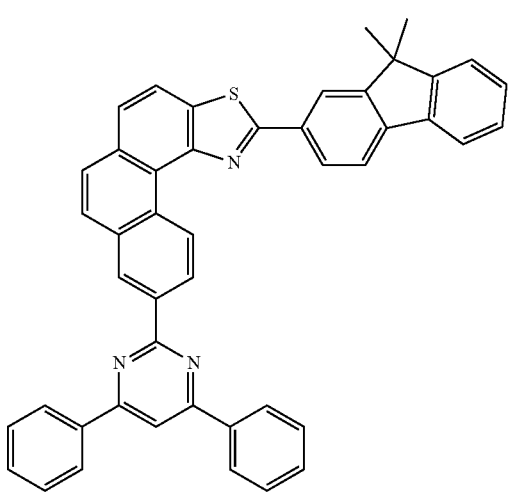
C-70
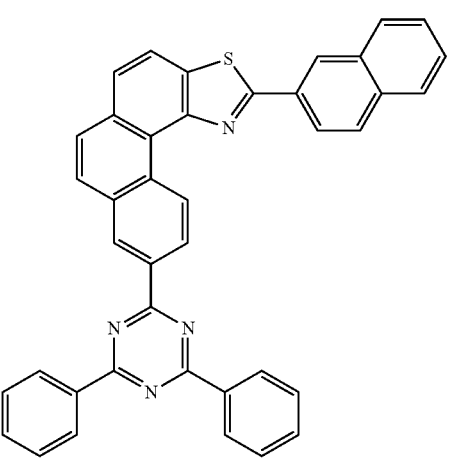
C-73

C-74
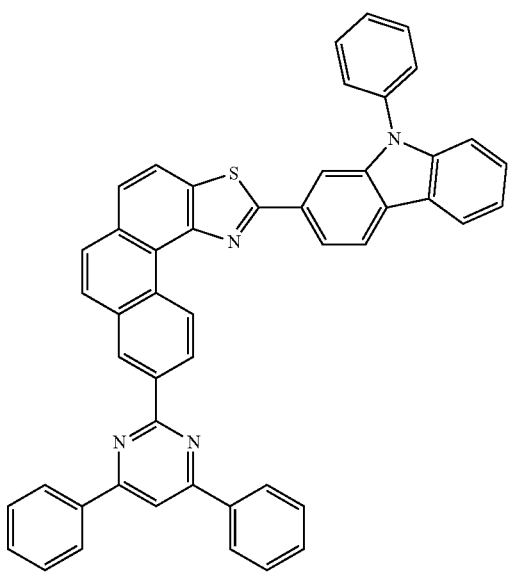
C-75
C-76
C-77
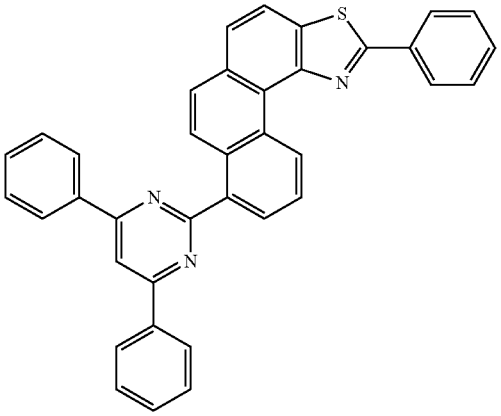
C-78
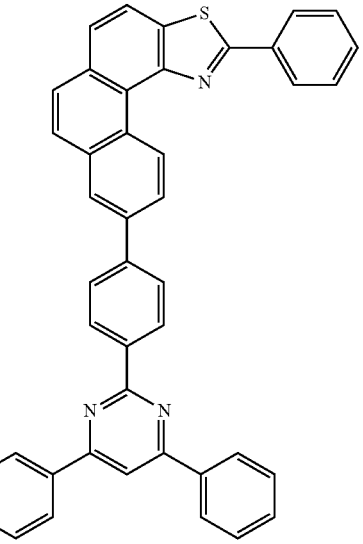
C-79
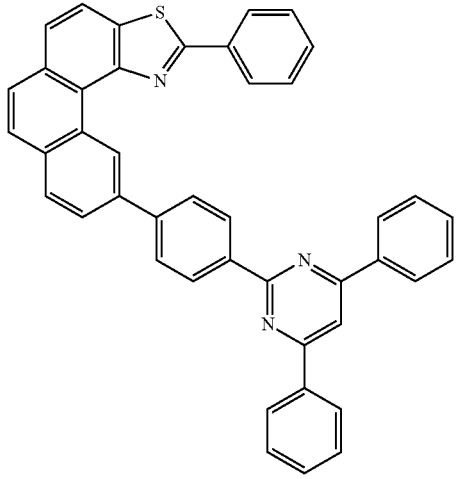

C-80
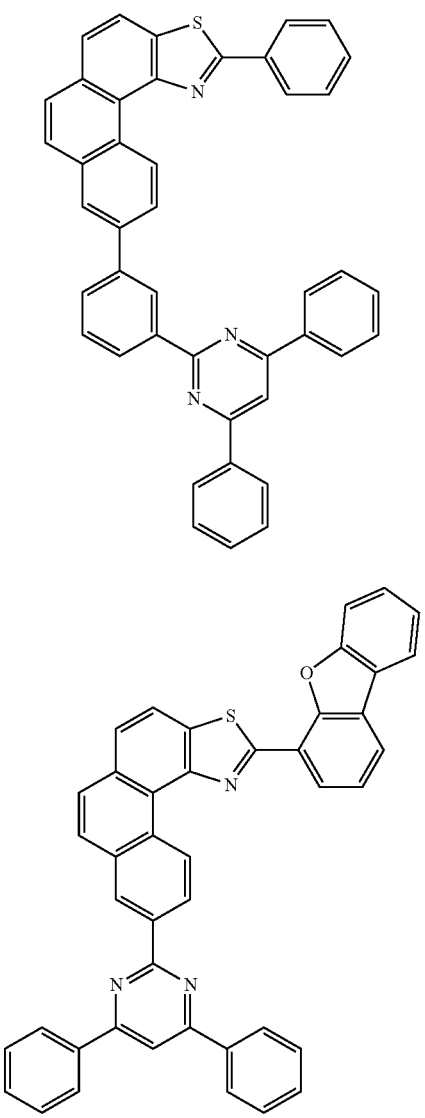
C-81
C-82
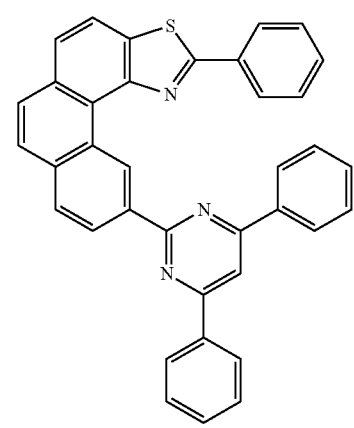
C-83
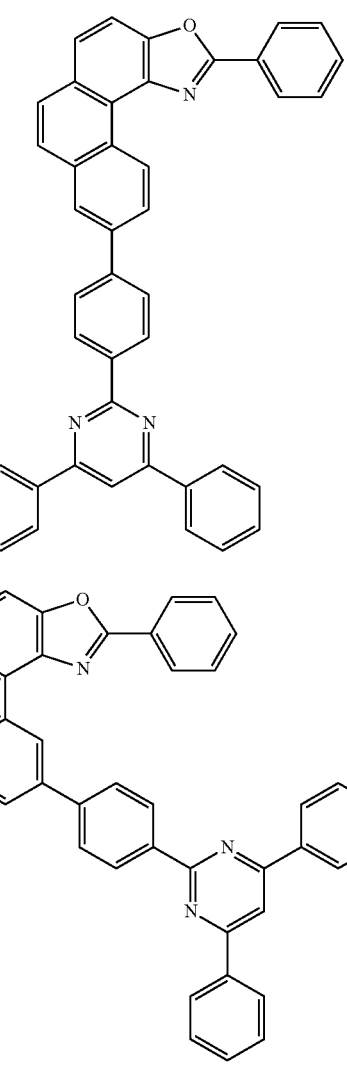
C-84
C-85
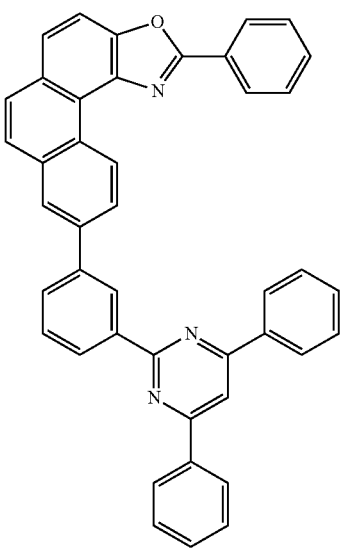

C-86
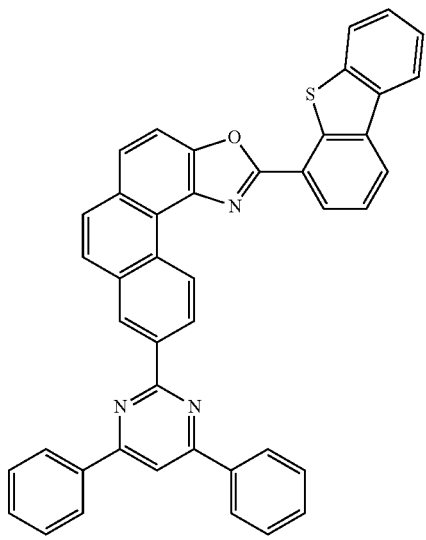
C-87
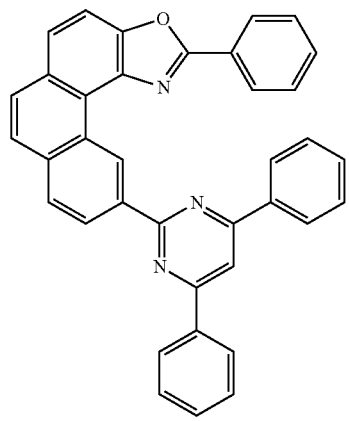
C-88
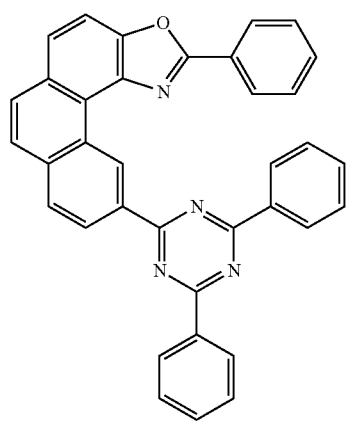
C-89
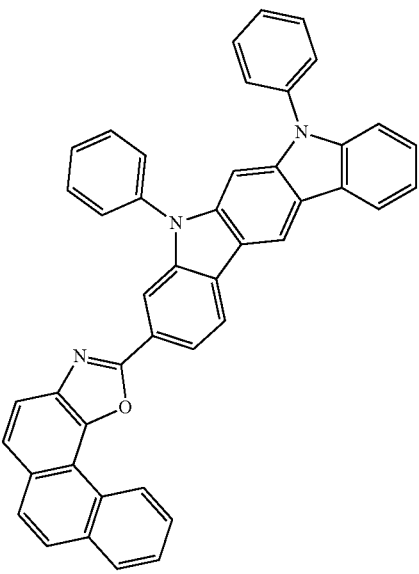
C-90
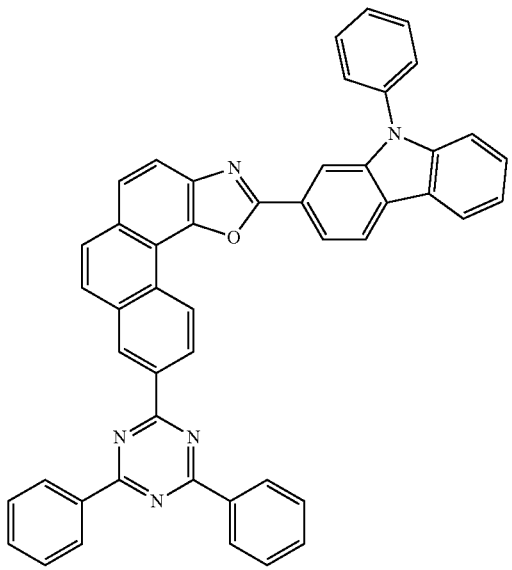
C-91
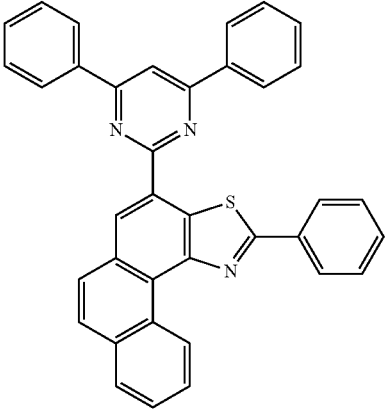

-continued
C-92
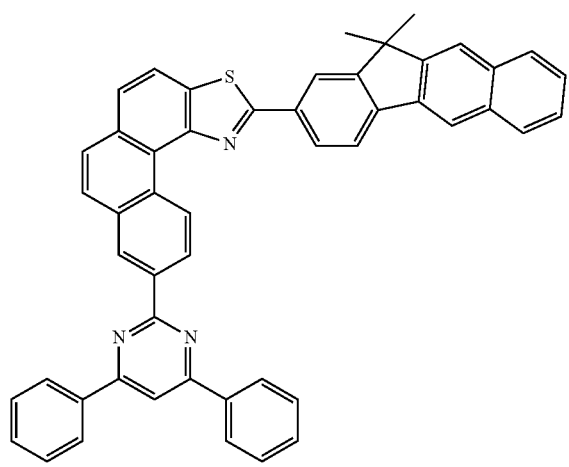
C-93
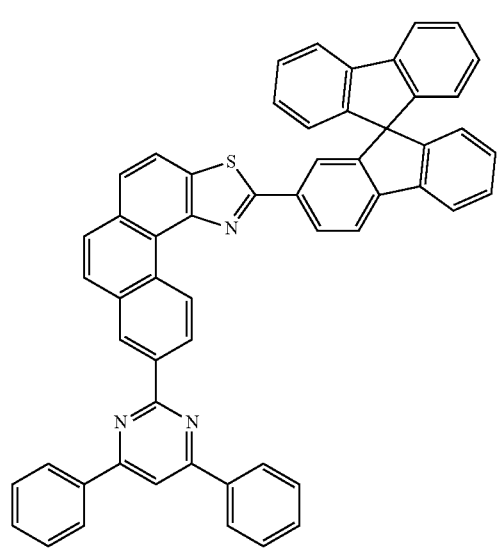
C-94
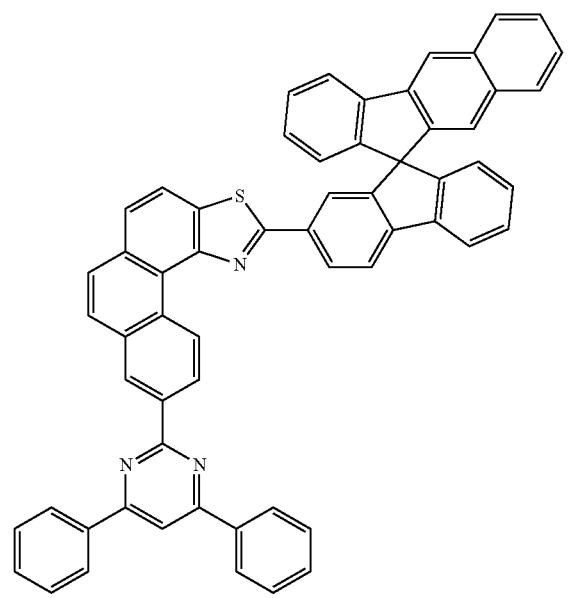
-continued
C-95
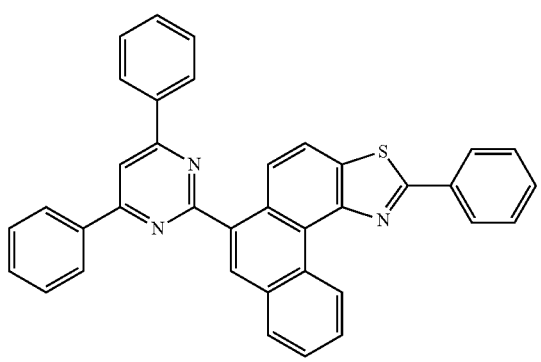
C-96
C-97
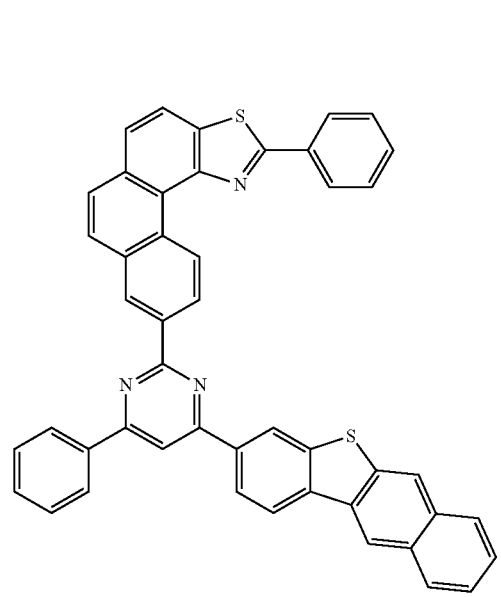

C-98
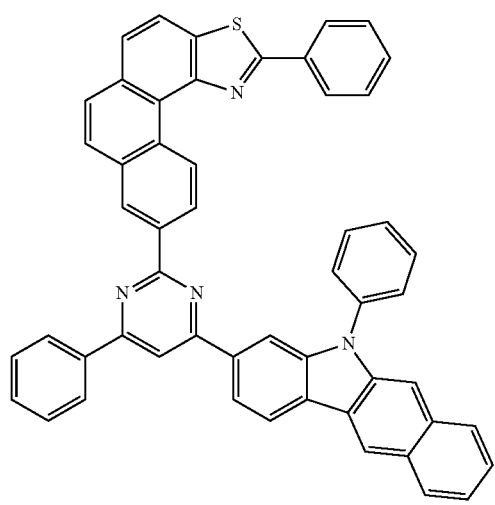
C-99
C-100
C-101
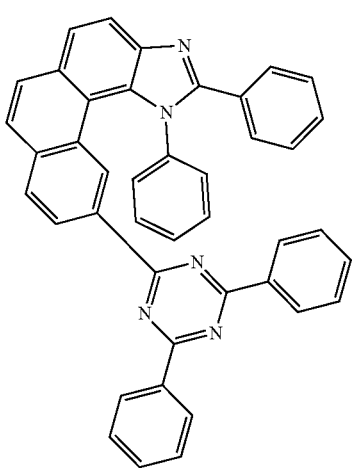
C-102
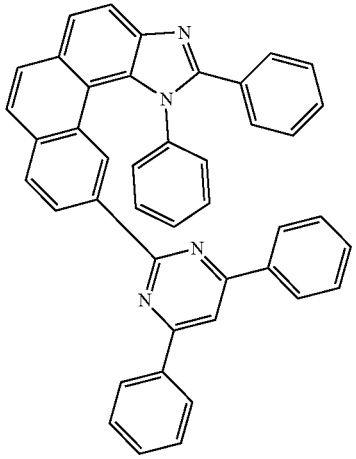
C-103
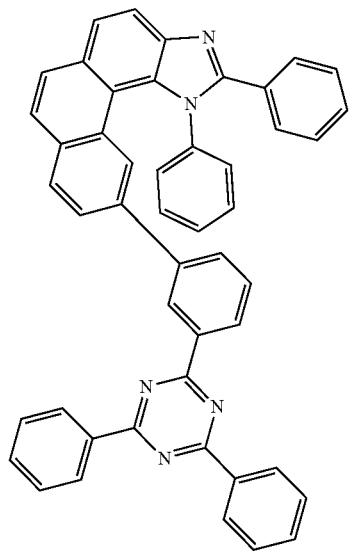

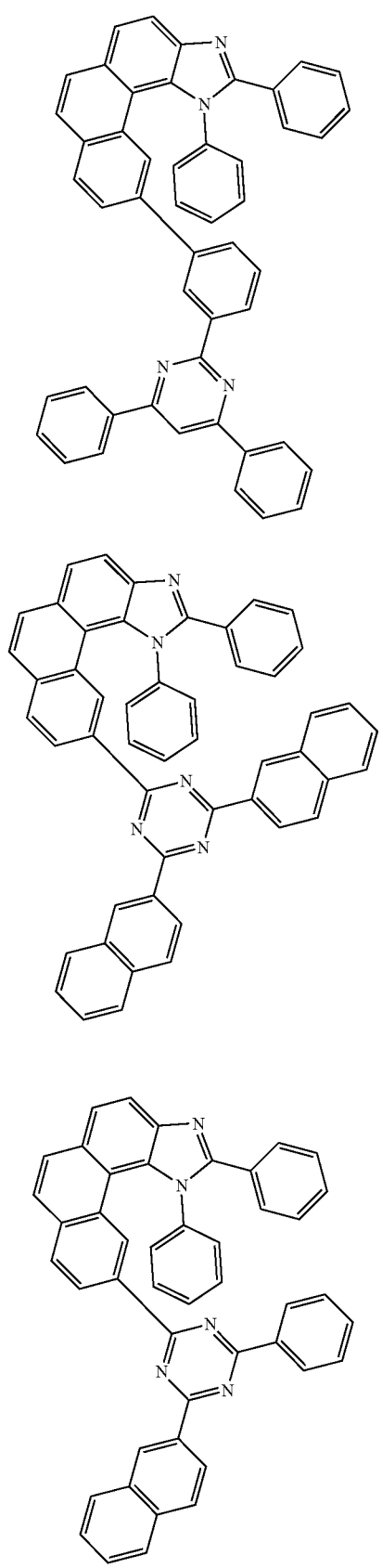
C-104
C-105
C-106
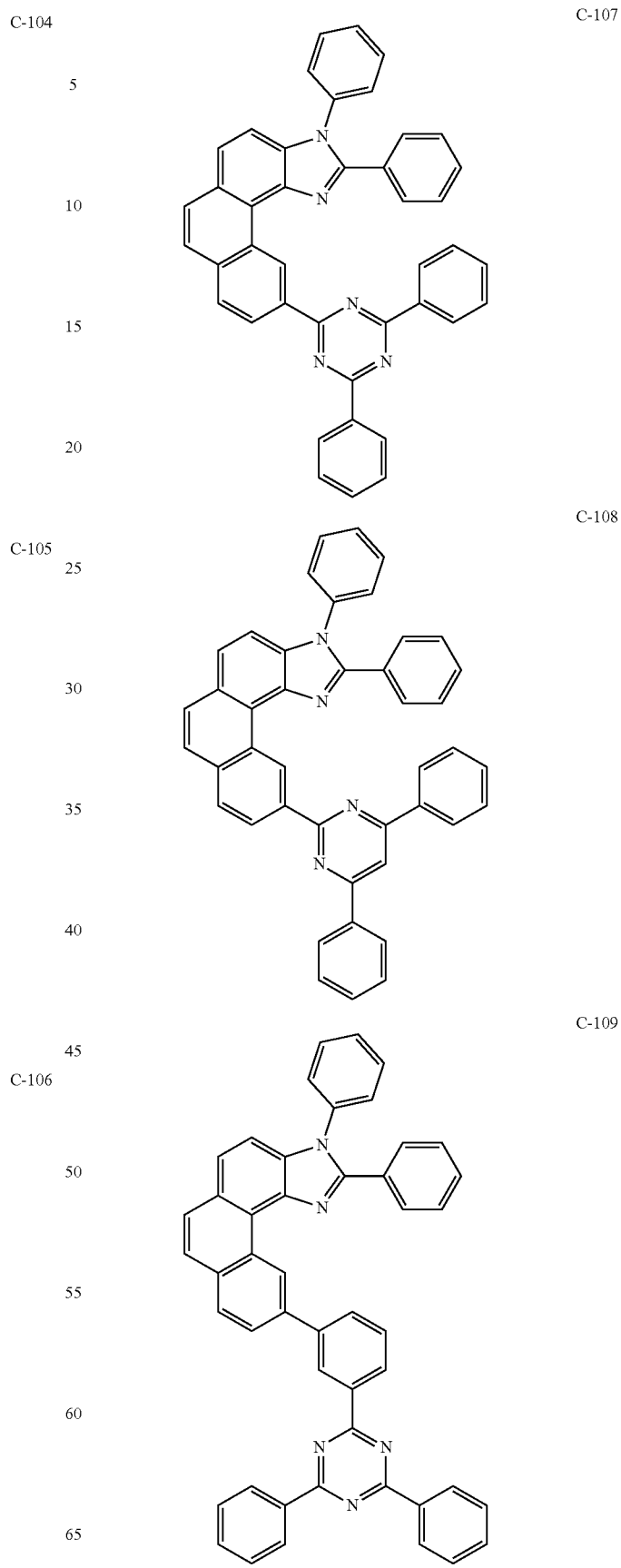
C-107
C-108
C-109

C-110
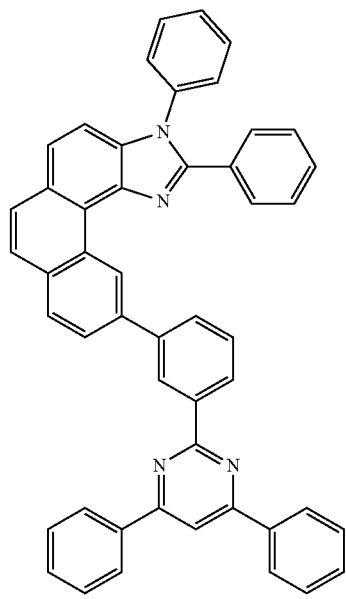
C-111
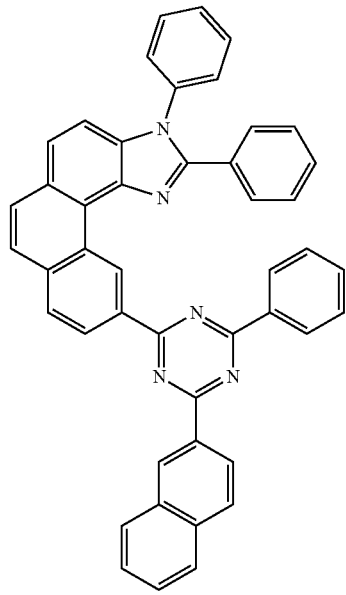
C-112
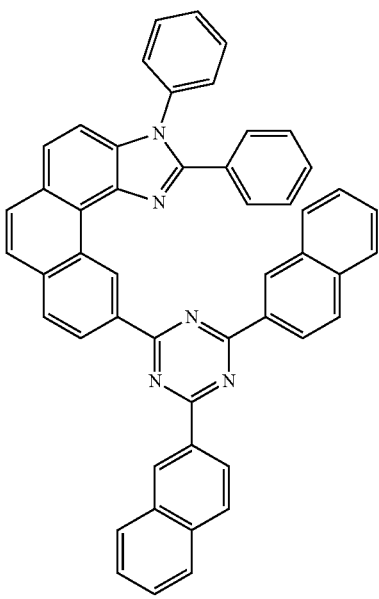
C-113
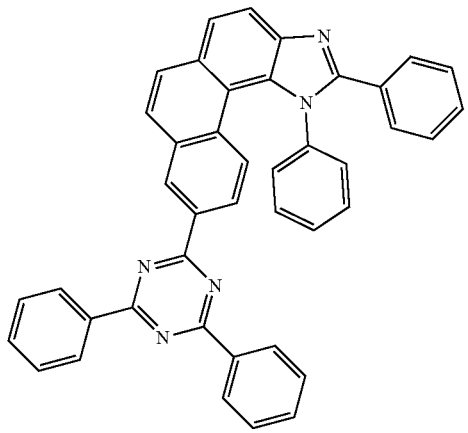
C-114
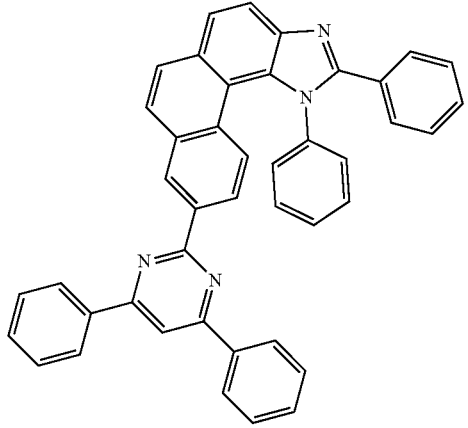

-continued
C-115
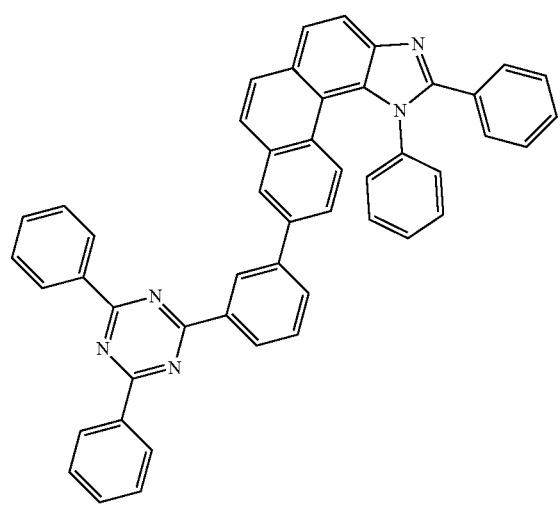
C-116
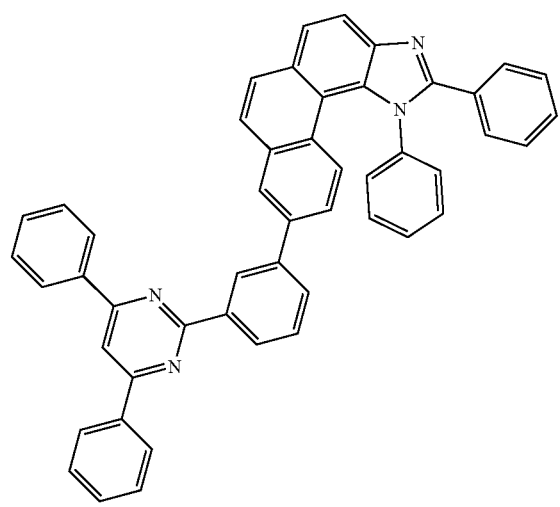
C-117
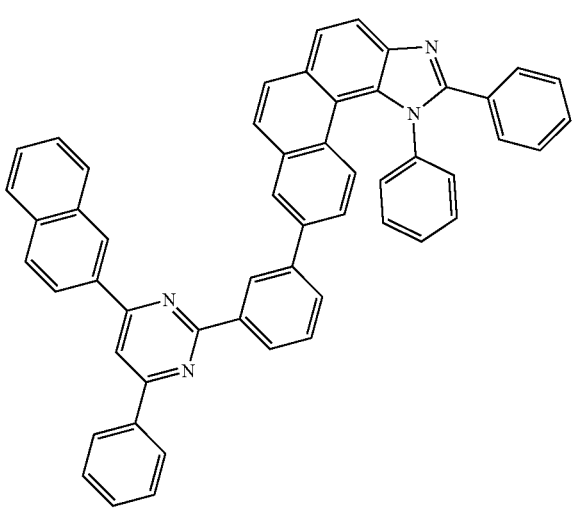
C-118
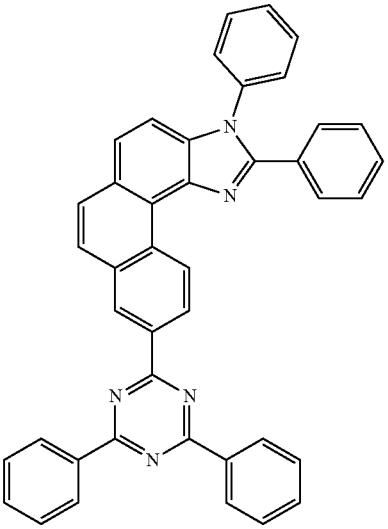
C-119

C-120
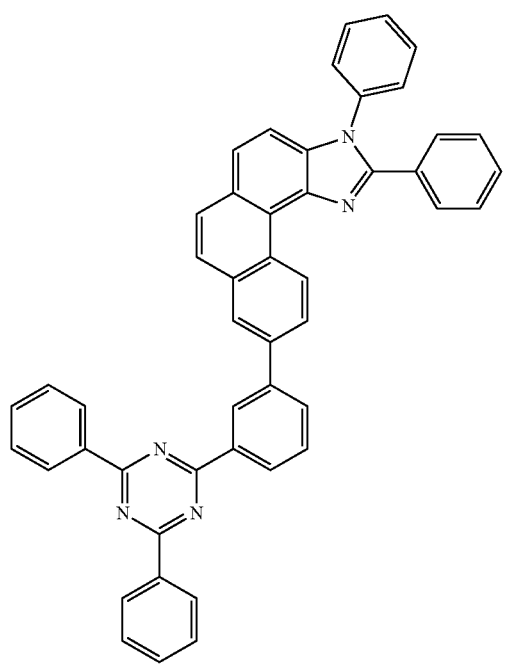
C-121
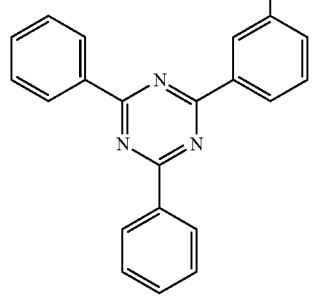
C-122
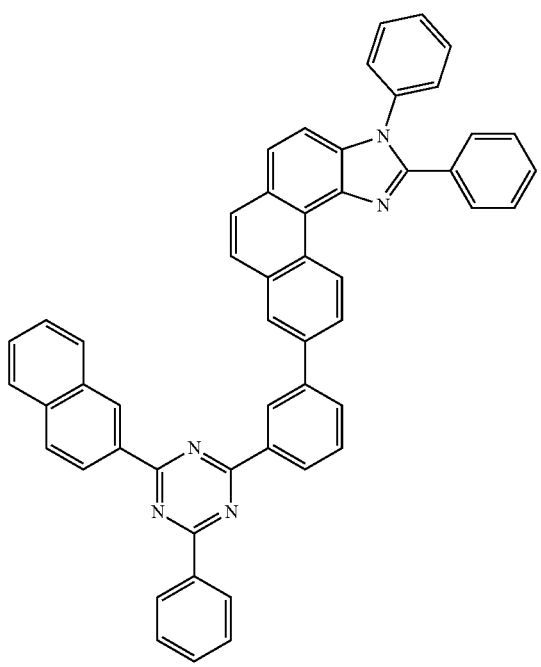
C-123
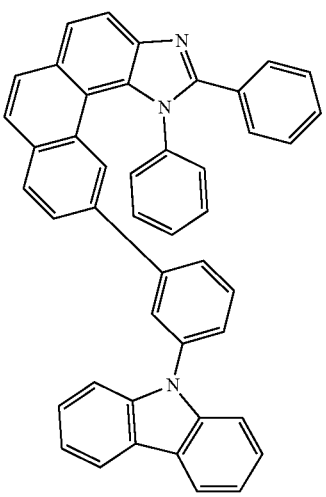

-continued
C-124
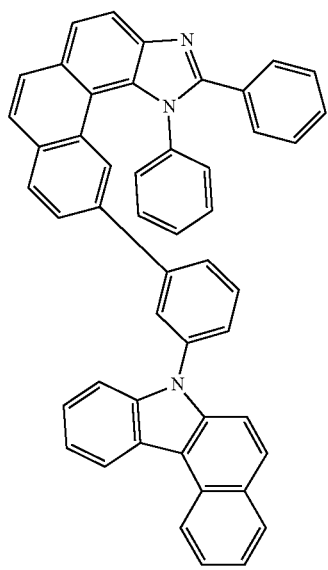
C-125
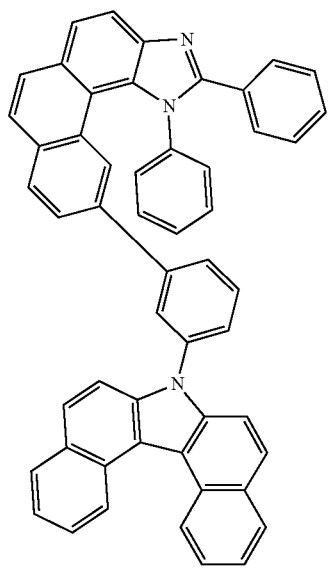
C-126
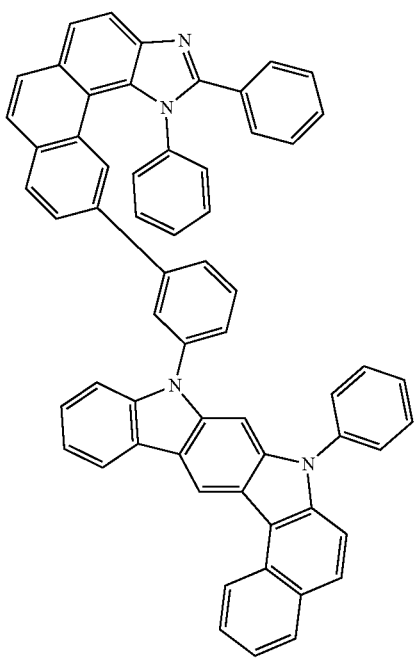
C-127
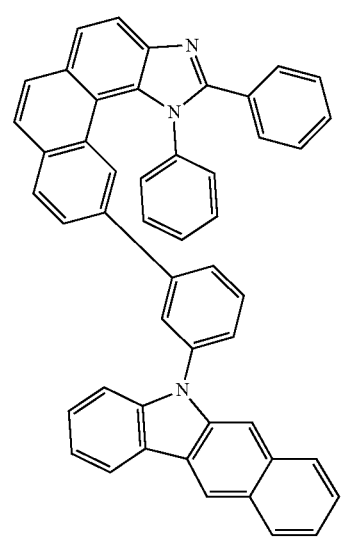
C-128
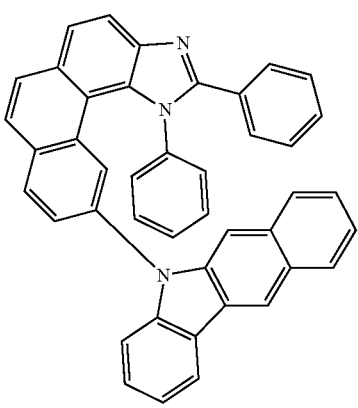

C-129
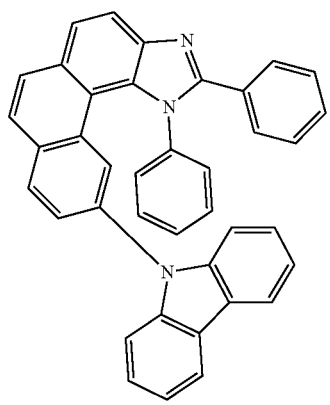
C-130
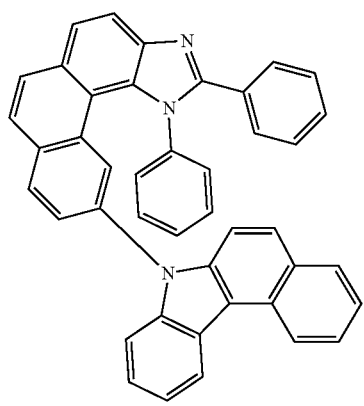
C-131
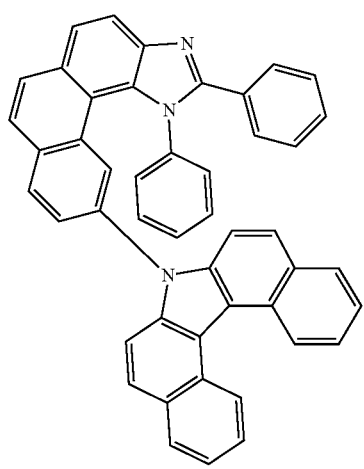
C-132
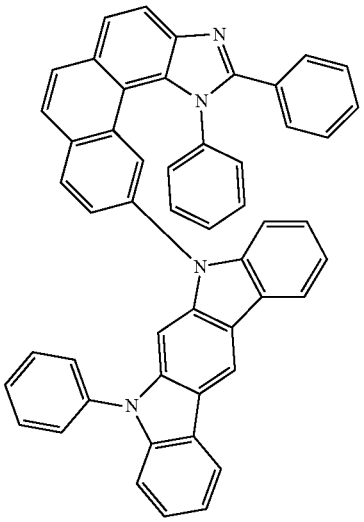
C-133
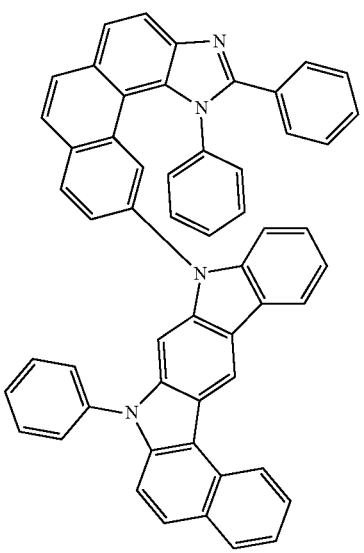
C-134
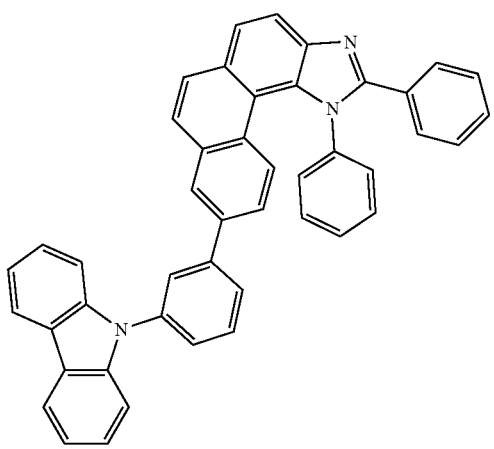

C-135
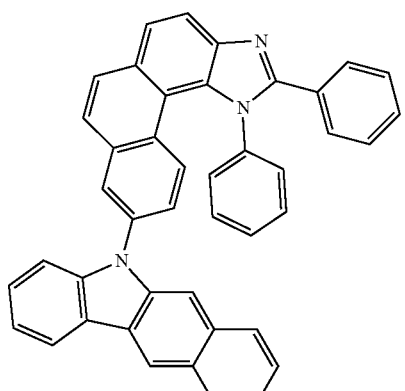
C-136
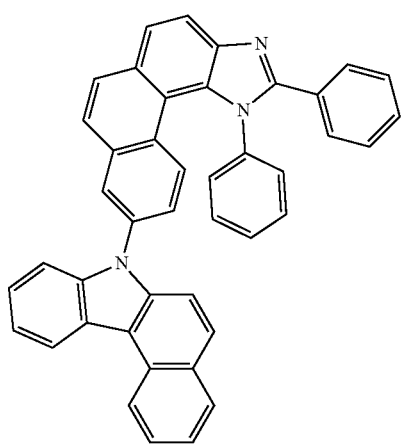
C-137
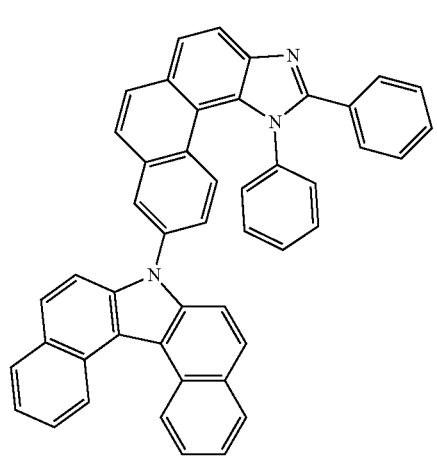
C-138
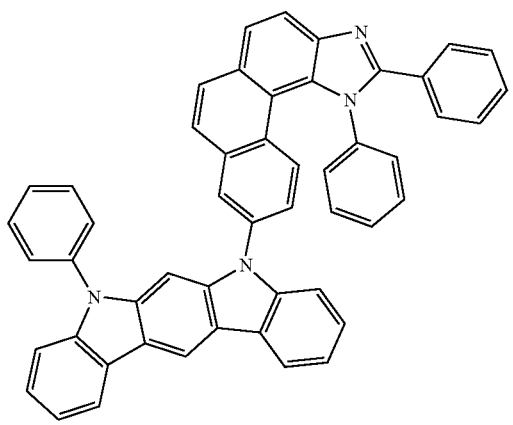
C-139
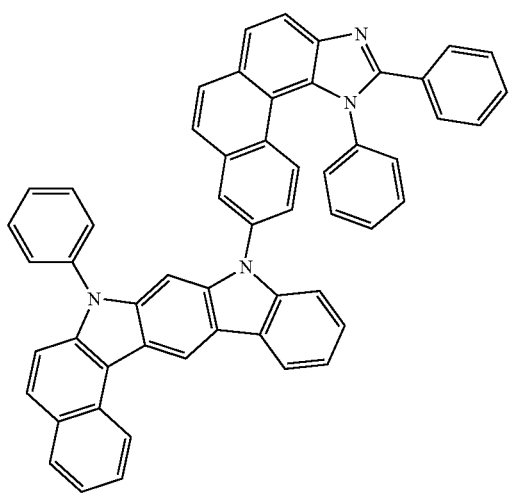
C-140
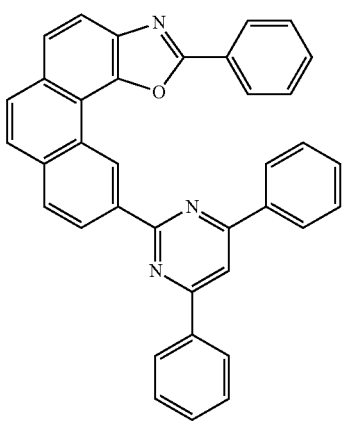

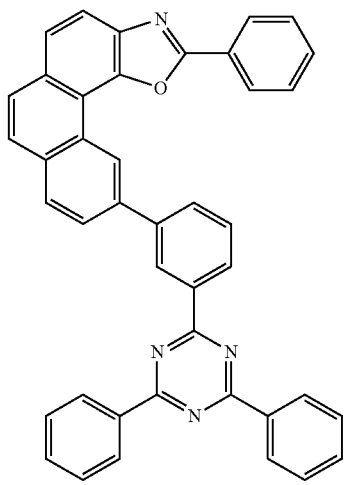

C-141

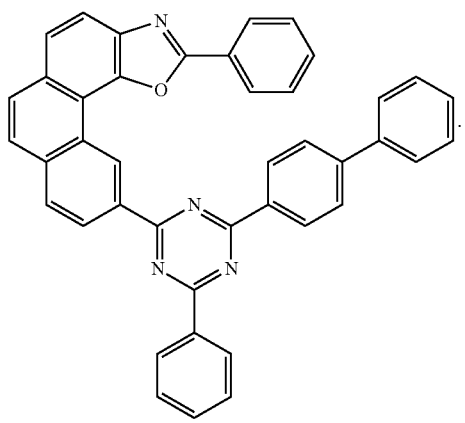

C-142

The compound of formulae 1 and 2 according to the present disclosure can be prepared by known methods to a person skilled in the art, and can be prepared, for example, by Bromination, Suzuki reaction, Buchwald-Hartwig reaction, Ullmann reaction, etc.

The host compound to be used in the present disclosure may be a phosphorescent host compound or a fluorescent host compound. The kinds of host compound to be used are not particularly limited, and may be compounds having the aforementioned LUMO energy level and selected from compounds known in the art. Specifically, the host compound may be a fluorescent host compound. The fluorescent host compound may be an anthracene-based compound represented by the following formula 30:

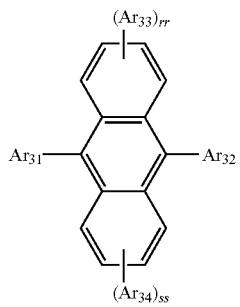

(30)

wherein $Ar_{31}$ and $Ar_{32}$, each independently, represent a substituted or unsubstituted (C6-C30)aryl, or a substituted or unsubstituted (5- to 30-membered) heteroaryl; $Ar_{33}$ and $Ar_{34}$, each independently, represent hydrogen, deuterium, a halogen, a cyano, a nitro, a hydroxy, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30)cycloalkyl, a substituted or unsubstituted (C1-C30)alkoxy, a substituted or unsubstituted (C1-C30)alkylsilyl, a substituted or unsubstituted (C6-C30)arylsilyl, a substituted or unsubstituted (C6-C30)aryl(C1-C30)alkylsilyl, or —$NR_{41}R_{42}$; $R_{41}$ and $R_{42}$, each independently, represent hydrogen, a substituted or unsubstituted (C6-C30)aryl, or a substituted or unsubstituted (5- to 30-membered) heteroaryl, or may be bonded to each other to form a mono- or polycyclic, (C3-C30) alicyclic, aromatic, or a combination of alicyclic and aromatic ring whose carbon atom(s) may be replaced with at least one heteroatom selected from nitrogen, oxygen, and sulfur; rr and ss, each independently, represent an integer of 1 to 4; and where rr or ss is an integer of 2 or more, each of $Ar_{33}$ or $Ar_{34}$ may be the same or different.

Specifically, the compound of formula 30 includes the following compounds, but is not limited thereto:

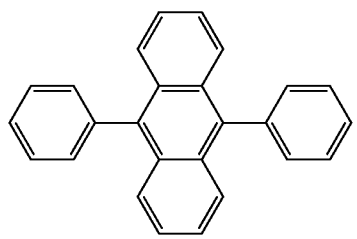

H-1

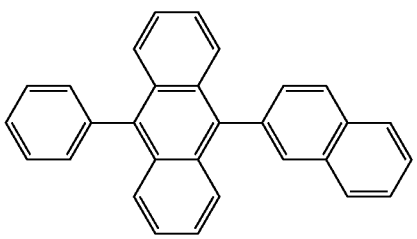

H-2

-continued
H-3
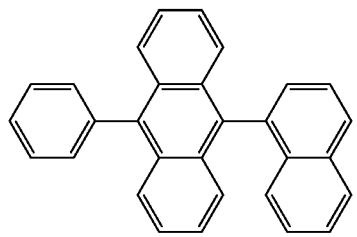
H-4
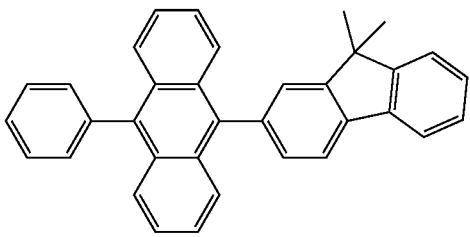
H-5
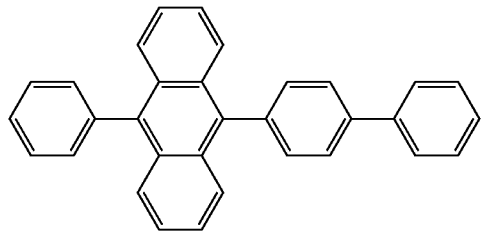
H-6
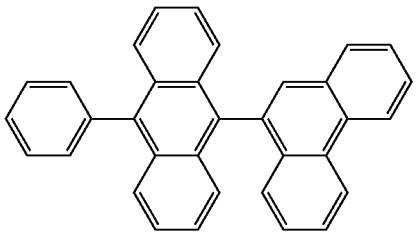
H-7
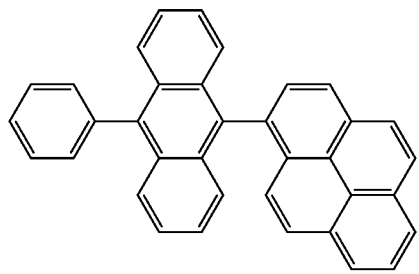
H-8
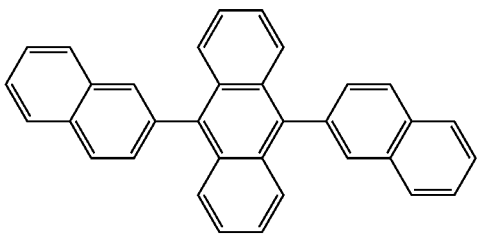
H-9
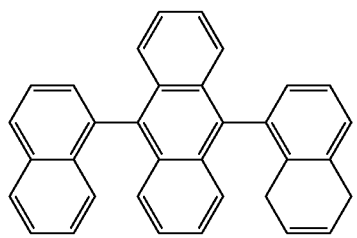
H-10
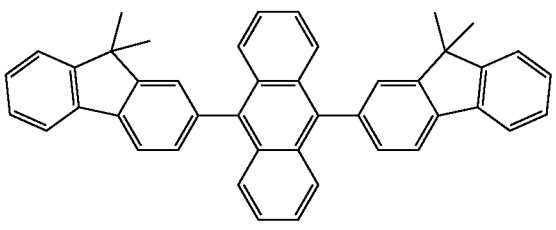
H-11
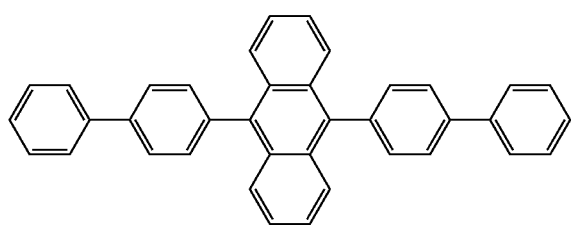
H-12
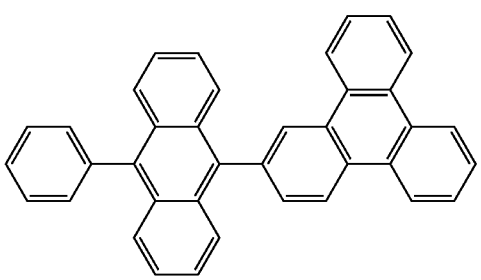
H-13
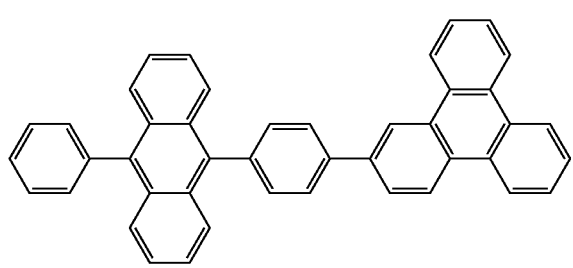
H-14
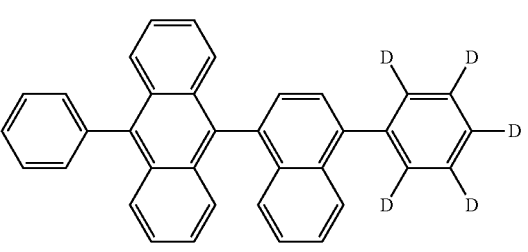

-continued
H-15
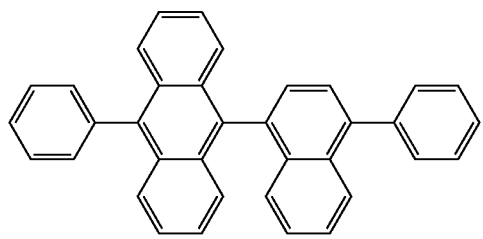
H-16
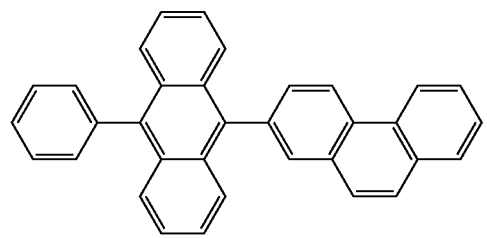
H-17
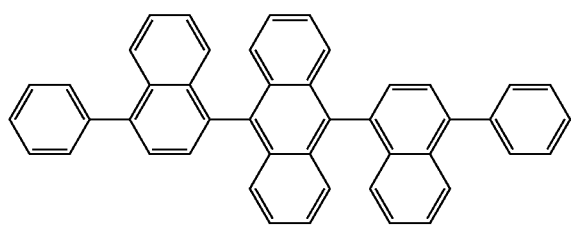
H-18
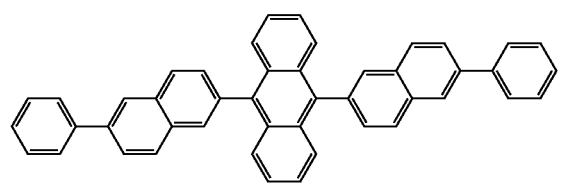
H-19
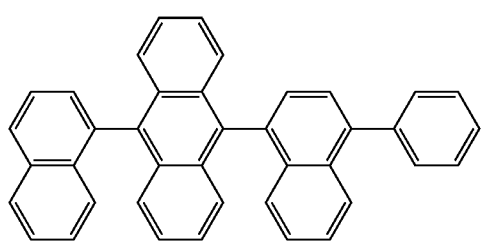
H-20
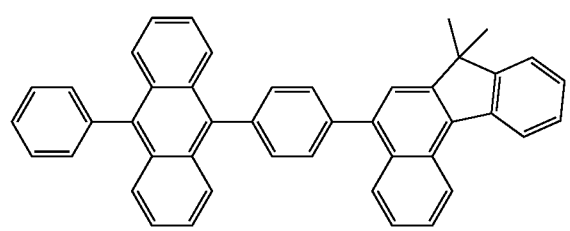
H-21
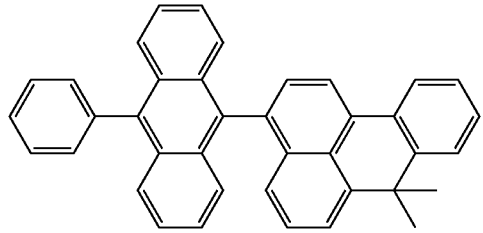
H-22
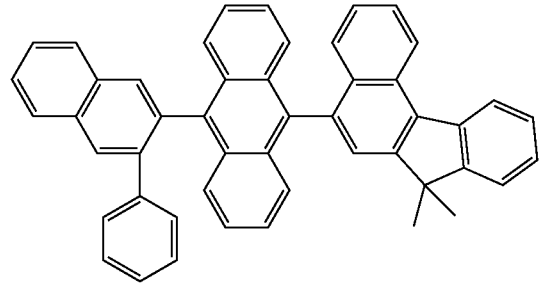
H-23
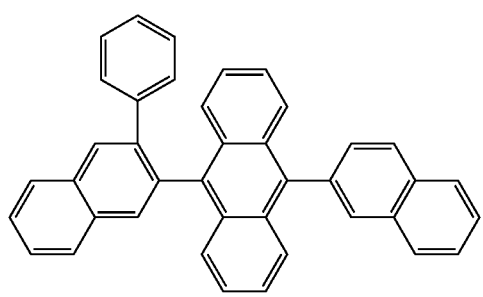
H-24
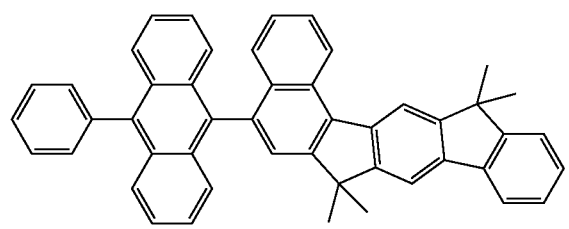
H-25
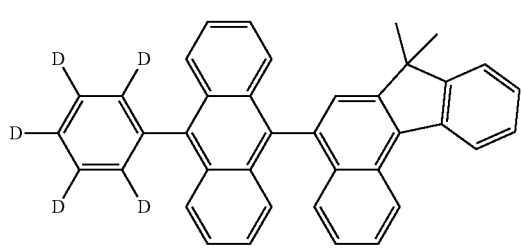
H-26
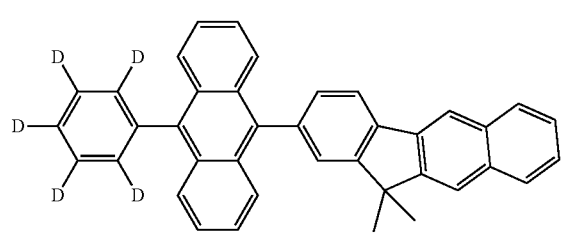

-continued
H-27
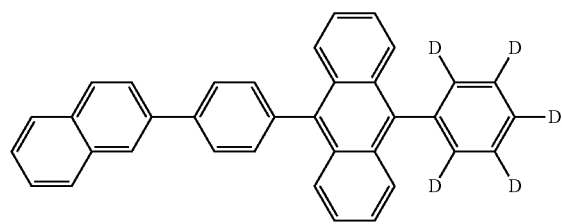
H-28
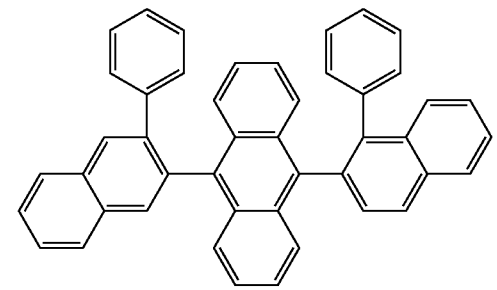
H-29
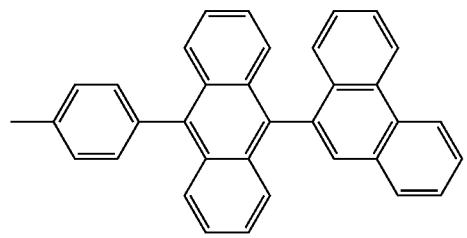
H-30
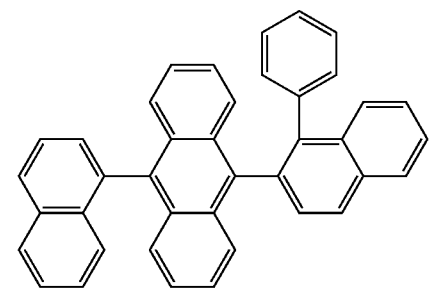
H-31
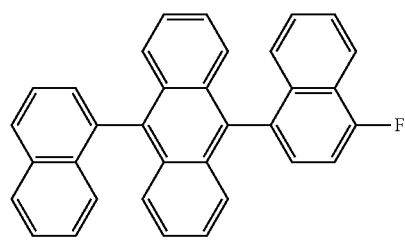
H-32
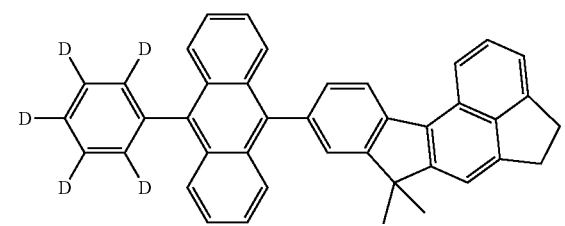
H-33
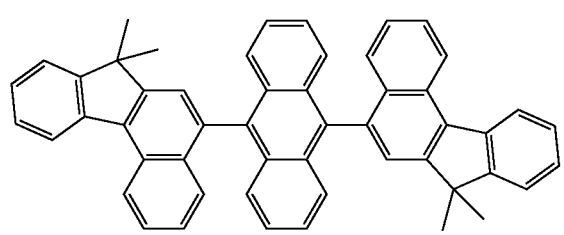
H-34
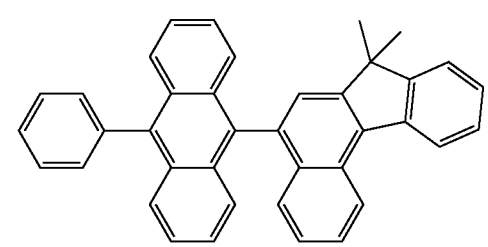
H-35
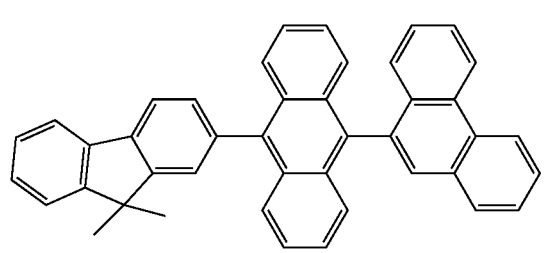
H-36
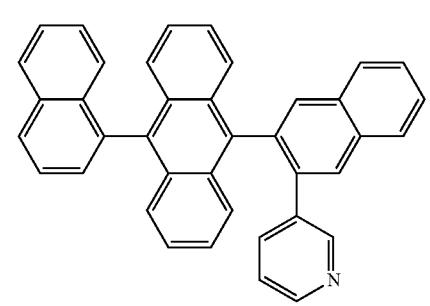

-continued
H-37
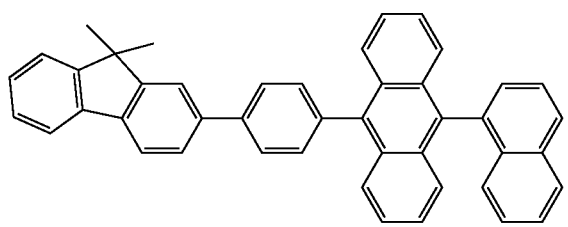
H-38
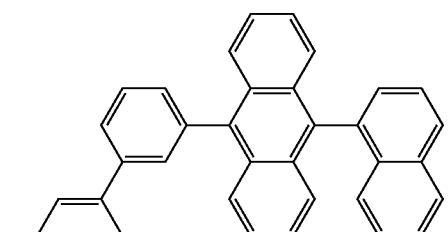
H-39
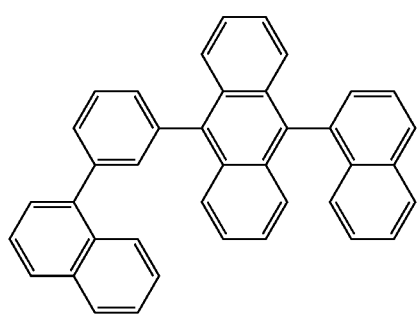
H-40
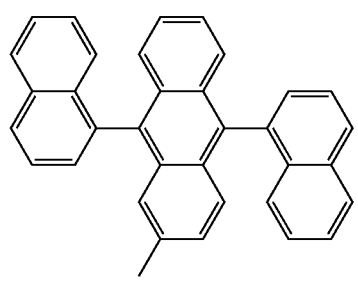
H-41
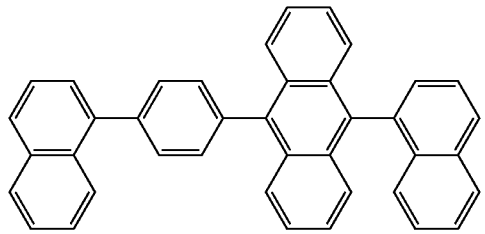
H-42
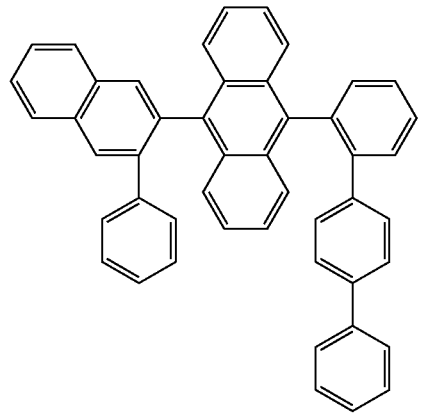
H-43
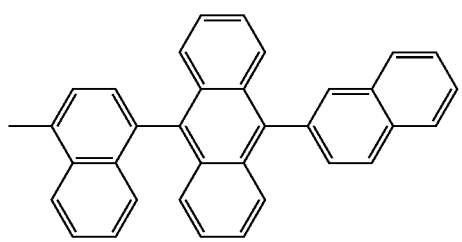
H-44
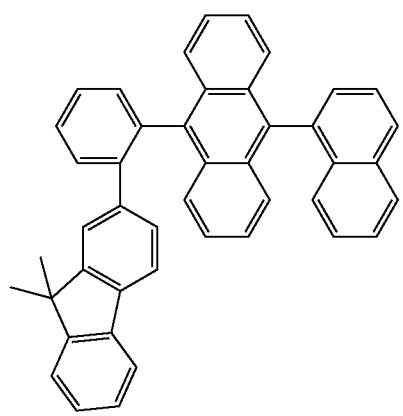

-continued
H-45
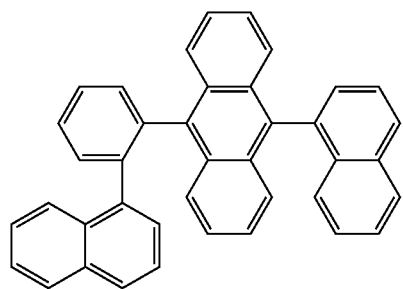
H-46
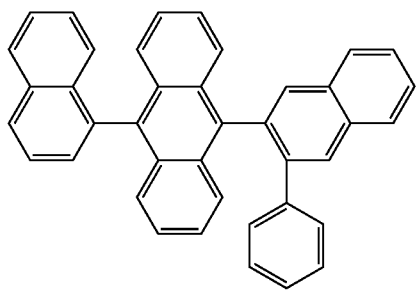
H-47
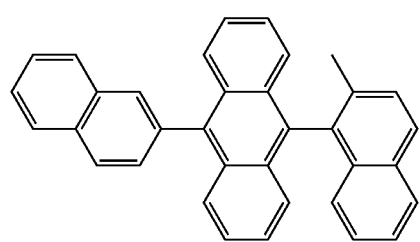
H-48
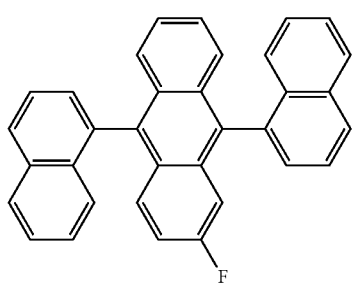
H-49
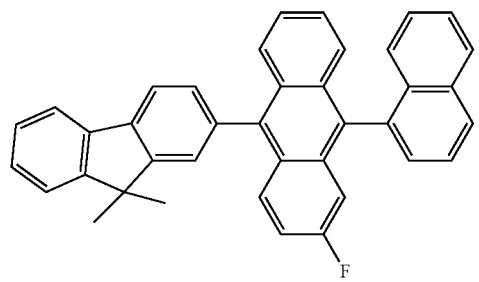
H-50
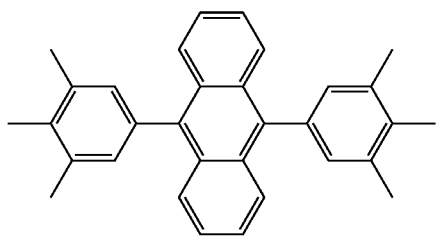
H-51
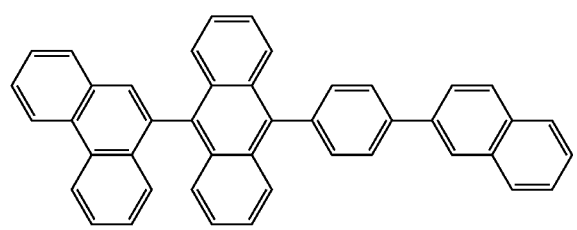
H-52
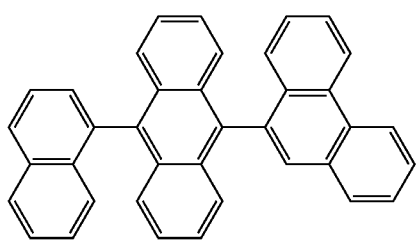
H-53
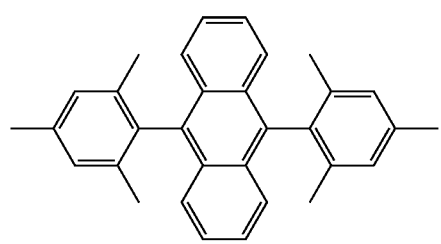
H-54
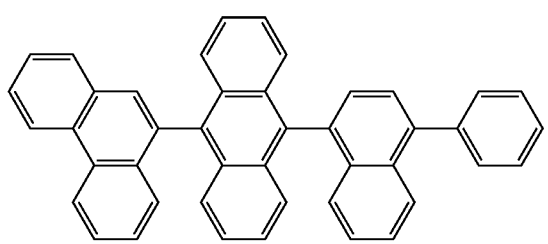

-continued
H-55
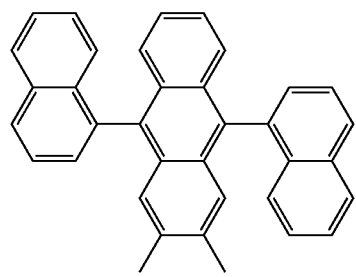
H-56
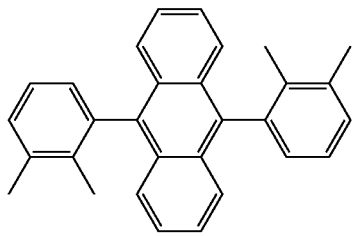
H-57
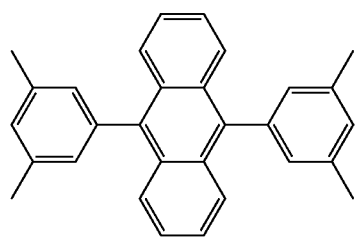
H-58
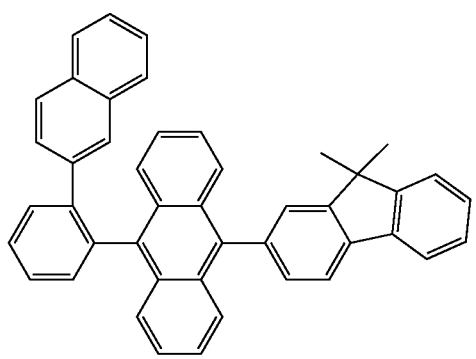
H-59
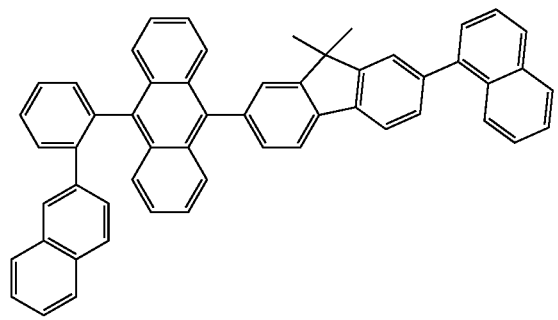
H-60
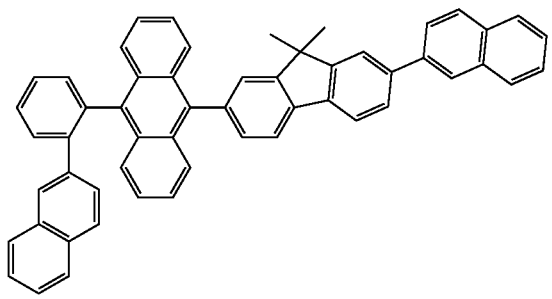
H-61
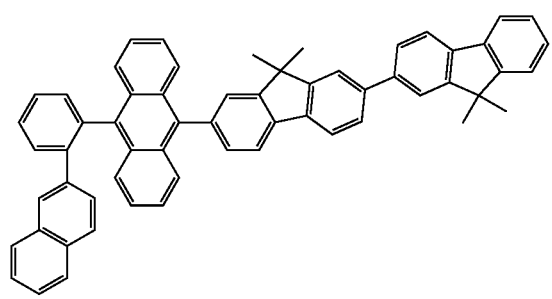
H-62
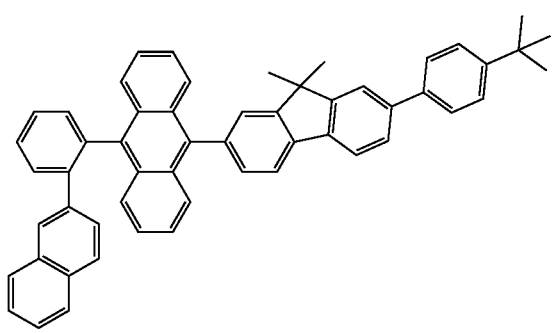

-continued
H-63
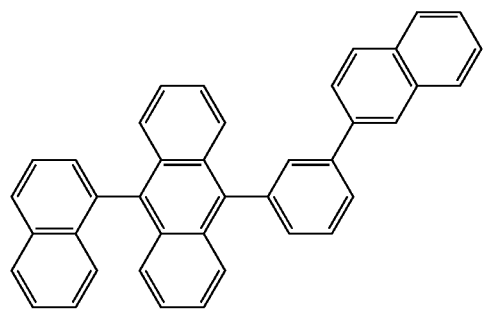
H-64
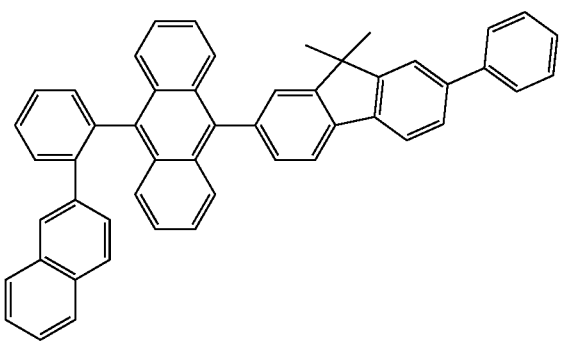
H-65
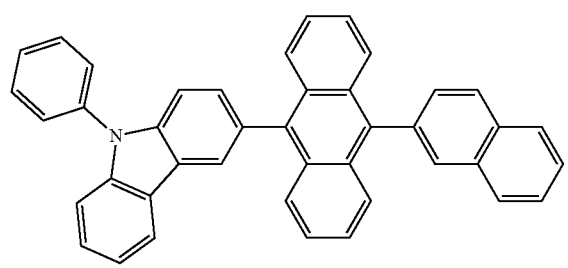
H-66
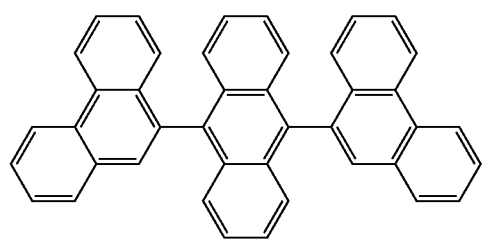
H-67
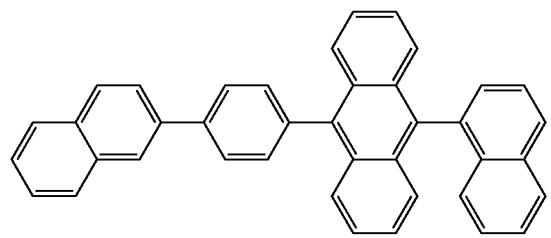
H-68
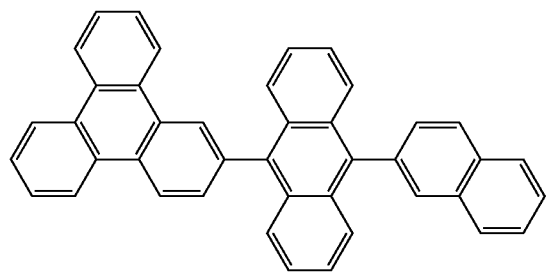
H-69
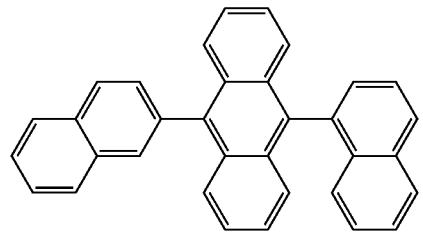
H-70
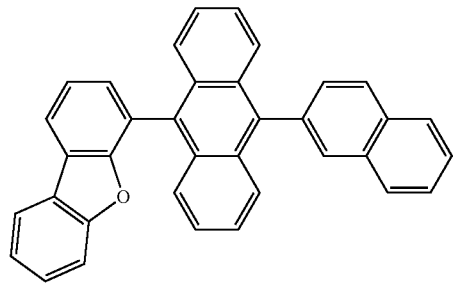
H-71
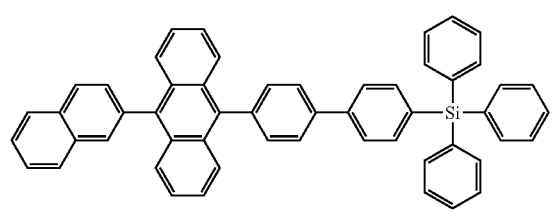
H-72
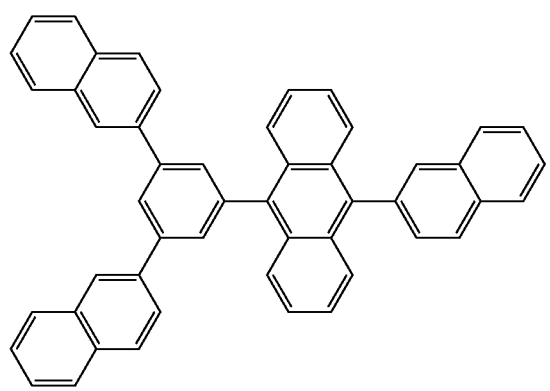

H-73
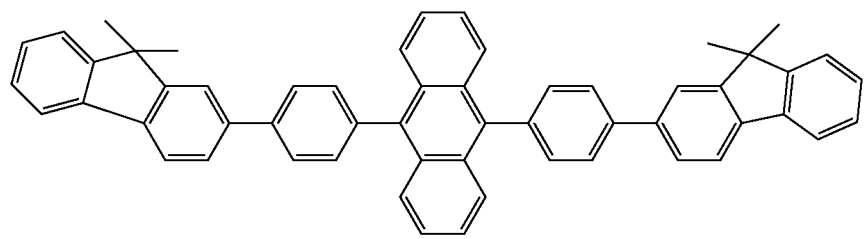
H-74
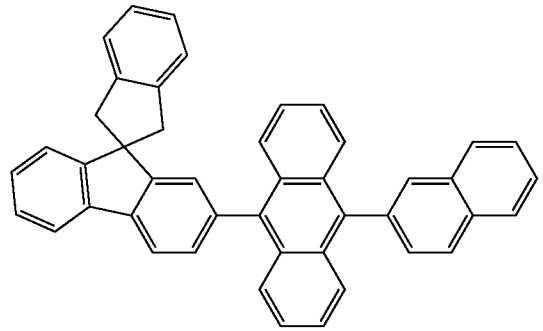
H-75
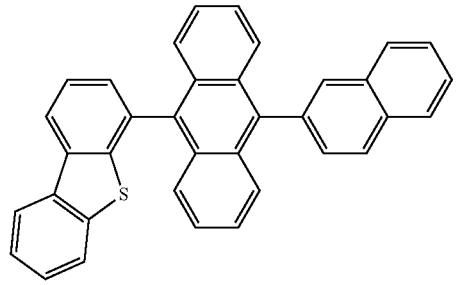
H-76
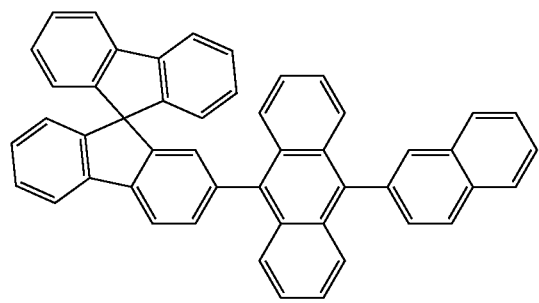
H-77
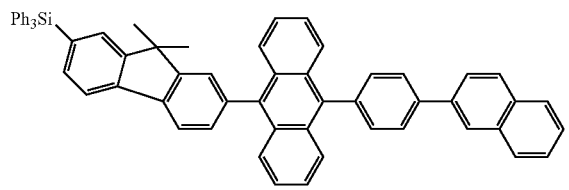
H-78
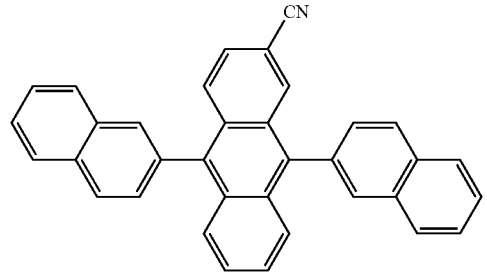
H-79
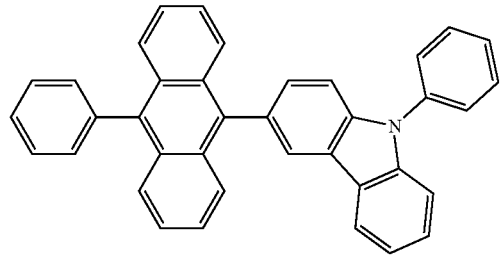
H-80
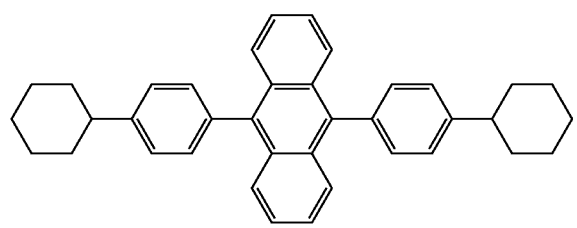
H-81
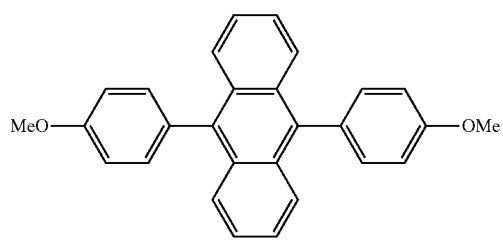

H-82

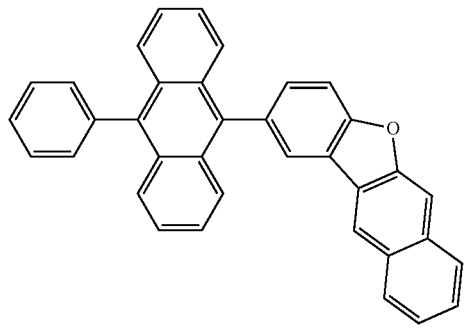

The dopant compound to be used in the present disclosure may be a phosphorescent dopant compound or a fluorescent dopant compound. Specifically, the dopant compound may be a fluorescent dopant compound. The fluorescent dopant compound may be a condensed polycyclic amine derivative represented by the following formula 40:

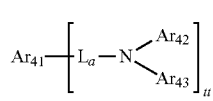 (40)

wherein $Ar_{41}$ represents a substituted or unsubstituted (C6-C50) aryl or styryl; La represents a single bond, a substituted or unsubstituted (C6-C30)arylene, or a substituted or unsubstituted (3- to 30-membered)heteroarylene; $Ar_{42}$ and $Ar_{43}$, each independently, represent hydrogen, deuterium, a halogen, a substituted or unsubstituted (C1-C30)alkyl, a substituted or unsubstituted (C6-C30)aryl, or a substituted or unsubstituted (3- to 30-membered)heteroaryl, or may be linked to an adjacent substituent(s) to form a mono- or polycyclic, (C3-C30) alicyclic, aromatic, or a combination of alicyclic and aromatic ring whose carbon atom(s) may be replaced with at least one heteroatom selected from nitrogen, oxygen, and sulfur; tt represents 1 or 2; and where tt is 2, each of

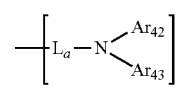

may be the same or different.

A preferable aryl for $Ar_{41}$ includes a substituted or unsubstituted phenyl, a substituted or unsubstituted fluorenyl, a substituted or unsubstituted anthryl, a substituted or unsubstituted pyrenyl, a substituted or unsubstituted chrysenyl, a substituted or unsubstituted benzofluorenyl, and spiro[fluoren-benzofluorene], etc.

Specifically, the compound of formula 40 includes the following compounds, but is not limited thereto:

D-1

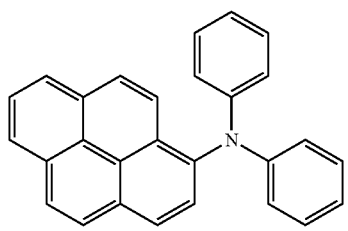

D-2

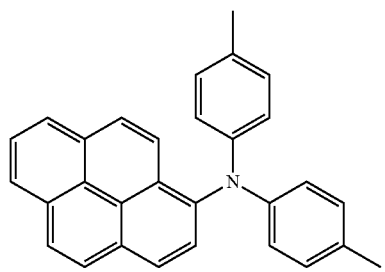

D-3

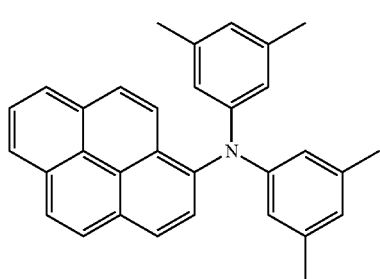

D-4

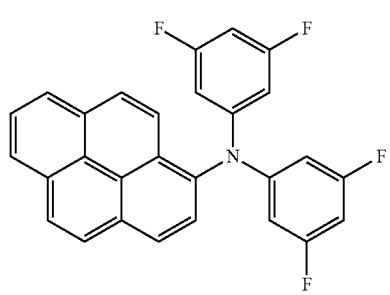

-continued
D-5
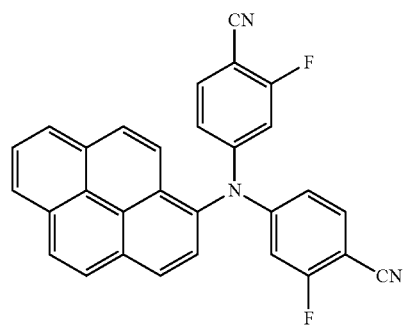
D-6
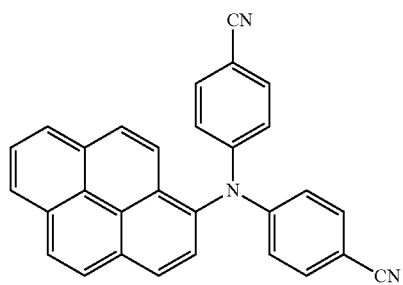
D-7
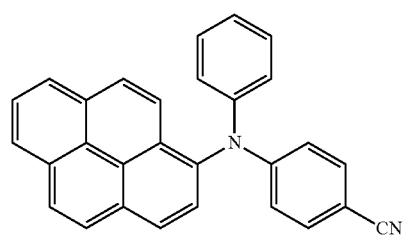
D-8
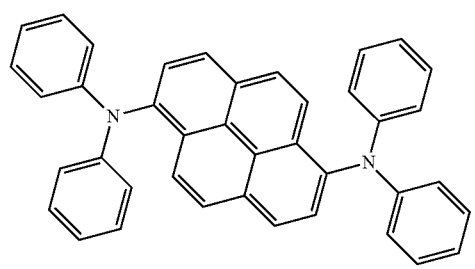
D-9
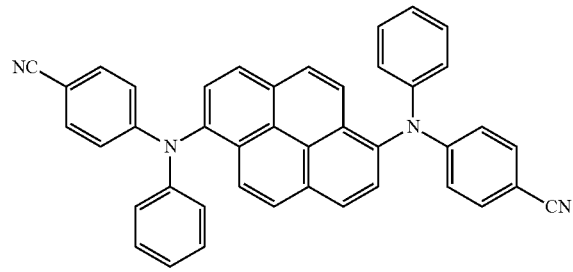
D-10
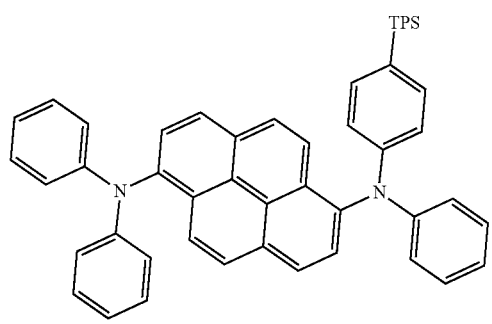
D-11
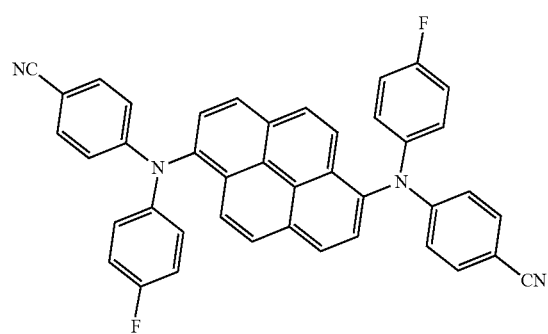
D-12
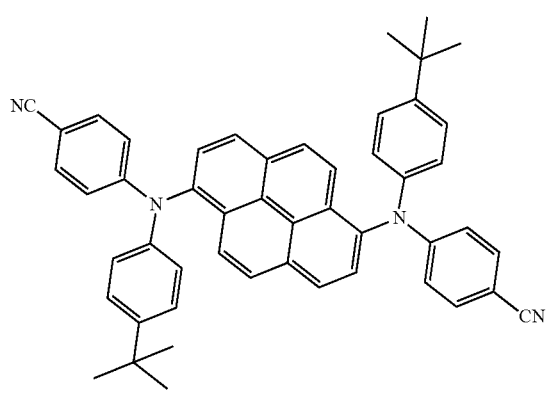

-continued
D-13
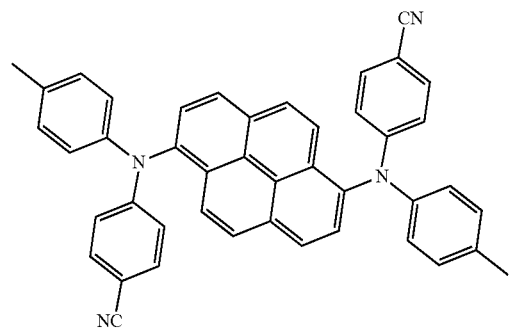
D-14
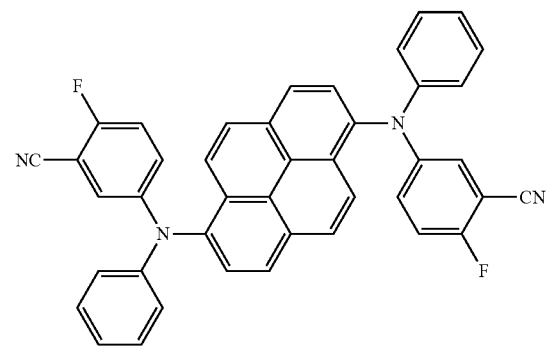
D-15
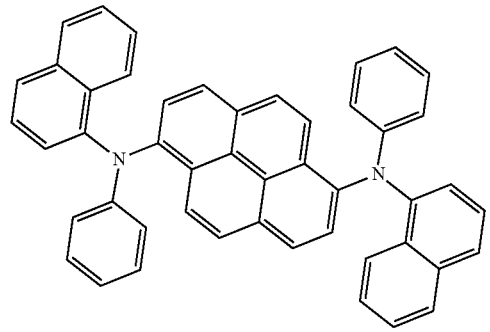
D-16
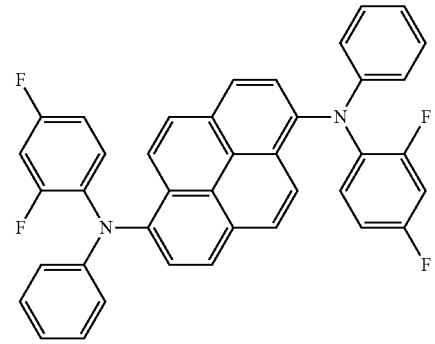
D-17
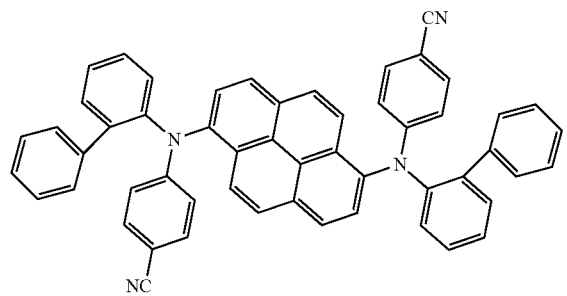
D-18
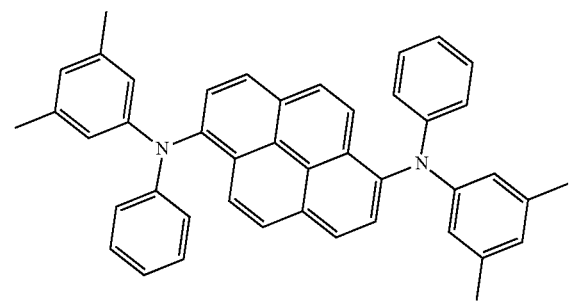
D-19
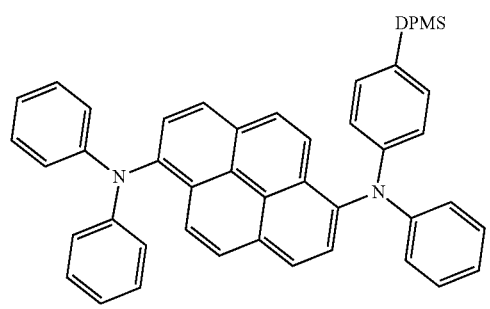
D-20
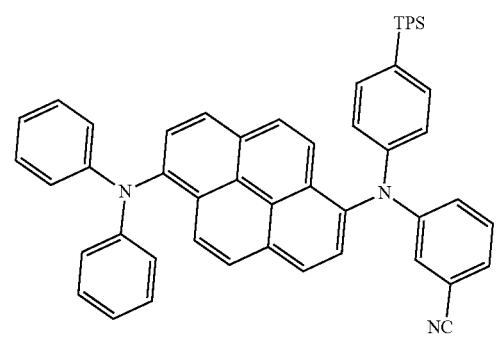

-continued
D-21
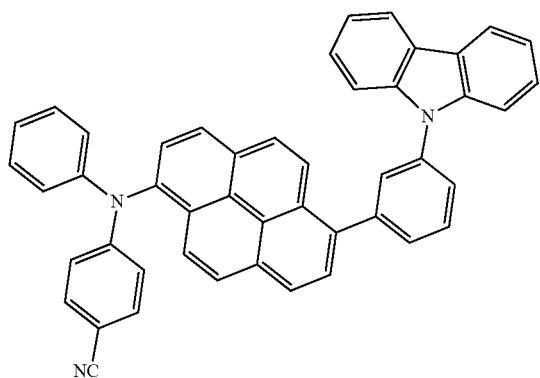
D-22
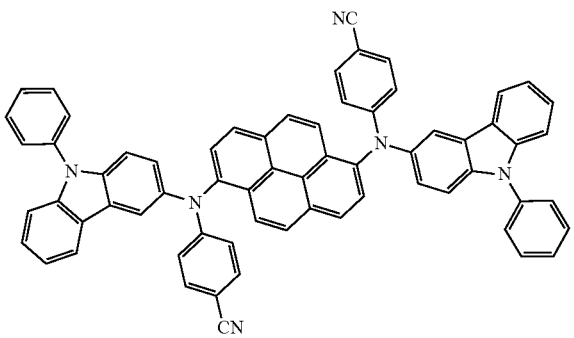
D-23
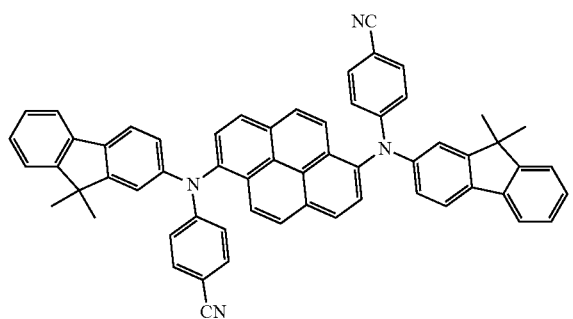
D-24
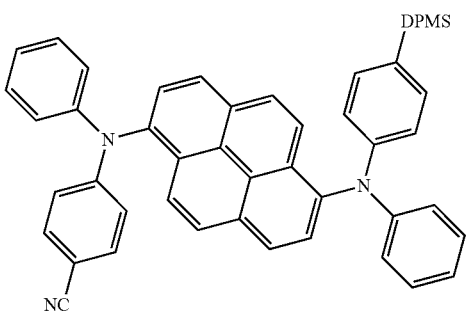
D-25
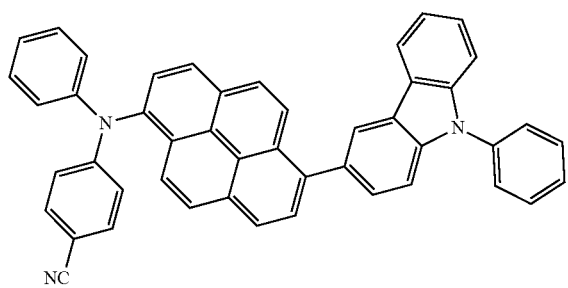
D-26
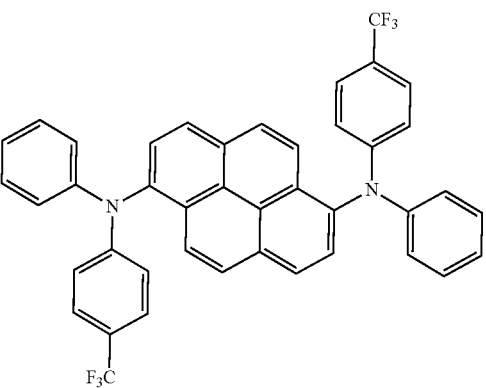
D-27
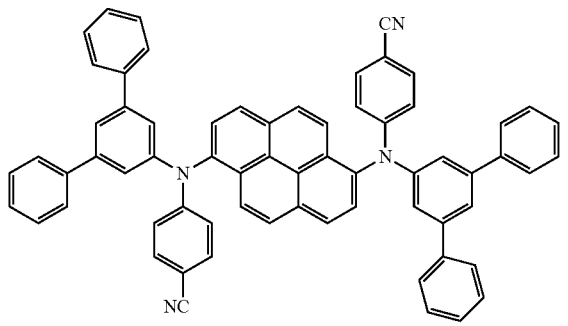
D-28
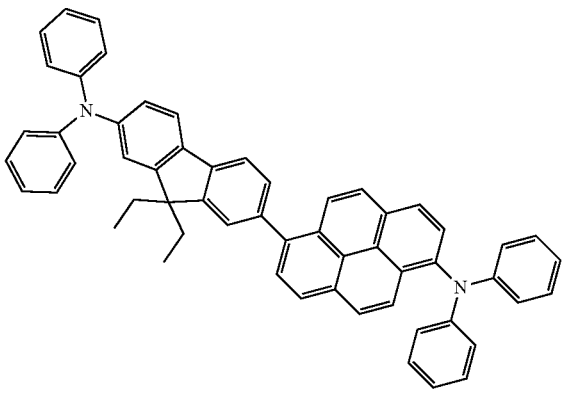

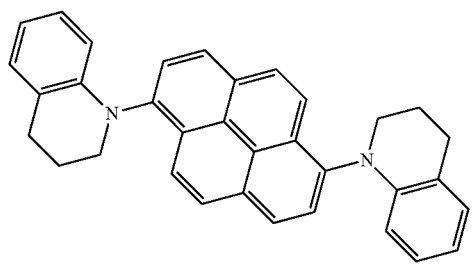
D-29
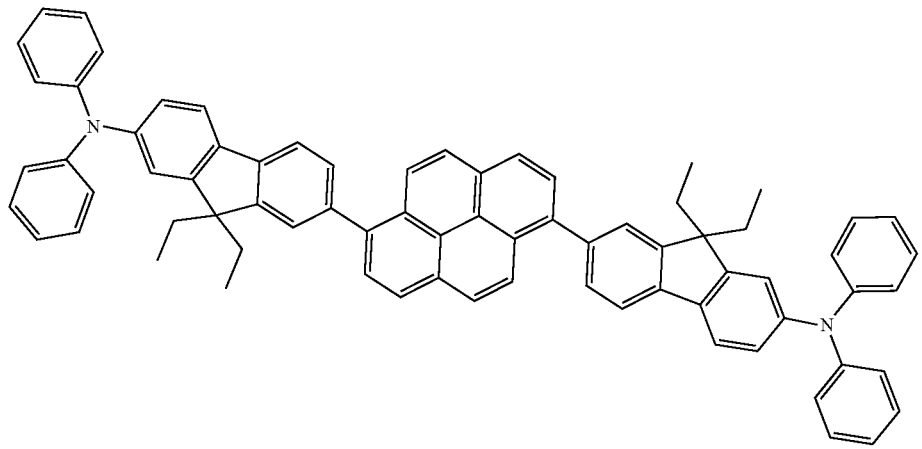
D-30
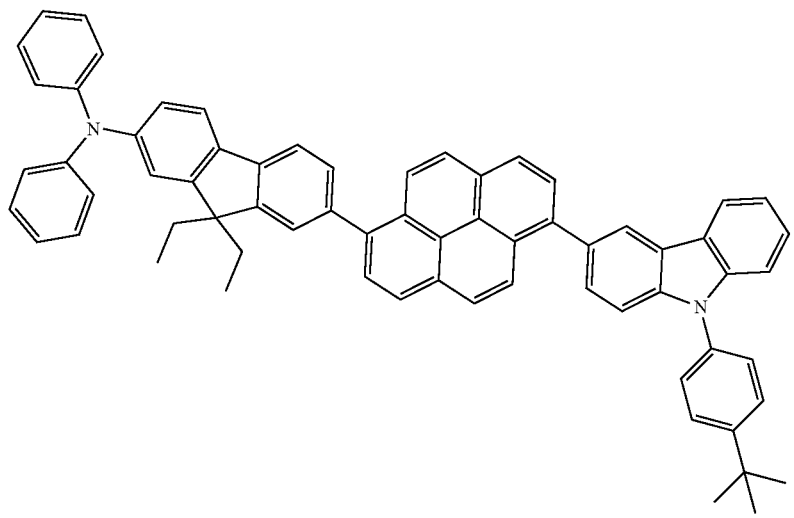
D-31
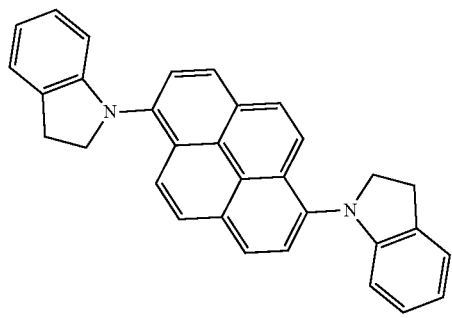
D-32

-continued
D-33
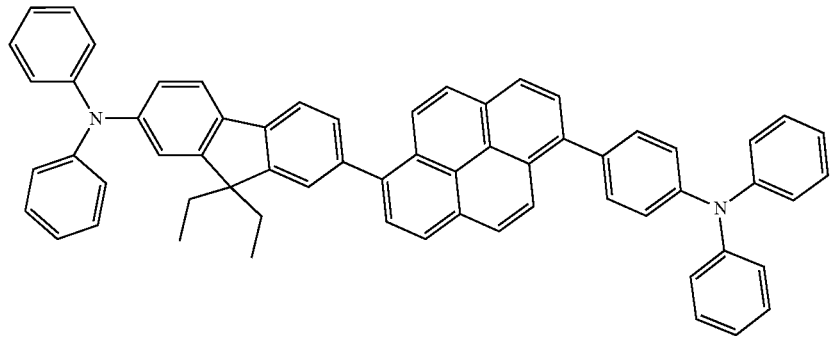
D-34
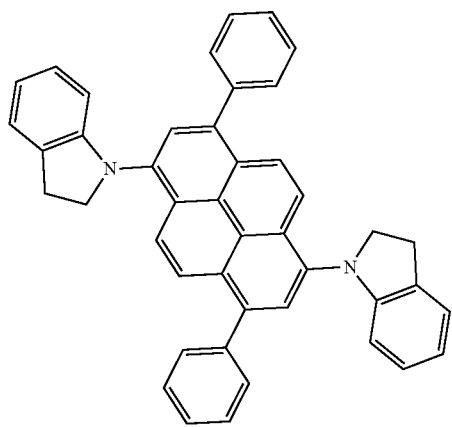
D-35
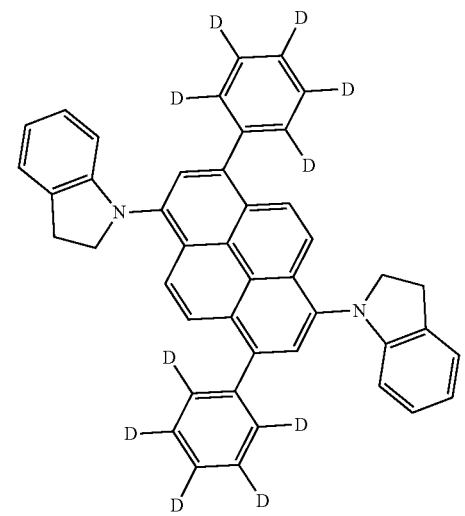
D-36
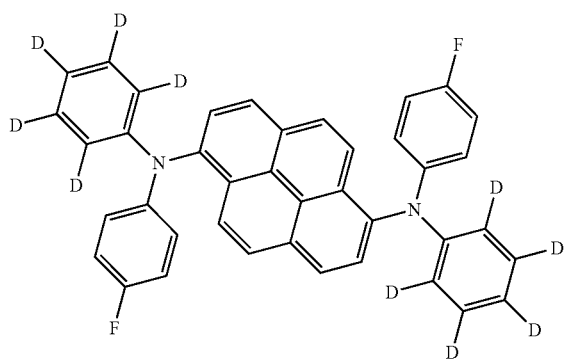
D-37
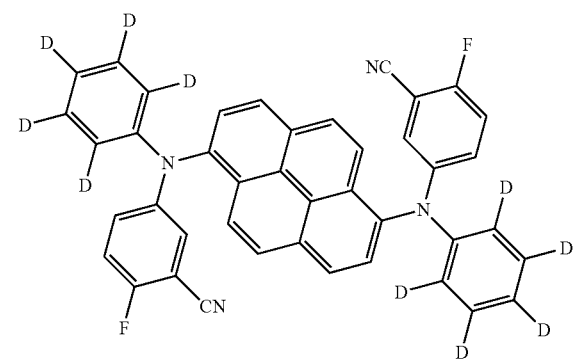
D-38
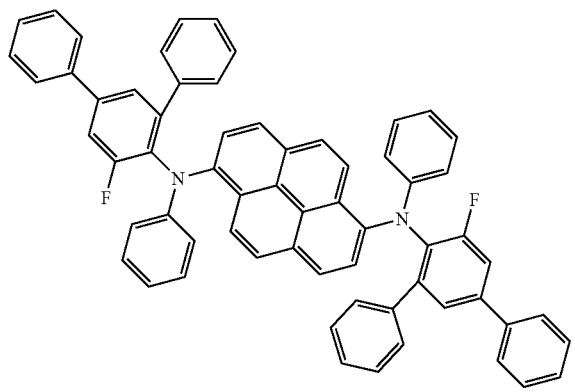
D-39
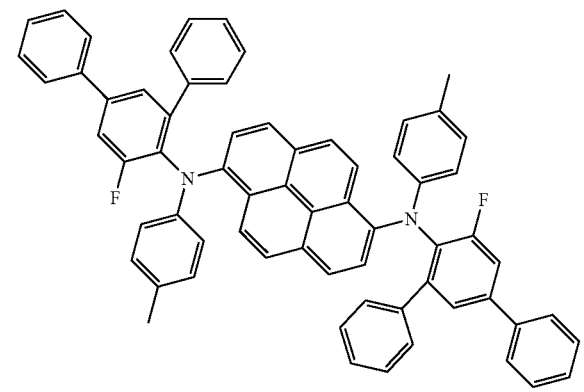

-continued
D-40
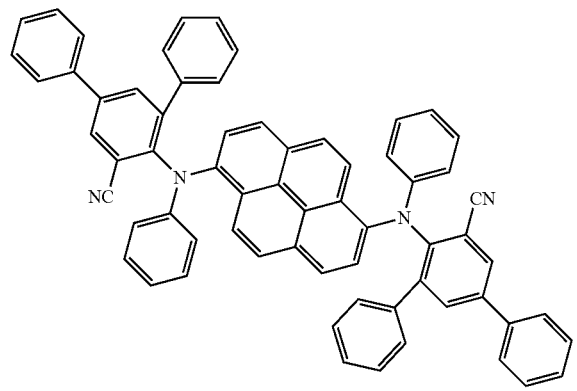
D-41
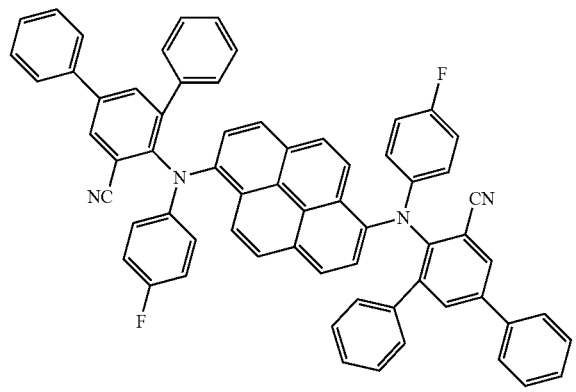
D-42
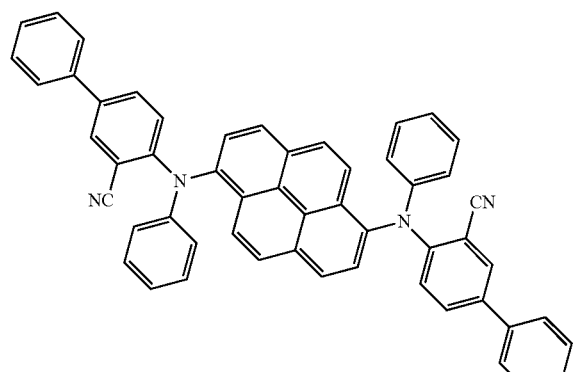
D-43
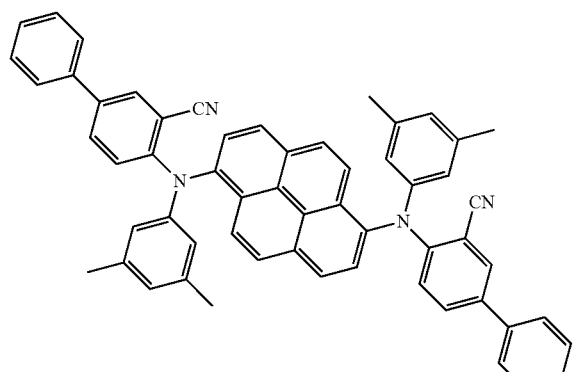
D-44
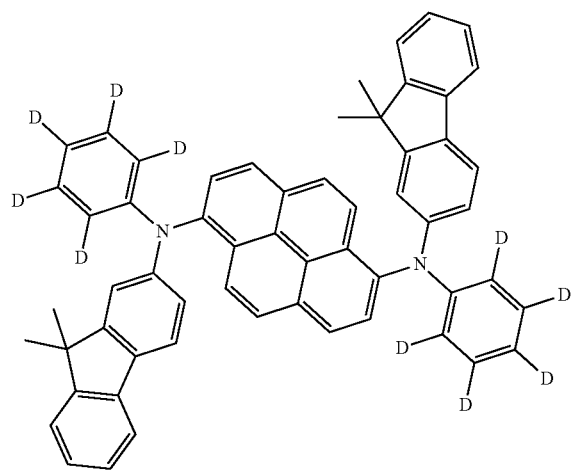
D-45
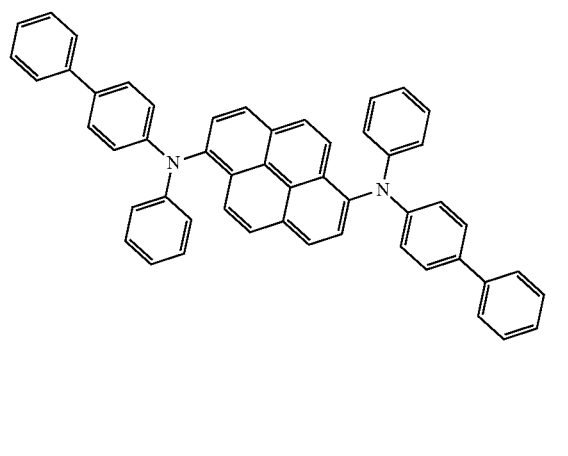
D-46
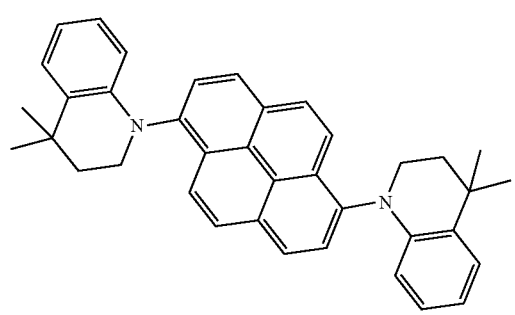
D-47
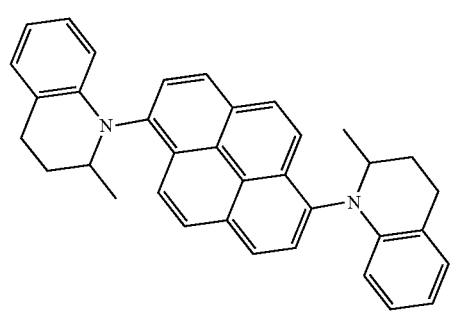

-continued
D-48
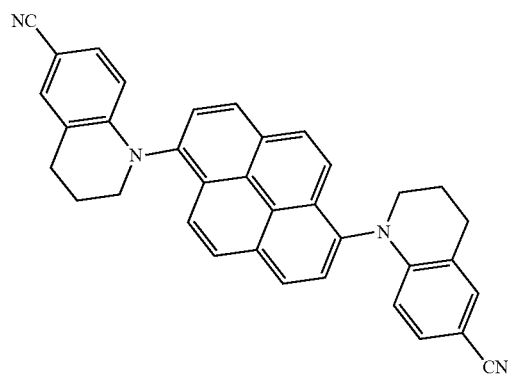
D-49
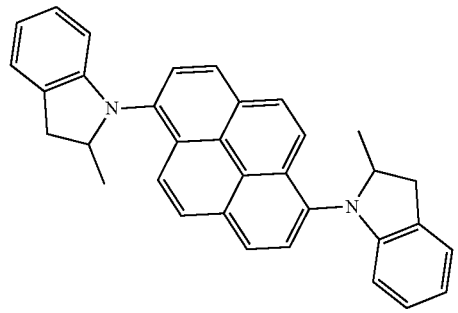
D-50
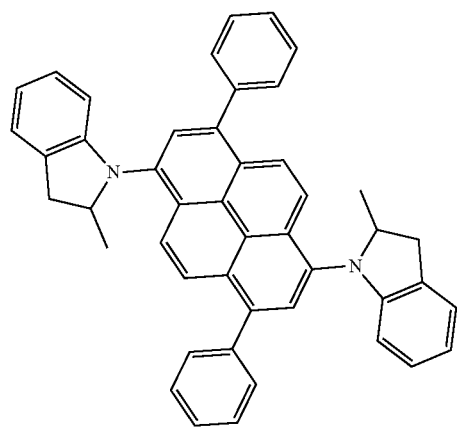
D-51
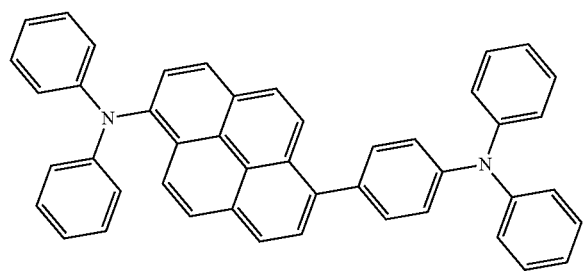
D-52
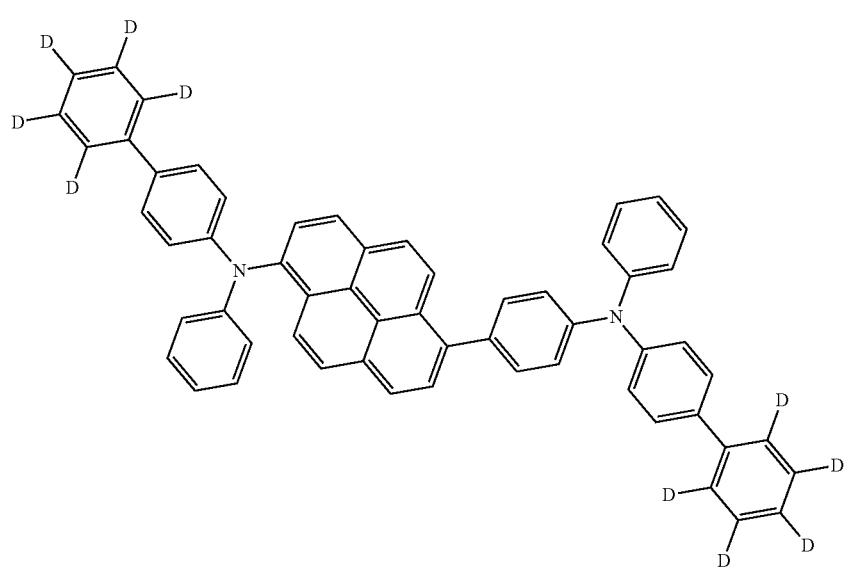

-continued
D-53
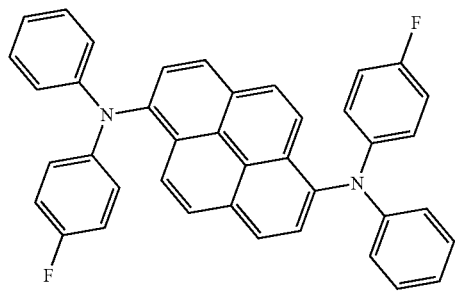
D-54
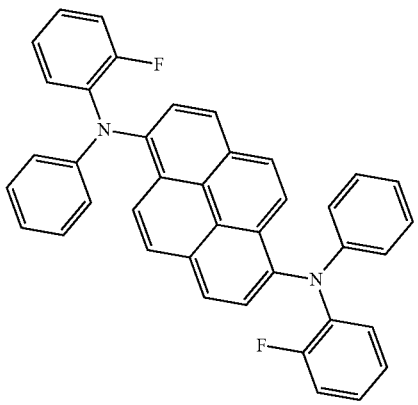
D-55
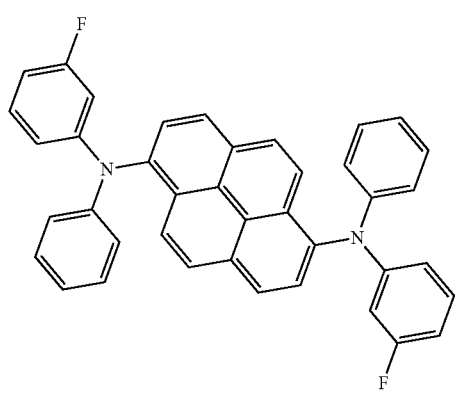
D-56
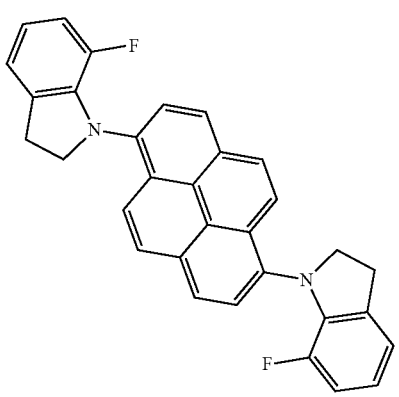
D-57
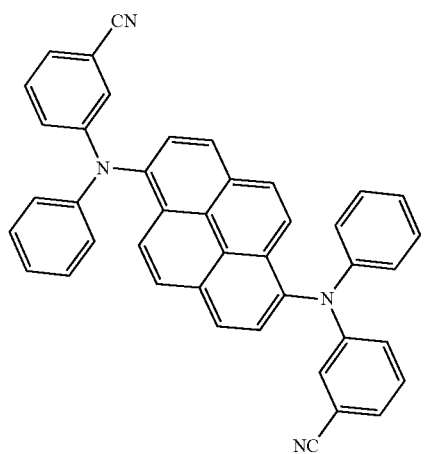
D-58
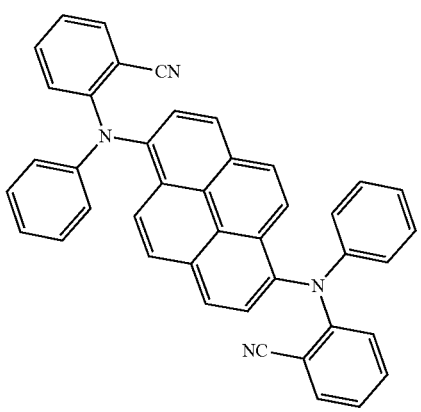
D-59
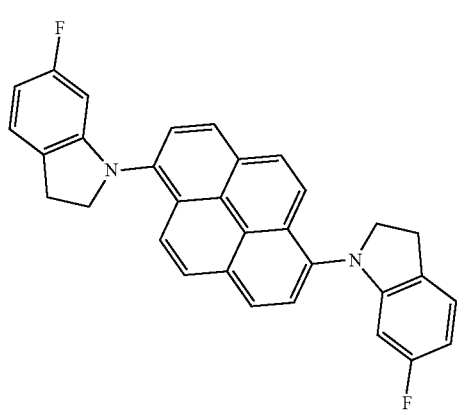
D-60
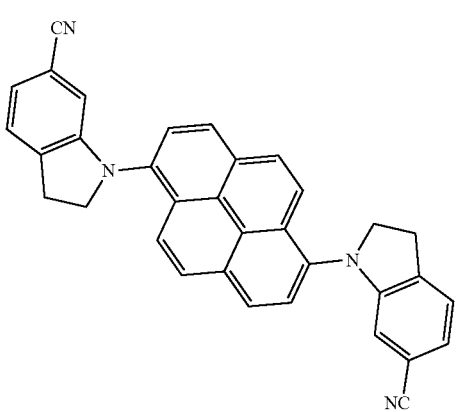

-continued
D-61
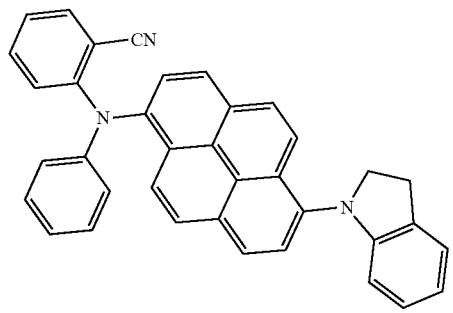
D-62
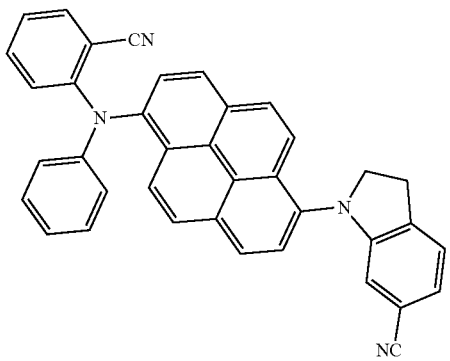
D-63
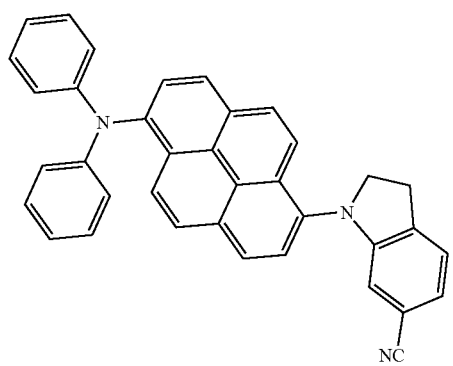
D-64
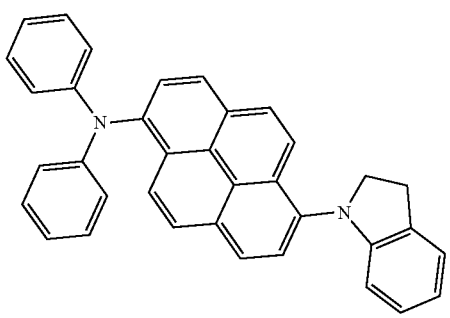
D-65
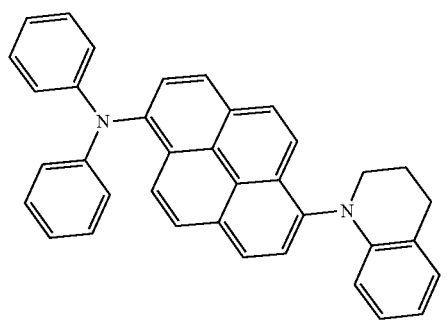
D-66
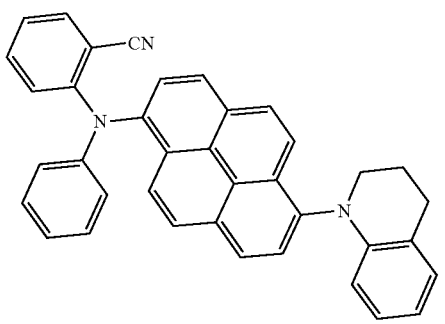
D-67
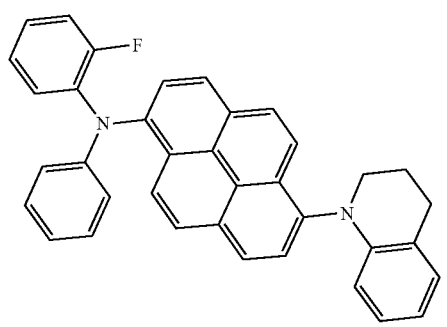
D-68
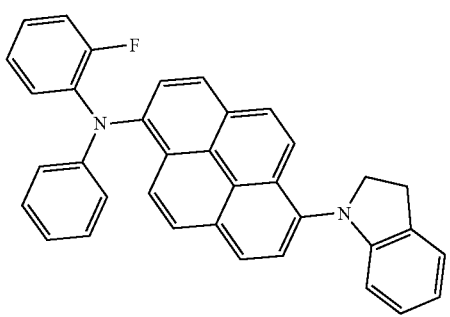

-continued
D-69
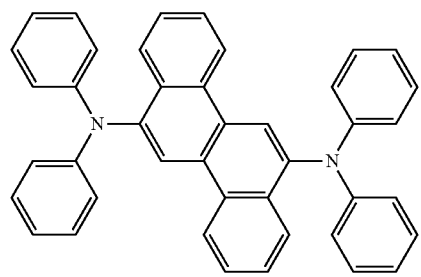
D-70
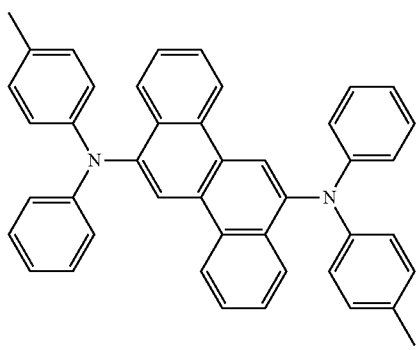
D-71
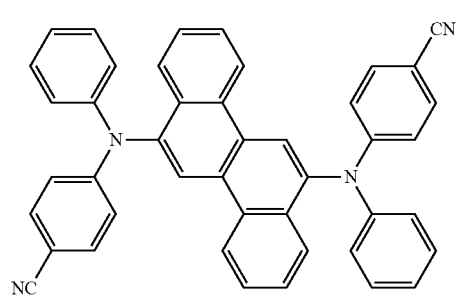
D-72
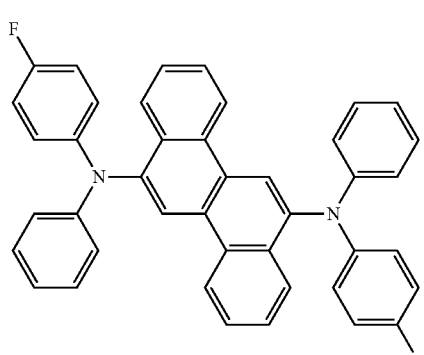
D-73
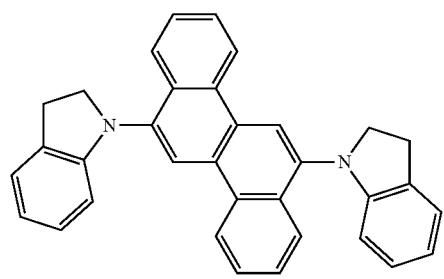
D-74
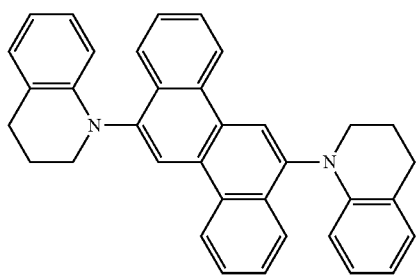
D-75
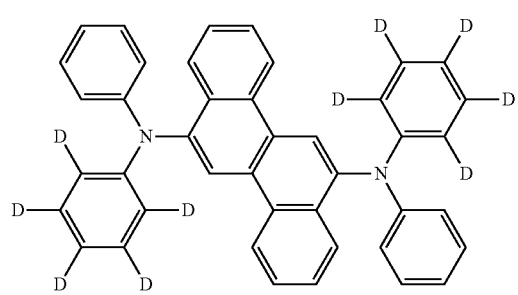
D-76
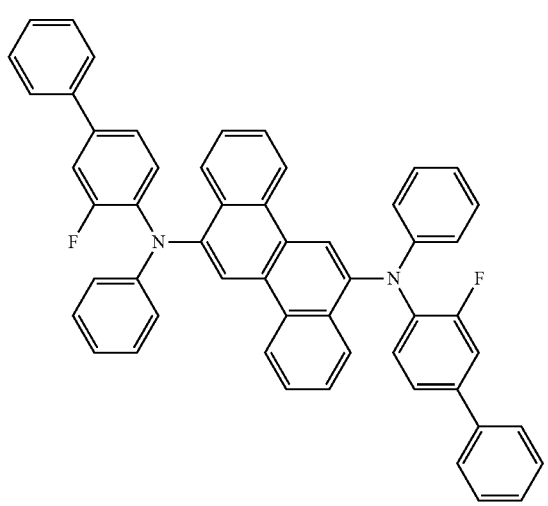

-continued
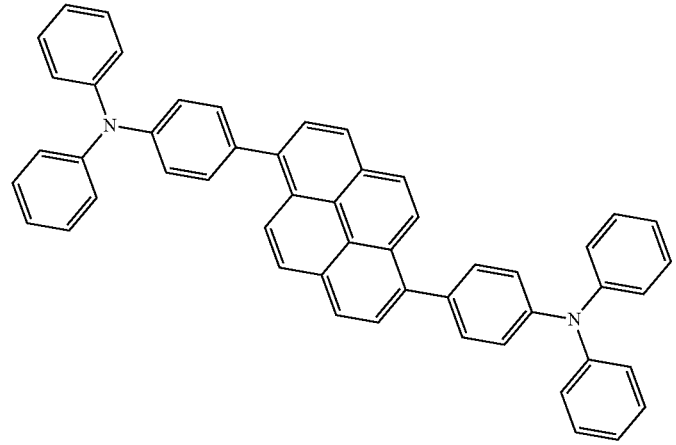
D-77
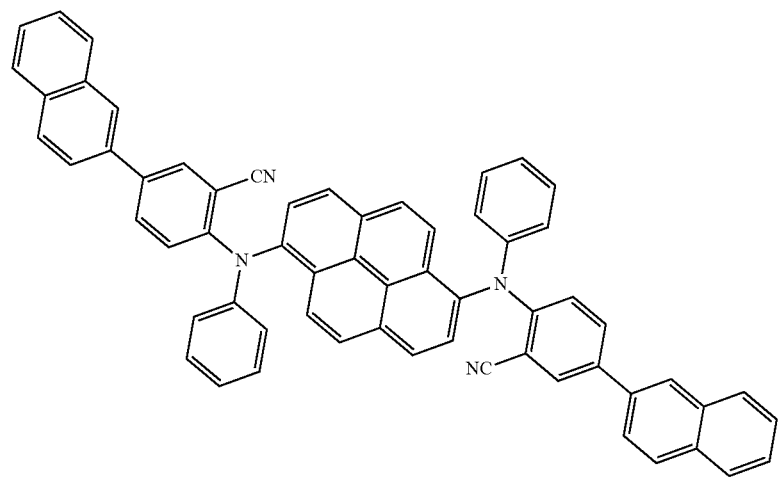
D-78
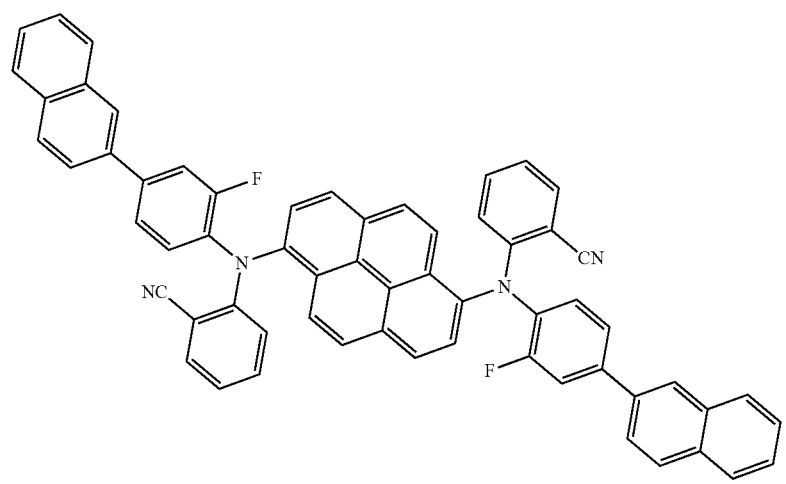
D-79

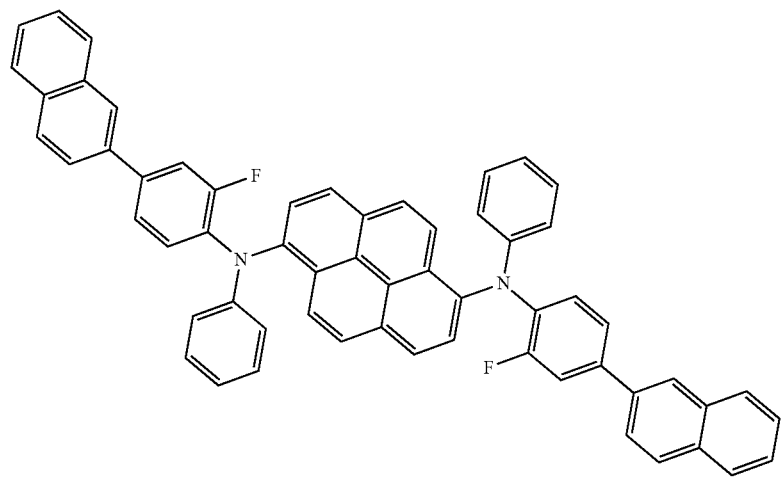
D-80
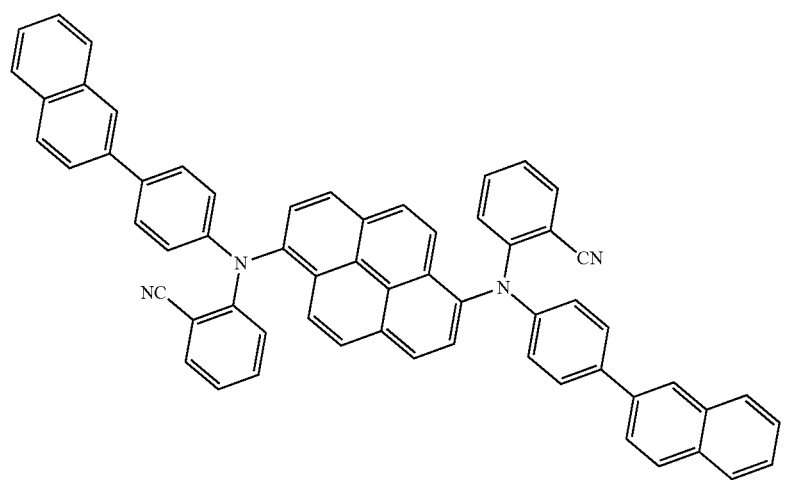
D-81
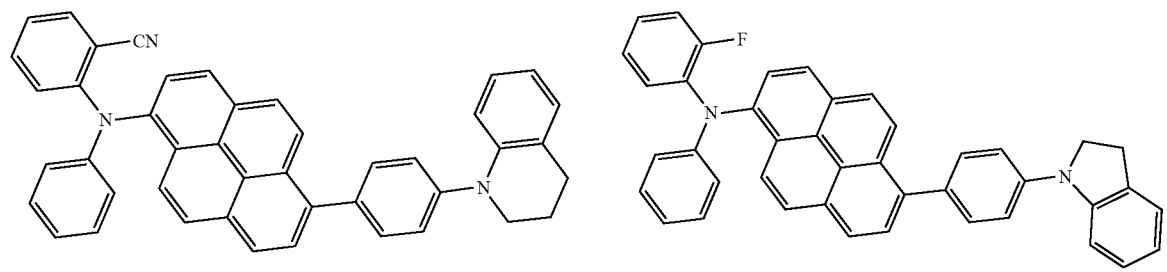
D-82
D-83

-continued
D-84
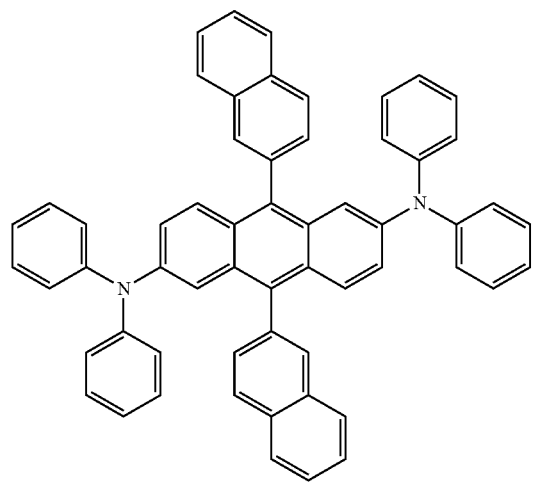
D-85
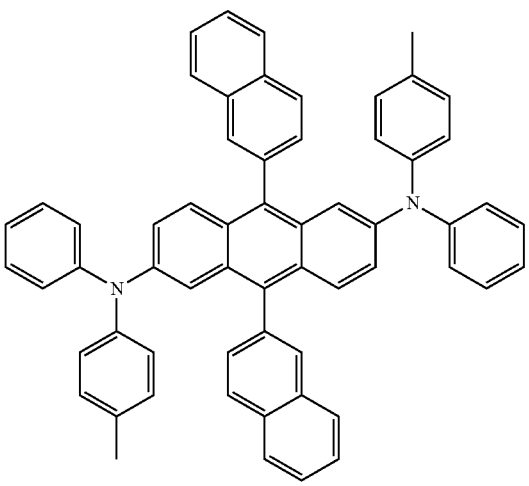
D-86
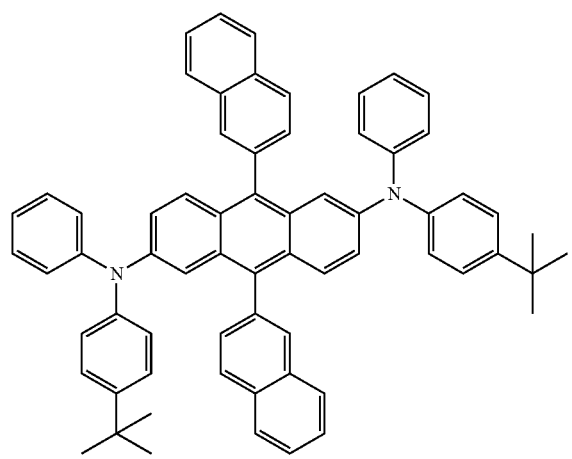
D-87
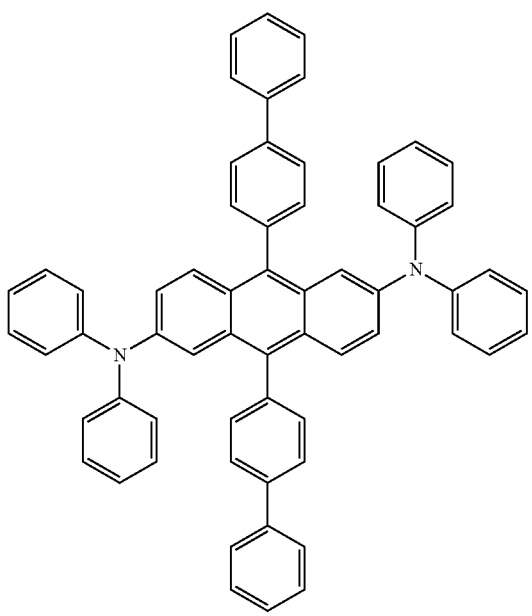

-continued
D-88
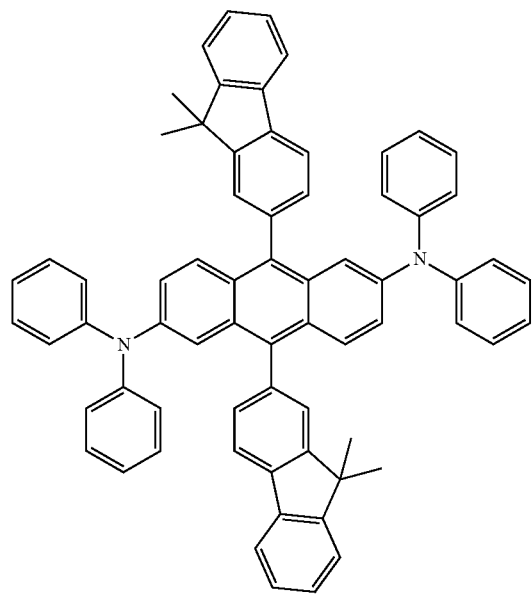
D-89
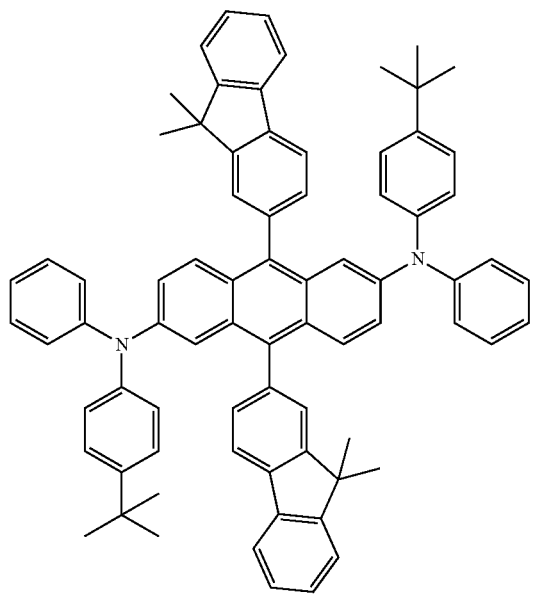
D-90
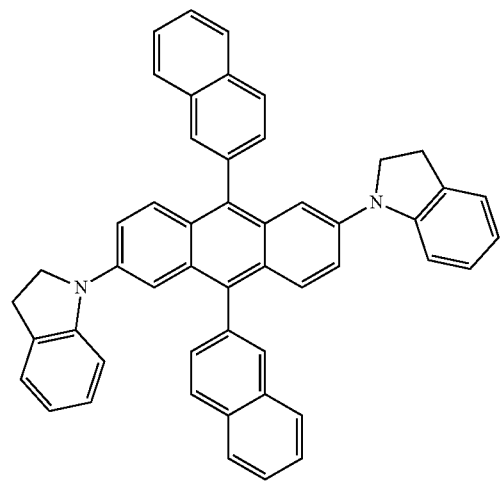
D-91
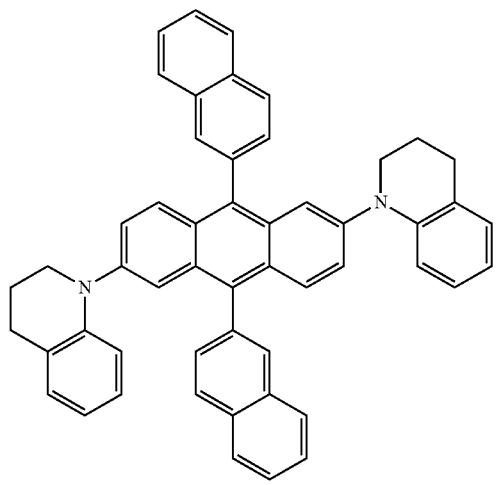
D-92
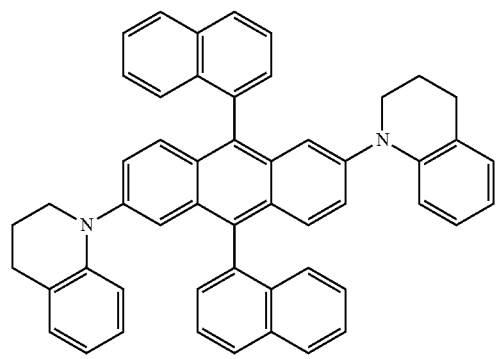
D-93
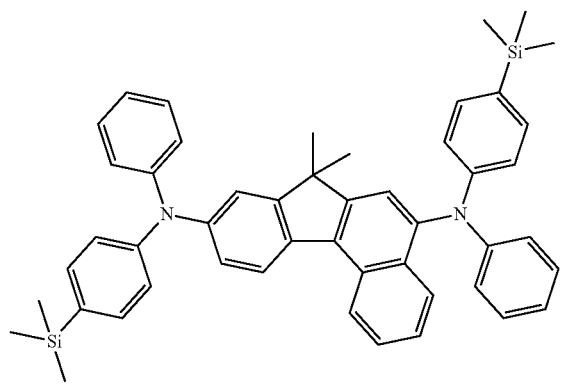

-continued
D-94
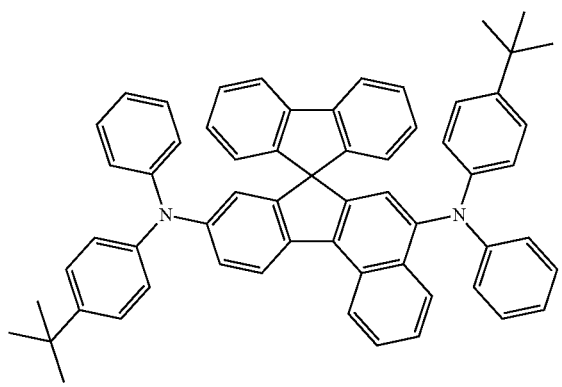
D-95
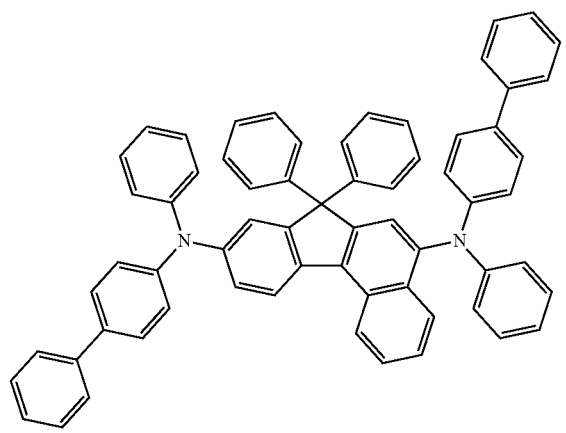
D-96
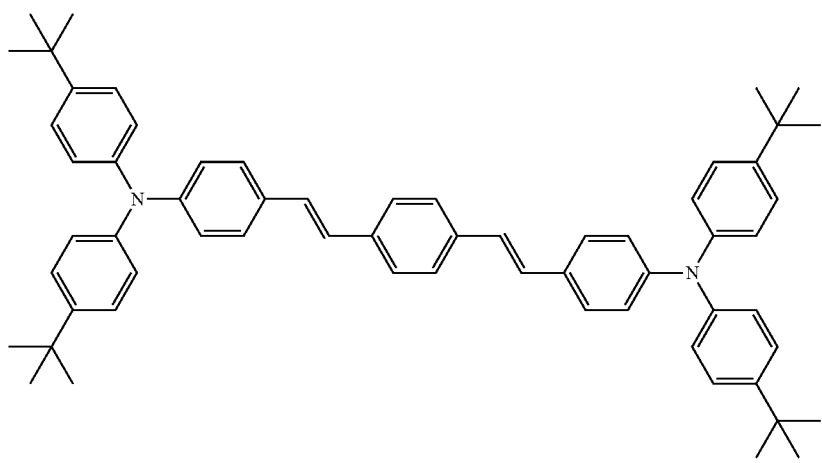
D-97
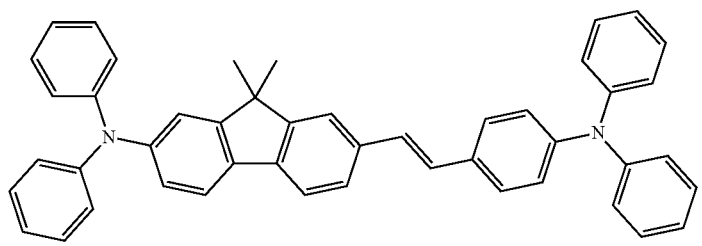
D-98
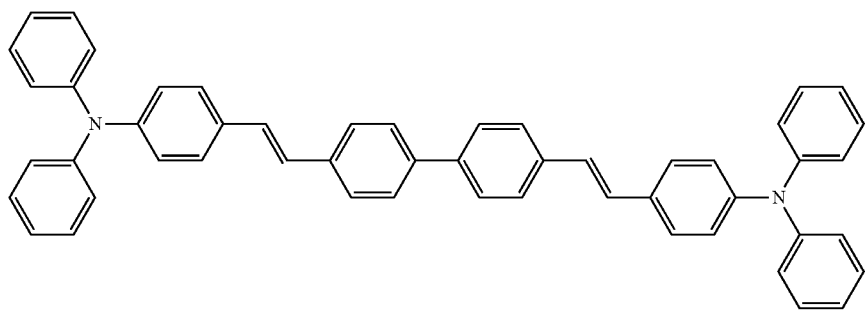

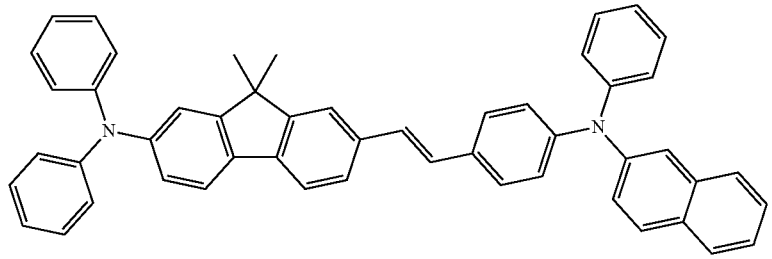

D-99

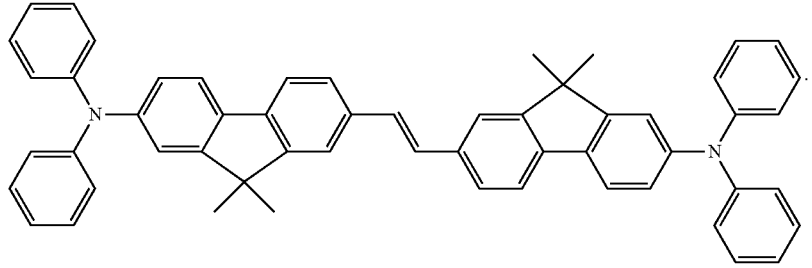

D-100

The organic electroluminescent device of the present disclosure may further comprise a hole injection layer or a hole transport layer between the first electrode and the light-emitting layer.

Hereinafter, referring to FIG. 1, the structure of an organic electroluminescent device, and a method for preparing it will be described in detail.

FIG. 1 illustrates a schematic sectional view of an organic electroluminescent device according to one embodiment of the present disclosure.

FIG. 1 shows an organic electroluminescent device 100 comprising a substrate 101, a first electrode 110 formed on the substrate 101, an organic layer 120 formed on the first electrode 110, and a second electrode 130 formed on the organic layer 120 and facing the first electrode 110.

The organic layer 120 comprises a hole injection layer 122, a hole transport layer 123 formed on the hole injection layer 122, a light-emitting layer 125 formed on the hole transport layer 123, an electron buffer layer 126 formed on the light-emitting layer 125, and an electron transport zone 129 formed on the electron buffer layer 126; and the electron transport zone 129 comprises an electron transport layer 127 formed on the electron buffer layer 126, and an electron injection layer 128 formed on the electron transport layer 127.

The light-emitting layer 125 may be prepared with a host compound and a dopant compound. The kinds of host compound and dopant compound to be used are not particularly limited, and may be selected from compounds known in the art. The examples of the host compound and the dopant compound are as described above. When the light-emitting layer 125 comprises a host and a dopant, the dopant can be doped in an amount of less than about 25 wt %, and preferably less than 17 wt %, based on the total amount of the dopant and host of the light-emitting layer. When the light emitting layer 125 is composed of two or more layers, each of the layers may be prepared to emit color different from one another. For example, the device may emit white light by preparing three light-emitting layers 125 which emit blue, red, and green colors, respectively. Furthermore, the device may include light-emitting layers which emit yellow or orange color, if necessary.

The electron buffer layer 126 may employ the compound of formula 1 of the present disclosure or other compounds for the electron buffer. The thickness of the electron buffer layer 126 is 1 nm or more, but is not particularly limited thereto. Specifically, the thickness of the electron buffer layer 126 may be in the range of from 2 nm to 200 nm. The electron buffer layer 126 may be formed on the light-emitting layer 125 by using known various methods such as vacuum deposition, wet film-forming methods, laser induced thermal imaging, etc. The electron buffer layer indicates a layer controlling an electron flow. Therefore, the electron buffer layer may be, for example, a layer which traps electrons, blocks electrons, or lowers an energy barrier between an electron transport zone and a light-emitting layer.

The electron transport zone 129 means a zone in which electrons are transported from the second electrode to the light-emitting layer. The electron transport zone 129 can comprise an electron transport compound, a reductive dopant, or a combination thereof. The electron transport compound can be at least one selected from a group comprising phenanthrene-based compounds, oxazole-based compounds, isoxazole-based compounds, triazole-based compounds, isothiazole-based compounds, oxadiazole-based compounds, thiadiazole-based compounds, perylene-based compounds, anthracene-based compounds, aluminum complexes, and gallium complexes. The reductive dopant may be selected from alkali metals, alkali metal compounds, alkaline earth metals, rare-earth metals, and halides, oxides, and complexes thereof. Specifically, the reductive dopant includes lithium quinolate, sodium quinolate, cesium quinolate, potassium quinolate, LiF, NaCl, CsF, $Li_2O$, BaO, and $BaF_2$, but are not limited thereto. In addition, the electron transport zone 129 can comprise an electron transport layer 127, an electron injection layer 128, or both of them. The electron transport layer 127 and the electron injection layer 128 can each be composed of two or more layers. The electron transport layer 127 can comprise an electron transport material including the compound represented by formula 2. In addition, the electron transport layer 127 can further comprise the reductive dopant above.

The electron injection layer 128 may be prepared with any electron injection material known in the art, which includes lithium quinolate, sodium quinolate, cesium quinolate, potassium quinolate, LiF, NaCl, CsF, Li$_2$O, BaO, and BaF$_2$, but is not limited thereto.

The aforementioned description regarding the organic electroluminescent device shown in FIG. 1 is intended to explain one embodiment of the invention, and is not meant in any way to restrict the scope of the invention. The organic electroluminescent device can be constructed in another way. For example, any one optional component such as a hole injection layer may not be comprised in the organic electroluminescent device of FIG. 1, except for a light-emitting layer and an electron buffer layer. In addition, an optional component may be further comprised therein, which includes one or more of an impurity layer such as n-doping layer and p-doping layer. The organic electroluminescent device may be a both side emission type in which a light-emitting layer is placed on each of both sides of the impurity layer. The two light-emitting layers on the impurity layer may emit different colors. The organic electroluminescent device may be a bottom emission type in which a first electrode is a transparent electrode and a second electrode is a reflective electrode. The organic electroluminescent device may be a top emission type in which a first electrode is a reflective electrode and a second electrode is a transparent electrode. The organic electroluminescent device may have an inverted type structure in which a cathode, an electron transport layer, a light-emitting layer, a hole transport layer, a hole injection layer, and an anode are sequentially stacked on a substrate.

Figure 2:
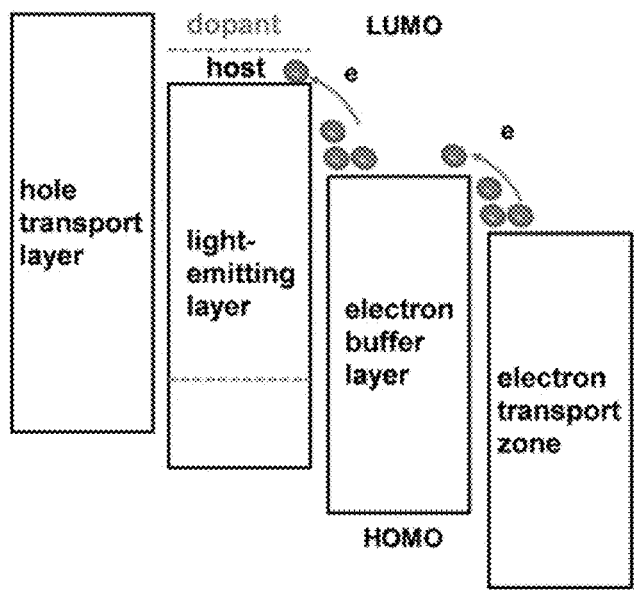
FIG. 2 illustrates an energy gap relationship among the layers of the organic electroluminescent device according to one embodiment of the present disclosure.

FIG. 2 illustrates an energy gap relationship among the layers of the organic electroluminescent device according to one embodiment of the present disclosure.

In FIG. 2, a hole transport layer 123, a light-emitting layer 125, an electron buffer layer 126, and an electron transport zone 129 are sequentially stacked. Electrons (e$^-$) injected from a cathode are transported to a light-emitting layer 125 through an electron transport zone 129 and an electron buffer layer 126.

The LUMO energy level of the electron buffer layer 126 has a medium value of the LUMO energy level of the host compound and the dopant compound of the light-emitting layer 125 and the LUMO energy level of the electron transport layer 127. Specifically, the LUMO energy levels of the layers have a relationship of the electron transport layer>electron buffer layer>light-emitting layer. As in FIG. 2, a LUMO energy gap of 0.5 eV or greater occurs between the light-emitting layer and the electron transport layer. However, by inserting an electron buffer layer, electrons can be actively transported.

According to one embodiment of the organic electroluminescent device of the present disclosure, the LUMO energy level of the light-emitting layer (Ah) is higher than the LUMO energy level of the dopant compound (Ad).

According to one embodiment of the organic electroluminescent device of the present disclosure, the LUMO energy level of the electron transport layer (Ae) is higher than the LUMO energy level of the electron buffer layer (Ab). In contrast, the LUMO energy level of the electron transport layer (Ae) may be lower than the LUMO energy level of the electron buffer layer (Ab).

According to one embodiment of the organic electroluminescent device of the present disclosure, the LUMO energy level of the light-emitting layer (Ah), the LUMO energy level of the electron buffer layer (Ab), and the LUMO energy level of the electron transport layer (Ae) satisfy the following equations (1) and (2).

$$|Ae-Ab| \leq 0.3 \text{ eV} \tag{1}$$

$$|Ab-Ah| \leq 0.4 \text{ eV} \tag{2}$$

For appropriate efficiency and long lifespan, equation (3) is preferably satisfied.

$$Ae \leq Ab+0.2 \text{ eV} \tag{3}$$

For high efficiency, equation (4) is preferably satisfied.

$$Ab \leq Ae+0.2 \text{ eV} \tag{4}$$

The electron injection characteristic can be controlled according to the combination of the electron buffer layer and the electron transport layer. High efficiency and long lifespan characteristics can be controlled according to the property and the LUMO energy level of the electron buffer layer. For example, when the LUMO energy levels of the light-emitting layer, the electron buffer layer, and the electron transport layer make a cascade as in FIG. 2, a high efficiency is possible due to fast electron injection characteristic (equation (4)). In contrast, when the LUMO energy level of the electron buffer layer is lower than the LUMO energy levels of the light-emitting layer and the electron transport layer, there is an advantage of long lifespan due to alleviation of the electron current (equation (3)). In particular, by using the combinations of the compounds of formulae 1 and 2 of the present disclosure, high efficiency and long lifespan can be simultaneously achieved.

The compound of formula 2 used in the electron transport layer comprises phenanthrooxazole-based and phenanthrothiazole-based compounds which have high electronegativity and electron-rich groups as well as a fused structure between a phenanthrene and an oxazole, or a phenanthrene and a thiazole providing a rigid characteristic. Thereby, the compounds represented by formula 2 above can provide easy intermolecular transition. Further, the build-up of such intermolecular stacking can provide easy horizontal molecular orientation, and then can provide rapid electron current characteristic. Furthermore, when a limited structure of a triazine and pyrimidine derivatives are used as a material of an electron buffer layer, an organic electroluminescent device can be provided wherein the intermolecular stacking effect with the electron transport layer is maintained while having a relatively low driving voltage due to advanced interfacial characteristic, and excellent luminous efficiency such as current and power efficiencies, and enabling color of high purity.

The results according to the relationship of the LUMO energy levels of the electron transport layer (Ae), electron buffer layer (Ab), and the light-emitting layer (Ah) are for explaining the rough tendency of the device in accordance with the overall LUMO energy groups, and so results other than the above can appear according to the inherent property of the specific derivatives, and the stability of the materials.

The electron buffer layer can be comprised in organic electroluminescent devices emitting every color including blue, red, and green. Preferably, it can be comprised in an organic electroluminescent device emitting blue light (i.e. the main peak wavelength is from 430 to 470 nm, preferably, in the 450's nm).

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the compounds of the present disclosure and the luminous properties of the organic electroluminescent device of the present disclosure will be explained in detail with reference to the representative compounds of the present disclosure.

[Example 1] Preparation of Compound C-24

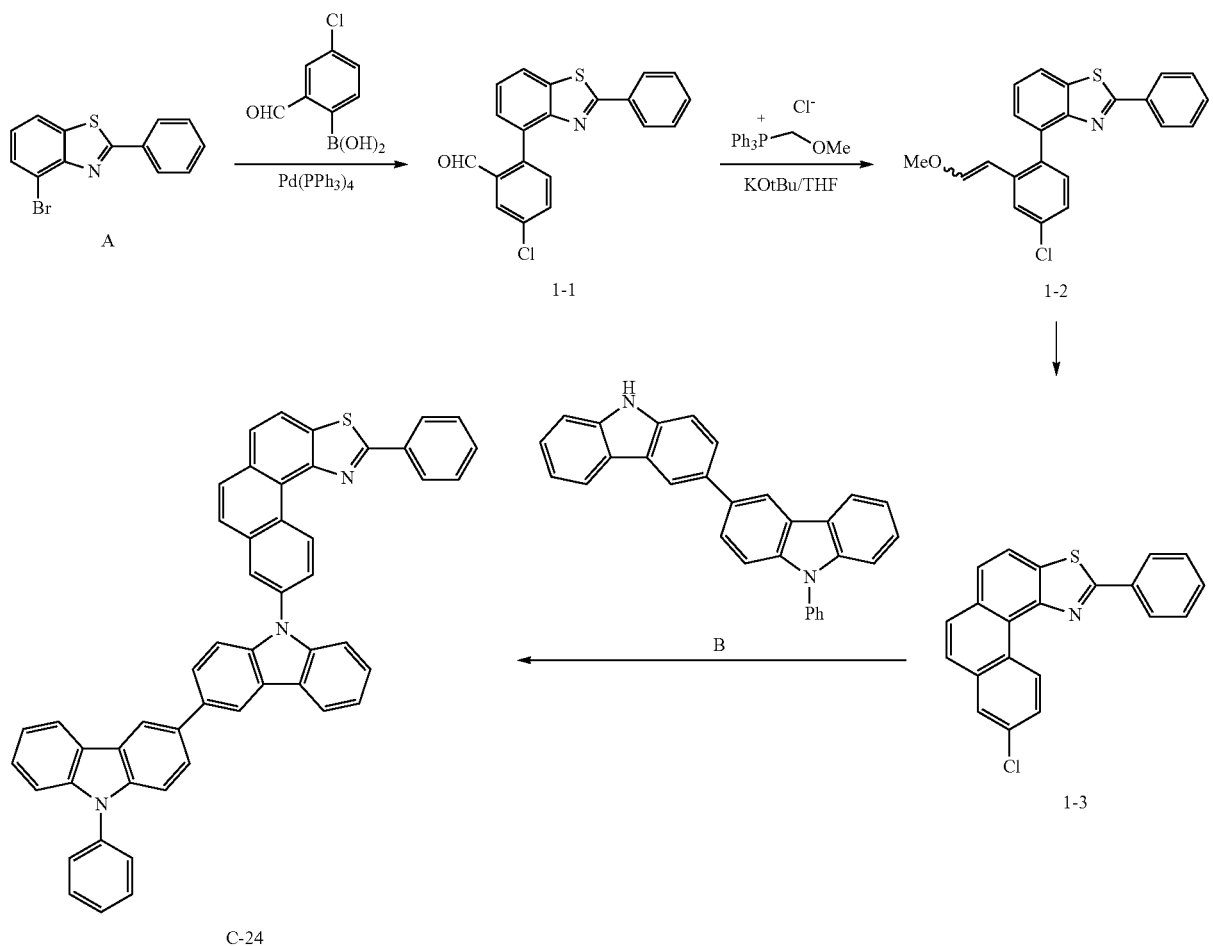

1) Preparation of Compound 1-1

After adding compound A (CAS: 1044146-16-8, 36 g, 124 mmol), 4-chloro-2-formylbenzene boronic acid (25.2 g, 136 mmol), tetrakis(triphenylphosphine)palladium (5.7 g, 5.0 mmol), sodium carbonate (33 g, 150 mmol), toluene (600 mL), EtOH (150 mL), and distilled water (150 mL) into a reaction vessel, the mixture was stirred at 140° C. for 3 hours. After completion of the reaction, the precipitated solid was washed with distilled water and MeOH. The obtained compound 1-1 was used in the next reaction without further purification.

2) Preparation of Compound 1-2

After introducing compound 1-1 (45.6 g, 130 mmol), (methoxymethyl)triphenylphosphonium chloride (74.3 g, 217 mmol), and tetrahydrofuran (1500 mL) into a reaction vessel, the reaction mixture was stirred for 5 minutes, and then potassium tert-butoxide (KOtBu) (1 M in THF, 220 mL) was slowly added dropwise thereto at 0° C. The mixture was warmed slowly to room temperature, and then additionally stirred for 3 hours. The reaction was completed by the addition of distilled water to the reaction mixture, and the mixture was then extracted with ethyl acetate. After the extracted organic layer was dried with magnesium sulfate, the solvent was removed therefrom with a rotary evaporator. The remaining product was purified by column chromatography to obtain compound 1-2 (48 g, yield: 97%).

3) Preparation of Compound 1-3

After introducing compound 1-2 (44.8 g, 119 mmol), Eaton's reagent (4.5 mL), and chlorobenzene (600 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 1-3 (36.3 g, yield: 89%).

4) Preparation of Compound C-24

After adding compound 1-3 (8 g, 23 mmol), compound B (CAS: 1060735-14-9, 9.5 g, 23 mmol), tris(dibenzylideneacetone)dipalladium (Pd$_2$(dba)$_3$) (1 g, 1.16 mmol), 2-dicyclohexylphosphino-2',6'-dimethoxybiphenyl(s-phos) (0.95 g, 2.31 mmol), sodium tert-butoxide (NaOtBu) (4.5 g, 46.3 mmol), and o-xylene (150 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-24 (8.7 g, yield: 68%).

[Example 2] Preparation of Compound C-1

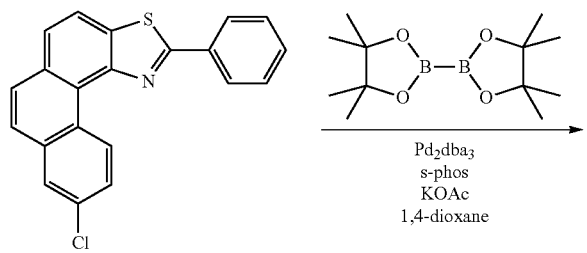

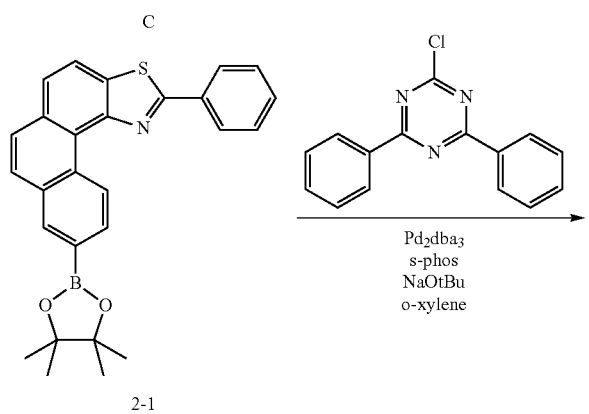

1) Preparation of Compound 2-1

After adding compound C (10 g, 29 mmol), bis(pinacolato)diborane (8.8 g, 34.8 mmol), tris(dibenzylideneacetone)dipalladium (Pd$_2$(dba)$_3$) (1.3 g, 1.45 mmol), 2-dicyclohexylphosphino-2',6'-dimethoxybiphenyl(s-phos) (1.2 g, 2.9 mmol), potassium acetate (KOAc) (8.5 g, 87 mmol), and 1,4-dioxane (150 mL) into a reaction vessel, the mixture was then stirred at 140° C. for 3 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 2-1 (10.4 g, yield: 82%).

2) Preparation of Compound C-1

After adding compound 2-1 (10 g, 23.8 mmol), 2-chloro-4,6-diphenyltriazine (CAS: 3842-55-5, 6.4 g, 23.8 mmol), tris(dibenzylideneacetone)dipalladium (Pd$_2$(dba)$_3$) (1 g, 1.16 mmol), 2-dicyclohexylphosphino-2',6'-dimethoxybiphenyl(s-phos) (1 g, 2.31 mmol), sodium tert-butoxide (NaOtBu) (4.5 g, 46.3 mmol), and o-xylene (150 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-1 (8.2 g, yield: 55%).

[Example 3] Preparation of Compound C-17

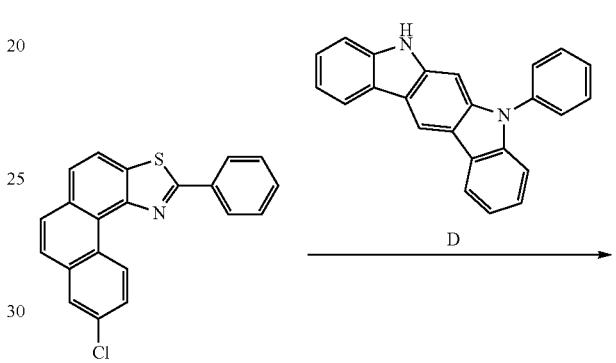

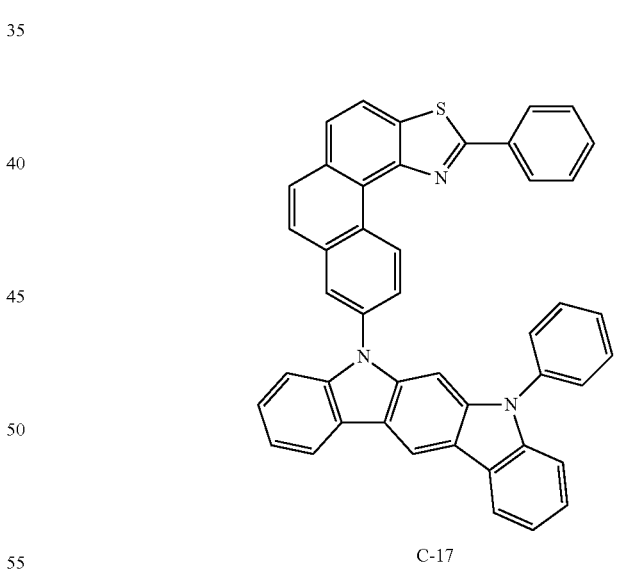

After adding compound C (8 g, 23.1 mmol), compound D (CAS: 1448296-00-1, 7.7 g, 23.1 mmol), tetrakis(triphenylphosphine)palladium (1.4 g, 1.19 mmol), K$_2$CO$_3$ (8.2 g, 60 mmol), toluene (90 mL), EtOH (30 mL), and distilled water (30 mL) into a reaction vessel, the mixture was stirred at 140° C. for 3 hours. After completion of the reaction, the precipitated solid was washed with distilled water and MeOH. The obtained compound was purified by column chromatography to obtain compound C-17 (8.7 g, yield: 77%).

[Example 4] Preparation of Compound C-39

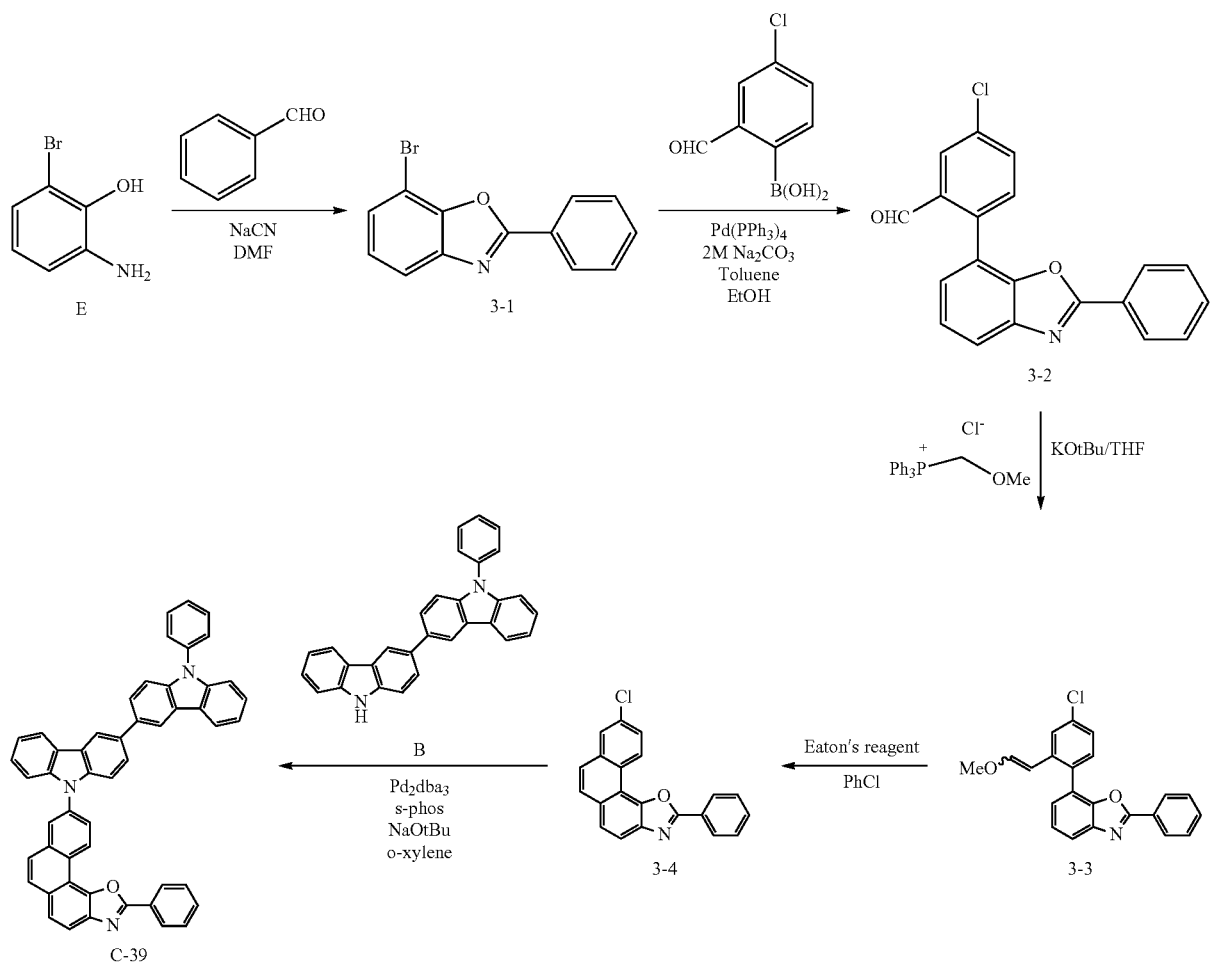

1) Preparation of Compound 3-1

After adding compound E (CAS: 913835-76-4, 40 g, 212.7 mmol), benzaldehyde (27 g, 255.29 mmol), sodium cyanide (10.4 g, 212.7 mmol), and N,N-dimethylformamide (DMF) (1000 mL) into a reaction vessel, the mixture was stirred at 100° C. for 3 hours. After the reaction solution was cooled to room temperature, the solution was extracted with ethyl acetate. The obtained compound 3-1 was used in the next reaction without further purification.

2) Preparation of Compound 3-2

After adding compound 3-1 (35 g, 128 mmol), 4-chloro-2-formylbenzene boronic acid (26 g, 141 mmol), tetrakis(triphenylphosphine)palladium (6 g, 5.1 mmol), sodium carbonate (34 g, 320 mmol), toluene (600 mL), EtOH (150 mL), and distilled water (150 mL) into a reaction vessel, the mixture was stirred at 140° C. for 3 hours. After completion of the reaction, the precipitated solid was washed with distilled water and MeOH. The obtained compound 3-2 was used in the next reaction without further purification.

3) Preparation of Compound 3-3

After introducing compound 3-2 (19 g, 56.9 mmol), (methoxymethyl)triphenylphosphonium chloride (29.3 g, 85.4 mmol), and tetrahydrofuran (500 mL) into a reaction vessel, the reaction mixture was stirred for 5 minutes, and then potassium tert-butoxide (KOtBu) (1 M in THF, 85 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 3-3 (16.4 g, yield: 80%).

4) Preparation of Compound 3-4

After introducing compound 3-3 (14.4 g, 39.8 mmol), Eaton's reagent (1.4 mL), and chlorobenzene (200 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 3-4 (11.1 g, yield: 79%).

5) Preparation of Compound C-39

After adding compound 3-4 (4 g, 12.1 mmol), compound B (CAS: 1060735-14-9, 4.9 g, 12.1 mmol), tris(dibenzylideneacetone)dipalladium ($Pd_2(dba)_3$) (0.5 g, 0.61 mmol), 2-dicyclohexylphosphino-2',6'-djimethoxybiphenyl(s-phos) (0.5 g, 1.21 mmol), sodium tert-butoxide (NaOtBu) (2.33 g, 24.3 mmol), and o-xylene (100 mL) into a reaction vessel, the mixture was stirred at 170° C. for 3 hours. After completion of the reaction, the mixture was added dropwise to MeOH, and then the resultant solid was filtered. The obtained solid was purified by column chromatography to obtain compound C-39 (8.7 g, yield: 47%).

[Example 5] Preparation of Compound C-49

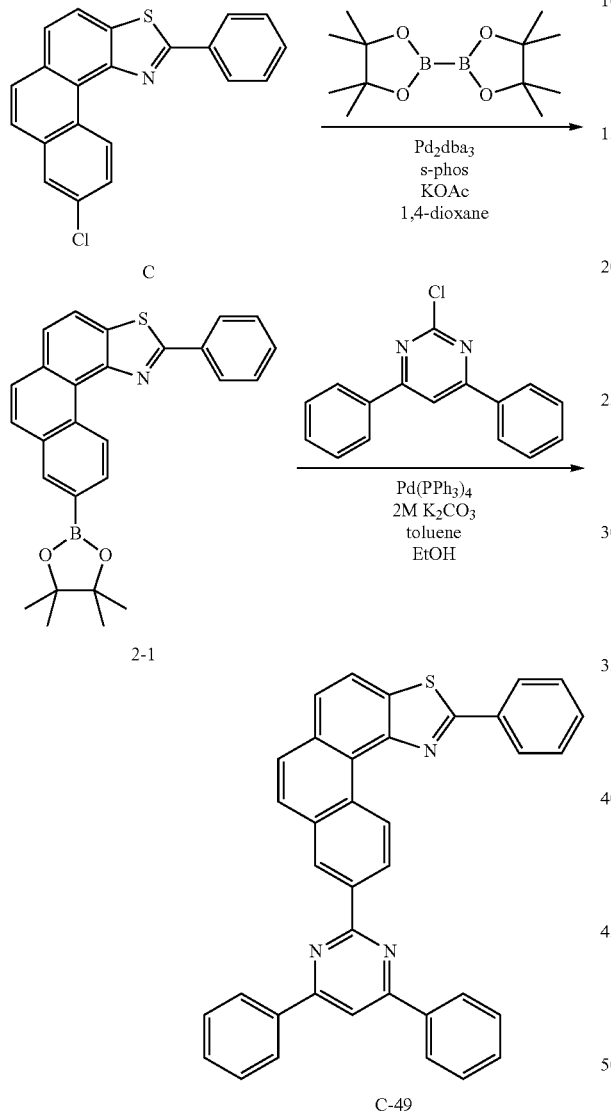

1) Preparation of Compound 2-1
Compound 2-1 was prepared in the same manner as in Example 2.

2) Preparation of Compound C-49
After adding compound 2-1 (4.5 g, 10 mmol), 2-chloro-4,6-diphenylpyrimidine (CAS: 2915-16-4, 2.7 g, 10 mmol), tetrakis(triphenylphosphine)palladium (0.47 g, 0.4 mmol), $K_2CO_3$ (3.6 g, 26 mmol), toluene (50 mL), EtOH (13 mL), and distilled water (13 mL) into a reaction vessel, the mixture was stirred at 120° C. for 4 hours. After completion of the reaction, the mixture was added dropwise to MeOH, and then the resultant solid was filtered. The obtained solid was purified by column chromatography to obtain compound C-49 (4.5 g, yield: 73%).

[Example 6] Preparation of Compound C-75

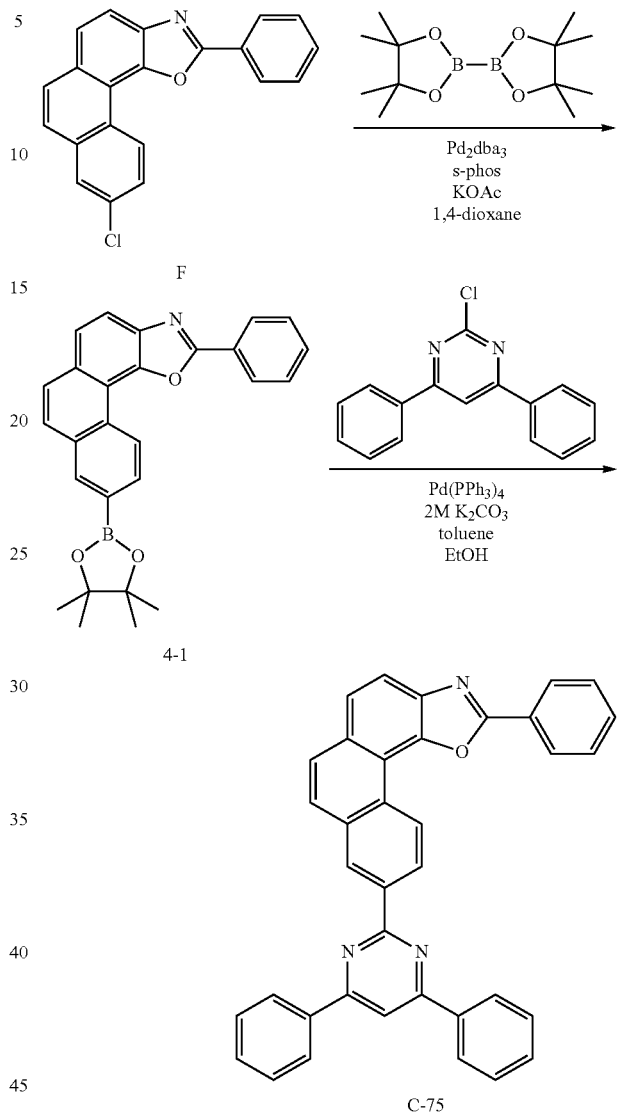

1) Preparation of Compound 4-1
After adding compound F (7.2 g, 21.8 mmol), bis(pinacolato)diborane (6.6 g, 26.2 mmol), tris(dibenzylideneacetone)dipalladium ($Pd_2(dba)_3$) (1.0 g, 1.1 mmol), 2-dicyclohexylphosphino-2',6'-dimethoxybiphenyl(s-phos) (0.89 g, 2.2 mmol), potassium acetate (KOAc) (6.4 g, 65 mmol), and 1,4-dioxane (150 mL) into a reaction vessel, the mixture was stirred at 140° C. for 3 hours. After completion of the reaction, the mixture was cooled to room temperature, and then the mixture was extracted with ethyl acetate. After the extracted organic layer was dried with magnesium sulfate, the solvent was removed therefrom with a rotary evaporator. The remaining product was purified by column chromatography to obtain compound 4-1 (5.2 g, yield: 57%).

2) Preparation of Compound C-75
After adding compound 4-1 (5.2 g, 12.3 mmol), 2-chloro-4,6-diphenylpyrimidine (CAS: 2915-16-4, 3.3 g, 12.3 mmol), tetrakis(triphenylphosphine)palladium (0.71 g, 0.62 mmol), $K_2CO_3$ (4.2 g, 30 mmol), toluene (60 mL), EtOH (20 mL), and distilled water (20 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystallization to obtain compound C-75 (5.3 g, yield: 82%).

[Example 7] Preparation of Compound C-140

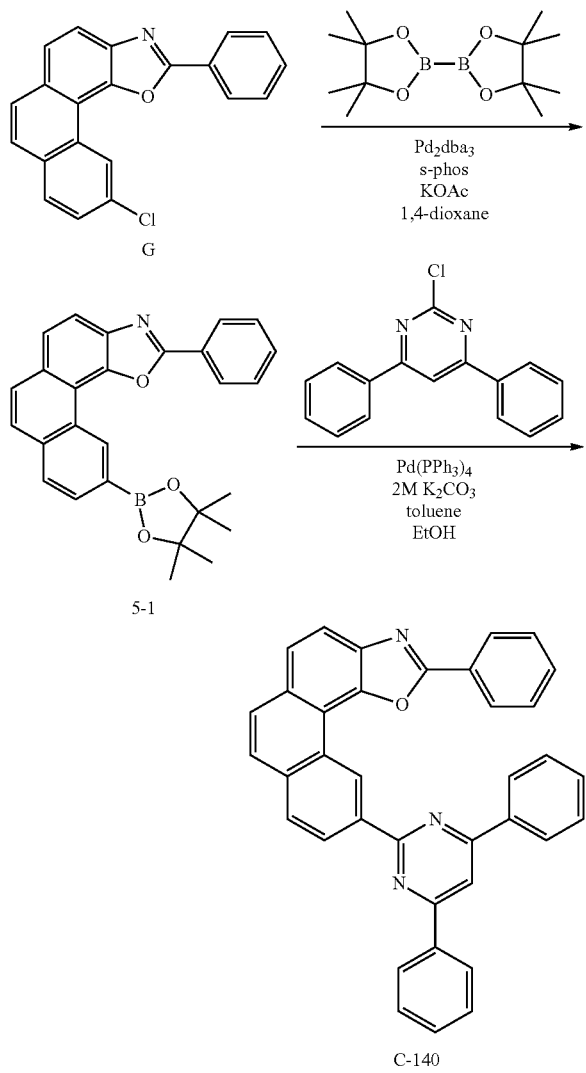

1) Preparation of Compound G

Compound G was prepared in the same manner as in the procedure for the preparation of compound 3-2 in Example 4, except that 4-chloro-2-formylbenzene boronic acid was replaced with 5-chloro-2-formyl boronic acid.

2) Preparation of Compound 5-1

After adding compound G (15 g, 45.5 mmol), bis(pinacolato)diborane (13.9 g, 54.6 mmol), tris(dibenzylideneacetone)dipalladium (Pd$_2$(dba)$_3$) (1.6 g, 1.8 mmol), 2-dicyclohexylphosphino-2',6'-dimethoxybiphenyl(s-phos) (0.9 g, 3.64 mmol), potassium acetate (KOAc) (13 g, 136 mmol), and 1,4-dioxane (350 mL) into a reaction vessel, the mixture was stirred at 140° C. for 3 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 5-1 (20 g, yield: 99%).

3) Preparation of Compound C-140

After adding compound 5-1 (10 g, 22.7 mmol), 2-chloro-4,6-diphenylpyrimidine (CAS: 2915-16-4, 5.5 g, 20.6 mmol), tetrakis(triphenylphosphine)palladium (1.2 g, 1.0 mmol), K$_2$CO$_3$ (7.1 g, 56 mmol), toluene (90 mL), EtOH (30 mL), and distilled water (30 mL) into a reaction vessel, the mixture was then stirred at 120° C. for 4 hours. After completion of the reaction, the mixture was added dropwise to MeOH, and then the resultant solid was filtered. The obtained solid was purified by column chromatography and recrystallization to obtain compound C-140 (5.5 g, yield: 51%).

[Example 8] Preparation of Compound C-100

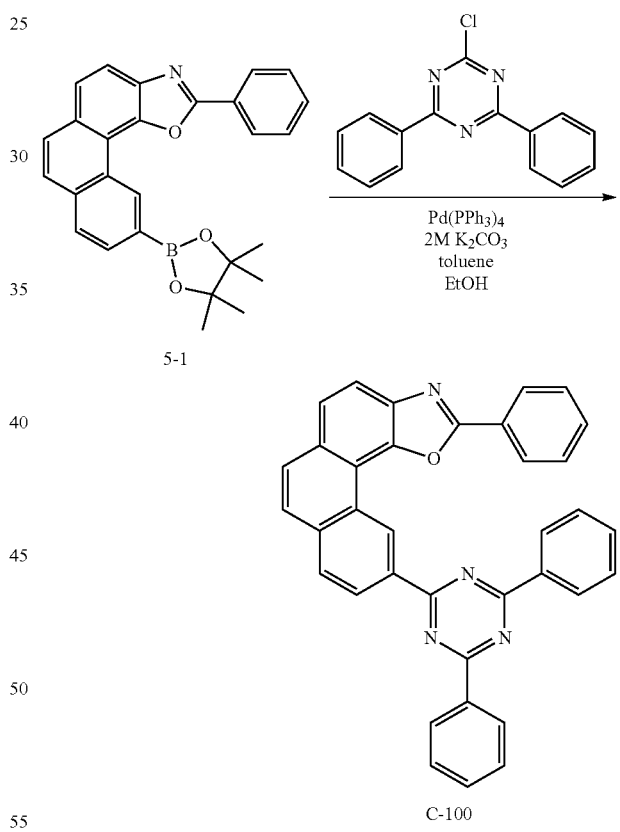

After adding compound 5-1 (10 g, 23.7 mmol), 2-chloro-4,6-diphenyltriazine (CAS: 3842-55-5, 5.8 g, 21.6 mmol), tetrakis(triphenylphosphine)palladium (1.2 g, 1.0 mmol), K$_2$CO$_3$ (7.5 g, 59 mmol), toluene (90 mL), EtOH (30 mL), and distilled water (30 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystallization to obtain compound C-100 (5.7 g, yield: 50%).

[Example 9] Preparation of Compound C-45

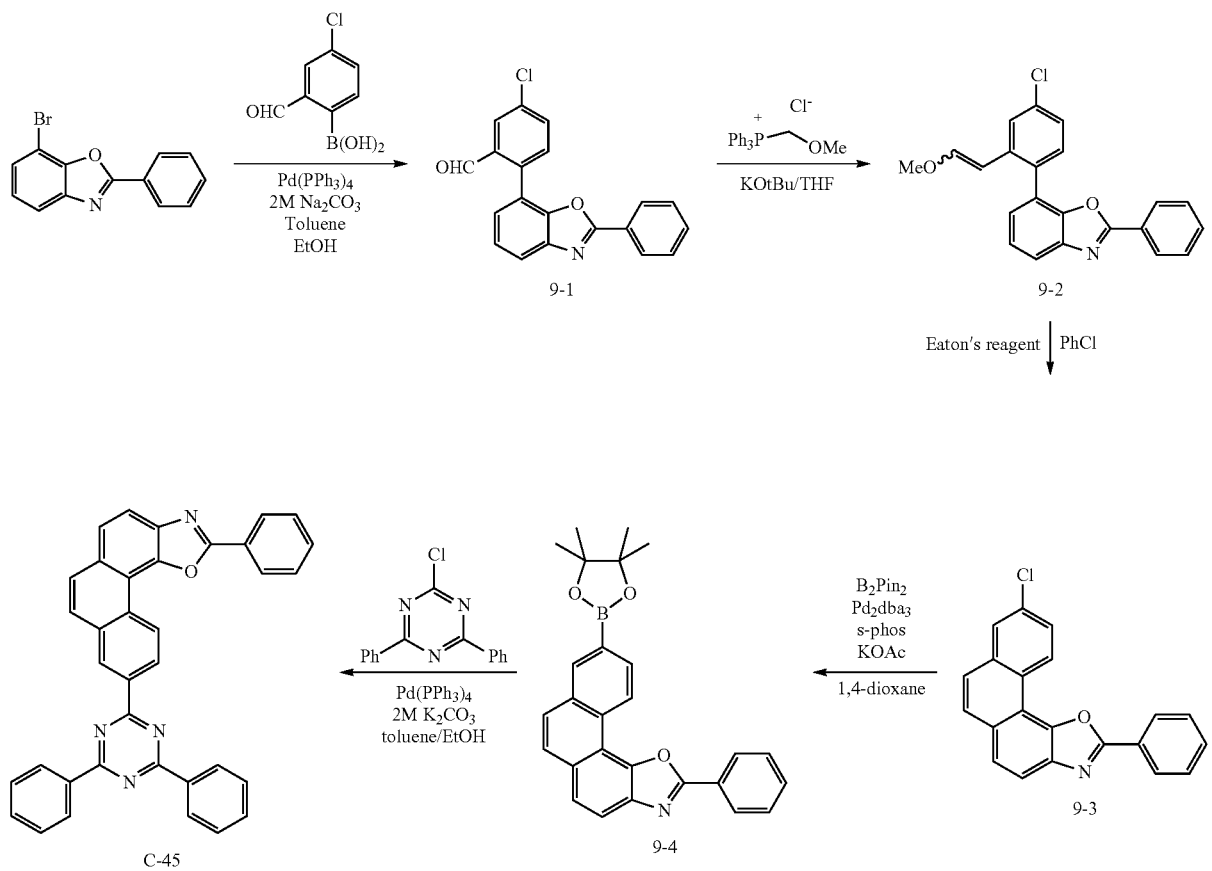

1) Preparation of Compound 9-1

After adding compound 7-bromo-2-phenyl-benzoxazole (37 g, 135 mmol), 4-chloro-2-formylbenzene boronic acid (25 g, 135 mmol), tetrakis(triphenylphosphine)palladium (7.8 g, 6.7 mmol), sodium carbonate (35 g, 338 mmol), toluene (680 mL), EtOH (170 mL), and distilled water (170 mL) into a reaction vessel, the mixture was stirred at 130° C. for 3 hours. After completion of the reaction, the precipitated solid was washed with distilled water and MeOH. The remaining product was purified by column chromatography to obtain compound 9-1 (26 g, yield: 60%).

2) Preparation of Compound 9-2

After introducing compound 9-1 (26 g, 80.2 mmol), (methoxymethyl)triphenylphosphonium chloride (41 g, 120 mmol), and tetrahydrofuran (800 mL) into a reaction vessel, the reaction mixture was stirred for 5 minutes, and then potassium tert-butoxide (KOtBu) (1 M in THF, 120 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 9-2 (25 g, yield: 87%).

3) Preparation of Compound 9-3

After introducing compound 9-2 (25 g, 70.2 mmol), Eaton's reagent (3 mL), and chlorobenzene (350 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 9-3 (13 g, yield: 56%).

4) Preparation of Compound 9-4

After adding compound 9-3 (13 g, 39 mmol), bis(pinacolato)diborane (12 g, 47 mmol), tris(dibenzylideneacetone)dipalladium (Pd$_2$(dba)$_3$) (1.8 g, 1.9 mmol), 2-dicyclohexylphosphino-2',6'-dimethoxybiphenyl(s-phos) (1.6 g, 3.9 mmol), potassium acetate (KOAc) (11 g, 118 mmol), and 1,4-dioxane (330 mL) into a reaction vessel, the mixture was stirred for at 130° C. for 4 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 9-4 (13 g, yield: 81%).

5) Preparation of Compound C-45

After adding compound 9-4 (13 g, 31 mmol), 2-chloro-4,6-diphenyltriazine (8 g, 30 mmol), tetrakis(triphenylphosphine)palladium (1.7 g, 1.5 mmol), K$_2$CO$_3$ (10 g, 75 mmol), toluene (140 mL), EtOH (35 mL), and distilled water (35 mL) into a reaction vessel, the mixture was stirred at 130° C. for 4 hours. After completion of the reaction, the precipitated solid was washed with distilled water and MeOH.

The remaining product was purified by column chromatography to obtain compound C-45 (7.7 g, yield: 49%).

[Example 10] Preparation of Compound C-141

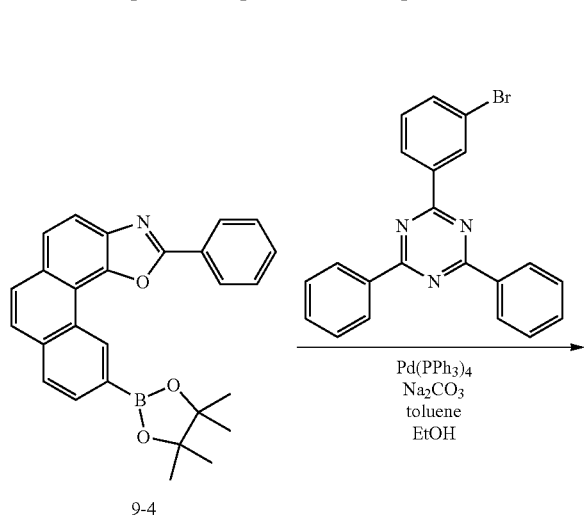

[Example 11] Preparation of Compound C-142

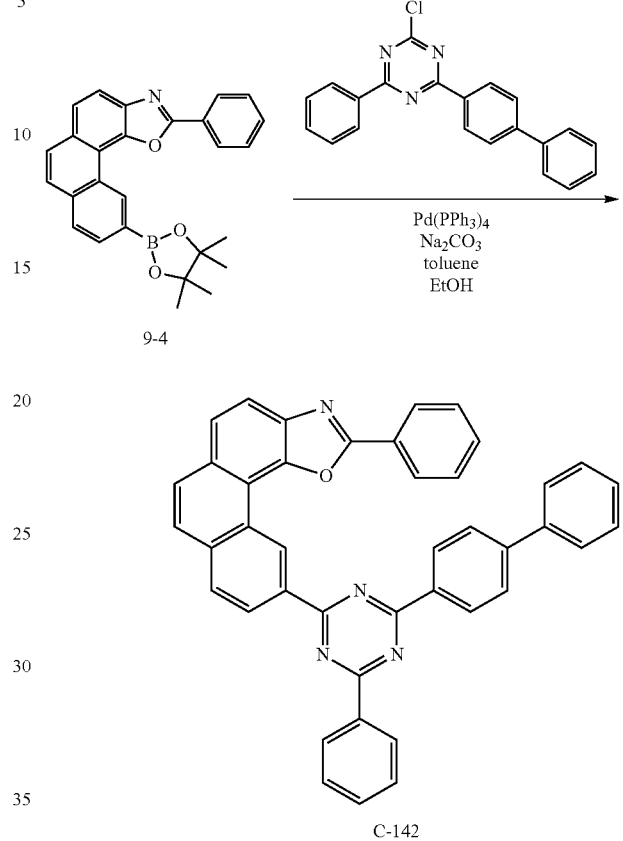

After adding compound 9-4 (3.48 g, 8.3 mmol), 2-([1,1'-biphenyl]-4-yl)-4-chloro-6-phenyl-1,3,5-triazine (CAS: 1472062-94-4, 3.53 g, 9.1 mmol), tetrakis(triphenylphosphine)palladium (0.48 g, 0.41 mmol), sodium carbonate (2.2 g, 20.7 mmol), toluene (28 mL), EtOH (7 mL), and distilled water (7 mL) into a reaction vessel, the mixture was stirred at 120° C. for 5 hours. After completion of the reaction, the mixture was added dropwise to MeOH, and then the resultant solid was filtered. The obtained solid was purified by column chromatography and recrystallization to obtain compound C-142 (3.7 g, yield: 74%).

[Example 12] Preparation of Compound C-101

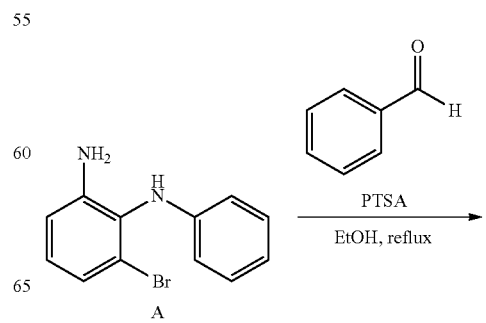

After adding compound 9-4 (3 g, 7.1 mmol), 2-(3-bromophenyl)-4,6-diphenyl-1,3,5-triazine (CAS: 864377-31-1, 3.04 g, 7.8 mmol), tetrakis(triphenylphosphine)palladium (0.41 g, 0.36 mmol), sodium carbonate (1.9 g, 17.8 mmol), toluene (24 mL), EtOH (6 mL), and distilled water (6 mL) into a reaction vessel, the mixture was stirred at 120° C. for 4 hours. After completion of the reaction, the mixture was added dropwise to MeOH, and then the resultant solid was filtered. The obtained solid was purified by column chromatography and recrystallization to obtain compound C-141 (2.3 g, yield: 54%).

-continued

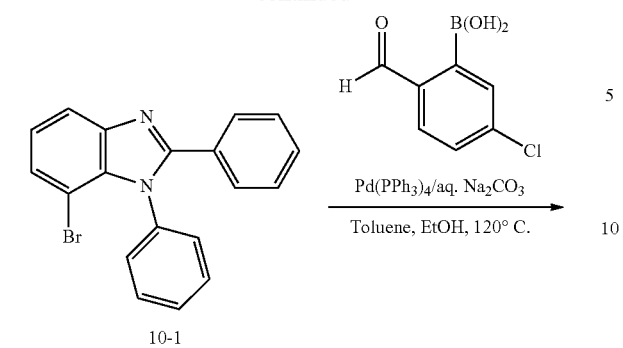

10-1

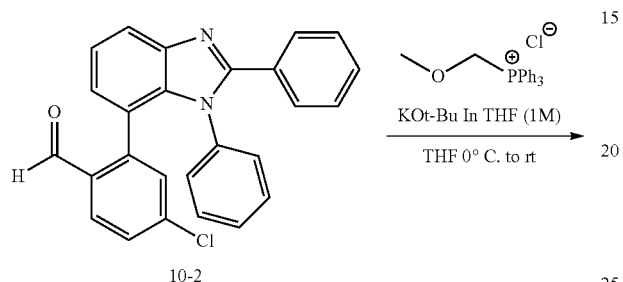

10-2

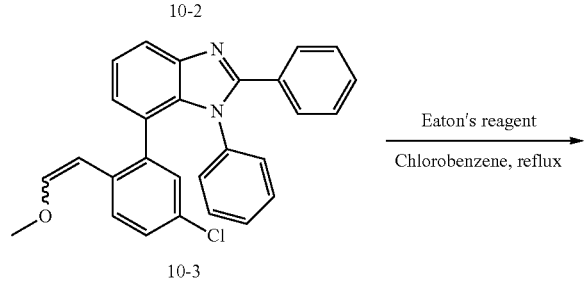

10-3

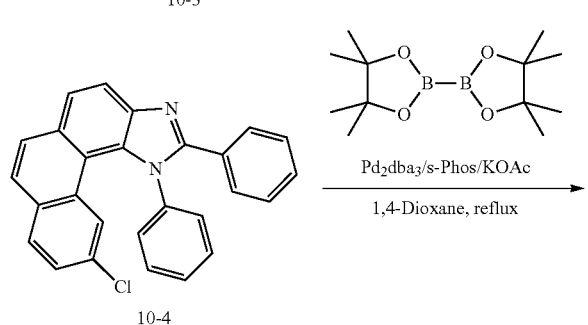

10-4

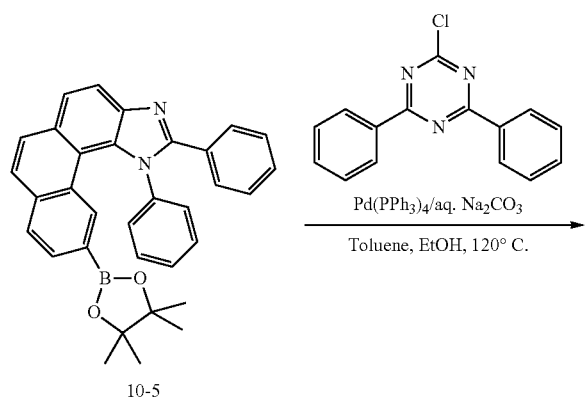

10-5

-continued

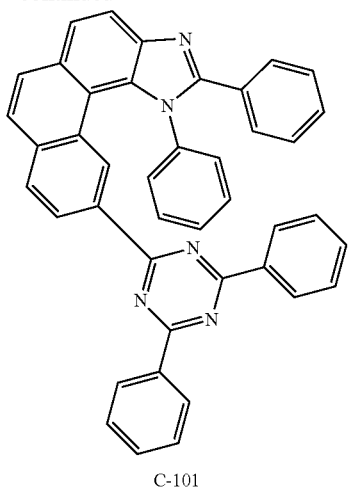

C-101

1) Preparation of Compound 10-1

After adding compound A (20 g, 76.0 mmol), benzaldehyde (8.1 g, 76.0 mmol), para-toluenesulfonic acid (1.5 g, 7.6 mmol), and EtOH (380 mL) into a reaction vessel, the mixture was stirred under reflux for 24 hours. After completion of the reaction, the precipitated solid was washed with distilled water and MeOH. The remaining product was purified by column chromatography to obtain compound 10-1 (20 g, yield: 75%).

2) Preparation of Compound 10-2

After adding compound 10-1 (20 g, 57.3 mmol), 4-chloro-2-formylbenzene boronic acid (10.6 g, 57.3 mmol), tetrakis(triphenylphosphine)palladium (2.0 g, 1.7 mmol), sodium carbonate (15.2 g, 143.3 mmol), toluene (300 mL), EtOH (100 mL), and distilled water (100 mL) into a reaction vessel, the mixture was stirred at 120° C. for 3 hours. After completion of the reaction, the precipitated solid was washed with distilled water and MeOH. The remaining product was purified by column chromatography to obtain compound 10-2 (16.5 g, yield: 70%).

3) Preparation of Compound 10-3

After introducing compound 10-2 (16.5 g, 40.4 mmol), (methoxymethyl)triphenyl phosphonium chloride (21 g, 61 mmol), and tetrahydrofuran (400 mL) into a reaction vessel, the reaction mixture was stirred for 5 minutes, and then potassium tert-butoxide (KOtBu) (1 M in THF, 60 mL) was slowly added dropwise thereto at 0° C. The mixture was warmed slowly to room temperature, and then additionally stirred for 3 hours. After distilled water was added to the reaction solution to stop the reaction, the solution was extracted with ethyl acetate. After the extracted organic layer was dried with magnesium sulfate, the solvent was removed therefrom with a rotary evaporator. The remaining product was purified by column chromatography to obtain compound 10-3 (12 g, yield: 68%).

4) Preparation of Compound 10-4

After introducing compound 10-3 (12 g, 27.5 mmol), Eaton's reagent (1.2 mL), and chlorobenzene (140 mL) into a reaction vessel, the mixture was stirred under reflux for 2 hours. After completing the reaction, the mixture was cooled to room temperature, and then was extracted with methylene chloride (MC). After the extracted organic layer was dried with magnesium sulfate, the solvent was removed therefrom with a rotary evaporator. The remaining product was purified by column chromatography to obtain compound 10-4 (8 g, yield: 72%).

5) Preparation of Compound 10-5

After adding compound 10-4 (8 g, 19.8 mmol), bis(pinacolato)diborane (6 g, 23.7 mmol), tris(dibenzylideneacetone)dipalladium (Pd$_2$(dba)$_3$) (0.7 g, 0.8 mmol), 2-dicyclohexylphosphino-2',6'-dimethoxybiphenyl(s-phos) (0.7 g, 1.6 mmol), potassium acetate (KOAc) (5.8 g, 59.4 mmol), and 1,4-dioxane (100 mL) into a reaction vessel, the mixture was stirred under reflux at 130° C. for 4 hours. After completion of the reaction, the mixture was cooled to room temperature, and then was extracted with ethyl acetate. After the extracted organic layer was dried with magnesium sulfate, the solvent was removed therefrom with a rotary evaporator. The remaining product was purified by column chromatography to obtain compound 10-5 (7 g, yield: 71%).

6) Preparation of Compound C-101

After adding compound 10-5 (5 g, 10.1 mmol), 2-chloro-4,6-diphenyltriazine (2.7 g, 30 mmol), tetrakis(triphenylphosphine)palladium (0.4 g, 0.3 mmol), sodium carbonate (3.5 g, 25.3 mmol), toluene (50 mL), EtOH (12 mL), and distilled water (12 mL) into a reaction vessel, the mixture was stirred at 120° C. for 4 hours. After completion of the reaction, the precipitated solid was washed with distilled water and MeOH. The remaining product was purified by column chromatography to obtain compound C-101 (4.1 g, yield: 67%).

Specific property data of the representative compounds are listed in Table 1 below:

TABLE 1

| Compound | Yield (%) | UV spectrum (in toluene, nm) | PL spectrum (in toluene, nm) | MP (° C.) | MS/EIMS Found | MS/EIMS Calculated |
|---|---|---|---|---|---|---|
| C-24 | 68 | 306 | 418 | 240 | 718.1 | 717.22 |
| C-1 | 55 | 306 | 426 | 276 | 543.2 | 542.16 |
| C-17 | 77 | 306 | 426 | 276 | 642.0 | 641.19 |
| C-39 | 47 | 304 | 400 | 230 | 702.1 | 701.25 |
| C-49 | 73 | 362 | 420 | 279 | 542.0 | 541.66 |
| C-75 | 82 | 260 | 392 | 300 | 526.1 | 525.18 |
| C-140 | 51 | 296 | 402 | 278 | 526.1 | 525.18 |
| C-100 | 50 | 290 | 427 | 291 | 527.1 | 526.18 |
| C-45 | 49 | 345 | 426 | 309 | 526.6 | 526.18 |
| C-141 | 54 | 358 | 401 | 298 | 602.7 | 602.21 |
| C-142 | 74 | 324 | 429 | 299 | 602.7 | 602.21 |
| C-101 | 67 | 324 | 499 | — | 601.7 | — |

Comparative Example 1: Producing a Blue Light-Emitting OLED Device not According to the Present Disclosure An OLED device not according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. Next, the ITO substrate was mounted on a substrate holder of a vacuum vapor deposition apparatus. N$^4$,N$^{4'}$-diphenyl-N$^4$, N$^{4'}$-bis(9-phenyl-9H-carbazol-3-yl)-[1,1'-biphenyl]-4,4'-diamine (Compound HI-1) was introduced into a cell of the vacuum vapor deposition apparatus, and the pressure in the chamber of the apparatus was then controlled to 10$^{-7}$ torr. Thereafter, an electric current was applied to the cell to evaporate the introduced material, thereby forming a first hole injection layer having a thickness of 60 nm on the ITO substrate. 1,4,5,8,9,12-hexaazatriphenylen-hexacarbonitrile (Compound HI-2) was then introduced into another cell of the vacuum vapor deposition apparatus, and an electric current was applied to the cell to evaporate the introduced material, thereby forming a second hole injection layer having a thickness of 5 nm on the first hole injection layer. N-([1,1'-biphenyl]-4-yl)-9,9-dimethyl-N-(4-(9-phenyl-9H-carbazol-3-yl)phenyl)-9H-fluorene-2-amine (Compound HT-1) was introduced into another cell of the vacuum vapor deposition apparatus. Thereafter, an electric current was applied to the cell to evaporate the introduced material, thereby forming a first hole transport layer having a thickness of 20 nm on the second hole injection layer. 9-(naphthalen-2-yl)-3-(4-(9-phenyl-9H-carbazol-3-yl)phenyl)-9H-carbazole (Compound HT-2) was then introduced into another cell of the vacuum vapor deposition apparatus, and an electric current was applied to the cell to evaporate the introduced material, thereby forming a second hole transport layer having a thickness of 5 nm on the first hole transport layer. After forming the hole injection layers and the hole transport layers, a light-emitting layer was then deposited as follows. Compound H-82 as a host was introduced into one cell of the vacuum vapor deposition apparatus and compound D-38 as a dopant was introduced into another cell of the apparatus. The two materials were evaporated at a different rate and the dopant was deposited in a doping amount of 2 wt %, based on the total weight of the host and dopant, to form a light-emitting layer having a thickness of 20 nm on the second hole transport layer. Next, BCP (compound ETL-1) as an electron transport material was introduced into one cell of the vacuum vapor deposition apparatus and evaporated to form an electron transport layer having a thickness of 35 nm on the light-emitting layer. After depositing lithium quinolate (compound EIL-1) as an electron injection layer having a thickness of 2 nm on the electron transport layer, an Al cathode having a thickness of 80 nm was deposited by another vacuum vapor deposition apparatus on the electron injection layer. Thus, an OLED device was produced. All the materials used for producing the OLED device were purified by vacuum sublimation at 10$^{-6}$ torr.

Figure 3:
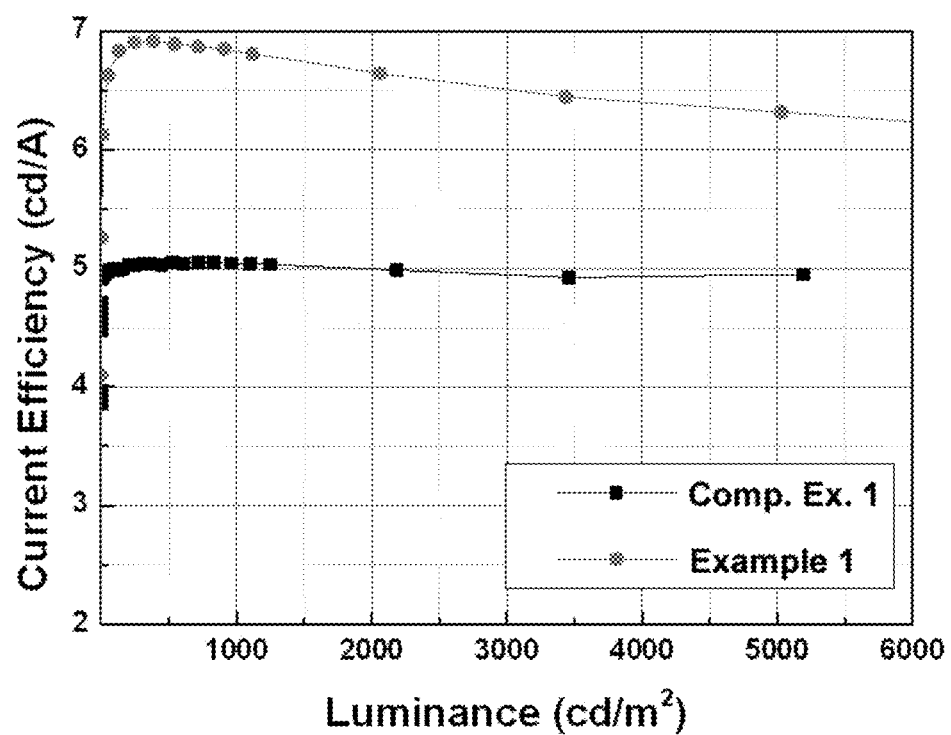
FIG. 3 is a graph illustrating a current efficiency versus a luminance of organic electroluminescent devices of Comparative Example 1 and Device Example 2.

The driving voltage, luminous efficiency, CIE color coordinates, and the time period for the luminance to decrease from 100% to 50% at a luminance of 1,000 nits of the produced OLED device are provided in Table 2 below. In addition, a current efficiency versus a luminance of the organic electroluminescent device of Comparative Example 1 is illustrated in FIG. 3 as a graph.

Comparative Example 2: Producing a Blue Light-Emitting OLED Device not According to the Present Disclosure An OLED device was produced in the same manner as in Comparative Example 1, except that Alq$_3$ (compound ETL-2) was used as an electron transport material, and evaluated. The evaluation results of the OLED device of Comparative Example 2 are provided in Table 2 below.

Comparative Examples 3 and 4: Producing a Blue Light-Emitting OLED Device not According to the Present Disclosure OLED devices were produced in the same manner as in Comparative Example 1, except that BCP (compound ETL-1) was evaporated as an electron buffer layer of 5 nm and Alq$_3$ (compound ETL-2) was evaporated as an electron transport layer of 30 nm (Comparative Example 3), and compound B-21 was evaporated as an electron buffer layer of 5 nm and compound ETL-3 and Liq in a weight ratio of 50:50 were evaporated as an electron transport layer of 30 nm (Comparative Example 4) instead of forming an electron transport layer of 35 nm, and evaluated. The evaluation results of the OLED device of Comparative Examples 3 and 4 are provided in Table 2 below.

Device Examples 1 to 5: Producing a Blue Light-Emitting OLED Device According to the Present Disclosure In Device Examples 1 to 5, OLED devices were produced in the same manner as in Comparative Example 1, except that compounds of Table 2 were evaporated as an electron buffer layer of 5 nm and compound C-45 and Liq in a weight ratio of 50:50 were evaporated as an electron transport layer of 30 nm, and evaluated. The evaluation results of the OLED device of Device Examples 1 to 5 are provided in Table 2 below. In addition, a current efficiency versus a luminance of the organic electroluminescent device of Device Example 1 is illustrated in FIG. 3 as a graph.

Comparative Examples 5 and 6: Producing a Blue Light-Emitting OLED Device not According to the Present Disclosure OILED devices were produced in the same manner as in Comparative Example 1, except for using compound H-15 as the host compound and using the electron transport material as in Table 3, and evaluated. The evaluation results (lifespan is the time period for the luminance to decrease from 100% to 90%) of the OILED device of Comparative Examples 5 and 6 are provided in Table 3 below.

Comparative Example 7: Producing a Blue Light-Emitting OLED Device not According to the Present Disclosure An OILED device was produced in the same manner as in Comparative Examples 5 and 6, except that BCP (compound ETL-1) was evaporated as an electron buffer layer of 5 nm and Alq$_3$ (compound ETL-2) was evaporated as an electron transport layer of 30 nm instead of forming an electron transport layer of 35 nm, and evaluated. The evaluation results of the OLED device of Comparative Example 7 are provided in Table 3 below.

Device Examples 6 to 9: Producing a Blue Light-Emitting OLED Device According to the Present Disclosure In Device Examples 6 to 9, OLED devices were produced in the same manner as in Comparative Examples 5 and 6, except that compounds of Table 3 were evaporated as an electron buffer layer of 5 nm and compound C-142 and Liq in a weight ratio of 50:50 were evaporated as an electron transport layer of 30 nm, and evaluated. The evaluation results of the OLED device of Device Examples 6 to 9 are provided in Table 3 below.

TABLE 2

| | Electron Buffer Material | Electron Transport Material | Driving Voltage (V) | Luminous Efficiency (cd/A) | Color Coordinate (x) | Color Coordinate (y) | Lifespan (T50, hr) |
|---|---|---|---|---|---|---|---|
| Comparative Example 1 | — | ETL-1 | 5.8 | 5.0 | 0.140 | 0.095 | 14.6 |
| Comparative Example 2 | — | ETL-2 | 4.6 | 4.3 | 0.144 | 0.105 | 213.8 |
| Comparative Example 3 | ETL-1 | ETL-2 | 5.2 | 4.2 | 0.141 | 0.097 | 36.5 |
| Comparative Example 4 | B-21 | ETL-3:Liq | 3.9 | 6.0 | 0.140 | 0.099 | 372.6 |
| Device Example 1 | B-2 | C-45:Liq (5:5) | 3.5 | 6.8 | 0.139 | 0.094 | 392.3 |
| Device Example 2 | B-21 | | 4.0 | 5.9 | 0.139 | 0.096 | 547.5 |
| Device Example 3 | B-19 | | 3.8 | 5.7 | 0.139 | 0.094 | 535.9 |
| Device Example 4 | B-79 | | 3.6 | 6.3 | 0.139 | 0.094 | 435.6 |
| Device Example 5 | B-28 | | 3.6 | 6.5 | 0.139 | 0.094 | 442.8 |

TABLE 3

| | Electron Buffer Material | Electron Transport Material | Driving Voltage (V) | Luminous Efficiency (cd/A) | Color Coordinate (x) | Color Coordinate (y) | Lifespan (T90, hr) |
|---|---|---|---|---|---|---|---|
| Comparative Example 5 | | ETL-1 | 6.4 | 4.7 | 0.140 | 0.089 | 0.13 |
| Comparative Example 6 | | ETL-2 | 5.2 | 4.0 | 0.146 | 0.105 | 1.9 |
| Comparative Example 7 | ETL-1 | ETL-2 | 5.8 | 4.0 | 0.141 | 0.091 | 0.56 |
| Device Example 6 | B-2 | C-142:Liq (5:5) | 4.0 | 6.5 | 0.139 | 0.087 | 39.4 |
| Device Example 7 | B-21 | | 4.3 | 5.4 | 0.140 | 0.090 | 67.1 |
| Device Example 8 | B-19 | | 4.2 | 5.5 | 0.139 | 0.089 | 62.4 |
| Device Example 9 | B-28 | | 4.1 | 6.2 | 0.139 | 0.088 | 60.5 |

From Tables 2 and 3 above, it can be seen that the OLED devices of Device Examples 1 to 5 and Device Examples 6 and 9 provide lower driving voltage, higher efficiency, and longer lifespan compared to Comparative Examples 1 to 4 and Comparative Examples 5 to 7, respectively, by appropriately combining the electron buffer layer and the electron transport layer of the present disclosure. Particularly, upon comparing Device Example 2 to Comparative Example 4, a lifespan characteristic of 30% or higher was increased. It is considered to be easily applied to flexible displays, lightings, and vehicle displays which require long lifespan.

TABLE 4

Compounds used in Comparative Examples and Device Examples

Hole Injection Layer/ Hole Transport Layer

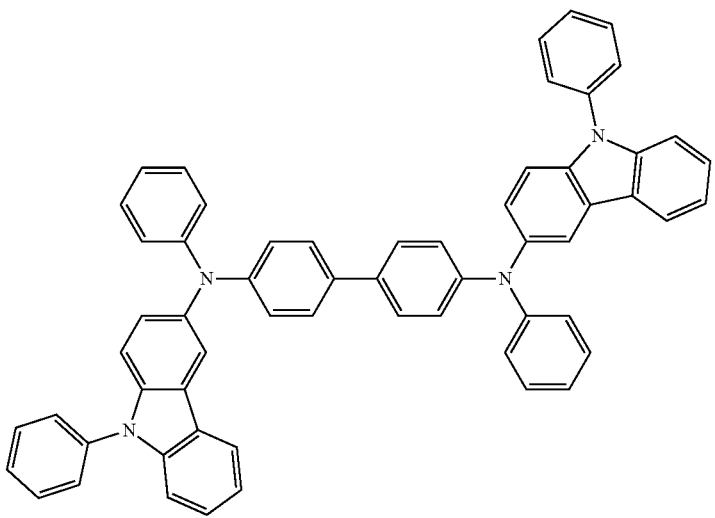

HI-1

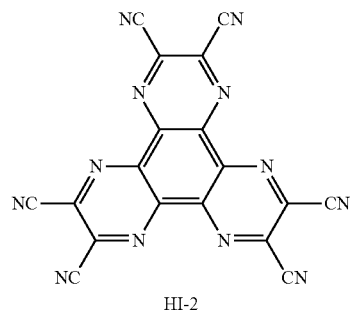

HI-2

TABLE 4-continued
Compounds used in Comparative Examples and Device Examples
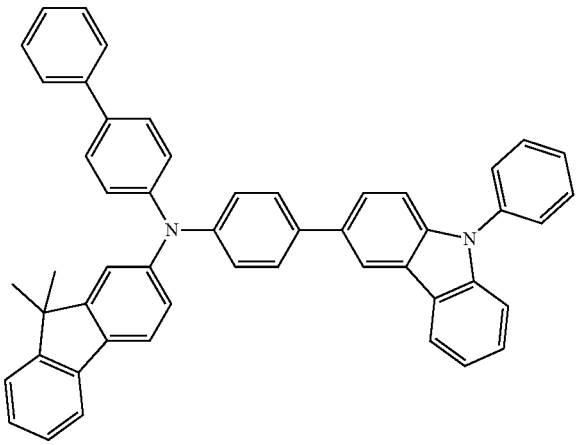
HT-1
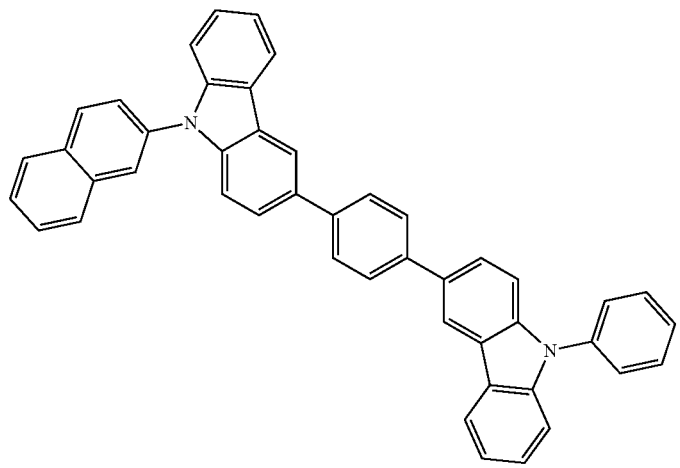
HT-2
Light-
Emitting
Layer
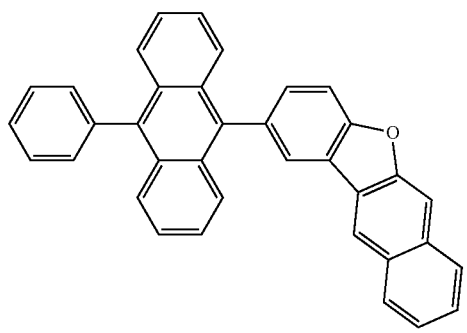
H-82

TABLE 4-continued
Compounds used in Comparative Examples and Device Examples
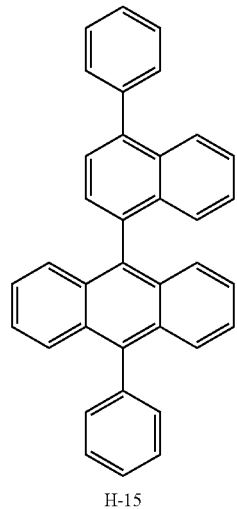
H-15
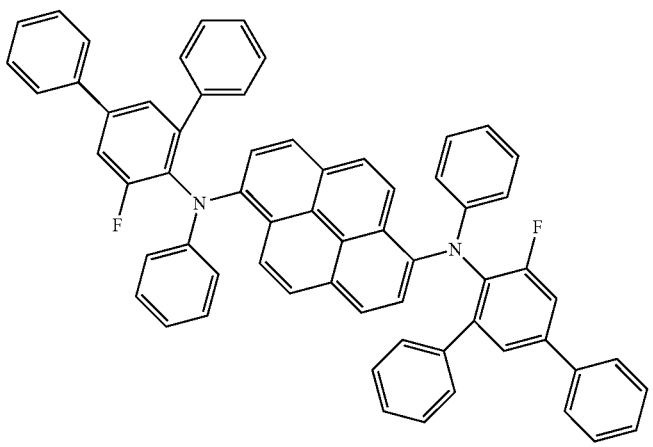
D-38

TABLE 4-continued
Compounds used in Comparative Examples and Device Examples
Electron Buffer Layer/ Electron Transport Layer/ Electron Injection Layer
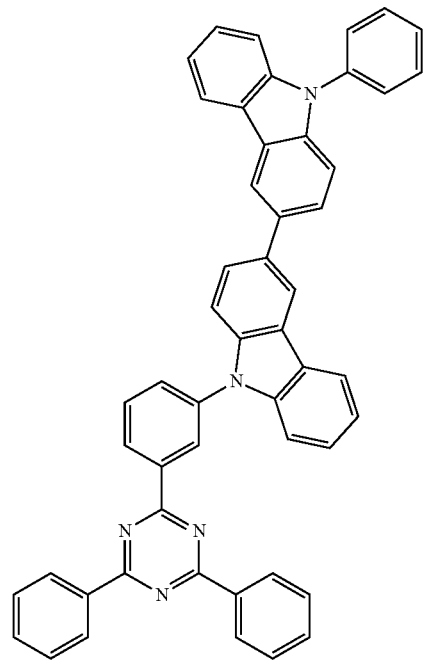
B-21
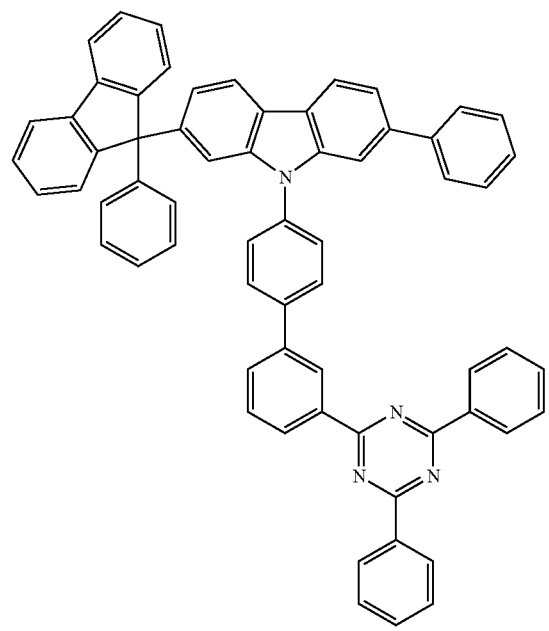
B-2

TABLE 4-continued

Compounds used in Comparative Examples and Device Examples

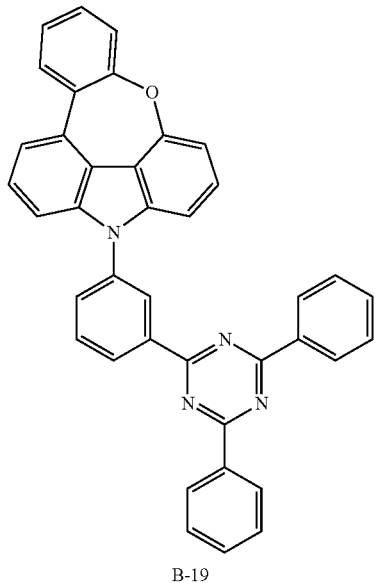

B-19

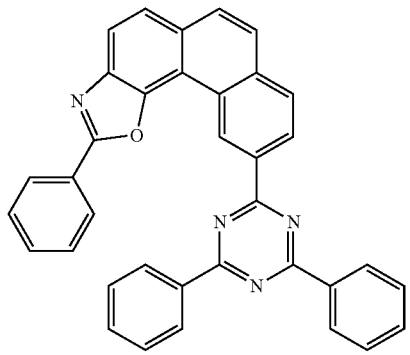

B-79

| Reference Numbers | |
|---|---|
| 100: organic electroluminescent device | 101: substrate |
| 110: first electrode | 120: organic layer |
| 122: hole injection layer | 123: hole transport layer |
| 125: light-emitting layer | 126: electron buffer layer |
| 127: electron transport layer | 128: electron injection layer |
| 129: electron transport zone | 130: second electrode |

The invention claimed is:

1. An organic electroluminescent device comprising a first electrode, a second electrode facing the first electrode, a light-emitting layer between the first electrode and the second electrode, and an electron transport layer and an electron buffer layer between the light-emitting layer and the second electrode, wherein the electron buffer layer comprises a compound represented by any one of the following formulae 5 to 8, and the electron transport layer comprises a compound represented by the following formula 2:

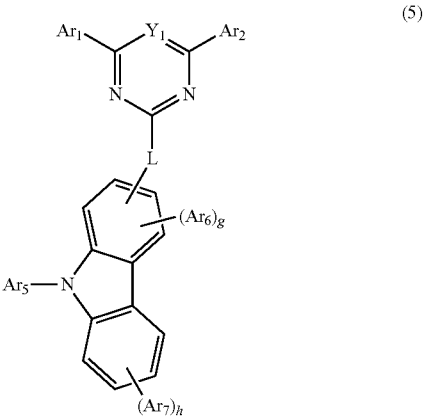

(5)

-continued

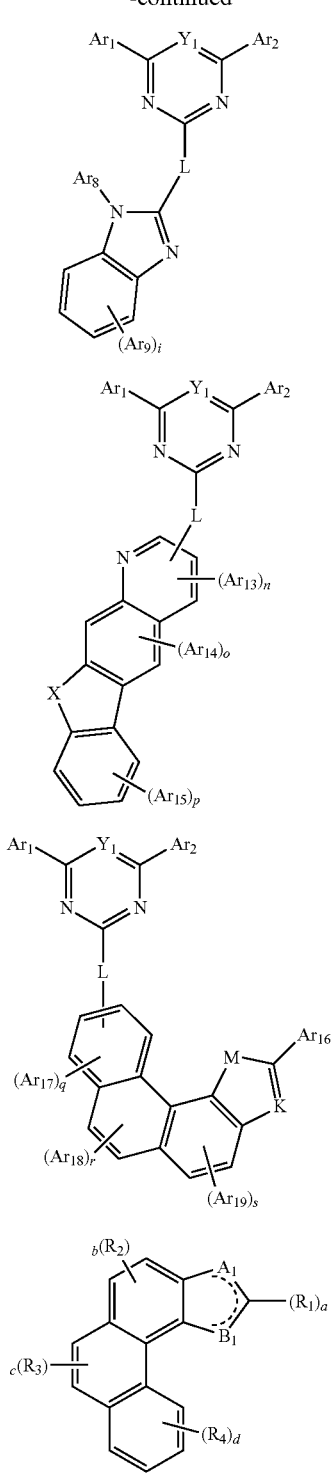

wherein
Y₁ represents N or CR₁₃;
Ar₁ and Ar₂, Ar₅ to Ar₉, and Ar₁₃ to A₁₉, each independently represent hydrogen, deuterium, a halogen, a cyano, a substituted or unsubstituted (C1-C30)alkyl, a substituted or unsubstituted (C6-C50)aryl, a substituted or unsubstituted (3- to 50-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur;

L represents a single bond, a substituted or unsubstituted (C6-C50)arylene, or a substituted or unsubstituted (5- to 50-membered)heteroarylene; and X represents CRaRb, NRc, O, or S, wherein Ra, Rb, and Rc are each independently identical to the definition of Ar₁;

K represents CRd or N, wherein Rd is identical to the definition of Ar₁;

M represents O or S;

A₁ represents —N═, —NR₇—, —O—, or —S—;

B₁ represents —N═, —NR₈—, —O—, or —S—, with a proviso that B₁ is —NR₈—, —O—, or —S— when A₁ is —N═, and B₁ is —N═, —O—, or —S— when A₁ is —NR₇—;

R₁ represents a substituted or unsubstituted (C6-C30)aryl wherein the substituents of the (C6-30)aryl are at least one selected from the group consisting of deuterium, a (C1-30)alkyl, a (C6-30)aryl(C1-C30)alkyl and a (C1-C30)alkyl(C6-30)aryl;

R₂ to R₄, R₇, and R₈ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, mono- or polycyclic, (C3-C30) alicyclic, aromatic, or a combination of alicyclic and aromatic ring, whose carbon atom(s) may be replaced with at least one heteroatom selected from nitrogen, oxygen, and sulfur;

h, i, and p each independently represent an integer of 1 to 4, q and q each independently represent an integer of 1 to 3, and n, o, r, and s each independently represent 1 or 2;

a represents 1, b and c each independently represent 1 or 2, and d represents an integer of 1 to 4; and the heteroaryl(ene) contains at least one heteroatom selected from B, N, O, S, Si, and P.

2. The organic electroluminescent device according to claim 1, wherein the compound represented by any one of formulae 5 to 8 is selected from the group consisting of:

-continued
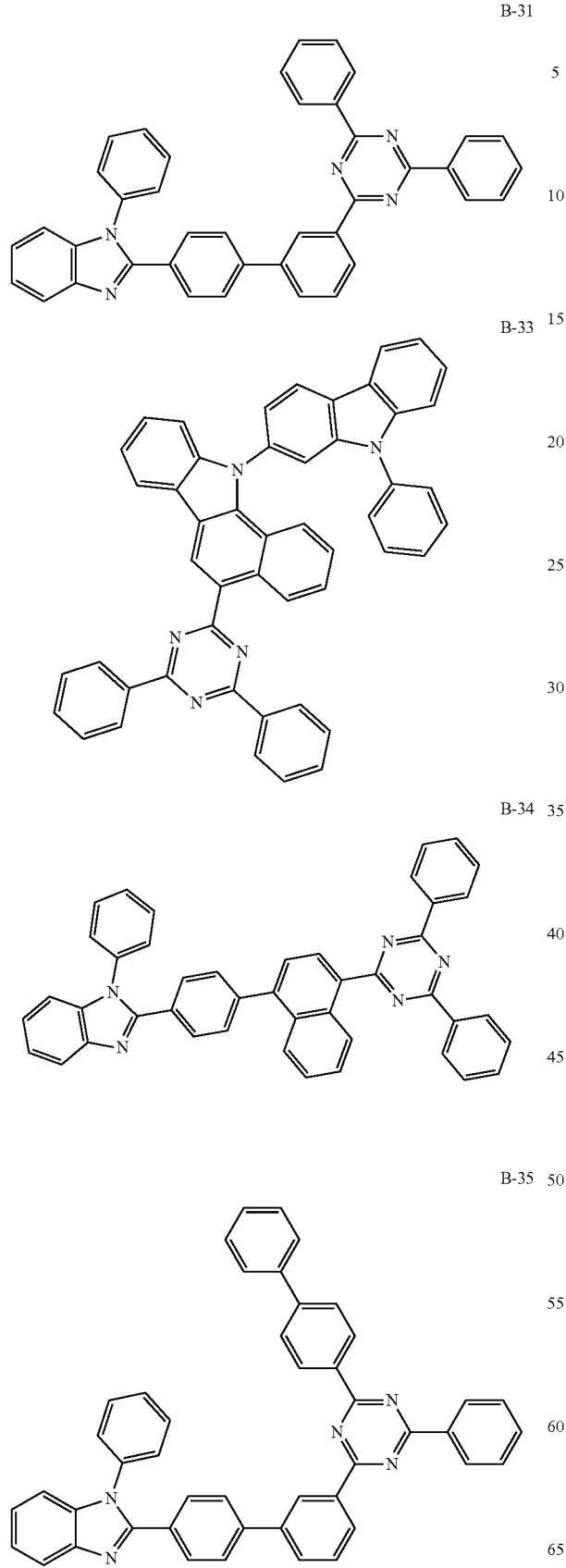
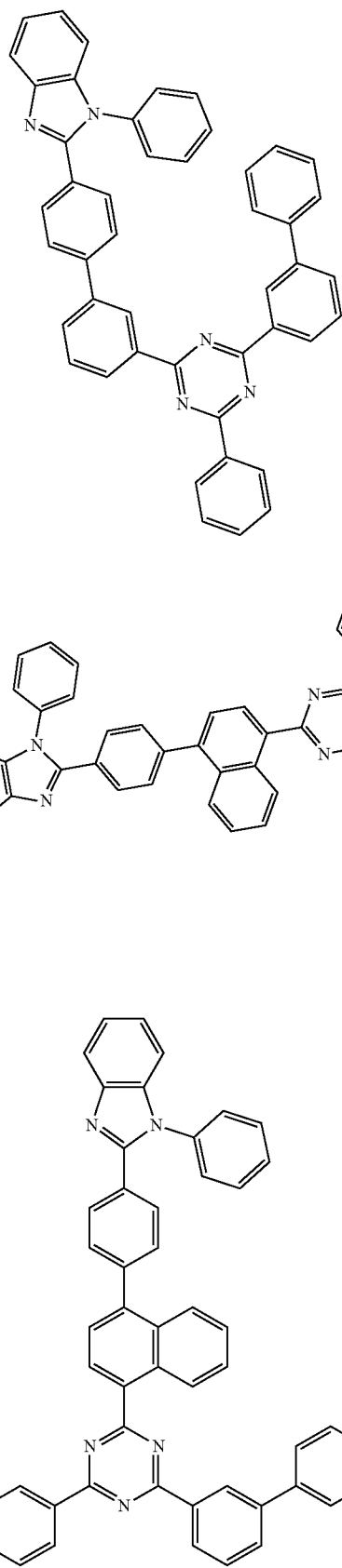

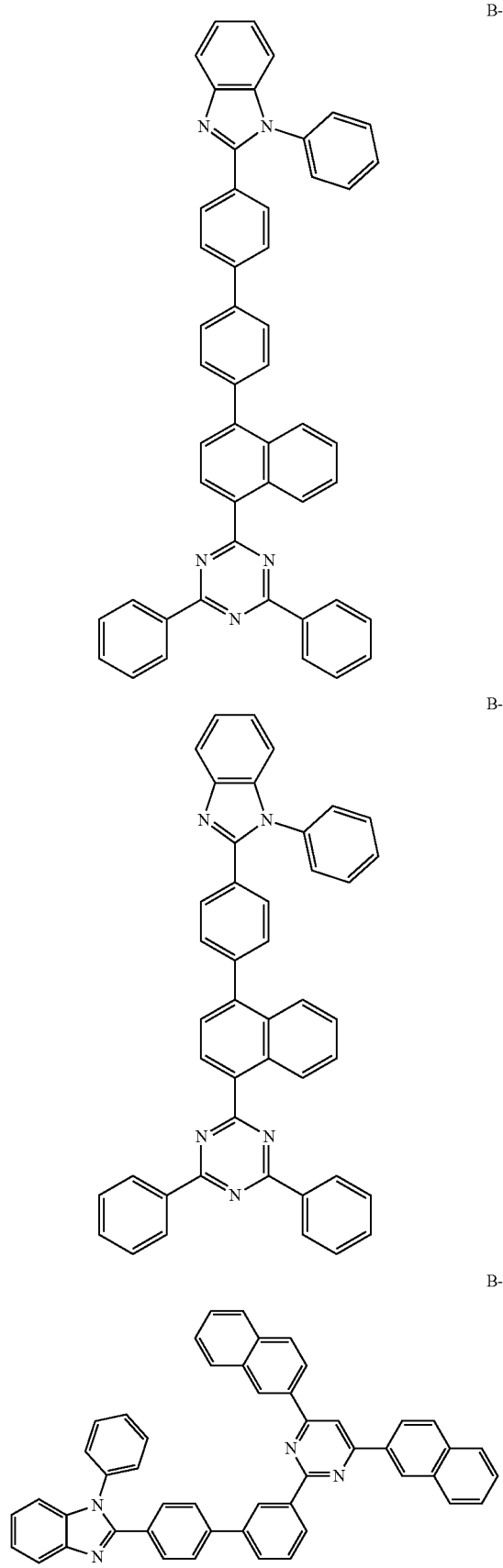
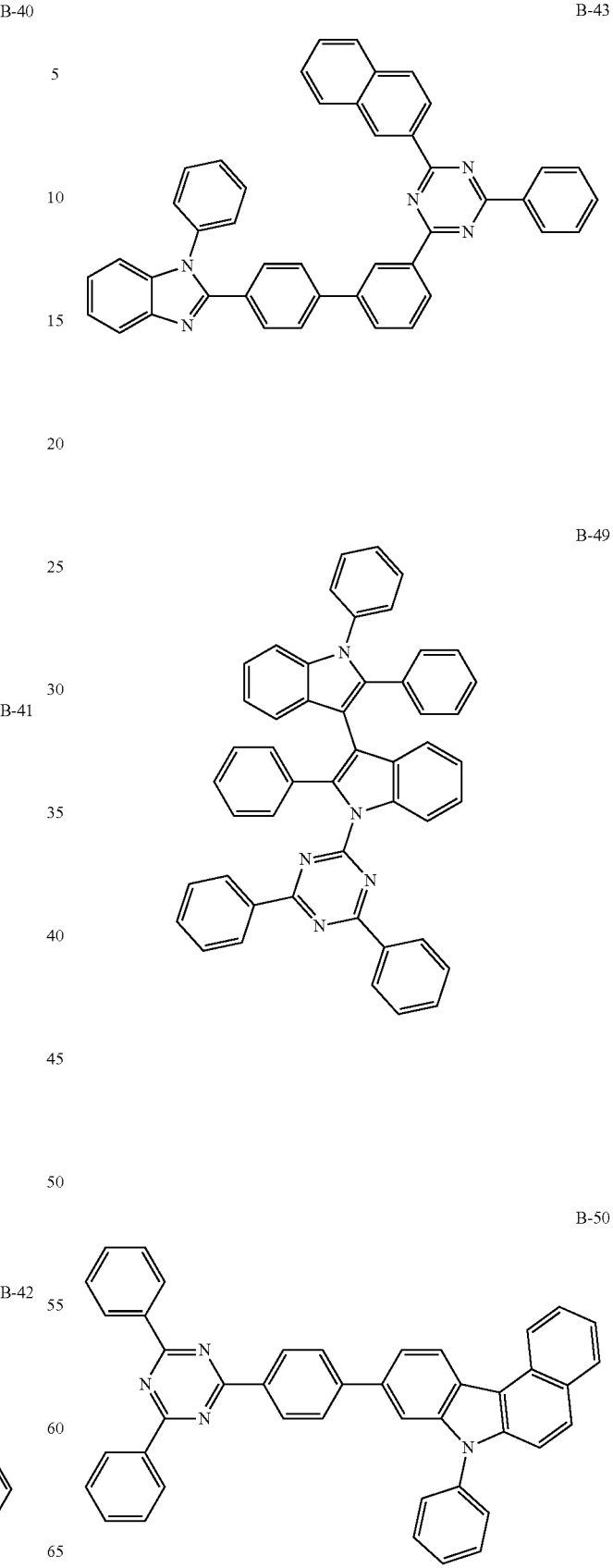

-continued
B-51
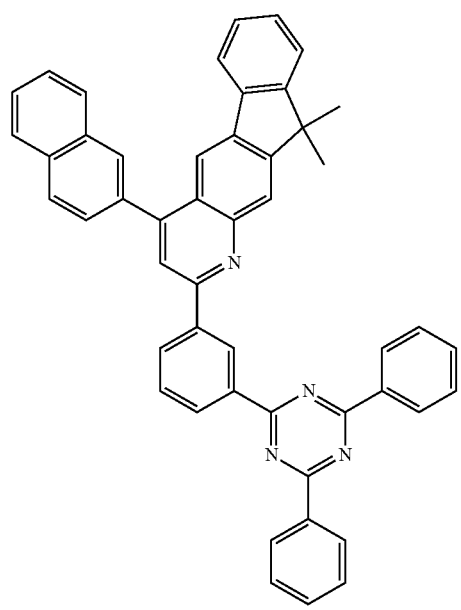
B-59
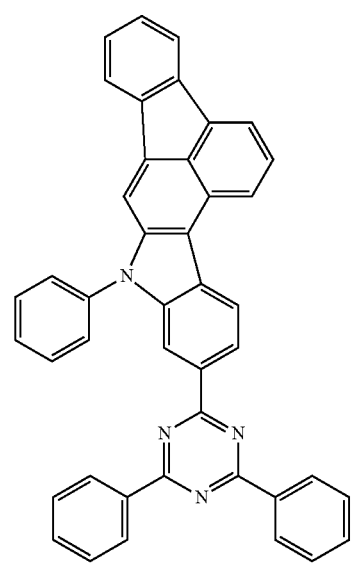
B-60
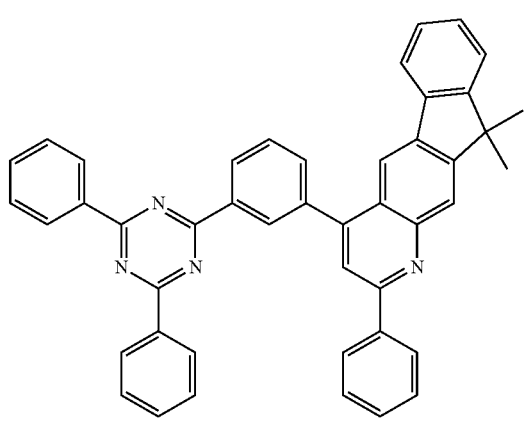
-continued
B-79
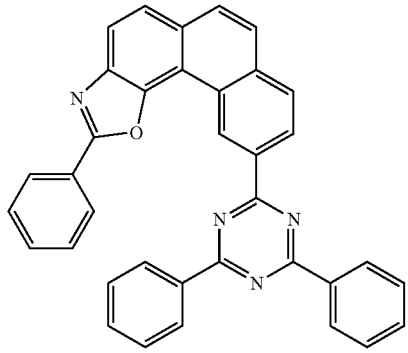
B-80
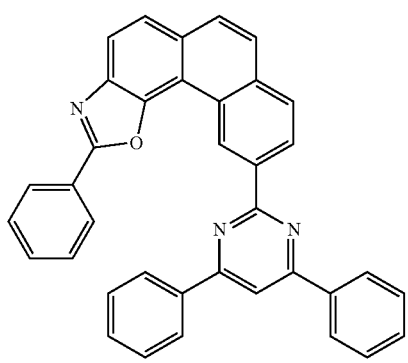
B-81
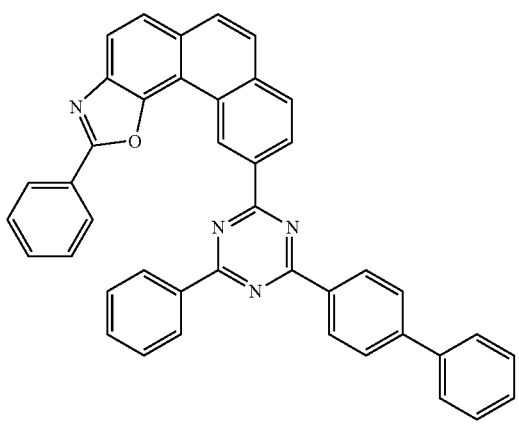
B-82
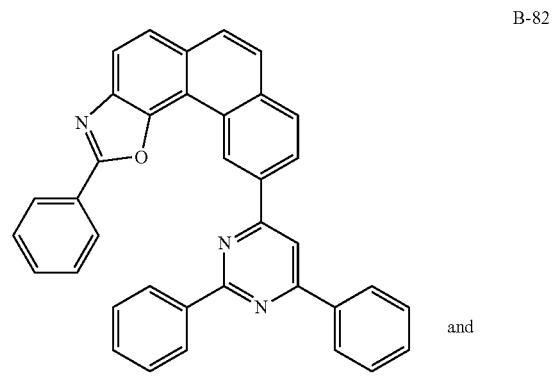
and

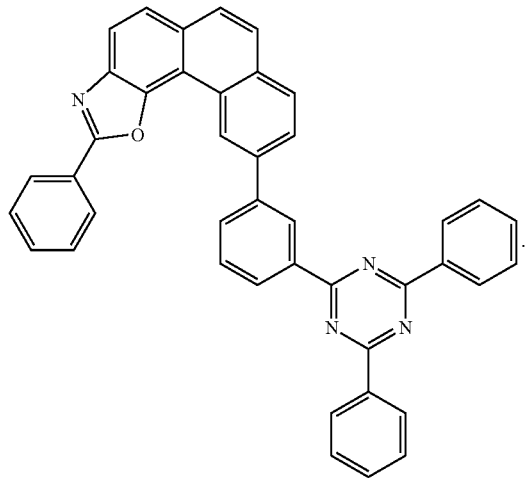
B-83
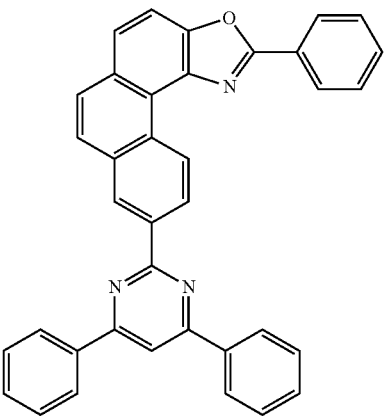
C-3
3. The organic electroluminescent device according to claim 1, wherein the compound represented by formula 2 is selected from the group consisting of:
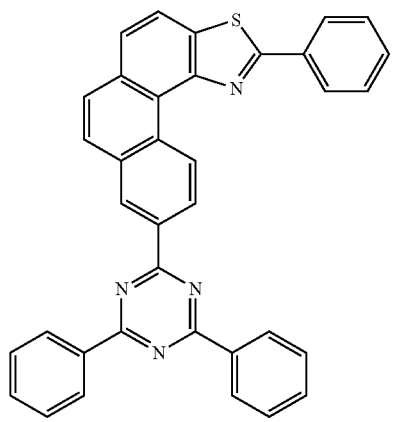
C-1
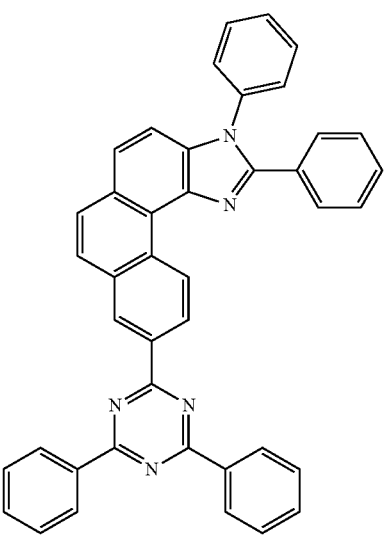
C-4
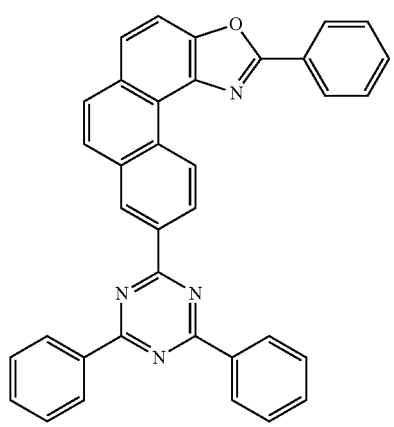
C-2
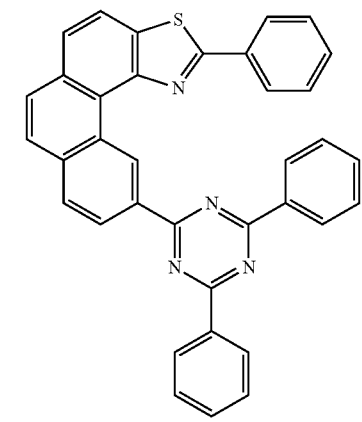
C-5

C-6
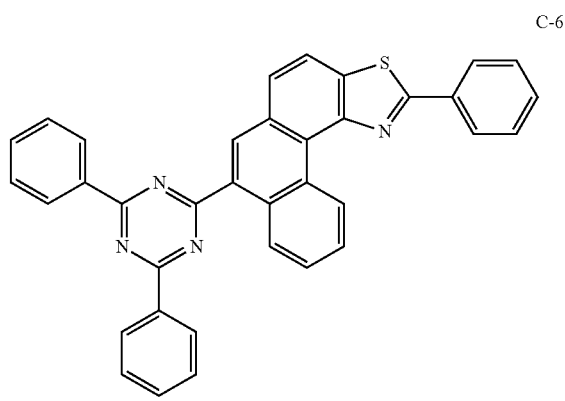
C-7
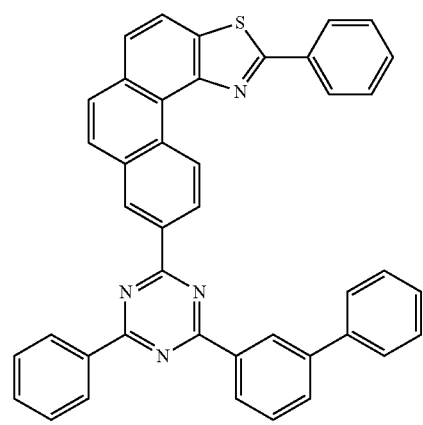
C-8
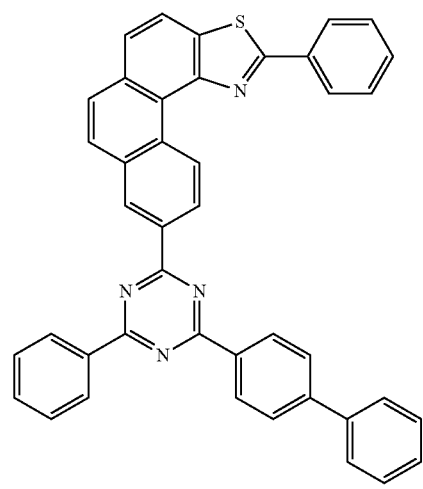
C-9
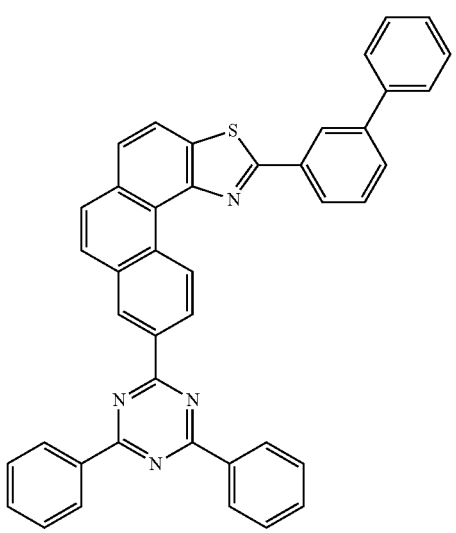
C-10
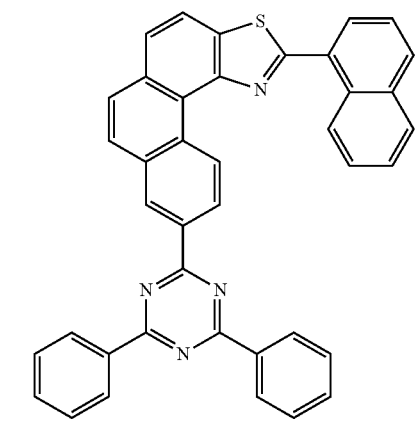
C-11
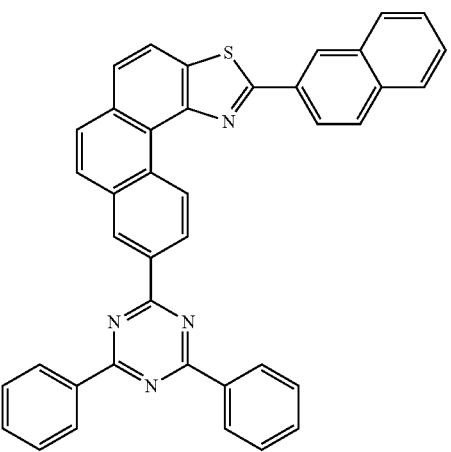

187
-continued
C-12
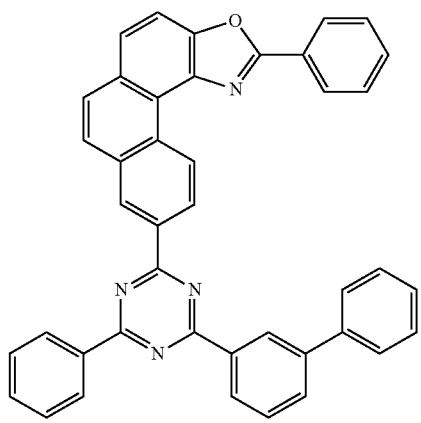
C-13
C-14
188
-continued
C-15
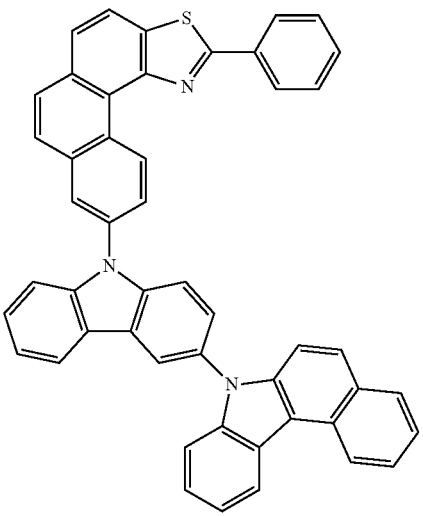
C-16
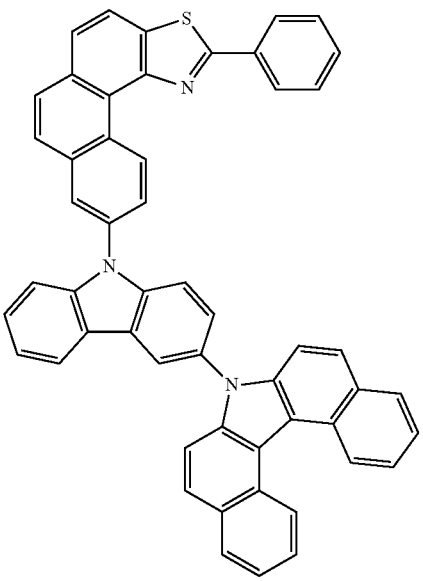
C-17
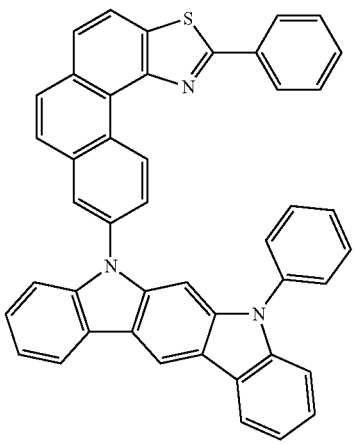

189
-continued
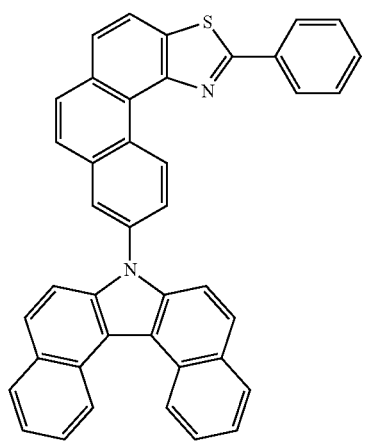
C-18
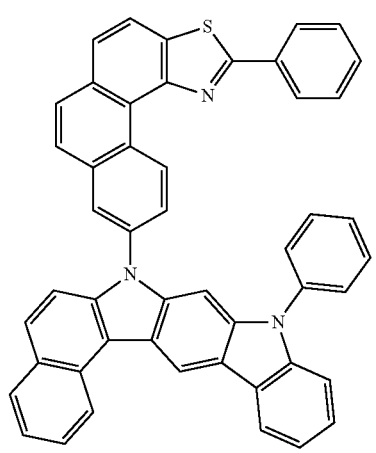
C-19
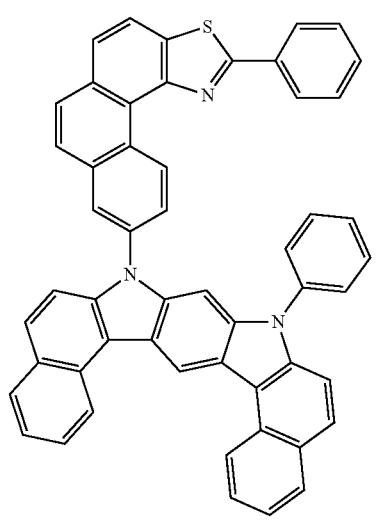
C-20
190
-continued
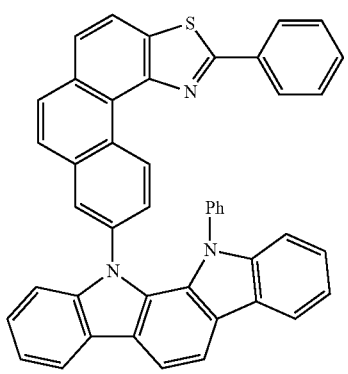
C-21
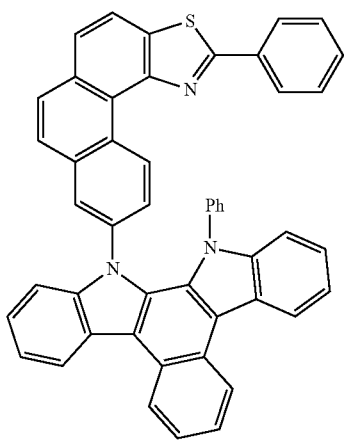
C-22
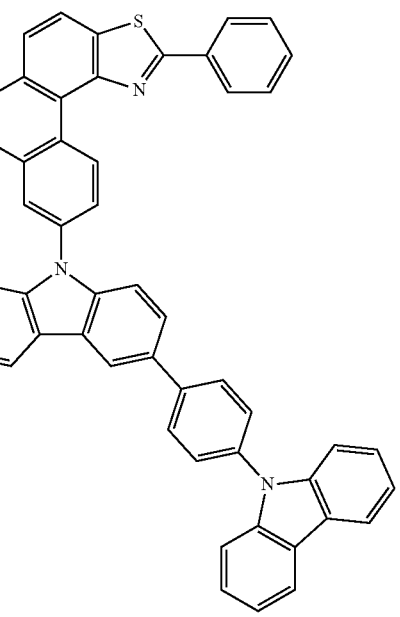
C-23

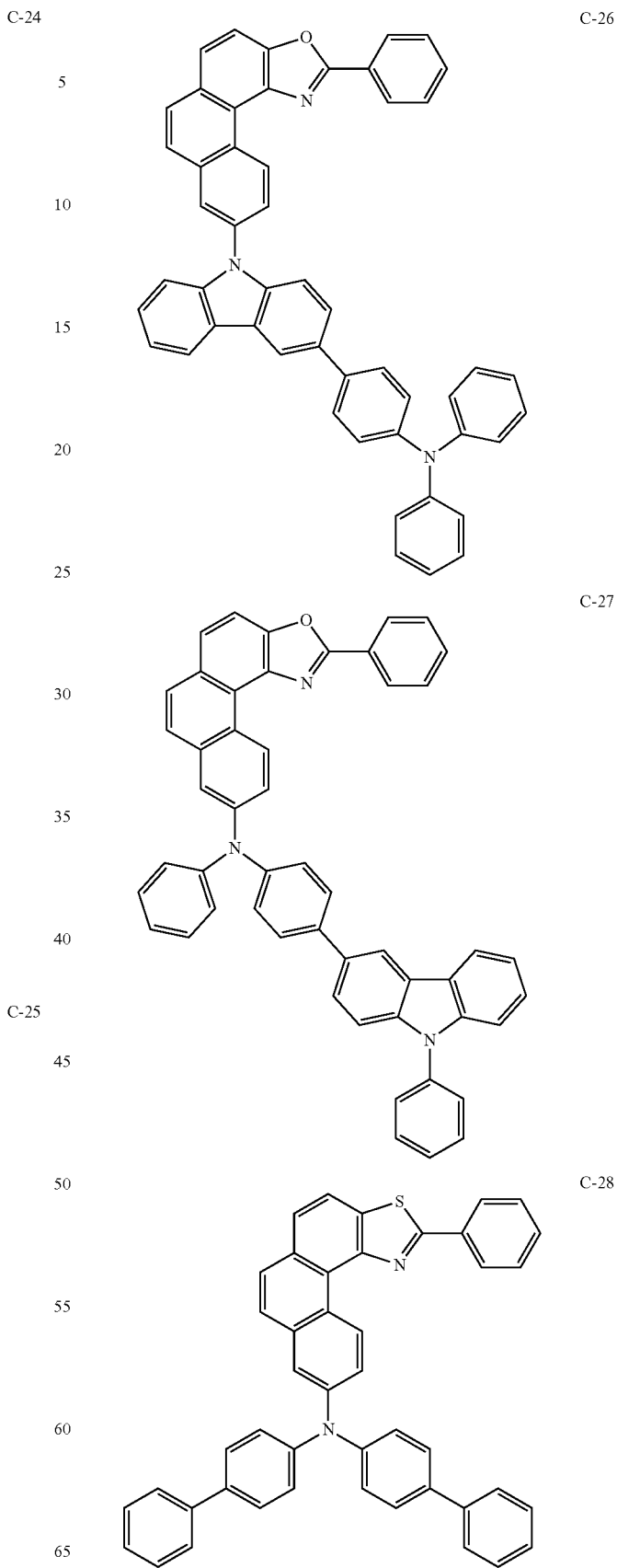

C-29
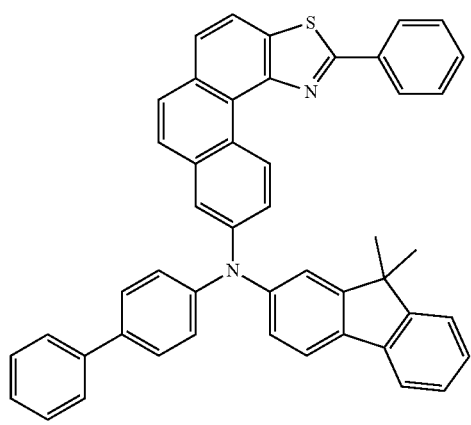
C-30
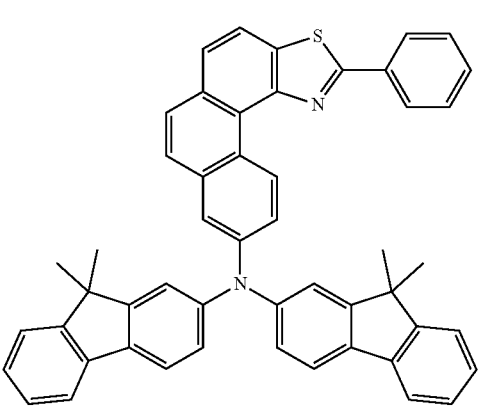
C-31
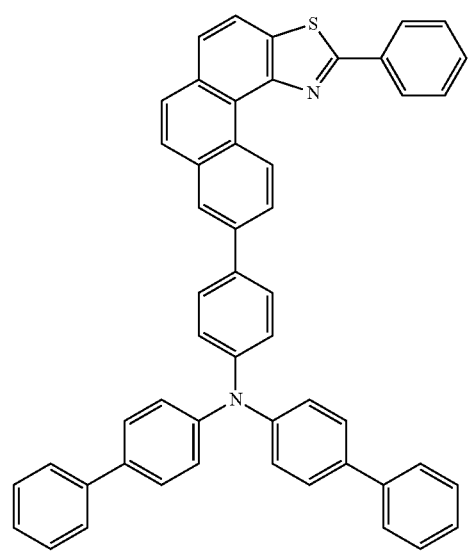
C-32
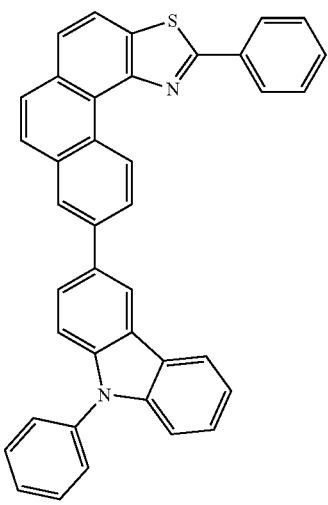
C-33
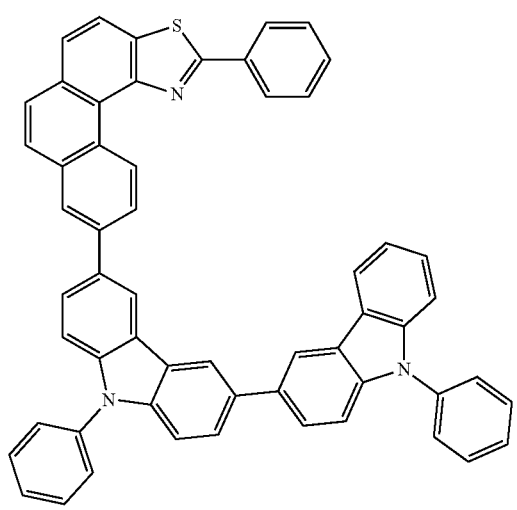
C-34
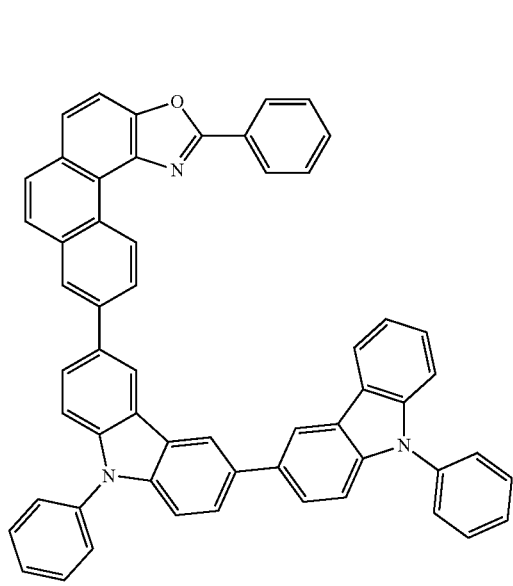

-continued
C-35
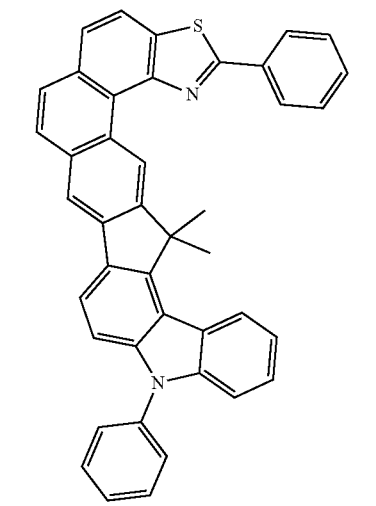
C-36
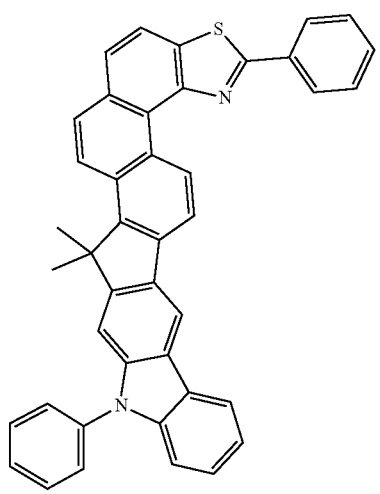
C-37
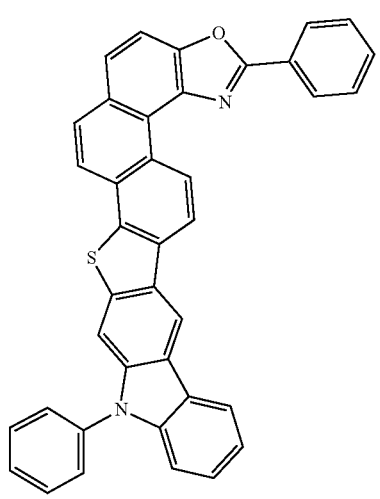
C-38
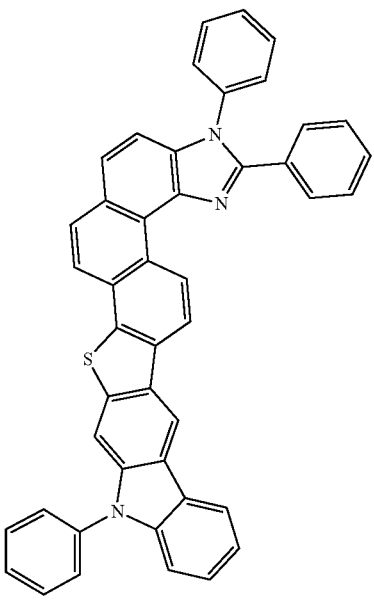
C-39
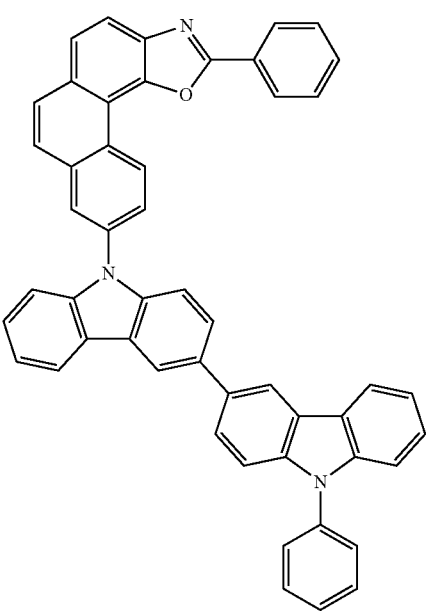

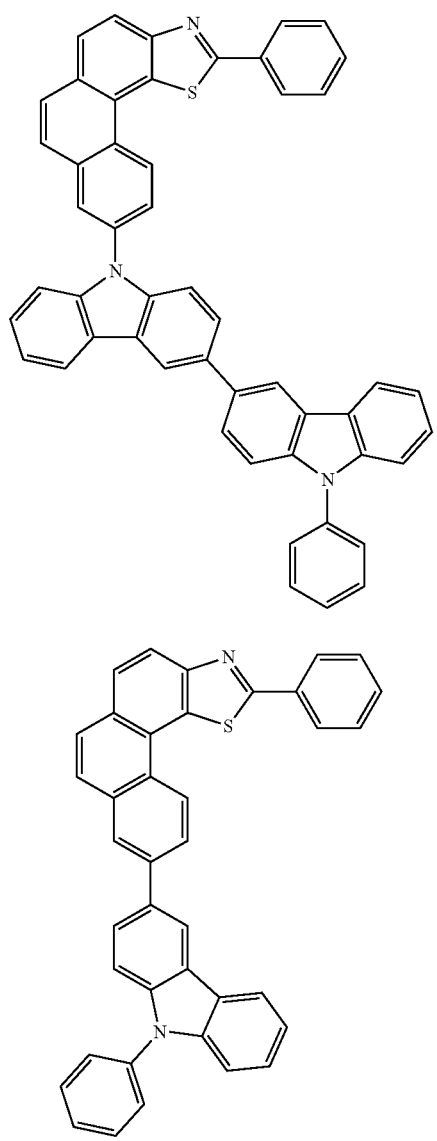
C-40
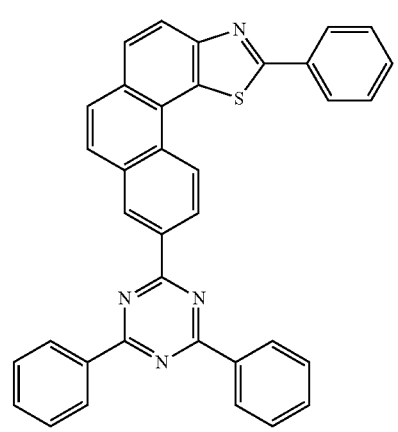
C-41
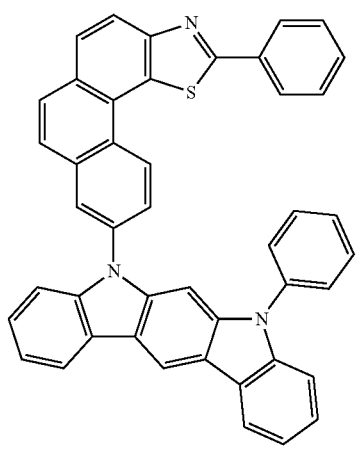
C-42
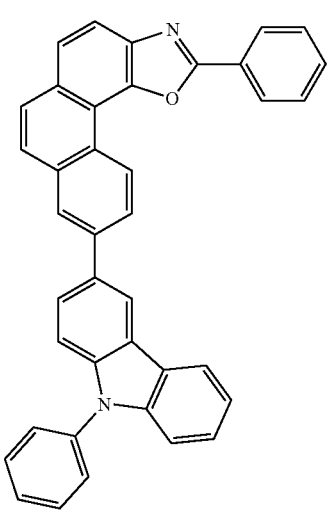
C-43
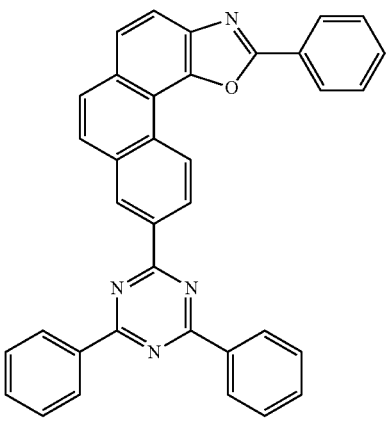
C-44
C-45

C-46
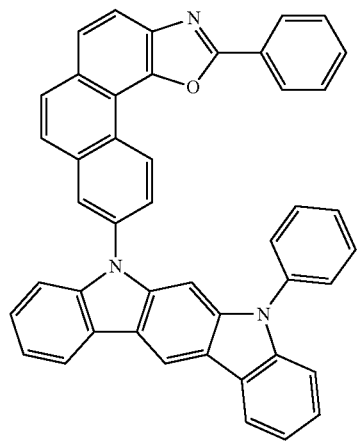
C-47
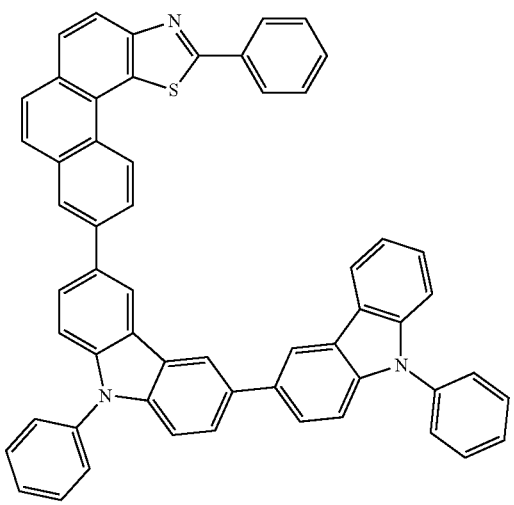
C-48
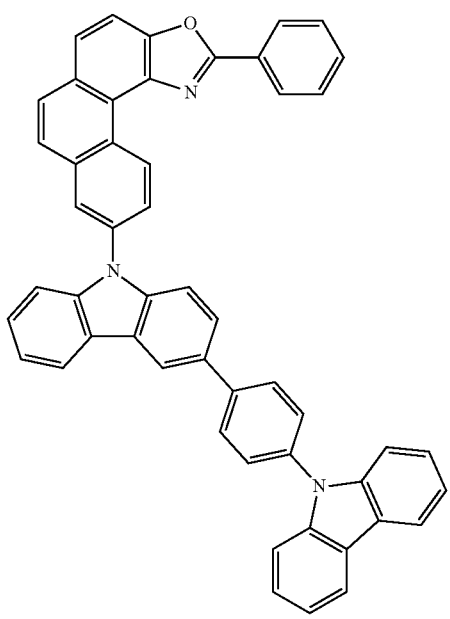
C-49
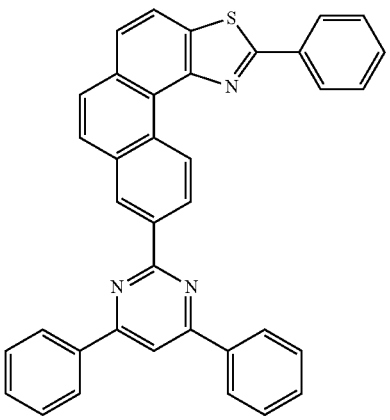
C-50
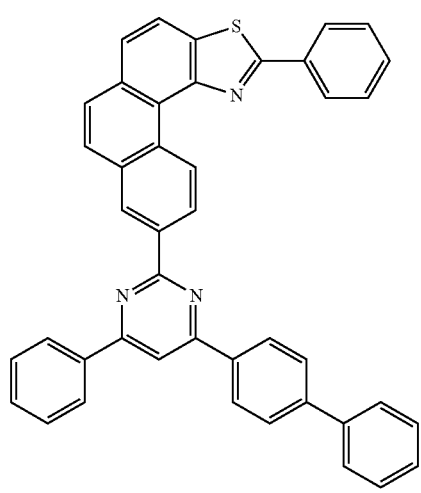
C-51
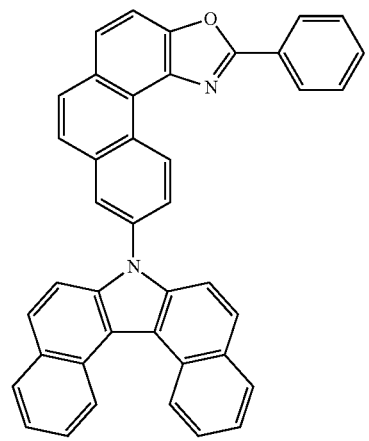

C-52
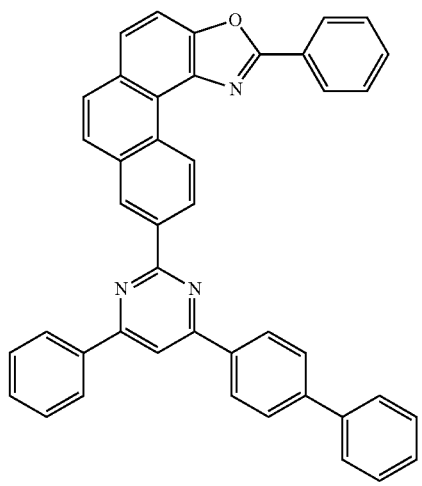
C-53
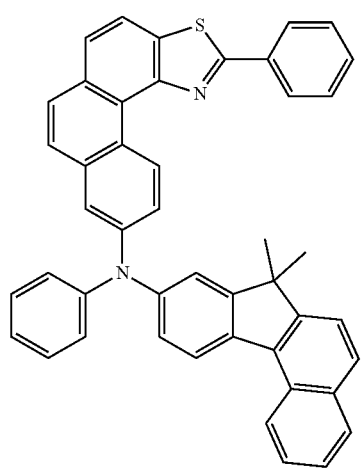
C-54
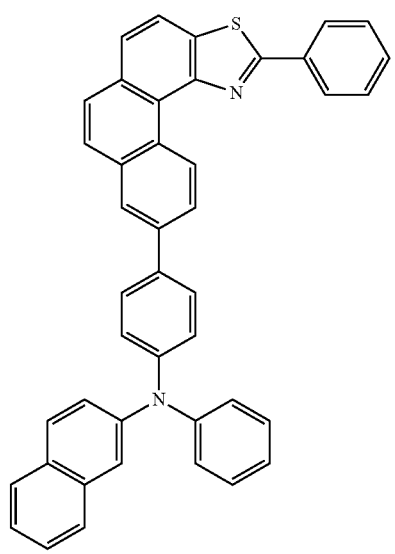
C-55
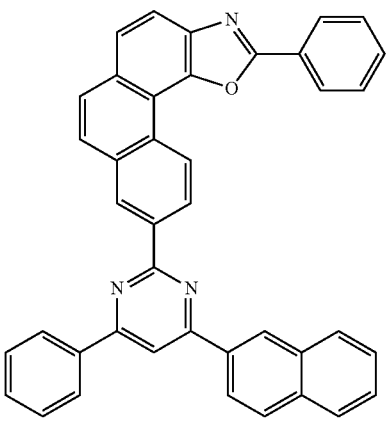
C-56
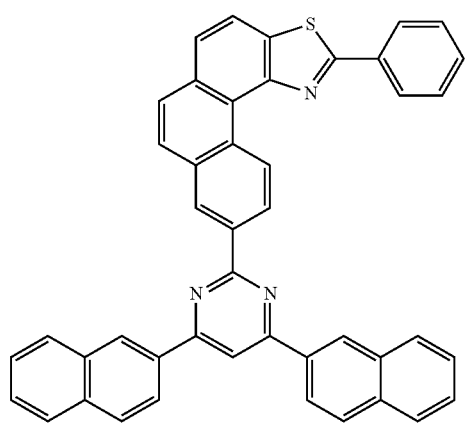
C-57

C-58 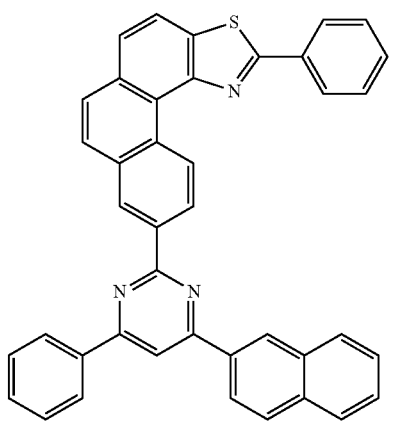
C-61 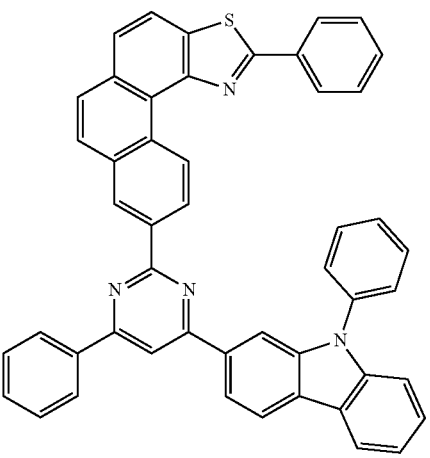
C-59 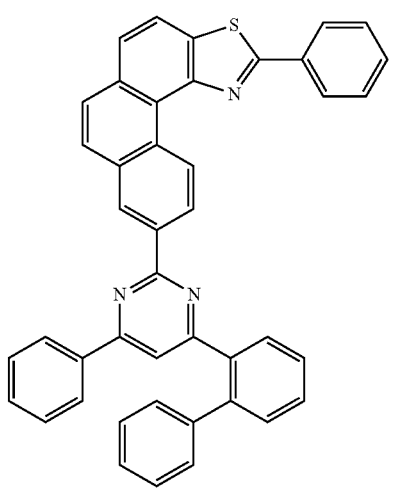
C-62 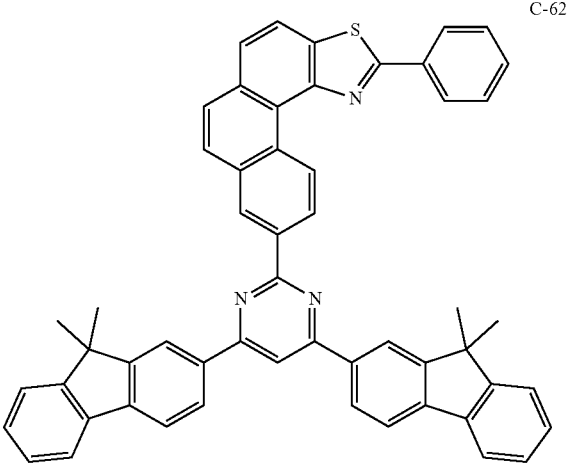
C-60 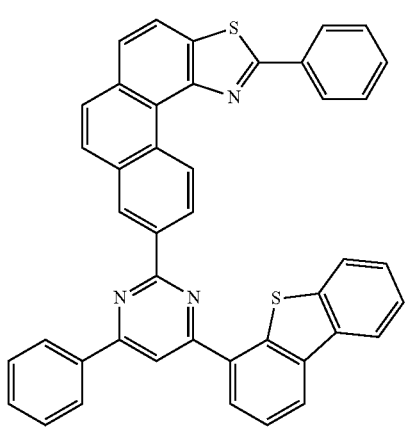
C-63 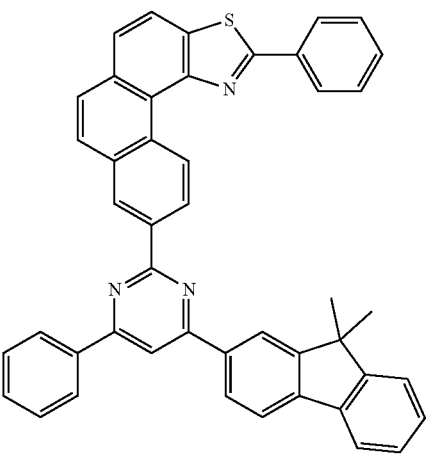

-continued
C-64
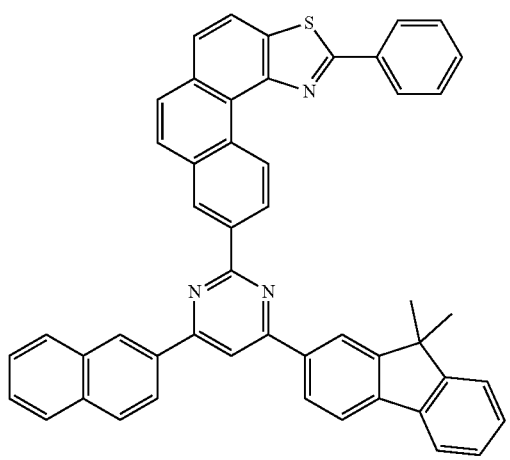
C-65
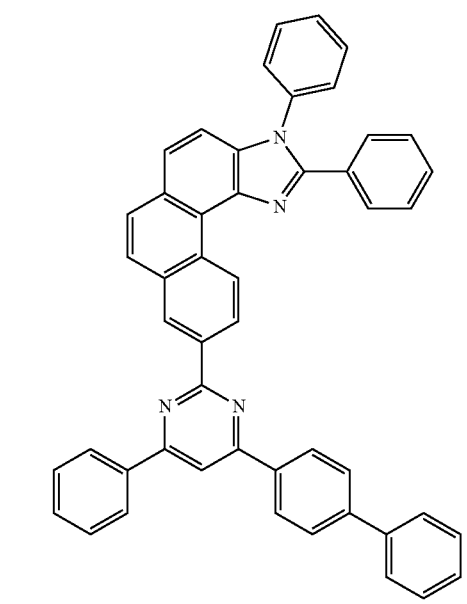
C-66
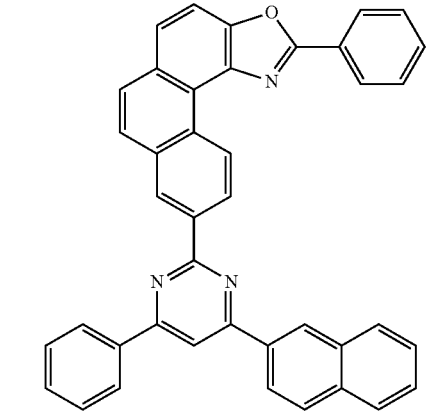
-continued
C-67
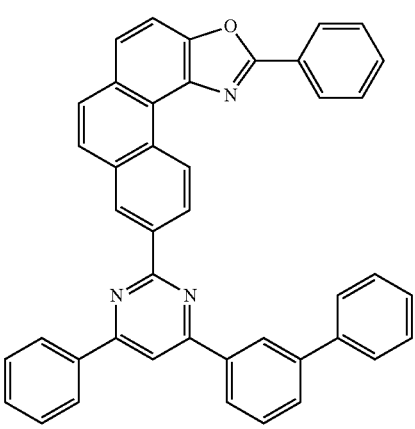
C-68
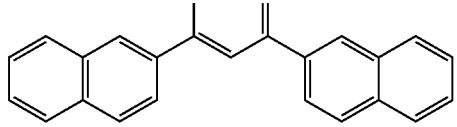
C-69

-continued
C-70
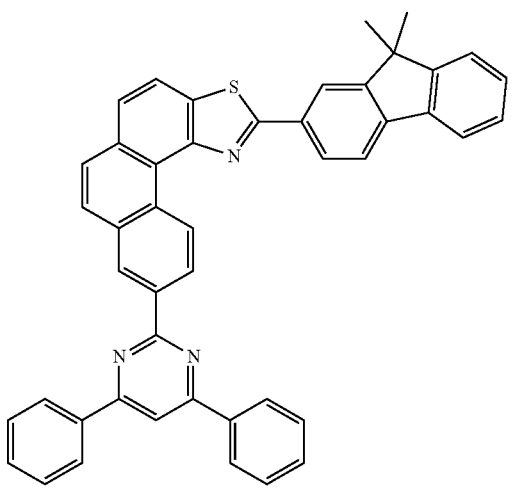
C-71
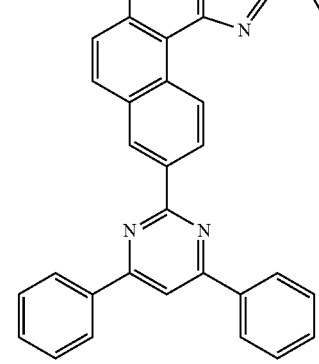
C-72
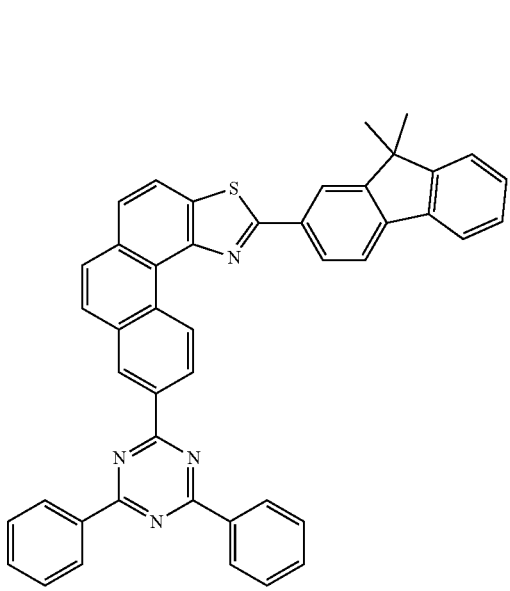
C-73
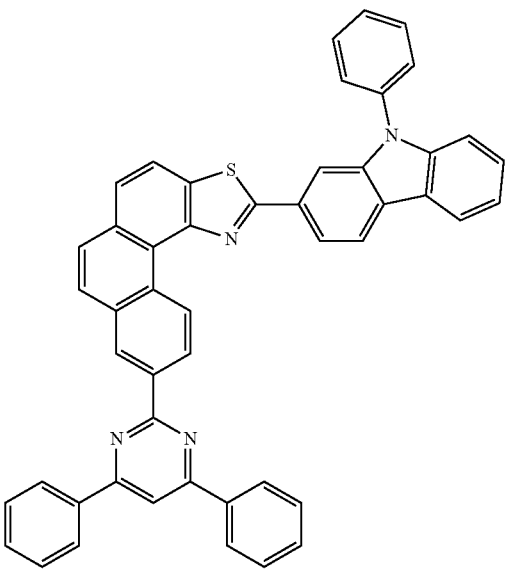
C-74
C-75
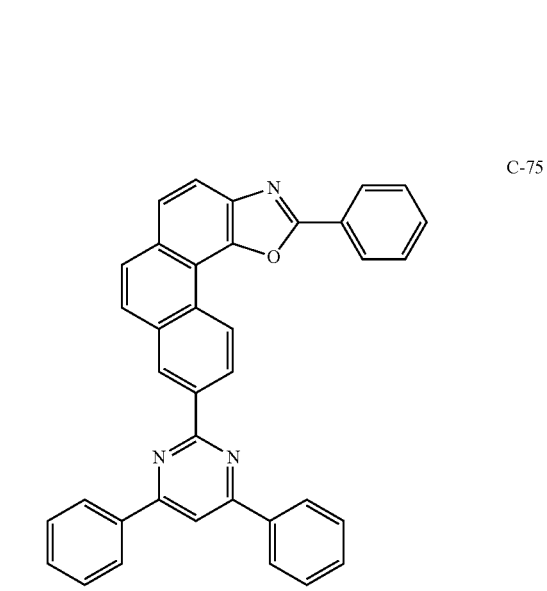

-continued
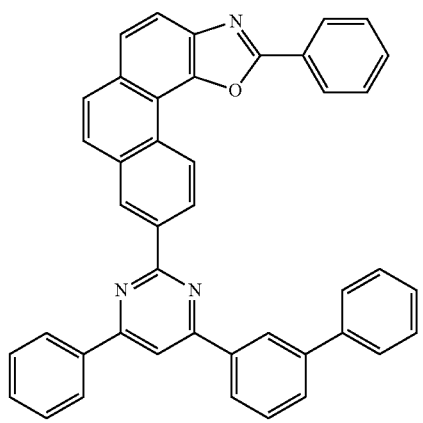
C-76
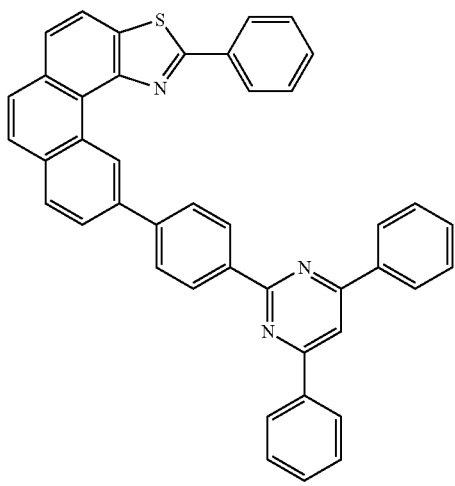
C-79
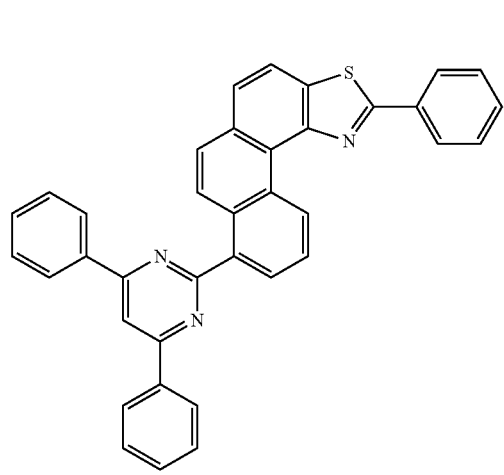
C-77
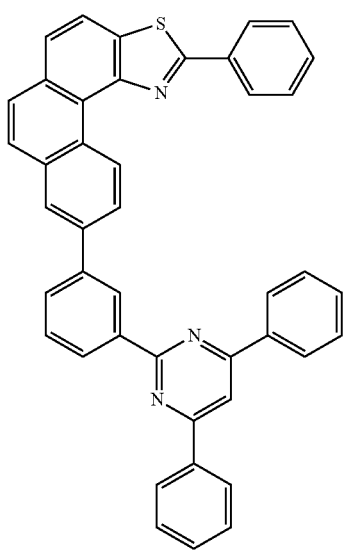
C-80
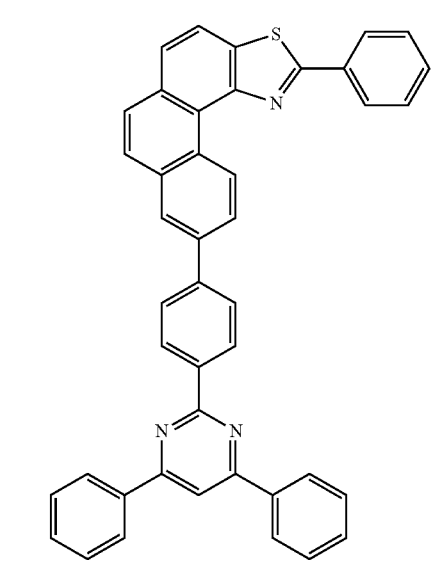
C-78
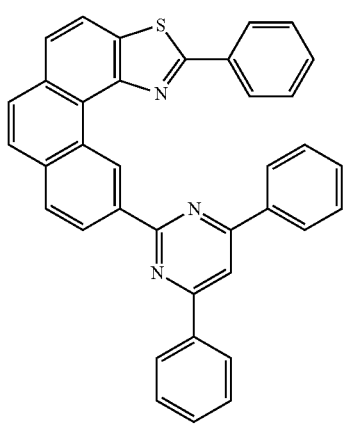
C-82

C-83 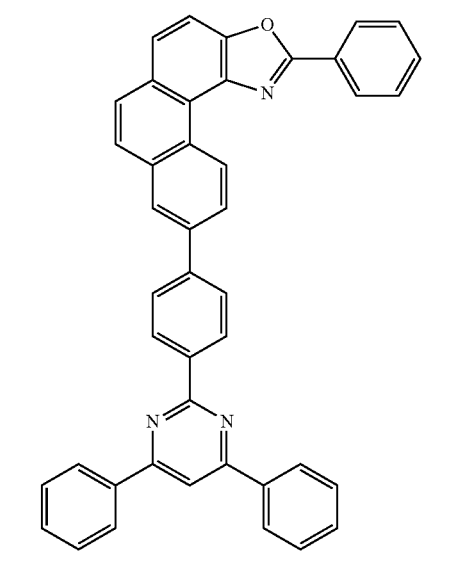
C-87 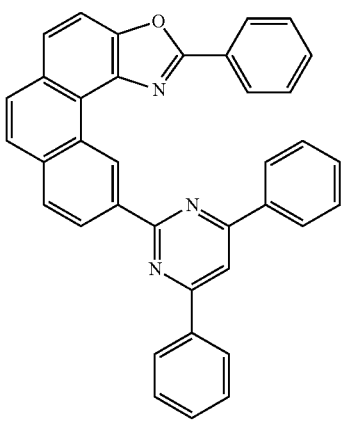
C-84 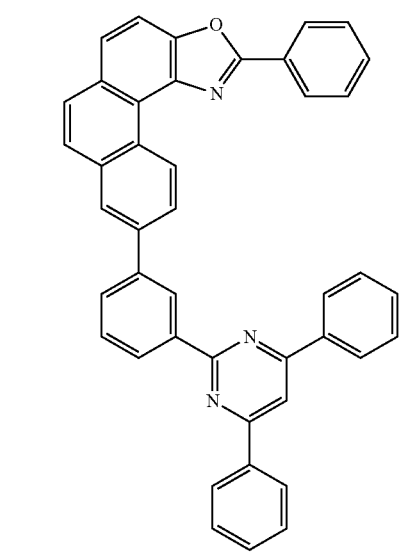
C-88 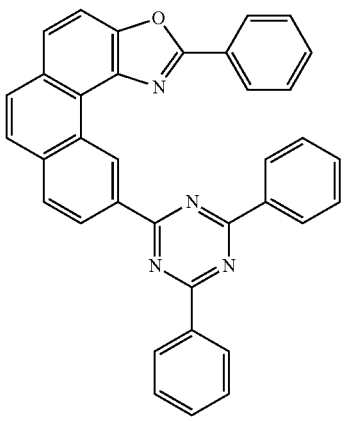
C-85
C-91 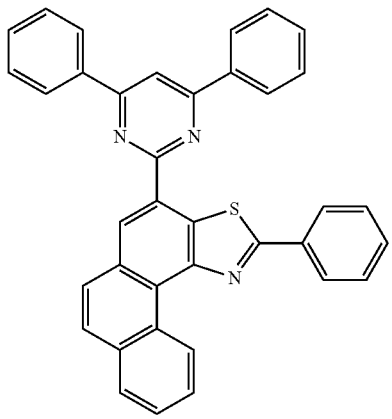

C-92
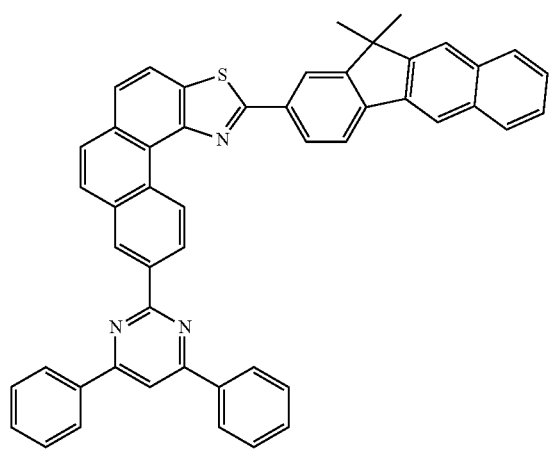
C-93
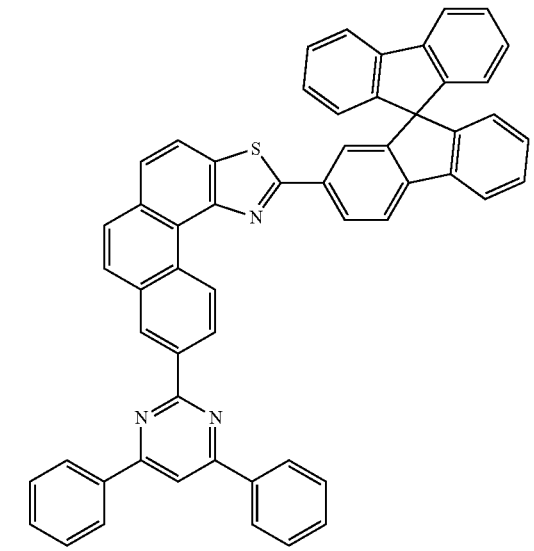
C-94
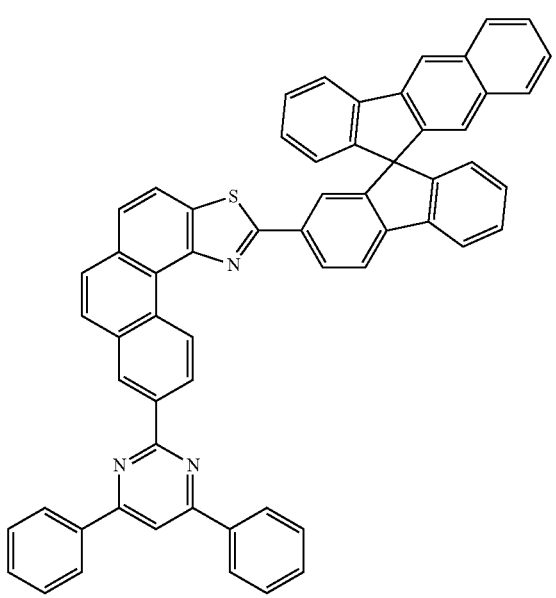
C-95
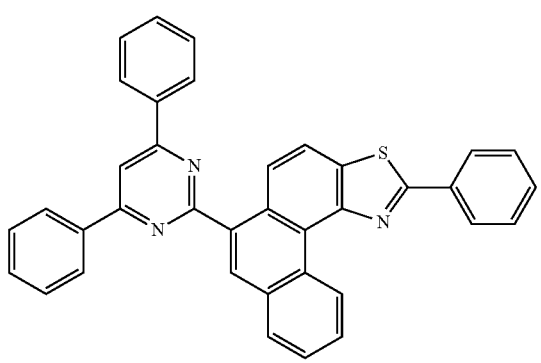
C-96
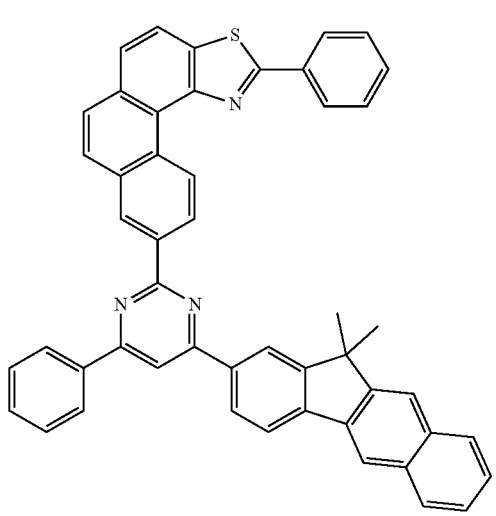
C-97
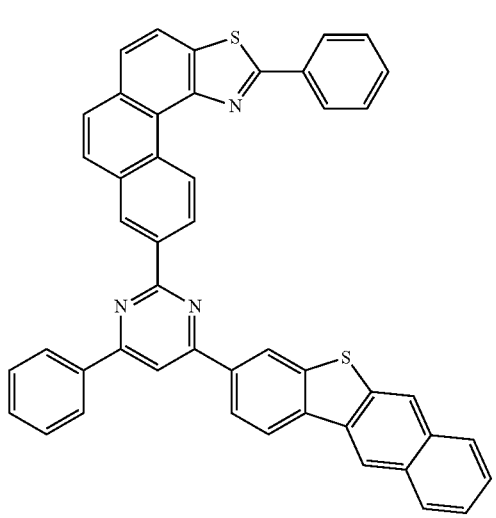

C-98
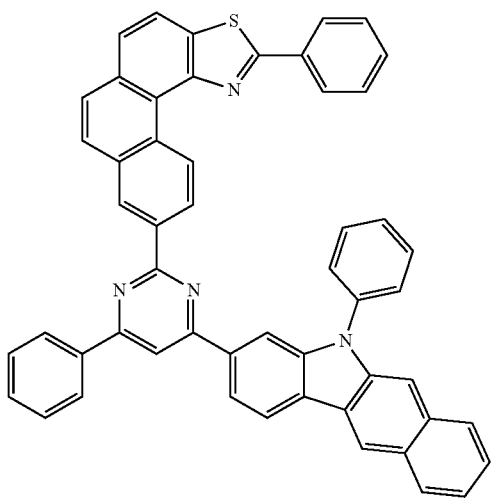
C-100
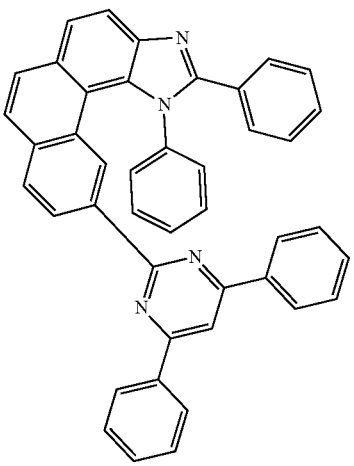
C-101
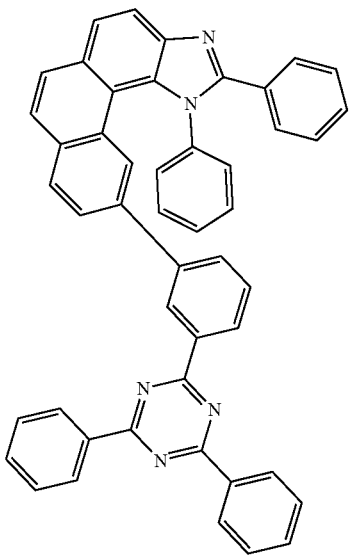
C-102
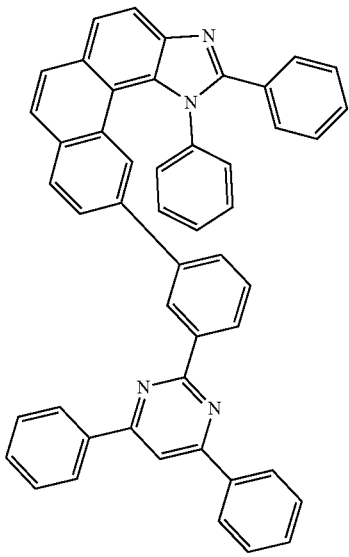
C-103
C-104

C-105
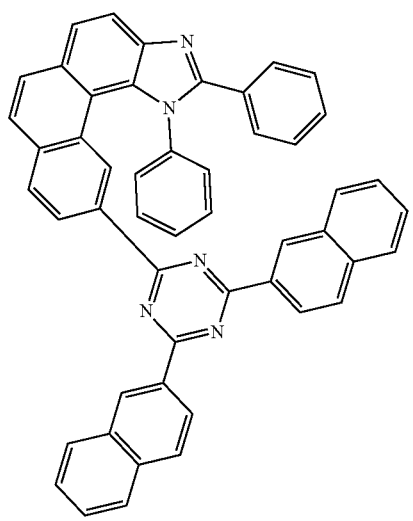
C-106
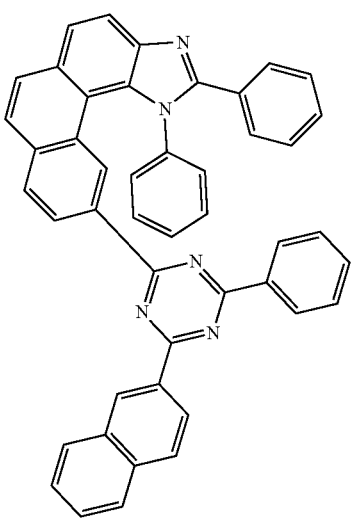
C-107
C-108
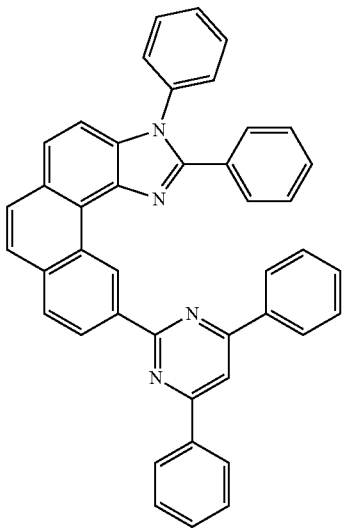
C-109
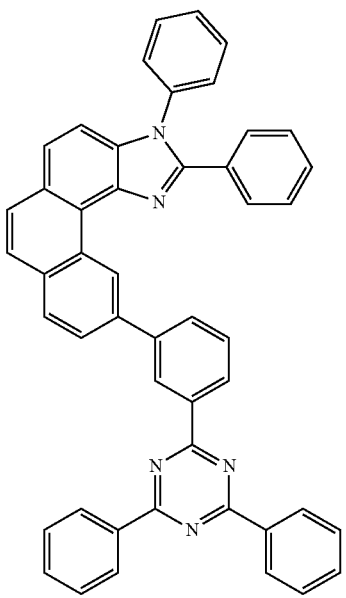

-continued
C-110
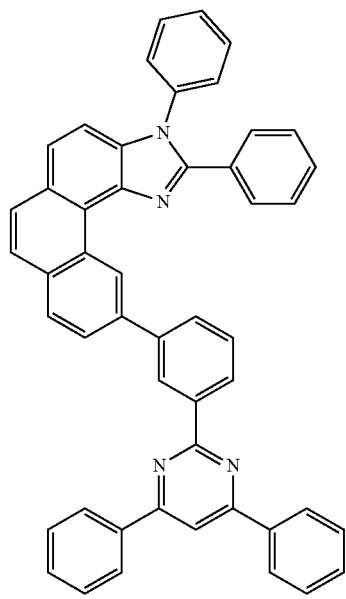
C-111
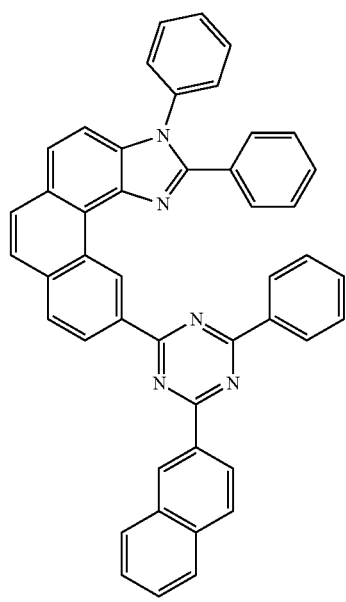
C-112
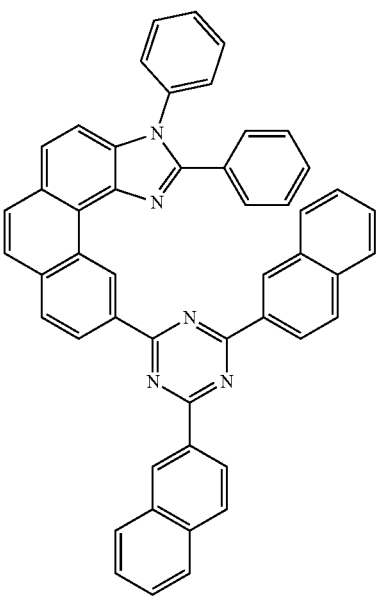
C-113
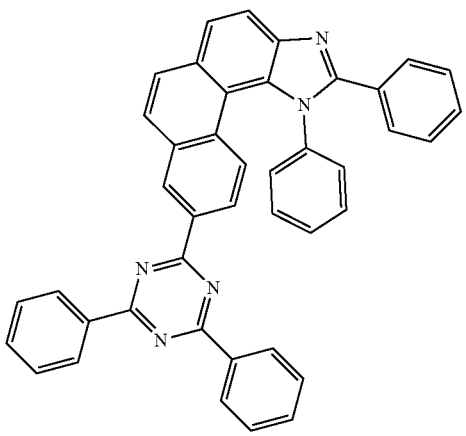
C-114
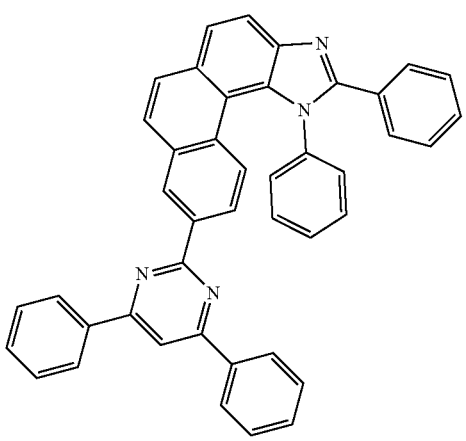

-continued
C-115
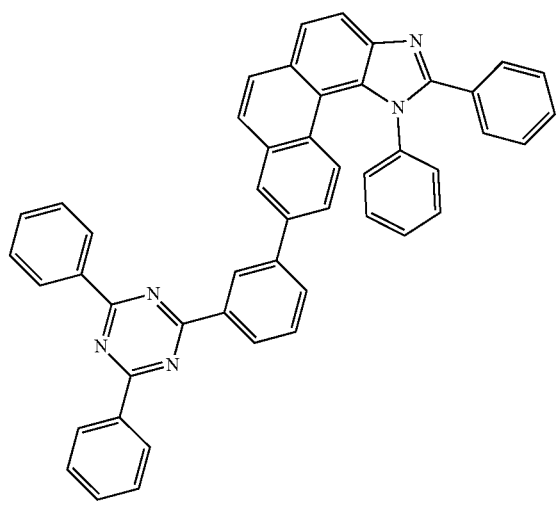
C-116
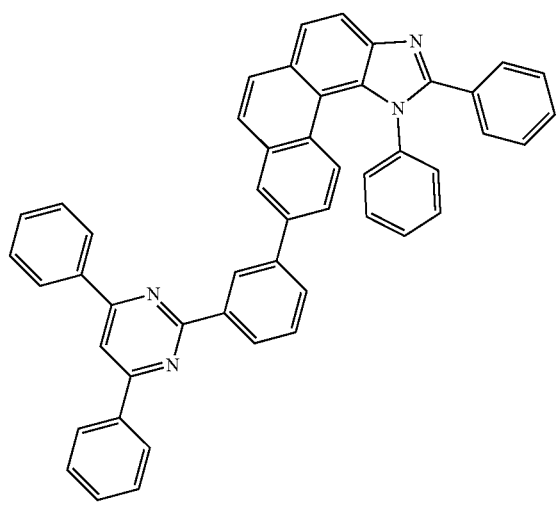
C-117
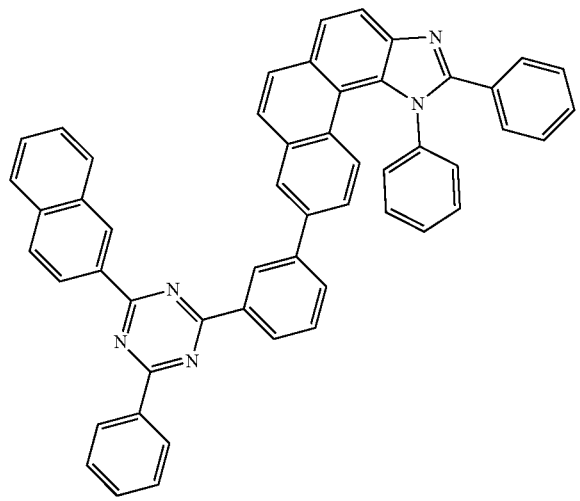
-continued
C-118
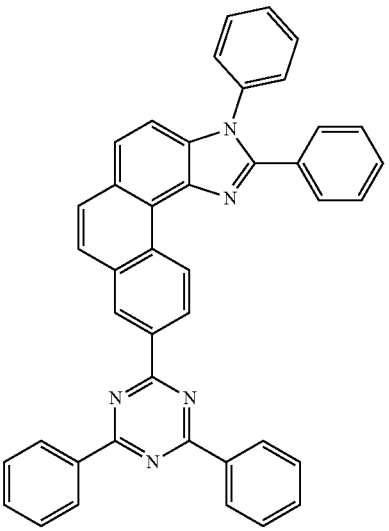
C-119
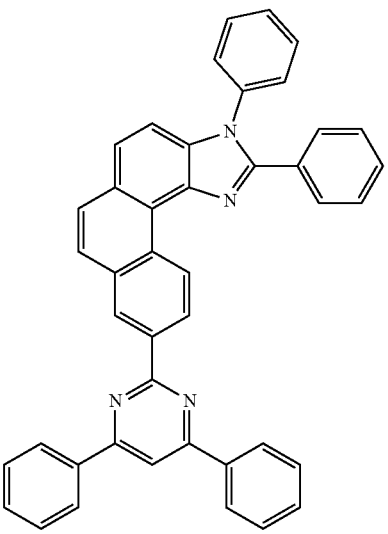

C-120
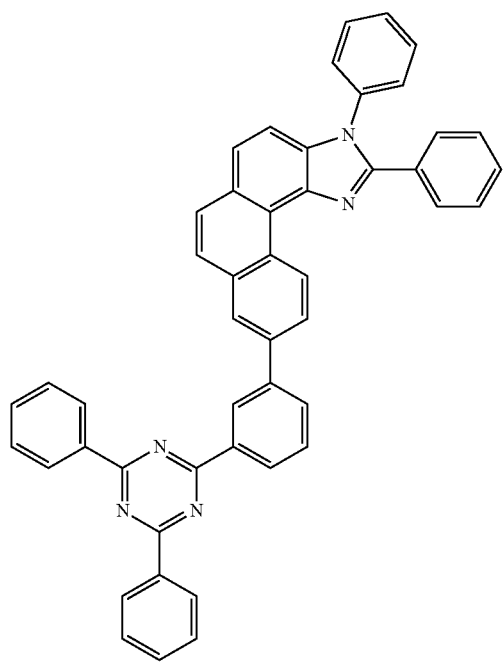
C-122
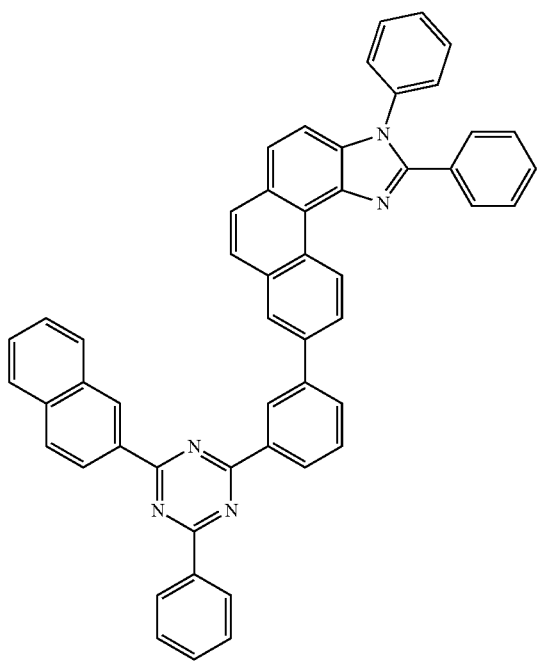
C-121
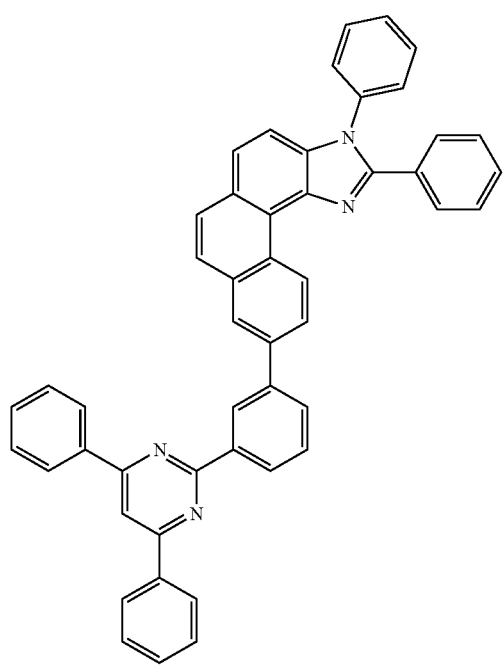
C-123
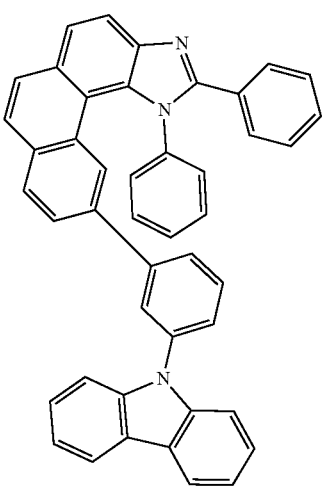

C-124
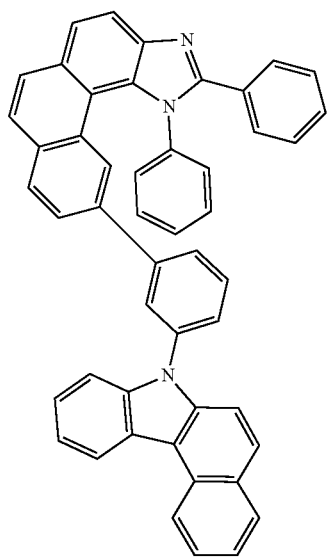
C-125
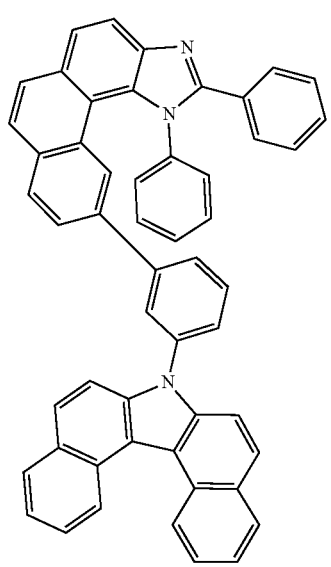
C-126
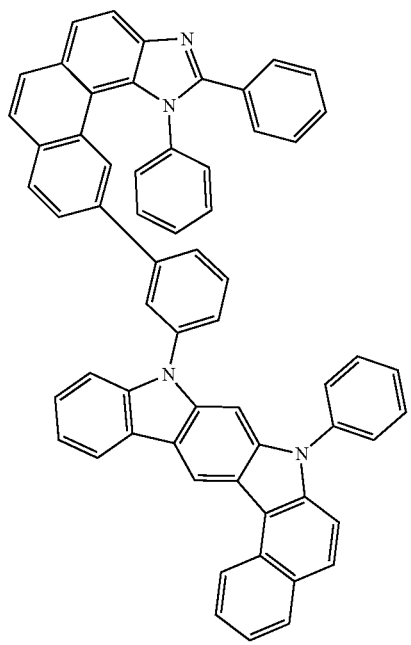
C-127
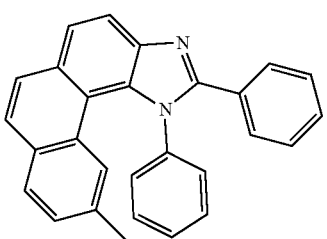
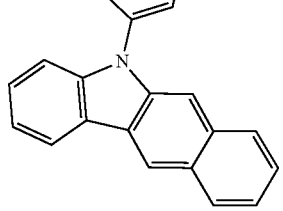
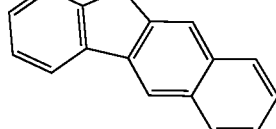
C-128
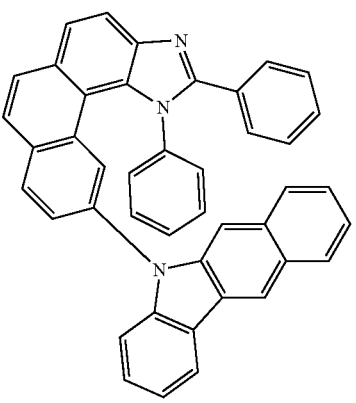

-continued
C-129
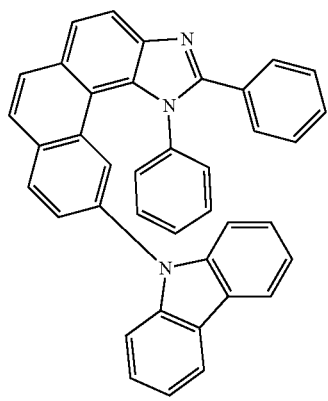
C-130
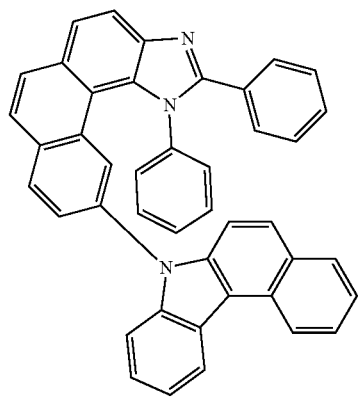
C-131
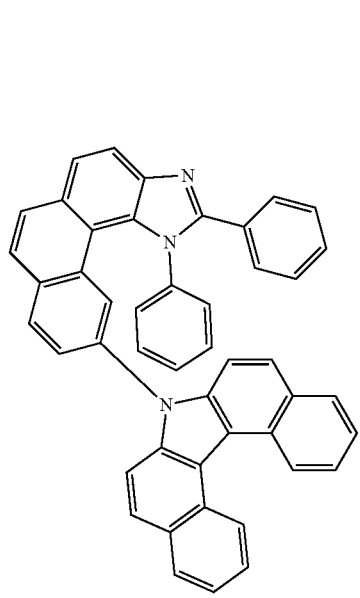
-continued
C-132
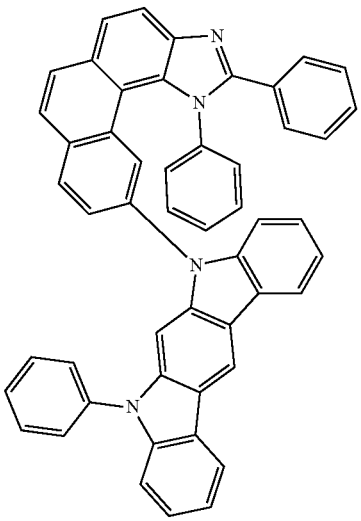
C-133
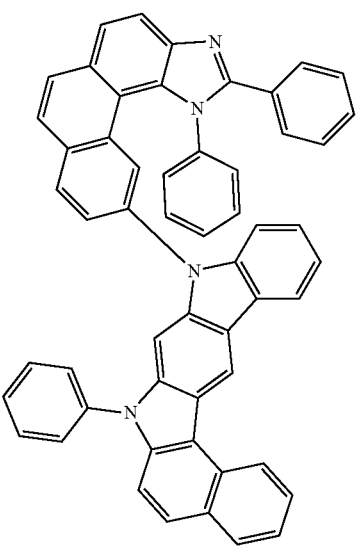
C-134
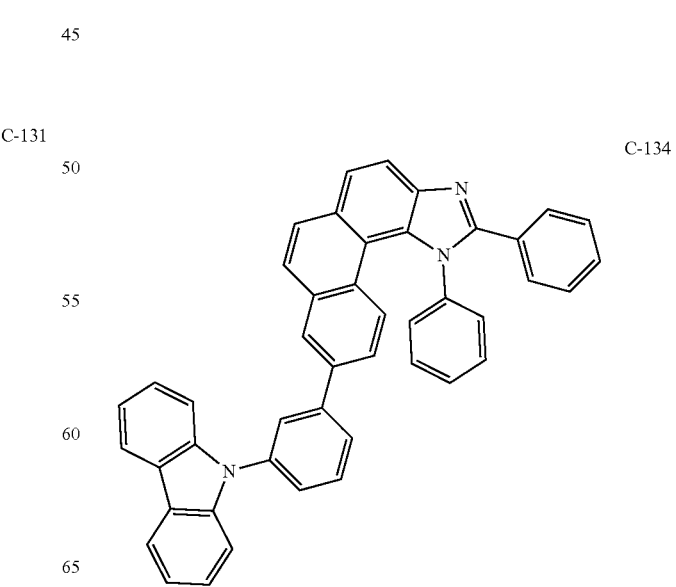

C-135 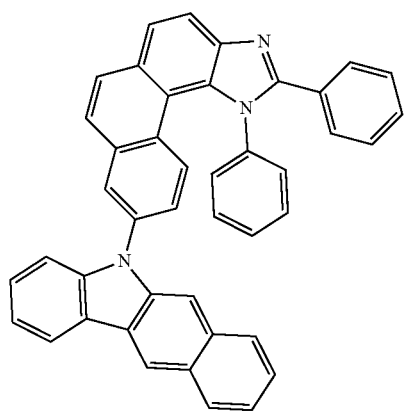
C-136 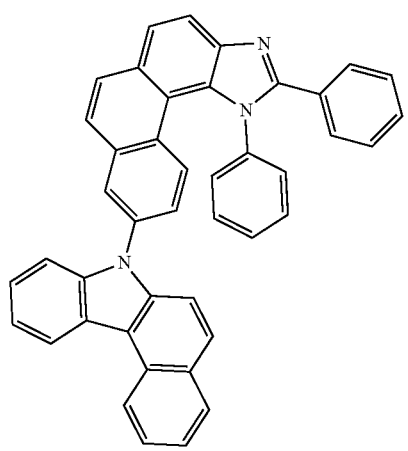
C-137 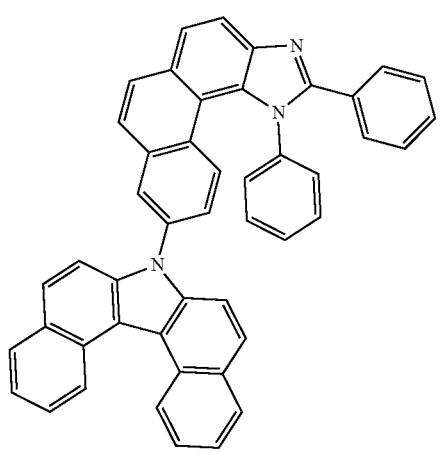
C-138 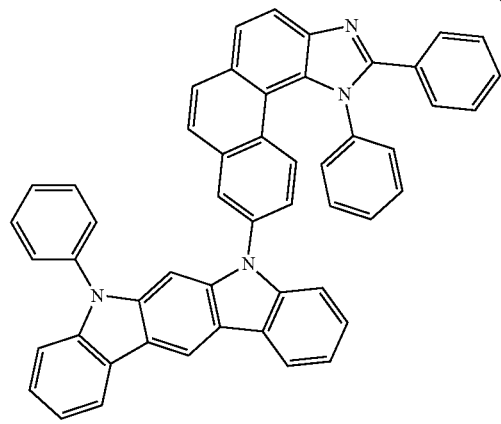
C-139 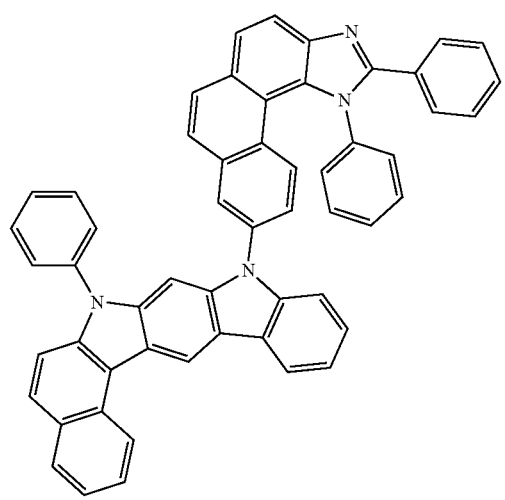
C-140 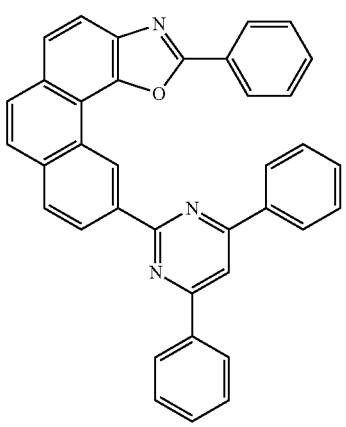

-continued

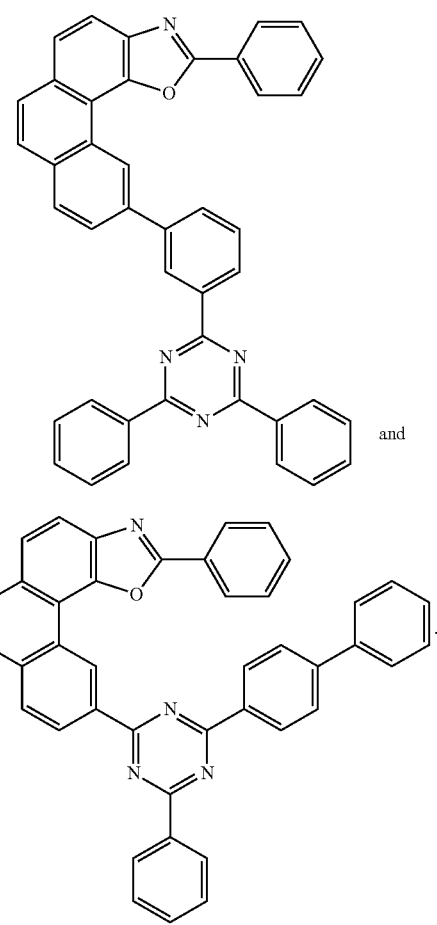

4. The organic electroluminescent device according to claim 1, wherein the light-emitting layer comprises a host compound and a dopant compound, the LUMO (lowest unoccupied molecular orbital) energy level of the electron buffer layer is higher than the LUMO energy level of the host compound, and the LUMO energy level of the electron transport layer is higher or lower than the LUMO energy level of the electron buffer layer.

5. The organic electroluminescent device according to claim 1, wherein the LUMO energy level of the light-emitting layer (Ah), the LUMO energy level of the electron buffer layer (Ab), and the LUMO energy level of the electron transport layer (Ae) satisfy the following equations (1) and (2):

$$|Ae-Ab| \leq 0.3 \text{ eV} \tag{1}$$

$$|Ab-Ah| \leq 0.4 \text{ eV} \tag{2}.$$

6. The organic electroluminescent device according to claim 1, wherein the LUMO energy level of the electron buffer layer (Ab) and the LUMO energy level of the electron transport layer (Ae) satisfy the following equation (3), equation (4), or both of them:

$$Ae \leq Ab+0.2 \text{ eV} \tag{3}$$

$$Ab \leq Ae+0.2 \text{ eV} \tag{4}.$$

7. The organic electroluminescent device according to claim 1, wherein the electron transport layer further comprises a reductive dopant.

* * * * *

UNITED STATES PATENT AND TRADEMARK OFFICE
CERTIFICATE OF CORRECTION

| | | |
|---|---|---|
| PATENT NO. | : 11,930,704 B2 | Page 1 of 1 |
| APPLICATION NO. | : 18/062715 | |
| DATED | : March 12, 2024 | |
| INVENTOR(S) | : Hee-Choon Ahn et al. | |

It is certified that error appears in the above-identified patent and that said Letters Patent is hereby corrected as shown below:

In the Specification

Column 164, Lines 6, 11 and 19 - 'OILED' should be 'OLED'.

Signed and Sealed this
Thirtieth Day of April, 2024

Katherine Kelly Vidal
*Director of the United States Patent and Trademark Office*